(12) United States Patent
Miller et al.

(10) Patent No.: US 12,089,972 B2
(45) Date of Patent: Sep. 17, 2024

(54) APPARATUS AND METHODS FOR BIOPSY AND ASPIRATION OF BONE MARROW

(71) Applicant: TELEFLEX LIFE SCIENCES LIMITED, Valletta (MT)

(72) Inventors: Larry J. Miller, Spring Branch, TX (US); David S. Bolleter, San Antonio, TX (US); Robert W. Titkemeyer, San Antonio, TX (US); Matthew T. Harmon, Santa Cruz, CA (US)

(73) Assignee: TELEFLEX LIFE SCIENCES LIMITED, Valletta (MT)

( * ) Notice: Subject to any disclaimer, the term of this patent is extended or adjusted under 35 U.S.C. 154(b) by 0 days.

(21) Appl. No.: 17/899,345

(22) Filed: Aug. 30, 2022

(65) Prior Publication Data
US 2022/0409321 A1    Dec. 29, 2022

Related U.S. Application Data

(60) Continuation of application No. 16/155,505, filed on Oct. 9, 2018, now Pat. No. 11,426,249, which is a
(Continued)

(51) Int. Cl.
*A61B 50/30* (2016.01)
*A61B 10/02* (2006.01)
(Continued)

(52) U.S. Cl.
CPC ........ *A61B 50/3001* (2016.02); *A61B 10/025* (2013.01); *A61B 17/3472* (2013.01);
(Continued)

(58) Field of Classification Search
CPC ............... A61B 50/3001; A61B 50/33; A61B 2050/3008; A61B 17/3472; A61B 10/025;
(Continued)

(56) References Cited

U.S. PATENT DOCUMENTS

| | | |
|---|---|---|
| 1,272,104 A | 7/1918 | Riethmueller |
| 1,539,637 A | 5/1925 | Bronner |

(Continued)

FOREIGN PATENT DOCUMENTS

| | | |
|---|---|---|
| CA | 2138842 A1 | 6/1996 |
| CA | 2366676 A1 | 9/2000 |

(Continued)

OTHER PUBLICATIONS

Office Action for U.S. Appl. No. 11/190,331, dated Mar. 23, 2009.
(Continued)

*Primary Examiner* — Anu Ramana
(74) *Attorney, Agent, or Firm* — BakerHostetler

(57) ABSTRACT

Medical procedure trays and related methods are provided to accommodate joining a first non-sterile medical device with a second sterile medical device and maintaining required sterilization of the second sterile medical device to perform an associated medical procedure. One example of such medical procedures includes biopsy of a bone and/or associated bone marrow using a non-sterile powered driver and a sterile biopsy needle or biopsy needle set. Each medical procedure tray may include a containment bag or sterile sleeve. A coupler assembly, one or more sharps protectors, a biopsy sample ejector and/or associated ejector funnel may also be included. Some medical procedure trays may allow engaging a non-sterile powered driver with one end of a coupler assembly and sealing the non-sterile powered driver in a sterile sleeve or containment bag without compromising sterility of other components in the medical procedure tray.

16 Claims, 38 Drawing Sheets

Related U.S. Application Data continuation of application No. 14/600,162, filed on Jan. 20, 2015, now abandoned, which is a division of application No. 12/407,651, filed on Mar. 19, 2009, now Pat. No. 8,944,069, which is a continuation-in-part of application No. 11/853,701, filed on Sep. 11, 2007, now Pat. No. 8,656,929.

(60) Provisional application No. 60/910,122, filed on Apr. 4, 2007, provisional application No. 60/825,325, filed on Sep. 12, 2006.

(51) Int. Cl.
| | | |
|---|---|---|
| *A61B 17/34* | (2006.01) | |
| *A61B 46/00* | (2016.01) | |
| *A61B 46/10* | (2016.01) | |
| *A61B 50/33* | (2016.01) | |
| *A61B 17/00* | (2006.01) | |
| *A61B 17/064* | (2006.01) | |
| *A61B 46/23* | (2016.01) | |
| *A61B 50/00* | (2016.01) | |
| *A61B 90/00* | (2016.01) | |
| *A61B 90/40* | (2016.01) | |

(52) U.S. Cl.
CPC .............. *A61B 46/00* (2016.02); *A61B 46/10* (2016.02); *A61B 50/30* (2016.02); *A61B 50/33* (2016.02); *A61B 2010/0208* (2013.01); *A61B 2010/0258* (2013.01); *A61B 2017/0046* (2013.01); *A61B 2017/00734* (2013.01); *A61B 2017/0649* (2013.01); *A61B 46/23* (2016.02); *A61B 2050/0065* (2016.02); *A61B 2050/3008* (2016.02); *A61B 2050/314* (2016.02); *A61B 2090/062* (2016.02); *A61B 90/40* (2016.02); *A61B 2562/247* (2013.01); *Y10T 29/49826* (2015.01)

(58) Field of Classification Search
CPC .. A61B 2010/0208; A61B 46/10; A61B 90/40
See application file for complete search history.

(56) References Cited

U.S. PATENT DOCUMENTS

| | | | |
|---|---|---|---|
| 1,686,482 | A | 10/1928 | Windle |
| 1,954,620 | A | 4/1934 | Connell |
| 2,080,202 | A | 5/1937 | Drake |
| 2,130,845 | A | 9/1938 | Von Issendorff |
| 2,138,842 | A | 12/1938 | Drew |
| 2,219,605 | A | 10/1940 | Turkel |
| 2,261,958 | A | 11/1941 | Burri |
| 2,317,648 | A | 4/1943 | Siqveland |
| 2,318,648 | A | 5/1943 | Penfold |
| 2,419,045 | A | 4/1947 | Whittaker |
| 2,426,535 | A | 8/1947 | Turkel |
| 2,525,588 | A | 10/1950 | Cameron et al. |
| 2,525,839 | A | 10/1950 | Sparklin |
| 2,590,516 | A | 3/1952 | De Von Breymann |
| 2,660,635 | A | 11/1953 | Wood |
| 2,714,026 | A | 7/1955 | Schultz |
| RE24,056 | E | 8/1955 | Johansen |
| 2,766,907 | A | 10/1956 | Wallace, Jr. |
| 2,773,501 | A | 12/1956 | Young |
| 2,817,648 | A | 12/1957 | Gould et al. |
| 2,860,635 | A | 11/1958 | Wilburn |
| 2,876,369 | A | 3/1959 | Doerner |
| 3,022,596 | A | 2/1962 | Cannon |
| 3,104,448 | A | 9/1963 | Morrow et al. |
| 3,120,845 | A | 2/1964 | Horner |
| 3,173,417 | A | 3/1965 | Horner |
| 3,175,554 | A | 3/1965 | Stewart |
| 3,269,046 | A | 8/1966 | Schaefer |
| 3,413,498 | A | 11/1968 | Bowen et al. |
| 3,507,276 | A | 4/1970 | Burgess et al. |
| 3,519,858 | A | 7/1970 | Morganson |
| 3,529,580 | A | 9/1970 | Stevens |
| 3,536,943 | A | 10/1970 | Bowen et al. |
| 3,543,966 | A | 12/1970 | Ryan et al. |
| 3,590,232 | A | 6/1971 | Sadowski |
| 3,598,108 | A | 8/1971 | Jamshidi et al. |
| 3,664,163 | A | 5/1972 | Foote |
| 3,671,699 | A | 6/1972 | Matthews |
| 3,697,223 | A | 10/1972 | Kovalcik et al. |
| 3,713,417 | A | 1/1973 | Shugart |
| 3,719,186 | A | 3/1973 | Merig |
| 3,734,207 | A | 5/1973 | Fishbein |
| 3,750,667 | A | 8/1973 | Pshenichny et al. |
| 3,802,555 | A | 4/1974 | Grasty et al. |
| 3,815,605 | A | 6/1974 | Schmidt et al. |
| 3,835,860 | A | 9/1974 | Garretson |
| 3,843,143 | A | 10/1974 | Laxson |
| 3,844,291 | A | 10/1974 | Moen |
| 3,850,158 | A | 11/1974 | Elias et al. |
| 3,893,445 | A | 7/1975 | Hofsess |
| 3,893,455 | A | 7/1975 | McNally |
| 3,935,909 | A | 2/1976 | Mabuchi et al. |
| 3,976,066 | A | 8/1976 | McCartney |
| 3,981,398 | A | 9/1976 | Boshoff |
| 3,991,765 | A | 11/1976 | Cohen |
| 3,999,110 | A | 12/1976 | Ramstrom et al. |
| 4,021,920 | A | 5/1977 | Kirschner et al. |
| 4,040,462 | A | 8/1977 | Hattan |
| 4,046,254 | A | 9/1977 | Kramer |
| 4,099,518 | A | 7/1978 | Baylis et al. |
| 4,124,026 | A | 11/1978 | Berner et al. |
| 4,142,517 | A | 3/1979 | Contreras et al. |
| 4,154,026 | A | 5/1979 | Palthe |
| 4,157,714 | A | 6/1979 | Foltz et al. |
| 4,170,993 | A | 10/1979 | Alvarez |
| 4,185,619 | A | 1/1980 | Reiss |
| 4,189,266 | A | 2/1980 | Koslow |
| 4,194,505 | A | 3/1980 | Schmitz |
| 4,200,111 | A | 4/1980 | Harris |
| 4,213,462 | A | 7/1980 | Sato |
| 4,256,119 | A | 3/1981 | Gauthier |
| 4,258,722 | A | 3/1981 | Sessions et al. |
| 4,262,676 | A | 4/1981 | Jamshidi |
| 4,266,555 | A | 5/1981 | Jamshidi |
| 4,269,192 | A | 5/1981 | Matsuo |
| 4,299,230 | A | 11/1981 | Kubota |
| 4,306,570 | A | 12/1981 | Matthews |
| 4,316,463 | A | 2/1982 | Schmitz et al. |
| 4,330,093 | A | 5/1982 | Chapman, Jr. |
| 4,333,459 | A | 6/1982 | Becker |
| 4,334,529 | A | 6/1982 | Wirth |
| 4,356,826 | A | 11/1982 | Kubota |
| 4,359,052 | A | 11/1982 | Staub |
| 4,373,518 | A | 2/1983 | Kaiser et al. |
| 4,378,053 | A | 3/1983 | Simpson |
| 4,381,777 | A | 5/1983 | Garnier |
| 4,393,872 | A | 7/1983 | Reznik et al. |
| 4,399,723 | A | 8/1983 | Marleau |
| 4,413,760 | A | 11/1983 | Paton |
| 4,416,503 | A | 11/1983 | Hayes |
| 4,420,085 | A | 12/1983 | Wilson et al. |
| 4,431,006 | A | 2/1984 | Trimmer et al. |
| 4,441,563 | A | 4/1984 | Walton, II |
| 4,461,305 | A | 7/1984 | Cibley |
| 4,469,109 | A | 9/1984 | Mehl |
| 4,484,577 | A | 11/1984 | Sackner et al. |
| 4,487,209 | A | 12/1984 | Mehl |
| 4,504,267 | A | 3/1985 | Parmelee et al. |
| 4,522,302 | A | 6/1985 | Paikoff |
| 4,543,966 | A | 10/1985 | Islam et al. |
| 4,553,539 | A | 11/1985 | Morris |
| 4,578,064 | A | 3/1986 | Sarnoff et al. |
| 4,595,322 | A | 6/1986 | Clement |
| 4,605,011 | A | 8/1986 | Naslund |
| 4,620,539 | A | 11/1986 | Andrews et al. |
| 4,623,335 | A | 11/1986 | Jackson |
| 4,630,616 | A | 12/1986 | Tretinyak |

(56) References Cited

U.S. PATENT DOCUMENTS

| | | |
|---|---|---|
| 4,645,492 A | 2/1987 | Weeks |
| 4,646,731 A | 3/1987 | Brower |
| 4,654,030 A | 3/1987 | Moll et al. |
| 4,654,492 A | 3/1987 | Koerner et al. |
| 4,655,226 A | 4/1987 | Lee |
| 4,659,329 A | 4/1987 | Annis |
| 4,670,008 A | 6/1987 | Von Albertini |
| 4,671,292 A | 6/1987 | Matzuk |
| 4,691,929 A | 9/1987 | Neumaier et al. |
| 4,692,073 A | 9/1987 | Martindell |
| 4,696,308 A | 9/1987 | Meller et al. |
| 4,702,261 A | 10/1987 | Cornell et al. |
| 4,711,636 A | 12/1987 | Bierman |
| 4,713,061 A | 12/1987 | Tarello et al. |
| 4,716,901 A | 1/1988 | Jackson et al. |
| 4,720,881 A | 1/1988 | Meyers |
| 4,723,945 A | 2/1988 | Theiling |
| 4,728,876 A | 3/1988 | Mongeon et al. |
| 4,736,850 A | 4/1988 | Bowman et al. |
| 4,753,345 A | 6/1988 | Goodsir et al. |
| 4,758,225 A | 7/1988 | Cox et al. |
| 4,762,118 A | 8/1988 | Lia et al. |
| 4,772,261 A | 9/1988 | Von et al. |
| 4,782,833 A | 11/1988 | Einhorn |
| 4,787,893 A | 11/1988 | Villette |
| 4,793,363 A | 12/1988 | Ausherman et al. |
| 4,798,213 A | 1/1989 | Doppelt |
| 4,801,293 A | 1/1989 | Jackson |
| 4,810,248 A | 3/1989 | Masters et al. |
| 4,812,008 A | 3/1989 | Tokumaru et al. |
| 4,838,282 A | 6/1989 | Strasser et al. |
| 4,838,877 A | 6/1989 | Massau |
| 4,844,259 A | 7/1989 | Glowczewskie et al. |
| 4,867,158 A | 9/1989 | Sugg |
| 4,874,181 A | 10/1989 | Hsu |
| 4,883,470 A | 11/1989 | Haindl |
| 4,919,146 A | 4/1990 | Rhinehart et al. |
| 4,919,653 A | 4/1990 | Martinez et al. |
| 4,921,013 A | 5/1990 | Spalink et al. |
| 4,922,602 A | 5/1990 | Mehl |
| 4,935,010 A | 6/1990 | Cox et al. |
| 4,940,459 A | 7/1990 | Noce |
| 4,944,677 A | 7/1990 | Alexandre |
| 4,969,870 A | 11/1990 | Kramer et al. |
| 4,976,269 A | 12/1990 | Mehl |
| 4,986,279 A | 1/1991 | O'Neill |
| 5,002,546 A | 3/1991 | Romano |
| 5,012,605 A | 5/1991 | Nishioka |
| 5,025,797 A | 6/1991 | Baran |
| 5,036,860 A | 8/1991 | Leigh et al. |
| 5,040,542 A | 8/1991 | Gray |
| 5,057,085 A | 10/1991 | Kopans |
| 5,064,426 A | 11/1991 | Huebsch |
| 5,074,311 A | 12/1991 | Hasson |
| 5,075,994 A | 12/1991 | Nishioka |
| 5,104,382 A | 4/1992 | Brinkerhoff et al. |
| 5,116,324 A | 5/1992 | Brierley et al. |
| 5,120,312 A | 6/1992 | Wigness et al. |
| 5,122,114 A | 6/1992 | Miller et al. |
| 5,133,359 A | 7/1992 | Kedem |
| 5,137,500 A | 8/1992 | Lhotak |
| 5,137,518 A | 8/1992 | Mersch |
| 5,139,500 A | 8/1992 | Schwartz |
| RE34,056 E | 9/1992 | Lindgren et al. |
| 5,145,369 A | 9/1992 | Lustig et al. |
| 5,148,813 A | 9/1992 | Bucalo |
| 5,156,399 A | 10/1992 | Gauer |
| 5,159,163 A | 10/1992 | Bahjat et al. |
| 5,172,700 A | 12/1992 | Bencini et al. |
| 5,172,701 A | 12/1992 | Leigh |
| 5,172,702 A | 12/1992 | Leigh et al. |
| 5,176,415 A | 1/1993 | Choksi |
| 5,176,643 A | 1/1993 | Kramer et al. |
| 5,183,054 A | 2/1993 | Burkholder et al. |
| 5,184,611 A | 2/1993 | Turnbull |
| 5,187,422 A | 2/1993 | Izenbaard et al. |
| 5,195,985 A | 3/1993 | Hall |
| 5,203,056 A | 4/1993 | Funk et al. |
| 5,204,670 A | 4/1993 | Stinton |
| 5,207,303 A | 5/1993 | Oswalt et al. |
| 5,207,697 A | 5/1993 | Carusillo et al. |
| 5,209,721 A | 5/1993 | Wilk |
| 5,210,376 A | 5/1993 | Caviar |
| 5,217,478 A | 6/1993 | Rexroth |
| D338,270 S | 8/1993 | Stephens et al. |
| 5,235,981 A | 8/1993 | Hascoet et al. |
| 5,244,619 A | 9/1993 | Burnham |
| 5,249,583 A | 10/1993 | Mallaby |
| 5,257,632 A | 11/1993 | Turkel et al. |
| 5,257,972 A | 11/1993 | Gurmarnik |
| 5,261,877 A | 11/1993 | Fine et al. |
| 5,261,891 A | 11/1993 | Brinkerhoff et al. |
| 5,269,785 A | 12/1993 | Bonutti |
| 5,271,380 A | 12/1993 | Riek et al. |
| 5,271,414 A | 12/1993 | Partika et al. |
| 5,271,744 A | 12/1993 | Kramer et al. |
| 5,279,306 A | 1/1994 | Mehl |
| 5,300,070 A | 4/1994 | Gentelia et al. |
| 5,312,351 A | 5/1994 | Gerrone |
| 5,312,361 A | 5/1994 | Zadini et al. |
| 5,312,364 A | 5/1994 | Jacobs |
| 5,312,408 A | 5/1994 | Brown |
| 5,313,733 A | 5/1994 | Meade |
| 5,315,737 A | 5/1994 | Ouimet |
| 5,318,543 A | 6/1994 | Ross et al. |
| 5,318,589 A | 6/1994 | Lichtman |
| 5,320,110 A | 6/1994 | Wang |
| 5,324,300 A | 6/1994 | Elias et al. |
| 5,330,480 A | 7/1994 | Meloul et al. |
| 5,331,972 A | 7/1994 | Wadhwani et al. |
| 5,332,398 A | 7/1994 | Miller et al. |
| 5,333,790 A | 8/1994 | Christopher |
| 5,334,169 A | 8/1994 | Brown et al. |
| 5,334,204 A | 8/1994 | Clewett et al. |
| 5,339,831 A | 8/1994 | Thompson |
| 5,341,316 A | 8/1994 | Nishigaki |
| 5,341,816 A | 8/1994 | Allen |
| 5,341,823 A | 8/1994 | Manosalva et al. |
| 5,344,420 A | 9/1994 | Hilal et al. |
| 5,348,022 A | 9/1994 | Leigh et al. |
| 5,354,287 A | 10/1994 | Wacks |
| 5,356,006 A | 10/1994 | Alpern et al. |
| 5,357,974 A | 10/1994 | Baldridge |
| 5,357,979 A | 10/1994 | Imran |
| 5,361,853 A | 11/1994 | Takamura et al. |
| 5,366,445 A | 11/1994 | Haber et al. |
| 5,368,046 A | 11/1994 | Scarfone et al. |
| 5,372,583 A | 12/1994 | Roberts et al. |
| 5,383,859 A | 1/1995 | Sewell, Jr. |
| 5,385,151 A | 1/1995 | Scarfone et al. |
| 5,385,553 A | 1/1995 | Hart et al. |
| 5,389,553 A | 2/1995 | Grubisich et al. |
| 5,394,875 A | 3/1995 | Lewis et al. |
| 5,400,798 A | 3/1995 | Baran |
| 5,405,348 A | 4/1995 | Anspach et al. |
| 5,405,362 A | 4/1995 | Kramer et al. |
| 5,407,243 A | 4/1995 | Riemann |
| 5,421,821 A | 6/1995 | Janicki et al. |
| 5,423,796 A | 6/1995 | Shikhman et al. |
| 5,423,824 A | 6/1995 | Akerfeldt et al. |
| 5,431,151 A | 7/1995 | Riek et al. |
| 5,431,655 A | 7/1995 | Melker et al. |
| 5,432,459 A | 7/1995 | Thompson et al. |
| 5,436,566 A | 7/1995 | Thompson et al. |
| 5,437,119 A | 8/1995 | Womack |
| 5,449,370 A | 9/1995 | Vaitekunas |
| 5,451,210 A | 9/1995 | Kramer et al. |
| 5,454,791 A | 10/1995 | Tovey et al. |
| 5,462,062 A | 10/1995 | Rubinstein et al. |
| 5,476,102 A | 12/1995 | Como et al. |
| 5,480,388 A | 1/1996 | Zadini et al. |
| 5,484,442 A | 1/1996 | Melker et al. |
| 5,497,787 A | 3/1996 | Nemesdy et al. |
| 5,499,997 A | 3/1996 | Sharpe et al. |

(56) References Cited

U.S. PATENT DOCUMENTS

| | | |
|---|---|---|
| 5,505,710 A | 4/1996 | Dorsey, III |
| 5,505,737 A | 4/1996 | Gosselin et al. |
| D369,858 S | 5/1996 | Baker et al. |
| 5,514,097 A | 5/1996 | Knauer |
| 5,522,398 A | 6/1996 | Goldenberg |
| 5,526,820 A | 6/1996 | Khoury |
| 5,526,821 A | 6/1996 | Jamshidi |
| 5,526,822 A | 6/1996 | Burbank et al. |
| 5,527,290 A | 6/1996 | Zadini et al. |
| 5,529,580 A | 6/1996 | Kusunoki et al. |
| 5,533,843 A | 7/1996 | Chung |
| 5,549,565 A | 8/1996 | Ryan et al. |
| 5,554,154 A | 9/1996 | Rosenberg |
| 5,556,399 A | 9/1996 | Huebner |
| 5,558,737 A | 9/1996 | Brown et al. |
| 5,571,133 A | 11/1996 | Yoon |
| 5,586,847 A | 12/1996 | Mattern et al. |
| 5,591,119 A | 1/1997 | Adair |
| 5,591,188 A | 1/1997 | Waisman |
| 5,595,186 A | 1/1997 | Rubinstein et al. |
| 5,599,347 A | 2/1997 | Hart et al. |
| 5,599,348 A | 2/1997 | Gentelia et al. |
| 5,601,559 A | 2/1997 | Melker et al. |
| 5,624,214 A | 4/1997 | Carroll |
| 5,632,747 A | 5/1997 | Scarborough et al. |
| 5,634,473 A | 6/1997 | Goldenberg |
| 5,649,547 A | 7/1997 | Ritchart et al. |
| 5,651,419 A | 7/1997 | Holzer et al. |
| 5,672,155 A | 9/1997 | Riley et al. |
| 5,685,820 A | 11/1997 | Riek et al. |
| 5,687,802 A | 11/1997 | Spooner et al. |
| 5,693,031 A | 12/1997 | Ryan et al. |
| 5,709,275 A | 1/1998 | Neumaier |
| 5,712,543 A | 1/1998 | Sjostrom |
| 5,713,149 A | 2/1998 | Cady et al. |
| 5,713,368 A | 2/1998 | Leigh |
| 5,724,873 A | 3/1998 | Hillinger |
| 5,728,124 A | 3/1998 | Cockburn et al. |
| 5,733,262 A | 3/1998 | Paul |
| 5,738,177 A | 4/1998 | Schell et al. |
| 5,752,923 A | 5/1998 | Terwilliger |
| 5,758,655 A | 6/1998 | Como Rodriguez |
| 5,762,498 A | 6/1998 | Gonzalez |
| 5,762,639 A | 6/1998 | Gibbs |
| 5,766,221 A | 6/1998 | Benderev et al. |
| 5,769,086 A | 6/1998 | Ritchart et al. |
| 5,779,708 A | 7/1998 | Wu |
| 5,800,389 A | 9/1998 | Burney et al. |
| 5,801,454 A | 9/1998 | Leininger |
| 5,807,275 A | 9/1998 | Jamshidi |
| 5,807,277 A | 9/1998 | Swaim |
| 5,809,653 A | 9/1998 | Everts et al. |
| 5,810,826 A | 9/1998 | Angstrom et al. |
| 5,817,052 A | 10/1998 | Johnson et al. |
| 5,823,970 A | 10/1998 | Terwilliger |
| D403,405 S | 12/1998 | Terwilliger |
| 5,843,001 A | 12/1998 | Goldenberg |
| D404,458 S | 1/1999 | Pruitt |
| 5,858,005 A | 1/1999 | Kriesel |
| 5,865,711 A | 2/1999 | Chen |
| 5,868,711 A | 2/1999 | Kramer et al. |
| 5,868,750 A | 2/1999 | Schultz |
| 5,873,499 A | 2/1999 | Leschinsky et al. |
| 5,873,510 A | 2/1999 | Hirai et al. |
| 5,873,580 A | 2/1999 | Swenson et al. |
| 5,885,226 A | 3/1999 | Rubinstein et al. |
| 5,891,085 A | 4/1999 | Lilley et al. |
| 5,893,851 A | 4/1999 | Umber et al. |
| 5,906,797 A | 5/1999 | Orihara et al. |
| 5,910,121 A | 6/1999 | Avaltroni et al. |
| 5,911,701 A | 6/1999 | Miller et al. |
| 5,911,708 A | 6/1999 | Teirstein |
| 5,916,229 A | 6/1999 | Evans |
| 5,919,172 A | 7/1999 | Golba, Jr. |
| 5,921,562 A | 7/1999 | Robison |
| 5,921,987 A | 7/1999 | Stone |
| 5,924,864 A | 7/1999 | Loge et al. |
| 5,926,989 A | 7/1999 | Oliver, Sr. |
| 5,927,976 A | 7/1999 | Wu |
| 5,928,164 A | 7/1999 | Burbank et al. |
| 5,928,238 A | 7/1999 | Scarborough et al. |
| 5,928,241 A | 7/1999 | Menut et al. |
| 5,938,636 A | 8/1999 | Kramer et al. |
| 5,941,706 A | 8/1999 | Ura |
| 5,941,841 A | 8/1999 | Mutch et al. |
| 5,941,851 A | 8/1999 | Coffey et al. |
| 5,945,896 A | 8/1999 | Miyamoto |
| 5,947,989 A | 9/1999 | Shikhman et al. |
| 5,951,026 A | 9/1999 | Harman et al. |
| 5,954,671 A | 9/1999 | O'Neill |
| 5,954,701 A | 9/1999 | Matalon |
| 5,960,575 A | 10/1999 | Chiovitt et al. |
| 5,960,797 A | 10/1999 | Kramer et al. |
| 5,980,469 A | 11/1999 | Burbank et al. |
| 5,980,545 A | 11/1999 | Pacala et al. |
| 5,984,020 A | 11/1999 | Meyer et al. |
| 5,984,919 A | 11/1999 | Hilal et al. |
| 5,989,257 A | 11/1999 | Tidwell et al. |
| 5,993,417 A | 11/1999 | Yerfino et al. |
| 5,993,454 A | 11/1999 | Longo |
| 6,007,481 A | 12/1999 | Riek et al. |
| 6,007,496 A | 12/1999 | Brannon |
| 6,015,391 A | 1/2000 | Rishton et al. |
| 6,017,348 A | 1/2000 | Hart et al. |
| 6,018,094 A | 1/2000 | Fox |
| 6,018,230 A | 1/2000 | Casey |
| 6,022,324 A | 2/2000 | Skinner |
| 6,025,683 A | 2/2000 | Philipp |
| 6,027,458 A | 2/2000 | Janssens |
| 6,033,369 A | 3/2000 | Goldenberg |
| 6,033,408 A | 3/2000 | Gage et al. |
| 6,033,411 A | 3/2000 | Preissman |
| 6,042,585 A | 3/2000 | Norman |
| 6,049,725 A | 4/2000 | Emmert et al. |
| 6,050,754 A | 4/2000 | Thomas |
| 6,050,955 A | 4/2000 | Bryan et al. |
| 6,053,923 A | 4/2000 | Veca et al. |
| 6,059,806 A | 5/2000 | Hoegerle |
| 6,063,037 A | 5/2000 | Mittermeier et al. |
| 6,066,938 A | 5/2000 | Hyodo et al. |
| 6,071,284 A | 6/2000 | Fox |
| 6,080,115 A | 6/2000 | Rubinstein |
| 6,083,176 A | 7/2000 | Terwilliger |
| 6,086,543 A | 7/2000 | Anderson et al. |
| 6,086,544 A | 7/2000 | Hibner et al. |
| 6,092,355 A | 7/2000 | Ishmael |
| 6,096,042 A | 8/2000 | Herbert |
| 6,098,042 A | 8/2000 | Huynh |
| 6,102,887 A | 8/2000 | Altman |
| 6,102,915 A | 8/2000 | Bresler et al. |
| 6,106,484 A | 8/2000 | Terwilliger |
| 6,110,128 A | 8/2000 | Andelin et al. |
| 6,110,129 A | 8/2000 | Terwilliger |
| 6,110,174 A | 8/2000 | Nichter |
| 6,120,462 A | 9/2000 | Hibner et al. |
| 6,126,670 A | 10/2000 | Walker et al. |
| 6,129,106 A | 10/2000 | Kornelson et al. |
| 6,135,769 A | 10/2000 | Kwan |
| 6,152,918 A | 11/2000 | Padilla et al. |
| 6,154,995 A | 12/2000 | Lenoir et al. |
| 6,159,163 A | 12/2000 | Strauss et al. |
| 6,162,203 A | 12/2000 | Haaga |
| 6,171,276 B1 | 1/2001 | Lippe et al. |
| 6,183,442 B1 | 2/2001 | Athanasiou et al. |
| 6,187,768 B1 | 2/2001 | Welle et al. |
| 6,210,376 B1 | 4/2001 | Grayson |
| 6,217,561 B1 | 4/2001 | Gibbs |
| 6,221,029 B1 | 4/2001 | Mathis et al. |
| 6,228,049 B1 | 5/2001 | Schroeder et al. |
| 6,228,088 B1 | 5/2001 | Miller et al. |
| 6,231,996 B1 | 5/2001 | Umeno et al. |
| 6,238,355 B1 | 5/2001 | Daum |
| 6,241,734 B1 | 6/2001 | Scribner et al. |
| 6,242,009 B1 | 6/2001 | Batarseh et al. |

(56) References Cited

U.S. PATENT DOCUMENTS

| | | |
|---|---|---|
| 6,247,110 B1 | 6/2001 | Huppenthal et al. |
| 6,247,928 B1 | 6/2001 | Meller et al. |
| 6,248,110 B1 | 6/2001 | Reiley et al. |
| 6,257,351 B1 | 7/2001 | Ark et al. |
| 6,261,272 B1 | 7/2001 | Gross et al. |
| 6,267,763 B1 | 7/2001 | Castro |
| 6,270,087 B1 | 8/2001 | Mickel et al. |
| 6,272,007 B1 | 8/2001 | Kitlas et al. |
| 6,273,715 B1 | 8/2001 | Meller et al. |
| 6,273,862 B1 | 8/2001 | Privitera et al. |
| 6,283,925 B1 | 9/2001 | Terwilliger |
| 6,283,970 B1 | 9/2001 | Lubinus |
| 6,287,114 B1 | 9/2001 | Meller et al. |
| 6,302,409 B1 | 10/2001 | Gutsche |
| 6,302,852 B1 | 10/2001 | Fleming et al. |
| 6,308,540 B1 | 10/2001 | Lee |
| 6,309,258 B1 | 10/2001 | Measley |
| 6,309,358 B1 | 10/2001 | Okubo |
| 6,312,394 B1 | 11/2001 | Fleming, III |
| 6,315,737 B1 | 11/2001 | Skinner |
| 6,321,855 B1 | 11/2001 | Barnes |
| 6,325,806 B1 | 12/2001 | Fox |
| 6,328,701 B1 | 12/2001 | Terwilliger |
| 6,328,744 B1 | 12/2001 | Harari et al. |
| 6,340,351 B1 | 1/2002 | Goldenberg |
| 6,349,496 B1 | 2/2002 | Neely |
| 6,358,252 B1 | 3/2002 | Shapira |
| 6,382,212 B1 | 5/2002 | Borchard |
| 6,402,701 B1 | 6/2002 | Kaplan et al. |
| 6,416,484 B1 | 7/2002 | Miller et al. |
| 6,419,490 B1 | 7/2002 | Kitchings Weathers, Jr. |
| 6,425,388 B1 | 7/2002 | Korinchock |
| 6,425,888 B1 | 7/2002 | Embleton et al. |
| 6,428,487 B1 | 8/2002 | Burdorff et al. |
| 6,443,910 B1 | 9/2002 | Krueger et al. |
| 6,446,734 B1 | 9/2002 | Williams et al. |
| 6,450,973 B1 | 9/2002 | Murphy |
| 6,451,023 B1 | 9/2002 | Salazar et al. |
| 6,458,117 B1 | 10/2002 | Pollins, Sr. |
| 6,461,296 B1 | 10/2002 | Desai |
| 6,468,248 B2 | 10/2002 | Gibbs |
| 6,478,751 B1 | 11/2002 | Krueger et al. |
| 6,488,636 B2 | 12/2002 | Bryan et al. |
| 6,494,590 B1 | 12/2002 | Paganini et al. |
| 6,520,971 B1 | 2/2003 | Perry et al. |
| 6,523,698 B1 | 2/2003 | Dennehey et al. |
| 6,527,736 B1 | 3/2003 | Attinger et al. |
| 6,527,778 B2 | 3/2003 | Athanasiou et al. |
| 6,537,242 B1 | 3/2003 | Palmer |
| 6,540,694 B1 | 4/2003 | Van et al. |
| 6,540,697 B2 | 4/2003 | Chen |
| 6,547,451 B1 | 4/2003 | Nishikawa et al. |
| 6,547,511 B1 | 4/2003 | Adams |
| 6,547,561 B2 | 4/2003 | Meller et al. |
| 6,547,755 B1 | 4/2003 | Lippe et al. |
| 6,549,511 B1 | 4/2003 | Prikryl |
| 6,550,786 B2 | 4/2003 | Gifford et al. |
| 6,554,778 B1 | 4/2003 | Fleming, III |
| 6,554,779 B2 | 4/2003 | Viola et al. |
| 6,555,212 B2 | 4/2003 | Boiocchi et al. |
| 6,572,563 B2 | 6/2003 | Ouchi |
| 6,575,745 B2 | 6/2003 | Meller et al. |
| 6,575,919 B1 | 6/2003 | Reiley et al. |
| 6,582,399 B1 | 6/2003 | Smith et al. |
| 6,585,622 B1 | 7/2003 | Shum et al. |
| 6,595,362 B2 | 7/2003 | Penney et al. |
| 6,595,911 B2 | 7/2003 | Lovuolo |
| 6,595,979 B1 | 7/2003 | Epstein et al. |
| 6,613,054 B2 | 9/2003 | Scribner et al. |
| 6,616,632 B2 | 9/2003 | Sharp et al. |
| 6,620,111 B2 | 9/2003 | Stephens et al. |
| 6,622,731 B2 | 9/2003 | Daniel et al. |
| 6,626,173 B2 | 9/2003 | Genova et al. |
| 6,626,848 B2 | 9/2003 | Neuenfeldt |
| 6,626,887 B1 | 9/2003 | Wu |
| 6,638,235 B2 | 10/2003 | Miller et al. |
| 6,641,395 B2 | 11/2003 | Kumar et al. |
| 6,656,133 B2 | 12/2003 | Voegele et al. |
| 6,689,072 B2 | 2/2004 | Kaplan et al. |
| 6,690,308 B2 | 2/2004 | Hayami |
| 6,695,786 B2 | 2/2004 | Wang et al. |
| 6,702,760 B2 | 3/2004 | Krause et al. |
| 6,702,761 B1 | 3/2004 | Damadian et al. |
| 6,706,016 B2 | 3/2004 | Cory et al. |
| 6,716,192 B1 | 4/2004 | Orosz, Jr. |
| 6,716,215 B1 | 4/2004 | David et al. |
| 6,716,216 B1 | 4/2004 | Boucher et al. |
| 6,718,196 B1 | 4/2004 | Mah et al. |
| 6,726,649 B2 | 4/2004 | Swenson et al. |
| 6,730,043 B2 | 5/2004 | Krueger et al. |
| 6,730,044 B2 | 5/2004 | Stephens et al. |
| 6,733,458 B1 | 5/2004 | Steins et al. |
| 6,749,576 B2 | 6/2004 | Bauer |
| 6,752,768 B2 | 6/2004 | Burdorff et al. |
| 6,752,816 B2 | 6/2004 | Culp et al. |
| 6,758,824 B1 | 7/2004 | Miller et al. |
| 6,761,726 B1 | 7/2004 | Findlay et al. |
| 6,770,070 B1 | 8/2004 | Balbierz |
| 6,783,532 B2 | 8/2004 | Steiner et al. |
| 6,796,957 B2 | 9/2004 | Carpenter et al. |
| 6,839,789 B2 | 1/2005 | Kraemer et al. |
| 6,846,314 B2 | 1/2005 | Shapira |
| 6,849,051 B2 | 2/2005 | Sramek et al. |
| 6,855,148 B2 | 2/2005 | Foley et al. |
| 6,860,860 B2 | 3/2005 | Viola |
| 6,871,759 B2 | 3/2005 | Rake et al. |
| 6,872,187 B1 | 3/2005 | Stark et al. |
| 6,875,163 B2 | 4/2005 | Cercone et al. |
| 6,875,179 B2 | 4/2005 | Ferguson et al. |
| 6,875,183 B2 | 4/2005 | Cervi |
| 6,875,219 B2 | 4/2005 | Arramon et al. |
| 6,884,245 B2 | 4/2005 | Spranza, III |
| 6,887,209 B2 | 5/2005 | Kadziauskas et al. |
| 6,890,308 B2 | 5/2005 | Islam |
| 6,896,141 B2 | 5/2005 | McMichael et al. |
| 6,902,559 B2 | 6/2005 | Taufig |
| 6,905,466 B2 | 6/2005 | Salgo et al. |
| 6,905,486 B2 | 6/2005 | Gibbs |
| 6,916,292 B2 | 7/2005 | Morawski et al. |
| 6,930,461 B2 | 8/2005 | Rutkowski |
| 6,942,669 B2 | 9/2005 | Kurc |
| 6,947,669 B2 | 9/2005 | Wu et al. |
| 6,969,373 B2 | 11/2005 | Schwartz et al. |
| 7,001,342 B2 | 2/2006 | Faciszewski |
| 7,008,381 B2 | 3/2006 | Janssens |
| 7,008,383 B1 | 3/2006 | Damadian et al. |
| 7,008,394 B2 | 3/2006 | Geise et al. |
| 7,014,614 B2 | 3/2006 | Casula |
| 7,018,343 B2 | 3/2006 | Plishka |
| 7,025,732 B2 | 4/2006 | Thompson et al. |
| 7,033,324 B2 | 4/2006 | Giusti et al. |
| 7,063,672 B2 | 6/2006 | Schramm |
| 7,063,703 B2 | 6/2006 | Reo |
| 7,081,123 B2 | 7/2006 | Merboth et al. |
| 7,108,696 B2 | 9/2006 | Daniel et al. |
| 7,134,815 B2 | 11/2006 | Steer |
| 7,137,985 B2 | 11/2006 | Jahng |
| 7,169,127 B2 | 1/2007 | Epstein et al. |
| 7,182,752 B2 | 2/2007 | Stubbs et al. |
| 7,186,257 B2 | 3/2007 | Kim |
| 7,201,722 B2 | 4/2007 | Krueger |
| 7,207,949 B2 | 4/2007 | Miles et al. |
| 7,212,011 B2 | 5/2007 | Shimizu et al. |
| 7,226,450 B2 | 6/2007 | Athanasiou et al. |
| 7,229,401 B2 | 6/2007 | Kindlein |
| 7,278,972 B2 | 10/2007 | Lamoureux et al. |
| 7,285,112 B2 | 10/2007 | Stubbs et al. |
| 7,331,462 B2 | 2/2008 | Steppe |
| 7,331,930 B2 | 2/2008 | Faciszewski |
| 7,338,456 B2 | 3/2008 | Goldenberg |
| 7,338,473 B2 | 3/2008 | Campbell et al. |
| 7,413,559 B2 | 8/2008 | Stubbs et al. |
| 7,513,722 B2 | 4/2009 | Greenberg et al. |
| 7,565,935 B1 | 7/2009 | Phillips |

(56) References Cited

U.S. PATENT DOCUMENTS

| | | |
|---|---|---|
| 7,615,043 B2 | 11/2009 | Zhou |
| 7,670,328 B2 | 3/2010 | Miller |
| 7,699,850 B2 | 4/2010 | Miller |
| 7,736,322 B2 | 6/2010 | Roe et al. |
| 7,798,331 B2 | 9/2010 | Hardin et al. |
| 7,811,260 B2 | 10/2010 | Miller et al. |
| 7,815,642 B2 | 10/2010 | Miller |
| 7,850,620 B2 | 12/2010 | Miller et al. |
| 7,854,724 B2 | 12/2010 | Stearns et al. |
| 7,899,528 B2 | 3/2011 | Miller et al. |
| 7,934,333 B1 | 5/2011 | Tuz |
| 7,951,089 B2 | 5/2011 | Miller |
| 7,988,643 B2 | 8/2011 | Hoffmann et al. |
| 7,998,086 B2 | 8/2011 | Boock |
| 8,038,664 B2 | 10/2011 | Miller et al. |
| 8,088,189 B2 | 1/2012 | Matula et al. |
| 8,092,457 B2 | 1/2012 | Oettinger et al. |
| 8,142,365 B2 | 3/2012 | Miller |
| 8,216,189 B2 | 7/2012 | Stubbs et al. |
| 8,217,561 B2 | 7/2012 | Fukuzawa et al. |
| 8,277,411 B2 | 10/2012 | Gellman |
| 8,282,565 B2 | 10/2012 | Mahapatra et al. |
| 8,308,693 B2 | 11/2012 | Miller et al. |
| 8,317,815 B2 | 11/2012 | Mastri et al. |
| 8,419,683 B2 | 4/2013 | Miller et al. |
| 8,480,632 B2 | 7/2013 | Miller et al. |
| 8,506,568 B2 | 8/2013 | Miller |
| 8,641,715 B2 | 2/2014 | Miller |
| 8,656,929 B2 | 2/2014 | Miller et al. |
| 8,668,698 B2 | 3/2014 | Miller et al. |
| 8,684,978 B2 | 4/2014 | Miller et al. |
| 8,690,791 B2 | 4/2014 | Miller |
| 8,715,219 B2 | 5/2014 | Stearns et al. |
| 8,715,287 B2 | 5/2014 | Miller |
| 8,720,097 B2 | 5/2014 | Derman |
| 8,812,101 B2 | 8/2014 | Miller et al. |
| 8,814,807 B2 | 8/2014 | Hulvershorn et al. |
| 8,870,872 B2 | 10/2014 | Miller |
| 8,876,826 B2 | 11/2014 | Miller |
| 8,920,388 B2 | 12/2014 | Slocum et al. |
| 8,926,525 B2 | 1/2015 | Hulvershorn et al. |
| 8,944,069 B2 | 2/2015 | Miller et al. |
| 8,961,451 B2 | 2/2015 | Stearns et al. |
| 8,974,410 B2 | 3/2015 | Miller et al. |
| 8,974,569 B2 | 3/2015 | Matula et al. |
| 8,992,535 B2 | 3/2015 | Miller |
| 8,998,348 B2 | 4/2015 | Frank |
| 8,998,848 B2 | 4/2015 | Miller et al. |
| 9,067,030 B2 | 6/2015 | Stearns et al. |
| 9,072,543 B2 | 7/2015 | Miller et al. |
| 9,078,637 B2 | 7/2015 | Miller |
| 9,095,372 B2 | 8/2015 | Stearns et al. |
| 9,110,104 B2 | 8/2015 | Chung et al. |
| 9,186,172 B2 | 11/2015 | Velez Rivera |
| 9,199,047 B2 | 12/2015 | Stearns et al. |
| 9,295,487 B2 | 3/2016 | Miller et al. |
| 9,314,228 B2 | 4/2016 | Miller |
| 9,314,270 B2 | 4/2016 | Miller |
| 9,393,364 B2 | 7/2016 | Fischer, Jr. |
| 9,414,815 B2 * | 8/2016 | Miller ............... A61B 10/0266 |
| 9,439,667 B2 | 9/2016 | Miller |
| 9,451,968 B2 | 9/2016 | Miller et al. |
| 9,504,477 B2 | 11/2016 | Miller et al. |
| 9,510,910 B2 | 12/2016 | Miller |
| 9,545,243 B2 | 1/2017 | Miller et al. |
| 9,662,160 B2 | 5/2017 | Beale et al. |
| 9,717,564 B2 | 8/2017 | Miller et al. |
| 9,717,847 B2 | 8/2017 | Miller et al. |
| 9,826,984 B2 | 11/2017 | McGinley et al. |
| 9,872,703 B2 | 1/2018 | Miller et al. |
| 9,883,853 B2 * | 2/2018 | Woodard ............... B23Q 3/12 |
| 10,016,217 B2 | 7/2018 | Miller |
| 10,052,111 B2 | 8/2018 | Miller et al. |
| 10,064,630 B2 * | 9/2018 | Forman ............ A61B 17/1626 |
| 10,081,414 B2 | 9/2018 | Le Devehat et al. |
| 10,130,343 B2 | 11/2018 | Miller |
| 10,149,686 B2 | 12/2018 | Anderson |
| 10,245,010 B2 | 4/2019 | Miller et al. |
| 10,258,783 B2 | 4/2019 | Miller et al. |
| 10,456,149 B2 | 10/2019 | Miller |
| 10,512,474 B2 | 12/2019 | Miller et al. |
| 10,722,247 B2 | 7/2020 | Browne et al. |
| 10,806,491 B2 | 10/2020 | Miller et al. |
| 10,820,913 B2 | 11/2020 | Miller |
| 10,893,875 B2 | 1/2021 | Miller |
| 10,933,474 B2 * | 3/2021 | Woodard ............ B23B 31/1071 |
| 11,090,032 B2 | 8/2021 | Miller |
| 11,103,281 B2 | 8/2021 | Miller |
| 11,103,282 B1 | 8/2021 | Miller et al. |
| 11,234,683 B2 | 2/2022 | Miller |
| 11,291,472 B2 | 4/2022 | Miller |
| 11,298,202 B2 | 4/2022 | Miller |
| 11,337,728 B2 | 5/2022 | Miller |
| 11,426,249 B2 | 8/2022 | Miller |
| 2001/0005778 A1 | 6/2001 | Ouchi |
| 2001/0014439 A1 | 8/2001 | Meller et al. |
| 2001/0026051 A1 | 10/2001 | Gifford et al. |
| 2001/0034527 A1 | 10/2001 | Scribner et al. |
| 2001/0047183 A1 | 11/2001 | Privitera et al. |
| 2001/0053888 A1 | 12/2001 | Athanasiou et al. |
| 2002/0018102 A1 | 2/2002 | Nozawa |
| 2002/0022788 A1 | 2/2002 | Corvi et al. |
| 2002/0029007 A1 | 3/2002 | Bryan et al. |
| 2002/0042581 A1 | 4/2002 | Cervi |
| 2002/0050364 A1 | 5/2002 | Suzuki et al. |
| 2002/0055713 A1 | 5/2002 | Gibbs |
| 2002/0082519 A1 | 6/2002 | Miller et al. |
| 2002/0091039 A1 | 7/2002 | Reinbold et al. |
| 2002/0096343 A1 | 7/2002 | Potter et al. |
| 2002/0120197 A1 | 8/2002 | Kleffner et al. |
| 2002/0120212 A1 | 8/2002 | Ritchart et al. |
| 2002/0133148 A1 | 9/2002 | Daniel et al. |
| 2002/0138021 A1 | 9/2002 | Pflueger |
| 2002/0143269 A1 | 10/2002 | Neuenfeldt |
| 2002/0151821 A1 | 10/2002 | Castellacci |
| 2002/0151902 A1 | 10/2002 | Riedel et al. |
| 2002/0158102 A1 | 10/2002 | Patton et al. |
| 2002/0177822 A1 | 11/2002 | St. Cyr et al. |
| 2003/0009132 A1 | 1/2003 | Schwartz et al. |
| 2003/0023256 A1 | 1/2003 | Estes et al. |
| 2003/0028146 A1 | 2/2003 | Aves |
| 2003/0032939 A1 | 2/2003 | Gibbs |
| 2003/0036747 A1 | 2/2003 | Ie et al. |
| 2003/0050574 A1 | 3/2003 | Krueger |
| 2003/0078586 A1 | 4/2003 | Shapira |
| 2003/0078589 A1 | 4/2003 | Preissman |
| 2003/0114858 A1 | 6/2003 | Athanasiou et al. |
| 2003/0125639 A1 | 7/2003 | Fisher et al. |
| 2003/0144104 A1 | 7/2003 | Ryberg |
| 2003/0149436 A1 | 8/2003 | McDowell et al. |
| 2003/0153842 A1 | 8/2003 | Lamoureux et al. |
| 2003/0173178 A1 | 9/2003 | Sasaki |
| 2003/0191414 A1 | 10/2003 | Reiley et al. |
| 2003/0195436 A1 | 10/2003 | Van et al. |
| 2003/0195524 A1 | 10/2003 | Barner |
| 2003/0199787 A1 | 10/2003 | Schwindt |
| 2003/0199879 A1 | 10/2003 | Spranza |
| 2003/0205987 A1 | 11/2003 | Barlev et al. |
| 2003/0212343 A1 | 11/2003 | Plishka |
| 2003/0216667 A1 | 11/2003 | Viola |
| 2003/0225344 A1 | 12/2003 | Miller |
| 2003/0225364 A1 | 12/2003 | Kraft et al. |
| 2003/0225411 A1 | 12/2003 | Miller |
| 2003/0233114 A1 | 12/2003 | Merboth et al. |
| 2004/0010236 A1 | 1/2004 | Morawski et al. |
| 2004/0019297 A1 | 1/2004 | Angel |
| 2004/0019299 A1 | 1/2004 | Ritchart et al. |
| 2004/0031721 A1 | 2/2004 | Mann |
| 2004/0032179 A1 | 2/2004 | Du |
| 2004/0034280 A1 | 2/2004 | Privitera et al. |
| 2004/0049128 A1 | 3/2004 | Miller et al. |
| 2004/0049157 A1 | 3/2004 | Plishka et al. |
| 2004/0049205 A1 | 3/2004 | Lee et al. |
| 2004/0064136 A1 | 4/2004 | Papineau et al. |

(56) References Cited

U.S. PATENT DOCUMENTS

| | | |
|---|---|---|
| 2004/0073139 A1 | 4/2004 | Hirsch et al. |
| 2004/0077973 A1 | 4/2004 | Groenke |
| 2004/0092946 A1 | 5/2004 | Bagga et al. |
| 2004/0127814 A1 | 7/2004 | Negroni |
| 2004/0153003 A1 | 8/2004 | Cicenas et al. |
| 2004/0158172 A1 | 8/2004 | Hancock |
| 2004/0158173 A1 | 8/2004 | Voegele et al. |
| 2004/0162505 A1 | 8/2004 | Kaplan et al. |
| 2004/0167428 A1 | 8/2004 | Quick et al. |
| 2004/0191897 A1 | 9/2004 | Muschler |
| 2004/0210161 A1 | 10/2004 | Burdorff et al. |
| 2004/0210196 A1 | 10/2004 | Bush et al. |
| 2004/0210198 A1 | 10/2004 | Shih |
| 2004/0215102 A1 | 10/2004 | Ikehara et al. |
| 2004/0220497 A1 | 11/2004 | Findlay et al. |
| 2004/0249306 A1 | 12/2004 | Islam |
| 2004/0249389 A1 | 12/2004 | Kim |
| 2004/0259254 A1 | 12/2004 | Honmou et al. |
| 2005/0027210 A1 | 2/2005 | Miller |
| 2005/0033275 A1 | 2/2005 | Hoegerle et al. |
| 2005/0033304 A1 | 2/2005 | O'Heeron |
| 2005/0040060 A1 | 2/2005 | Andersen et al. |
| 2005/0043714 A1 | 2/2005 | Zhou |
| 2005/0075581 A1 | 4/2005 | Schwindt |
| 2005/0085838 A1 | 4/2005 | Thompson et al. |
| 2005/0101880 A1 | 5/2005 | Cicenas et al. |
| 2005/0113716 A1 | 5/2005 | Mueller et al. |
| 2005/0116673 A1 | 6/2005 | Carl et al. |
| 2005/0119660 A1 | 6/2005 | Bourlion et al. |
| 2005/0124915 A1 | 6/2005 | Eggers et al. |
| 2005/0131345 A1 | 6/2005 | Miller |
| 2005/0148940 A1 | 7/2005 | Miller |
| 2005/0159677 A1 | 7/2005 | Shabaz et al. |
| 2005/0165328 A1 | 7/2005 | Heske et al. |
| 2005/0165403 A1 | 7/2005 | Miller |
| 2005/0165404 A1 | 7/2005 | Miller |
| 2005/0171504 A1 | 8/2005 | Miller |
| 2005/0182394 A1 | 8/2005 | Spero et al. |
| 2005/0200087 A1 | 9/2005 | Vasudeva et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0228309 A1 | 10/2005 | Fisher et al. |
| 2005/0236940 A1 | 10/2005 | Rockoff |
| 2005/0261693 A1 | 11/2005 | Miller et al. |
| 2005/0267383 A1 | 12/2005 | Groenke |
| 2006/0011506 A1 | 1/2006 | Riley |
| 2006/0015066 A1 | 1/2006 | Turieo et al. |
| 2006/0036212 A1 | 2/2006 | Miller |
| 2006/0043685 A1 | 3/2006 | Kozak |
| 2006/0052790 A1 | 3/2006 | Miller |
| 2006/0074345 A1 | 4/2006 | Hibner |
| 2006/0074425 A1 | 4/2006 | Sutterlin et al. |
| 2006/0079774 A1 | 4/2006 | Anderson |
| 2006/0089565 A1 | 4/2006 | Schramm |
| 2006/0111724 A1 | 5/2006 | Yeung Wai Ping |
| 2006/0115066 A1 | 6/2006 | Levien et al. |
| 2006/0122535 A1 | 6/2006 | Daum |
| 2006/0129082 A1 | 6/2006 | Rozga |
| 2006/0144548 A1 | 7/2006 | Beckman et al. |
| 2006/0149163 A1 | 7/2006 | Hibner et al. |
| 2006/0151188 A1 | 7/2006 | Bodine et al. |
| 2006/0167377 A1 | 7/2006 | Ritchart et al. |
| 2006/0167378 A1 | 7/2006 | Miller |
| 2006/0167379 A1 | 7/2006 | Miller |
| 2006/0173480 A1 | 8/2006 | Zhang |
| 2006/0184063 A1 | 8/2006 | Miller |
| 2006/0189940 A1 | 8/2006 | Kirsch |
| 2006/0192350 A1 | 8/2006 | Kleine et al. |
| 2006/0206132 A1 | 9/2006 | Conquergood et al. |
| 2006/0237205 A1 | 10/2006 | Sia et al. |
| 2007/0010843 A1 | 1/2007 | Green |
| 2007/0016100 A1 | 1/2007 | Miller |
| 2007/0016138 A1 | 1/2007 | Swisher |
| 2007/0024013 A1 | 2/2007 | Hauptmann et al. |
| 2007/0049945 A1 | 3/2007 | Miller |
| 2007/0084742 A1 | 4/2007 | Miller et al. |
| 2007/0120331 A1 | 5/2007 | Manschitz et al. |
| 2007/0149920 A1 | 6/2007 | Michels et al. |
| 2007/0197935 A1 | 8/2007 | Reiley |
| 2007/0198042 A1 | 8/2007 | Richard |
| 2007/0209957 A1 | 9/2007 | Glenn et al. |
| 2007/0213735 A1 | 9/2007 | Saadat et al. |
| 2007/0256914 A1 | 11/2007 | Lohr et al. |
| 2007/0260255 A1 | 11/2007 | Haddock |
| 2007/0265548 A1 | 11/2007 | Goldenberg |
| 2007/0270712 A1 | 11/2007 | Wiksell et al. |
| 2007/0270775 A1 | 11/2007 | Miller et al. |
| 2008/0015467 A1 | 1/2008 | Miller |
| 2008/0015468 A1 | 1/2008 | Miller |
| 2008/0015623 A1 | 1/2008 | Deck |
| 2008/0045857 A1 | 2/2008 | Miller et al. |
| 2008/0045860 A1 | 2/2008 | Miller et al. |
| 2008/0045861 A1 | 2/2008 | Miller et al. |
| 2008/0045965 A1 | 2/2008 | Miller et al. |
| 2008/0072719 A1 | 3/2008 | Kozak |
| 2008/0086160 A1 | 4/2008 | Mastri et al. |
| 2008/0087448 A1 | 4/2008 | Happ |
| 2008/0140014 A1 | 6/2008 | Miller et al. |
| 2008/0177200 A1 | 7/2008 | Ikehara et al. |
| 2008/0215056 A1 | 9/2008 | Miller et al. |
| 2008/0221580 A1 | 9/2008 | Miller et al. |
| 2008/0243163 A1 | 10/2008 | Masseglia et al. |
| 2008/0262383 A1 | 10/2008 | Routhier et al. |
| 2008/0302551 A1 | 12/2008 | Komuro et al. |
| 2009/0069716 A1 | 3/2009 | Freeman et al. |
| 2009/0082697 A1 | 3/2009 | Goldenberg |
| 2009/0093677 A1 | 4/2009 | Smith |
| 2009/0131832 A1 | 5/2009 | Sacristan et al. |
| 2009/0194446 A1 | 8/2009 | Miller et al. |
| 2009/0248029 A1 | 10/2009 | Paulos |
| 2009/0311061 A1 | 12/2009 | Santamarina et al. |
| 2010/0137740 A1 | 6/2010 | Miller |
| 2010/0204611 A1 | 8/2010 | Zambelli |
| 2010/0298784 A1 | 11/2010 | Miller |
| 2011/0046477 A1 | 2/2011 | Hulvershorn et al. |
| 2011/0046507 A1 | 2/2011 | Herndon |
| 2011/0071572 A1 | 3/2011 | Sixto et al. |
| 2011/0082387 A1 | 4/2011 | Miller et al. |
| 2011/0098604 A1 | 4/2011 | Miller |
| 2011/0125084 A1 | 5/2011 | Stearns et al. |
| 2011/0184425 A1 | 7/2011 | Cheraux |
| 2011/0186456 A1 | 8/2011 | Bertazzoni et al. |
| 2011/0203821 A1 | 8/2011 | Puzio et al. |
| 2011/0251518 A1 | 10/2011 | Swisher et al. |
| 2011/0288405 A1 | 11/2011 | Razavi et al. |
| 2011/0306841 A1 | 12/2011 | Lozman et al. |
| 2012/0109061 A1 | 5/2012 | Miller et al. |
| 2012/0150101 A1 | 6/2012 | Stearns et al. |
| 2012/0165832 A1 | 6/2012 | Oostman et al. |
| 2012/0283582 A1 | 11/2012 | Mahapatra et al. |
| 2012/0323071 A1 | 12/2012 | Gellman |
| 2012/0330184 A1 | 12/2012 | Mahapatra et al. |
| 2013/0213843 A1 | 8/2013 | Knight et al. |
| 2014/0005657 A1 | 1/2014 | Brannan et al. |
| 2014/0188038 A1 | 7/2014 | Stearns et al. |
| 2014/0231302 A1 | 8/2014 | Goyal |
| 2014/0262408 A1 | 9/2014 | Woodard |
| 2014/0262880 A1* | 9/2014 | Yoon .................... A61B 50/30 53/469 |
| 2014/0276839 A1* | 9/2014 | Forman .............. A61B 17/1622 173/2 |
| 2014/0311302 A1 | 10/2014 | Taguchi et al. |
| 2014/0336567 A1 | 11/2014 | Stearns et al. |
| 2014/0343454 A1 | 11/2014 | Miller et al. |
| 2014/0358070 A1 | 12/2014 | Stearns et al. |
| 2015/0025363 A1 | 1/2015 | Hulvershorn et al. |
| 2015/0057530 A1 | 2/2015 | Roggeveen et al. |
| 2015/0112261 A1 | 4/2015 | Bassett et al. |
| 2015/0127006 A1 | 5/2015 | Miller |
| 2015/0129456 A1 | 5/2015 | Miller et al. |
| 2015/0173818 A1 | 6/2015 | Baroud et al. |
| 2015/0202390 A1 | 7/2015 | Stearns et al. |
| 2015/0202391 A1 | 7/2015 | Stearns et al. |

(56) References Cited

U.S. PATENT DOCUMENTS

| | | |
|---|---|---|
| 2015/0223786 A1 | 8/2015 | Morgan et al. |
| 2015/0230823 A1 | 8/2015 | Morgan et al. |
| 2015/0342635 A1 | 12/2015 | Tsamir et al. |
| 2015/0366569 A1 | 12/2015 | Miller |
| 2016/0081732 A1 | 3/2016 | Baroud |
| 2017/0036328 A1 | 2/2017 | Chen |
| 2017/0266790 A1 | 9/2017 | Chuang |
| 2018/0056095 A1 | 3/2018 | Messerly et al. |
| 2018/0353191 A1 | 12/2018 | Miller et al. |
| 2020/0054350 A1 | 2/2020 | Miller |
| 2020/0214722 A1 | 7/2020 | Miller |
| 2020/0237402 A1 | 7/2020 | Miller |
| 2021/0045753 A1 | 2/2021 | Miller et al. |
| 2021/0045755 A1 | 2/2021 | Miller |
| 2021/0052286 A1 | 2/2021 | Miller et al. |
| 2021/0170497 A1 | 6/2021 | Woodard |
| 2021/0282753 A1 | 9/2021 | Morgan |
| 2021/0298767 A1 | 9/2021 | Miller |
| 2022/0202399 A1 | 6/2022 | Miller |

FOREIGN PATENT DOCUMENTS

| | | |
|---|---|---|
| CA | 2454600 A1 | 2/2003 |
| CN | 2294028 Y | 10/1998 |
| CN | 2320209 Y | 5/1999 |
| CN | 2664675 Y | 12/2004 |
| DE | 10057831 A1 | 5/2002 |
| DE | 10057931 A1 | 8/2002 |
| EP | 0271775 A2 | 6/1988 |
| EP | 0517000 A2 | 12/1992 |
| EP | 0528478 A1 | 2/1993 |
| EP | 0807412 A1 | 11/1997 |
| EP | 0853349 A1 | 7/1998 |
| EP | 1099450 A1 | 5/2001 |
| EP | 1175870 A1 | 1/2002 |
| EP | 1314452 A1 | 5/2003 |
| EP | 1421907 A1 | 5/2004 |
| EP | 1447050 A2 | 8/2004 |
| EP | 2068725 A2 | 6/2009 |
| EP | 2177171 A1 | 4/2010 |
| EP | 3153116 A1 | 4/2017 |
| FR | 0853349 A | 3/1940 |
| FR | 2457105 A1 | 12/1980 |
| FR | 2516386 A1 | 5/1983 |
| FR | 2931451 A1 | 11/2009 |
| GB | 0322382 A | 12/1929 |
| GB | 0629824 | 9/1949 |
| GB | 2099703 A | 12/1982 |
| GB | 2130890 A | 6/1984 |
| GB | 2164277 A | 3/1986 |
| JP | 59-119808 A | 7/1984 |
| JP | 61-032633 Y2 | 9/1986 |
| JP | 61-032663 Y2 | 9/1986 |
| JP | 64-052433 A | 2/1989 |
| JP | 1052433 A | 2/1989 |
| JP | 06-132663 A | 5/1994 |
| JP | 10-052433 A | 2/1998 |
| JP | 2001-505076 A | 4/2001 |
| JP | 6132663 B2 | 5/2017 |
| WO | 92/08410 A1 | 5/1992 |
| WO | 93/07819 A2 | 4/1993 |
| WO | 93/25151 A1 | 12/1993 |
| WO | 94/07553 A1 | 4/1994 |
| WO | 96/31164 A1 | 10/1996 |
| WO | 98/06337 A1 | 2/1998 |
| WO | 98/52638 A2 | 11/1998 |
| WO | 99/18866 A1 | 4/1999 |
| WO | 99/52444 A1 | 10/1999 |
| WO | 00/09024 A1 | 2/2000 |
| WO | 00/10465 A1 | 3/2000 |
| WO | 00/56220 A1 | 9/2000 |
| WO | 01/78590 A1 | 10/2001 |
| WO | 01/93931 A1 | 12/2001 |
| WO | 02/41791 A1 | 5/2002 |
| WO | 02/41792 A1 | 5/2002 |
| WO | 02/96497 A1 | 12/2002 |
| WO | 03/15637 A1 | 2/2003 |
| WO | 2003/101307 A1 | 12/2003 |
| WO | 2005/072625 A2 | 8/2005 |
| WO | 2005/110259 A1 | 11/2005 |
| WO | 2005/112800 A2 | 12/2005 |
| WO | 2008/033871 A2 | 3/2008 |
| WO | 2008/033874 A2 | 3/2008 |
| WO | 2008/081438 A1 | 7/2008 |
| WO | 2009/070896 A1 | 6/2009 |
| WO | 2011/070593 A1 | 6/2011 |
| WO | 2011/123703 A1 | 10/2011 |
| WO | 2012/175946 A1 | 12/2012 |

OTHER PUBLICATIONS

Office Action for U.S. Appl. No. 11/253,467, dated Apr. 28, 2011.
Office Action for U.S. Appl. No. 11/253,467, dated Jul. 22, 2010.
Office Action for U.S. Appl. No. 11/253,467, dated Oct. 29, 2010.
Office Action for U.S. Appl. No. 11/253,959, dated Aug. 5, 2010.
Office Action for U.S. Appl. No. 11/253,959, dated Mar. 30, 2011.
Office Action for U.S. Appl. No. 11/253,959, dated Oct. 18, 2010.
Office Action for U.S. Appl. No. 11/427,501, dated Aug. 7, 2008.
Office Action for U.S. Appl. No. 11/427,501, dated Oct. 21, 2009.
Office Action for U.S. Appl. No. 11/427,501, dated May 13, 2009.
Office Action for U.S. Appl. No. 12/905,659, dated Mar. 21, 2011.
Office Action for U.S. Appl. No. 12/905,659, dated May 13, 2011.
Office Action in Canadian Patent Application No. 2,612,433, dated Aug. 22, 2014.
Office Action in Canadian Patent Application No. 2,612,483, dated Aug. 22, 2014.
Office Action in European Application No. 03756317.8 dated Dec. 28, 2006.
Office Action in European Application No. 08158699.2 dated Nov. 4, 2008.
Office Action issued in Chinese Application No. 200910006631.3, dated Mar. 22, 2011.
Office Action issued in Chinese Patent Application No. 201010144512.7, dated Feb. 23, 2011.
Office Action issued in Chinese Patent Application No. 201010144520.1, dated Jan. 27, 2011.
Office Action issued in European Application No. 09155111.9 dated Nov. 25, 2009.
Office Communication for European application 09150973.7-1269, dated Jan. 19, 2011.
Office Communication for European Patent Application No. 07842288.8, dated Mar. 12, 2015.
Office Communication in European Application No. 08021732.6, dated Jun. 20, 2013.
Office Communication in European Application No. 10153350.3, dated Jun. 14, 2011.
Office Communication issued in Chinese Patent Application No. 200910138130.0, dated Oct. 10, 2011.
Office Communication issued in European Patent Application No. 09150973.7, dated Dec. 22, 2011.
Office Communication issued in Taiwanese Patent Application No. 093134480, dated Jan. 15, 2011.
PCT Invitation to pay additional fees for international application PCT/US2006/025201, dated Oct. 26, 2006.
PCT Invitation to Pay Additional Fees in International Application No. PCT/US2007/072209 dated Dec. 3, 2007.
Pediatric Emergency, Intraosseous Infusion for Administration of Fluids and Drugs, www.cookgroup.com, 1 pg (2000).
Pediatrics, "2005 American Heart Association Guidelines for Cardiopulmonary Resuscitation and Emergency Cardiovascular Care of Pediatric and Neonatal Patients: Pediatric Advanced Life Support," Official Journal of the American Academy of Pediatrics. Downloaded from www.pediatrics.org on Feb. 21, 2007.
Request for Continued Examination and Amendment, U.S. Appl. No. 11/064,156, 22 pages, dated Nov. 19, 2009.
Response to Extended European Search Report in European Application No. 10153350.3, filed Jun. 30, 2010.

(56) References Cited

OTHER PUBLICATIONS

Response to Non-Final Office Action, U.S. Appl. No. 11/042,912, (11 pgs.), dated Oct. 23, 2009.
Response to Office Action for European application 07842284.7. Filed Nov. 10, 2012.
Response to Office Action for European application 07842285.4. Filed Nov. 13, 2012.
Response to Office Action for European application 07842286.2. Filed Nov. 8, 2012.
Response to Office Action for European application 07842288.8. Filed Nov. 9, 2012.
Response to Office Action for European application 10153350.3. Filed Mar. 17, 2011.
Response to Office Action for U.S. Appl. No. 10/449,476, filed Aug. 12, 2009.
Response to Office Action for U.S. Appl. No. 10/449,503, filed Jul. 1, 2009.
Response to Office Action for U.S. Appl. No. 11/427,501, filed Jul. 1, 2009.
Response to Office Communication in European Application No. 10153350.3, filed Feb. 9, 2012.
Response to Official Letter for European application 07842284.7. Filed Oct. 14, 2011.
Response to Official Letter for European application 07842285.4. Filed Oct. 14, 2011.
Response to Official Letter for European application 07842286.2. Filed Oct. 14, 2011.
Response to Official Letter for European application 07842288.8. Filed Oct. 14, 2011.
Riley, et al., "A Pathologists Perspective on Bone Marrow Aspiration Biopsy: Performing a Bone Marrow Examination" J Clin Lab Analysis. 18:70-90, 2004.
Search Report and Written Opinion in International Application No. PCT/US2006/025201 dated Jan. 29, 2007.
Search Report and Written Opinion in International Application No. PCT/US2007/072217 dated Mar. 12, 2007.
Notice of Allowance in U.S. Appl. No. 11/380,340 dated Aug. 22, 2014.
Notice of Allowance in U.S. Appl. No. 11/619,390 dated Jul. 3, 2014.
Notice of Allowance in U.S. Appl. No. 11/619,390 dated Nov. 6, 2014.
Notice of Allowance in U.S. Appl. No. 11/620,927 dated Jun. 3, 2014.
Notice of Allowance in U.S. Appl. No. 11/853,678 dated Jul. 11, 2013.
Notice of Allowance in U.S. Appl. No. 11/853,678, dated Nov. 8, 2013.
Notice of Allowance in U.S. Appl. No. 11/853,678, dated Oct. 11, 2013.
Notice of Allowance in U.S. Appl. No. 11/853,701 dated Jul. 3, 2013.
Notice of Allowance in U.S. Appl. No. 11/853,701, dated Oct. 11, 2013.
Notice of Allowance in U.S. Appl. No. 12/331,979 dated Jul. 17, 2013.
Notice of Allowance in U.S. Appl. No. 12/331,979, dated Dec. 23, 2013.
Notice of Allowance in U.S. Appl. No. 12/899,696 dated Aug. 27, 2013.
Notice of Allowance in U.S. Appl. No. 12/899,696 dated Jul. 18, 2013.
Notice of Allowance in U.S. Appl. No. 14/271,144 dated Jul. 22, 2014.
Notice of Allowance in U.S. Appl. No. 12/259,745 dated Nov. 7, 2014.
Notice of Allowance in U.S. Appl. No. 12/407,651 dated Jun. 11, 2014.
Notice of Allowance in U.S. Appl. No. 12/427,310, dated Nov. 29, 2013.
Notice of Allowance in U.S. Appl. No. 12/718,638, dated Aug. 3, 2015.
Notice of Allowance in U.S. Appl. No. 12/899,696, dated Nov. 12, 2013.
Notice of Allowance in U.S. Appl. No. 13/966,104, dated Aug. 17, 2015.
Notice of Allowance issued in U.S. Appl. No. 11/253,467, dated Mar. 29, 2013.
Notice of Allowance issued in U.S. Appl. No. 11/253,467, dated Mar. 4, 2014.
Notice of Allowance issued in U.S. Appl. No. 11/253,959 dated May 20, 2013.
Notice of Allowance issued in U.S. Appl. No. 11/253,959, dated Mar. 14, 2013.
Notice of Allowance issued in U.S. Appl. No. 11/853,678, dated Mar. 27, 2013.
Notice of Allowance issued in U.S. Appl. No. 11/853,701, dated Mar. 14, 2013.
Notice of Allowance issued in U.S. Appl. No. 12/427,310, dated Jun. 5, 2013.
Notice of Allowance issued in U.S. Appl. No. 12/554,664 dated Jul. 20, 2012.
Notice of Allowance issued in U.S. Appl. No. 12/554,708 dated Jul. 11, 2012.
Notice of Allowance issued in U.S. Appl. No. 12/718,606, dated Mar. 6, 2013.
Notice of Allowance issued in U.S. Appl. No. 12/718,606, dated Oct. 11. 2012.
Notification of First Chinese Office Action, Application No. 201410112780.9, dated May 27, 2015.
Notification of the First Chinese Office Action, Application No. 200580003261.8, 3 pages, dated Mar. 21, 2008.
Office Action Action for for Chinese application 200380000182.5 (English translation) dated Jun. 27, 2013.
Office Action for Canadian application 2,612,483, dated Dec. 27, 2013.
Office Action for Chinese application 201210169546.0 with English translation, dated Apr. 18, 2014.
Office Action for European application 03731475.4, dated Oct. 11, 2007.
Office Action for European application 05712091.7, dated Sep. 21, 2007.
Office Action for European application 07842284.7, dated May 3, 2012.
Office Action for European application 07842285.4, dated May 3, 2012.
Office Action for European application 07842286.2, dated Apr. 30, 2012.
Office Action for European application 07842288.8, dated May 3, 2012.
Office Action for European application 08021732.6, dated Oct. 2, 2013.
Office Action for European application 09155111.9-2310, dated Nov. 25, 2009.
Office Action for for Chinese application 201210169456.0 with English translation, dated Aug. 28, 2013.
Office Action for Japanese Application No. 2004-508670 with English Translation, dated Aug. 31, 2010.
Office Action for Taiwanese application 093134480 (English Translation), dated Feb. 11, 2011.
Office Action for U.S. Appl. No. 10/449,503, dated Apr. 1, 2009.
Office Action for U.S. Appl. No. 11/042,912, dated Mar. 19, 2010.
Office Action for U.S. Appl. No. 11/042,912, dated Nov. 28, 2008.
Search Report in European Application No. 08158699.2 dated Aug. 2008.
State Intellectual Property Office of the People's Republic of China, Notification of the Second Office Action for Chinese Application No. 200880000182.5, dated Mar. 12, 2012.
State Intellectual Property Office of the People's Republic of China, Notification of the Third Office Action for Chinese Application No. 200680000182.5, dated Dec. 13, 2012.

(56) References Cited

OTHER PUBLICATIONS

State Intellectual Property Office of the People's Republic of China, Reexamination Decision for Chinese Application No. 200880000182. 5, dated Nov. 20, 2013.
Taiwan Office Action, Application No. 94102179 (with English translation); 12 pages, dated May 13, 2010.
Trotty, "Technology (A Special Report)—The Wall Street Journal 2008 Technology Innovation Awards," The Wall Street Journal, Factiva. 2008.
Vidacare corporation comments to Intraosseous Vascular Access Position Paper, Infusion Nurses Society dated May 4, 2009.
Gunal et al., Compartment Syndrome After Intraosseous Infusion: An Experimental Study in Dogs, Journal od Pediatric Surgery, vol. 31, No. 11, pp. 1491-1493, Nov. 1996.
Hakan et al., "CT-guided Bone Biopsy Performed by Means of Coaxial Biopsy System with an Eccentric Drill," Radiology, pp. 549-552 (Aug. 1993).
International PCT Search Report and Written Opinion PCT /US2005/ 002484, 15 pages, dated Jul. 22, 2005.
International PCT Search Report and Written Opinion PCT/US2004/ 037753, 16 pages, dated Jul. 8, 2005.
International PCT Search Report PCT/US03/17167, 8 pages, dated Sep. 16, 2003.
International PCT Search Report PCT/US03/17203, 8 pages, dated Sep. 16, 2003.
International PCT Search Report PCT/US2004/037753, 6 pages, dated Apr. 19, 2005.
International Preliminary Report on Patent ability in International Application No. PCT/US2005/002484 dated Aug. 3, 2006.
International Preliminary Report on Patentability for international application PCT/US2006/025201, dated Feb. 7, 2008.
International Preliminary Report on Patentability for international application PCT/US2007/072202, dated Jan. 15, 2009.
International Preliminary Report on Patentability for international application PCT/US2007/078204, dated Apr. 2, 2009.
International Preliminary Report on Patentability for international application PCT/US2007/078205, dated Mar. 26, 2009.
International Preliminary Report on Patentability for international application PCT/US2007/078207, dated Mar. 26, 2009.
International Preliminary Report on Patentability for international application PCT/US2008/052943, dated Oct. 15, 2009.
International Preliminary Report on Patentability in International Application No. PCT/US/2007/072209, dated May 14, 2009.
International Preliminary Report on Patentability in International Application No. PCT/US/2008/050346, dated Jul. 23, 2009.
International Preliminary Report on Patentability in International Application No. PCT/US2007/072217 dated Feb. 12, 2009.
International Preliminary Report on Patentability in International Application No. PCT/US2007/078203, dated Mar. 26, 2009.
International Search Report and Written Opinion for international application PCT/US2007/078203, dated May 13, 2008.
International Search Report and Written Opinion for international application PCT/US2007/078204, dated May 15, 2008.
International Search Report and Written Opinion for international application PCT/US2007/078205, dated Sep. 11, 2007.
International Search Report and Written Opinion for international application PCT/US2007/078207, dated Apr. 7, 2008.
International Search Report and Written Opinion for international application PCT/US2008/0500346, dated May 22, 2008.
International Search Report and Written Opinion for international application PCT/US2008/050346 , dated May 22, 2008.
International Search Report and Written Opinion for International Patent Application No. PCT/US2007/072202, dated Mar. 25, 2008.
International Search Report and Written Opinion issued in PCT Application No. PCT/US2007/072209 dated Apr. 25, 2008.
International Search Report and Written Opinion issued in PCT Application No. PCT/US2007/072217 dated Mar. 31, 2008.
International Search Report and Written Opinion issued in PCT/ US2014/028594, dated Jul. 28, 2014.
International Search Report and Written Opinion, PCT/US08/52943 8 pages, dated Sep. 26, 2008.
International Search Report for international application PCT/ US2007/072209, dated Apr. 25, 2008.
Interview Summary dated Jul. 13, 2009 and Response to Interview Summary and Amendment filed Aug. 12, 2009, U.S. Appl. No. 11/190,331, 17 pages.
Interview Summary for U.S. Appl. No. 11/190,331, dated Jul. 13, 2009.
Japanese Office Action with English Transition; Application No. 2004-508670; PCT/US03/17203; pp. 7, dated Jan. 20, 2011.
Japanese Office Action, Application No. 2004-508669, (with English summary), (9 pages), dated Aug. 3, 2009.
Japanese Office Action, Application No. 2004-508670, (with English summary), (13 pages), dated Apr. 21, 2009.
Liakat A. Parapia, "Trepanning or trephines: a history of bone marrow biopsy," British Journal of Haematology, pp. 14-19 (2007).
Michael Totty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages (2008).
Non-Final Office Action dated Apr. 1, 2009 and Response to Office Action filed Jul. 1, 2009, U.S. Appl. No. 10/449,503, 19 pages.
Non-Final Office Action dated Mar. 23, 2009 and Response to Office Action filed Jun. 22, 2009, U.S. Appl. No. 11/190,331, 61 pages.
Non-Final Office Action dated May 29, 2009 and Response to Office Action filed Aug. 12, 2009, U.S. Appl. No. 10/449,476, 20 pages.
Non-Final Office Action, U.S. Appl. No. 10/449,476, 6 pages, dated May 29, 2009.
Non-Final Office Action, U.S. Appl. No. 10/449,476, 8 pages, dated Oct. 29, 2008.
Non-Final Office Action, U.S. Appl. No. 10/987,051, 9 pages, dated Nov. 10, 2009.
Non-Final Office Action, U.S. Appl. No. 11/042,912, 8 pages, dated Jul. 23, 2009.
Non-Final Office Action, U.S. Appl. No. 12/259,745,11 pages, dated Jul. 17, 2009.
Notice of Allowance dated Jun. 22, 2012 in U.S. Appl. No. 11/042,912.
Notice of Allowance dated Mar. 27, 2013 in U.S. Appl. No. 11/042,912.
Notice of Allowance dated Oct. 5, 2012 in U.S. Appl. No. 11/042,912.
Notice of Allowance in U.S. Appl. No. 11/042,912, dated Sep. 24, 2013.
Notice of Allowance in U.S. Appl. No. 11/253,467, dated Jun. 24, 2014.
"Proven reliability for quality bone marrow samples", Special Procedures, Cardinal Health, 6 pages, 2003.
Astrom, K. Gunnar, "CT-guided Transsternal Core Biopsy of Anterior Mediastinal Masses," Radiology, vol. 199, 1996, pp. 564-567.
Astrom, K.G., "Automatic Biopsy Instruments Used Through a Coaxial Bone Biopsy System with an Eccentric Drill Tip," Acta Radiological, 1995; 36:237-242.
Australian Exam Report on Patent Application No. 2003240970, 2 pages, dated Oct. 15, 2007.
Bio.Access.com, Single Use Small Bone Power Tool-How It Works, 1 pg, Jun. 9, 2008.
Buckley et al., "CT-guided bone biopsy: initial experience with commercially available hand held Black and Decker drill," European Journal of Radiology 61:176-180. 2007.
Chineese Office Action with English translation; Application No. 200910006631.3; pp. 12, dated Mar. 11, 2010.
Chinese Office Action w/english translation; Application No. 200680021872.X; pp. 8, dated Nov. 6, 2009.
Chinese Office Action with English translation, Application No. 2005800003261, 9 pgs, dated Jan. 16, 2009.
Chinese Office Action with English translation; Application No. 200380000022.0; pp. 10; dated Dec. 13, 2010.
Chinese Office Action with English translation; Application No. 200780000585.5; pp. 15, dated Nov. 19, 2010.
Chinese Office Action with English translation; Application No. 200780001190. 7; 12 pgs., dated Jun. 2, 2010.

(56) References Cited

OTHER PUBLICATIONS

Chinese Office Action with English translation; Application No. 200780001196; 12 pgs., dated Jul. 12, 2010.
Chinese Office Action with English translation; Application No. 200780001198.3; pp. 13, dated Apr. 27, 2010.
Chinese Office Action with English translation; Application No. 200830000022.0; pp, dated May 25, 2012.
Chinese Office Action with English translation; Application No. 200880000022.0; Pgs, dated Sep. 22, 2011.
Chinese Office Action with English translation; Application No. 200880000182.5; 12 pages, dated Sep. 10, 2010.
Chinese Office Action with English translation; Application No. 200910006631.3; pp. 9, dated Nov. 11, 2010.
Chinese Office Action, Application No. 200780000590.6, (with English translation), (13 pages), dated Aug. 21, 2009.
Chinese Office Action, Application No. 200780001188.X, (with English translation), (8 pgs) dated Nov. 9, 2010.
Chinese Office Action, Notification of the Fourth Office Action, Application No. 200880000022.0, dated Jan. 7, 2013.
Chinese Office Action, Notification of the Second Office Action, Application No. 200780000590.6, dated Mar. 1, 2010.
Communication Pursuant to Article 94(3) EPC in European Application No. 05712091.7 dated Apr. 8, 2008.
Communication relating to the results of the partial International Search Report for Mailed PCT/US2005/002484, 6 pages dated May 19, 2005.
Cummings et al.,"ACLS—Principles and Practice" ACLS—The Reference Textbook, American Heart Association, pp. 214-218, 2003.
Edited by Frederick A. Matsen III M.D., Compartmental Syndromes, About Compartmental Syndromes, Generic Trauma Content http://www.orthop.washington.edu/uw/ . . . ,pp. 1-45.
European Extended Search Report, Application No. EP08021732.6, 7 pages, dated Nov. 13, 2009.
European Extended Search Report, Application No. EP10153350.3, 5 pages, dated Mar. 11, 2010.
European Office Action and Search Report, Application No. 09150973.7, 8 pages, dated Oct. 23, 2009.
European Office Action dated Apr. 8, 2008 and Response dated May 15, 2008 , EP Application No. 05712091.7.
European Office Action dated Dec. 22, 2011 and Response dated Jun. 29, 2012 , EP Application No. 09150973.7.
European Office Action dated Feb. 21, 2007 and Response dated Jun. 27, 2007 , EP Application No. 05712091.7.
European Office Action dated Jan. 19, 2011 and Response dated Jul. 21, 2011 , EP Application No. 09150973.7.
European Office Action dated Sep. 21, 2007 and Response dated Nov. 26, 2007, EP Application No. 05712091.7.
European Office Action dated Sep. 8, 2010 and Response dated Mar. 17, 2011, EP Application No. 10153350.3.
European Patent Office, Communication from Examining Division for European Patent Application No. 08799753.2, dated Apr. 10, 2014.
European Patent Office, Communication from Examining Division for European Patent Application No. 08799753.2, dated May 18, 2015.
European Patent Office, Communication from Examining Division for European Patent Application No. 08799753.2, dated Sep. 29, 2014.
European Patent Office, European Search Report for European Patent Application No. 08799753.2, dated May 23, 2013.
European Search Report for European Patent Application No. 07842288.8, dated Mar. 16, 2011.
European Search Report issued in European Patent Application No. 17198059.2 dated Jan. 29, 2018.
European Telephone Consultation Report dated Apr. 21, 2009 and Response dated Jun. 24, 2009 , EP Application No. 08158699 .2.
European Telephone Consultation Report dated Sep. 23, 2009 and Response dated Oct. 28, 2009 , EP Application No. 08158699 .2.
Extended European Search Report for European application 07842285.4, dated Mar. 17, 2011.
Extended European Search Report for European application 07842286.2, dated Mar. 18, 2011.
F.A.S.T. 1 Intraosseous Infusion System with Depth-Control Mechanism Brochure, 6 pages, 2000.
Final Office Action, U.S. Appl. No. 11/064,156, 12 pages, dated Jun. 19, 2009.
Final Office Action, U.S. Appl. No. 11/781,568, 19 pages, dated Jun. 17, 2009.
Final Office Action, U.S. Appl. No. 11/781,597, 14 pages, dated Nov. 17, 2009.
Final Office Action, U.S. Appl. No. 11/853,685, 21 pages, dated Jun. 24, 2009.

\* cited by examiner

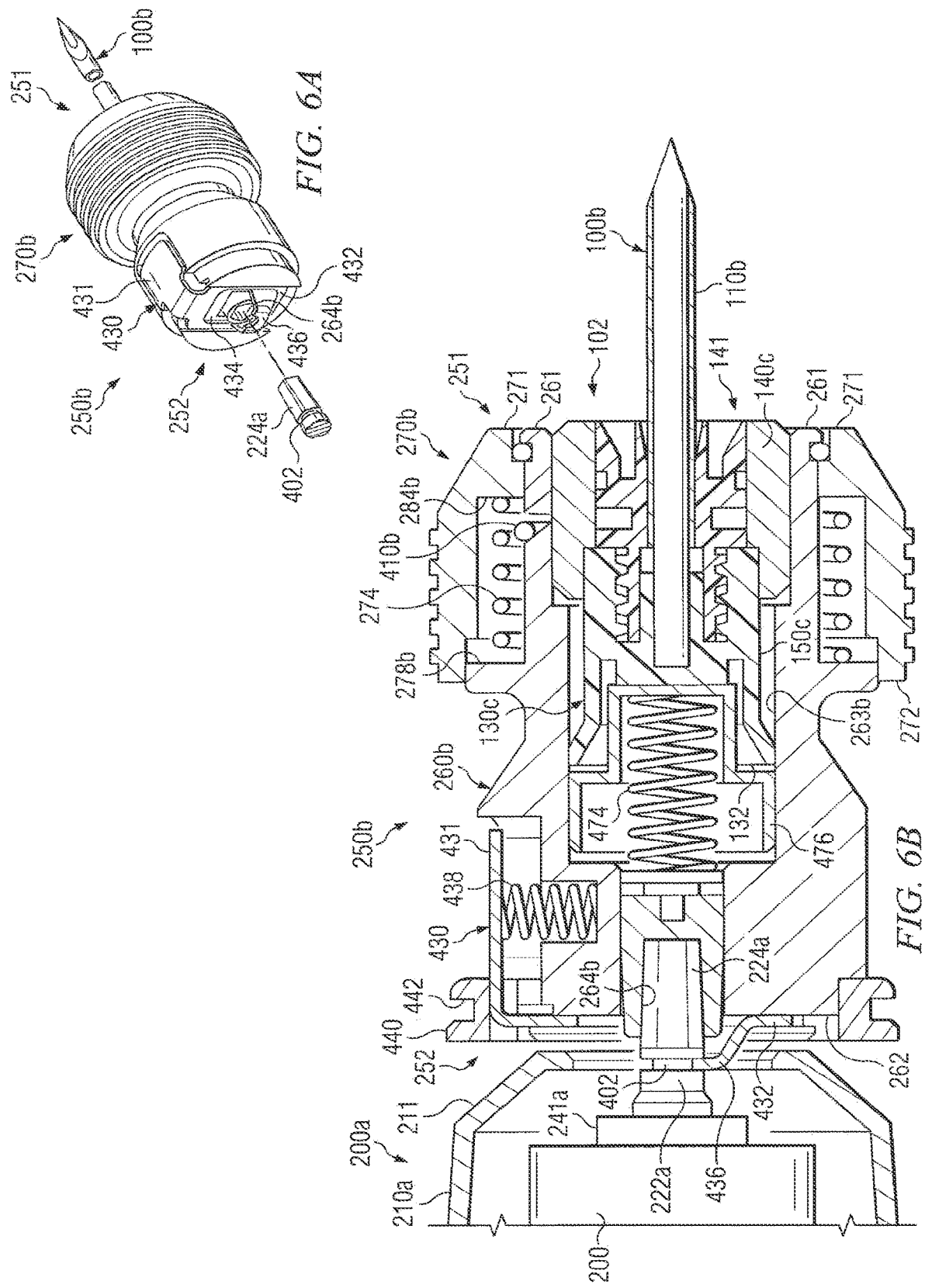

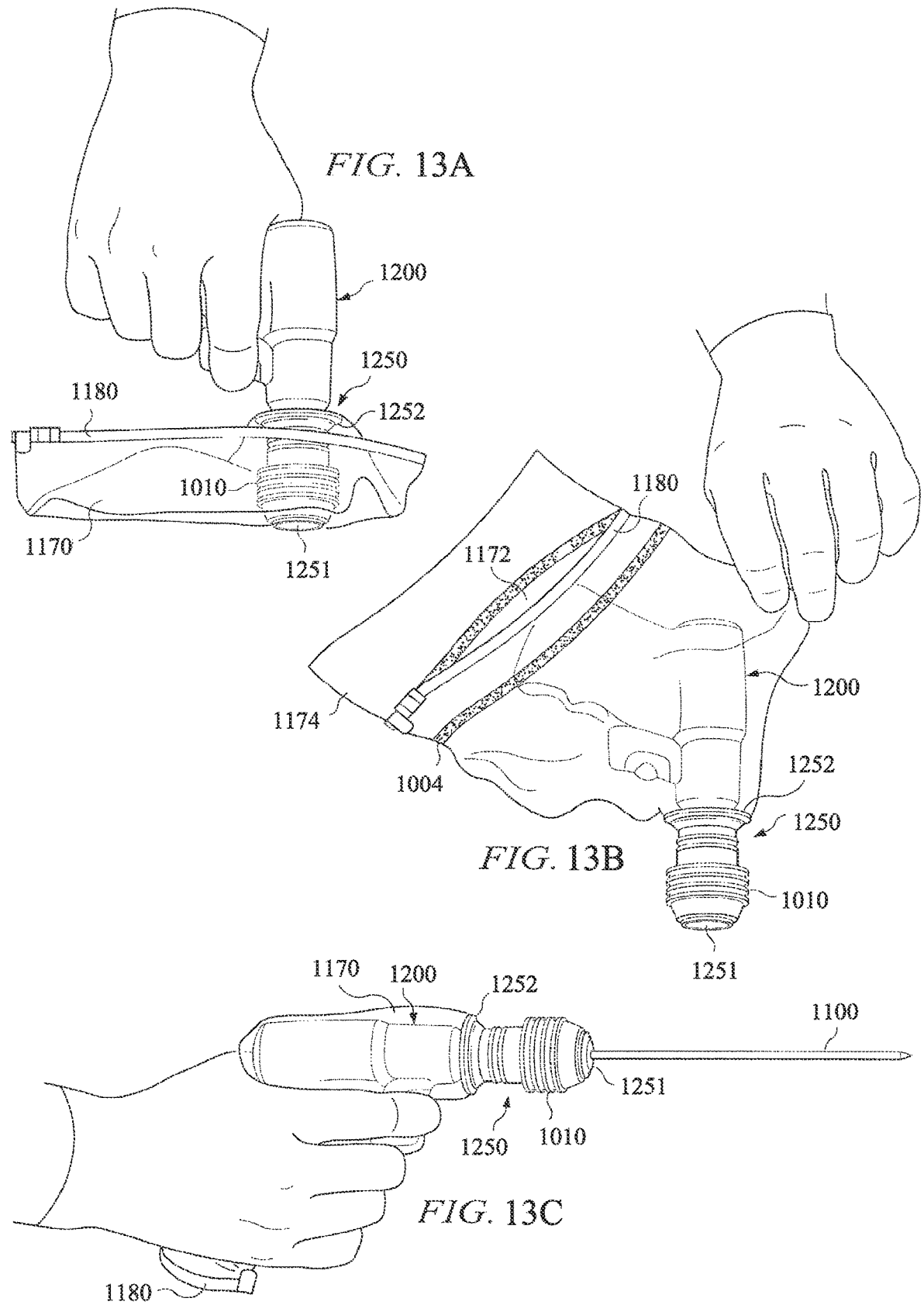

APPARATUS AND METHODS FOR BIOPSY AND ASPIRATION OF BONE MARROW

CROSS-REFERENCE TO RELATED APPLICATIONS

This application is a continuation application of U.S. patent application Ser. No. 16/155,505, filed Oct. 9, 2018, which is a continuation application of U.S. patent application Ser. No. 14/600,162, filed Jan. 20, 2015, which is a divisional application of U.S. patent application Ser. No. 12/407,651, filed Mar. 19, 2009, now U.S. Pat. No. 8,944,069, which is a continuation-in-part application of U.S. patent application Ser. No. 11/853,701, filed Sep. 11, 2007, now U.S. Pat. No. 8,656,929, which claims the benefit of U.S. Provisional Patent Application No. 60/825,325 entitled "Apparatus and Methods for Biopsy and Aspiration of Bone Marrow" filed Sep. 12, 2006, and claims the benefit of U.S. Provisional Patent Application No. 60/910,122 entitled "Powered Driver Intraosseous Device and Methods To Access Bone Marrow" filed Apr. 4, 2007. The contents of these applications are incorporated herein in their entirety by this reference.

TECHNICAL FIELD

The present disclosure is related generally to medical procedures such as aspiration and biopsy of bone marrow along with apparatus and methods associated with powered drivers, coupler assemblies, aspiration needles, biopsy needles, and associated medical procedure trays and kits. The present disclosure is also related generally to non-surgical medical procedures such as diagnosis, evaluation and treatment of bones, including factures, vertebral fractures, and/or other disease or injury to a patient's spine and to medical devices associated with such procedures. The disclosure also relates to medical procedure trays and kits for use in conjunction with diagnostic and therapeutic medical procedures for bone related disorders.

BACKGROUND OF THE DISCLOSURE

There are many clinical conditions where it is important to access and retrieve bone marrow. In some cases it may be necessary to treat diseases with bone marrow or stem cell transplants to restore functioning blood cells. Such conditions may include, but are not limited to, acute leukemia, brain tumors, breast cancer, Hodgkin's disease, multiple myeloma, neuroblastoma, non-Hodgkin's lymphomas, ovarian cancer, sarcoma and testicular cancer. In other cases it is necessary to access bone marrow to obtain a sample or specimen of the marrow for diagnostic testing. These conditions may include, but are not limited to, cancers of any type and hematologic disease of any origin.

In other cases it may be necessary to introduce a medicament or a therapeutic agent directly into bone tissue or bone marrow that may be useful to treat or ameliorate a clinical condition. For example, it may be necessary to treat diseases with bone marrow or stem cell transplants to restore functioning blood cells. Such conditions may include, but are not limited to, acute leukemia, brain tumors, breast cancer, Hodgkin's disease, multiple myeloma, neuroblastoma, non-Hodgkin's lymphomas, ovarian cancer, sarcoma and testicular cancer. In other cases, it may be necessary to treat conditions such as osteoporosis, degenerative bone disorders, or fractures by introducing a medicament into the bone or bone marrow.

Gaining access to bone and associated bone marrow for a small biopsy specimen or aspiration of a larger quantity of bone marrow may be difficult, traumatic and occasionally dangerous, depending on each selected target area for harvesting bone and/or associated bone marrow, operator expertise and patient anatomy. Currently available devices and techniques for gaining access to a bone and associated bone marrow may include an intraosseous (IO) needle with a removable trocar disposed therein. Various shapes and sizes of handles may be used to apply manual pressure and to manually rotate the IO needle and removable trocar as a set. Such manual IO devices often require substantial force to break through the outer cortex of a bone. Exertion of such force may cause pain to a patient and may sometimes damage the bone and/or IO device. Such force may cause damage when harvesting bone marrow from children with softer bone structures or any patient with bones deteriorated by disease (osteoporosis, cancer, fractures).

Occasionally a core specimen of bone and/or bone marrow may not be successfully retrieved using a standard biopsy needle. Thus, multiple insertions at different sites may be necessary to obtain a satisfactory bone and/or bone marrow biopsy specimen. Risks to health care personnel may be higher because of increased handling of blood contaminated sharp instruments. Accidental needle sticks and missed target areas may further complicate procedures and increase risks to health care personnel and/or patients.

Conventional bone marrow transplant techniques may require multiple penetration sites (up to 20 per patient) in order to obtain enough bone marrow to perform a routine bone marrow transplant. This procedure is often labor intensive. Conventional biopsy needles and/or aspiration needles are typically inserted with considerable manual force. This force may cause loss of control or operator fatigue. When the biopsy needle or aspiration needle is in place, an associated trocar is generally removed and a syringe attached to one end of the needle to aspirate a few cubic centimeters of bone marrow. The biopsy or aspiration needle is then withdrawn. A new insertion site may be penetrated, often about a centimeter from the first insertion site. The procedure may be repeated multiple times. There is a need for better apparatus and methods for accessing bone tissue.

Vertebroplasty may often be performed with a patient sedated but awake, in a x-ray suite or an operating room. During vertebroplasty, a bone cement is typically injected under pressure directly into a fractured vertebra. Once in position, the cement may harden in about ten minutes or less, depending upon the type of cement, congealing the fragments of the fractured vertebra and providing immediate stability.

SUMMARY OF THE DISCLOSURE

In accordance with teachings of the present disclosure, apparatus and methods are provided for aspiration and/or biopsy of bone marrow. Such apparatus and methods may also be used during various types of stem cell transplant procedures. Various teaching of the present disclosure may be used with other types of intraosseous devices and other types of medical procedures outside the field of providing vascular access for treatment of a patient. Examples of such procedures may include, but are not limited to, kyphoplasty, vertebral plasty, placement of wires and screws associated with replacement of joints and internal fixation of bone fractures and many other orthopedic procedures. Teachings of the present disclosure may also be incorporated into various gastroenterology-urology biopsy devices and procedures.

One aspect of the present disclosure may include a bone marrow aspiration system having an aspiration needle set along with a powered driver and coupler assembly operable to insert the aspiration needle set into a bone and associated bone marrow. The aspiration needle set may include a cannula having a single lumen and a trocar or stylet operable to be slidably disposed within the lumen of the cannula. Various types of connections including, but not limited to, Luer lock connections may be used to releasably engage the trocar within the cannula.

Another aspect of the present disclosure may include a bone and/or bone marrow biopsy system having a biopsy needle or biopsy needle set along with a powered driver or a manual driver. The powered driver and a coupler assembly may be used to insert the biopsy needle or biopsy needle set into a bone and associated bone marrow. The biopsy needle set may include a cannula having a single lumen and a trocar operable to be slidably or releasably disposed within the lumen of the cannula. Such needles and needle sets may be used in connection with detection and/or treatment of various cancers and other disease indications.

Still another aspect of the present disclosure may include accessing bone marrow by inserting an intraosseous needle or needle set into a bone and associated bone marrow using a powered driver and coupler assembly operable to rotate the intraosseous needle or needle set at an optimum speed to obtain a biopsy specimen of the bone and/or associated bone marrow. A single helical thread may be provided in one end of a biopsy needle to enhance capture of a biopsy specimen by screwing the single helical thread into associate cancellous bone to capture a bone marrow specimen or bone marrow core.

One aspect of the present disclosure may include placing a powered driver within a containment bag or sterile enclosure to provide isolation between the powered driver and an exterior environment. The containment bag may be formed from relatively flexible, lightweight, clear plastic-type materials. The containment bag may include a port assembly operable to be releasably engaged with one end of the powered driver and to maintain a fluid barrier with adjacent portions of a driver housing. An intraosseous device may be attached to one end of the port assembly. A drive shaft extending from the powered driver may be releasably engage with another end of the port assembly.

A further aspect of the present disclosure may include a biopsy kit having a biopsy needle and an ejector or ejector rod operable to remove a bone and/or bone marrow specimen from a biopsy needle. A funnel (sometimes referred to as an "ejector funnel") may also be included within the biopsy kit. The funnel may accommodate insertion of the ejector into one end of the biopsy needle. The funnel may include a reduced inside diameter portion formed in accordance with teachings of the present disclosure. For some embodiments, interior portions of the funnel may function as a "one way connector" which may allow the funnel to function as a sharps protector for one end of the biopsy needle disposed therein.

A further aspect of the present disclosure may include a coupler assembly operable to releasably engage an intraosseous device with portions of a drive shaft extending from one end of a powered driver. The coupler assembly may allow the powered driver to insert the intraosseous device at an insertion site (power in.) The coupler assembly may also allow the powered driver to "spin" the intraosseous device during removal from the insertion site (power out). This feature of the present disclosure may also be referred to as "power in and power out."

Apparatus and methods incorporating teachings of the present disclosure may: Reduced physical requirements to insert an IO device into bone and associated bone marrow. Better control of an IO device during insertion. Increased speed to complete an IO procedure. Reduced discomfort to patients. Simple, intuitive systems and procedures for an operator.

This summary contains only a limited number of examples of various embodiments and features of the present disclosure. Additional examples of embodiments and features will be discussed in the Detailed Description of the Disclosure.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 6A is a schematic drawing showing an alternative embodiment of a coupler assembly operable to releasably engage an intraosseous device with one end of a drive shaft extending from a powered driver in accordance with teachings of the present disclosure;

FIG. 6B is a schematic drawing in section with portions broken away showing portions of the powered driver, coupler assembly and intraosseous device of FIG. 6A;

FIG. 13A is a schematic drawing showing an isometric view of a user attaching a non-sterile powered driver to a sterile coupler assembly attached to a sterile container bag in accordance with teachings of the present disclosure;

FIG. 13B is a schematic drawing showing still another isometric view of a user raising a sterile container bag of FIG. 13A with a flap and adhesive strip to enclose the non-sterile powered driver coupled with a sterile coupler assembly in accordance with teachings of the present disclosure;

FIG. 13C is a schematic drawing showing an isometric view of a non-sterile powered driver enclosed in a sterile container bag comprising a flap and an adhesive strip, wherein the powered driver is releasably coupled with a sterile coupler assembly and is further releasably attached to an intraosseous device assembly, in accordance with teachings of the present disclosure;

DETAILED DESCRIPTION OF THE DISCLOSURE

Figure 1A:
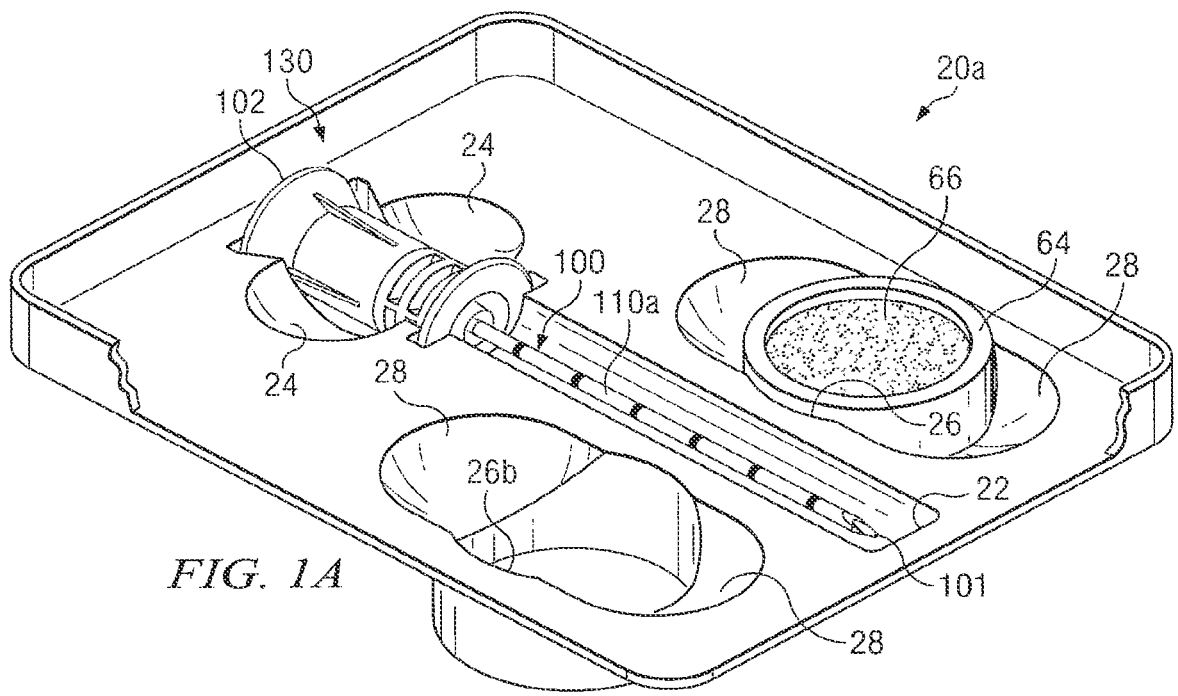
FIG. 1A is a schematic drawing showing an isometric view of one example of a aspiration needle set incorporating teachings of the present disclosure disposed in a kit.

Preferred embodiments of the disclosure and various advantages may be understood by reference to FIGS. 1A-19D, wherein like numbers refer to same and like parts.

The term "containment bag" as used in this application may include any sterile sleeve, sterile envelope, sterile glove, sterile enclosure or any other device incorporating teachings of the present disclosure and operable to allow engaging a non-sterile device with a sterile device and conducting a medical procedure requiring a sterile field or sterile environment.

For some applications a non-sterile powered driver may be placed in a containment bag incorporating teachings of the present disclosure and engaged with a sterile intraosseous device for use during various medical procedures requiring a sterile field or sterile environment. Such containment bags may be attached to a coupler assembly or any other device incorporating teachings of the present disclosure to prevent the non-sterile powered driver from contaminating the sterile intraosseous (TO) device during and after engagement of the non-sterile powered driver with the IO device.

The term "driver" as used in this application may include any type of powered driver satisfactory for inserting an intraosseous (TO) device into a selected portion of a patient's vascular system. Such powered drivers often rotate a drive shaft extending therefrom. However, various teachings of the present disclosure may be used with powered drivers that reciprocate an associated drive shaft (not expressly shown).

Various techniques may be satisfactorily used to releasably engage or attach an IO device with a powered driver in accordance with teachings of the present disclosure. For example a wide variety of coupler assemblies, port assemblies, connectors, receptacles, fittings, hubs, hub assemblies, latching mechanisms and/or other types of connecting devices incorporating teachings of the present disclosure may be satisfactorily used to releasably engage an IO device with a powered driver.

Various types of coupler assemblies incorporating teachings of the present disclosure may be satisfactorily used to releasably engage one end of a shaft extending from a driver with one end of an intraosseous device. For some embodiments the powered driver may include a drive shaft having one end with a generally hexagonal cross section operable to be releasably engaged with a latch mechanism disposed in one end of a coupler assembly. For some embodiments a coupler assembly incorporating teachings of the present disclosure may be referred to as a "hands free" coupler, a quick disconnect or quick release coupler and/or port assembly.

Respective latch mechanisms may be disposed proximate a first end and a second end of a coupler assembly in accordance with teachings of the present disclosure. Pushing one end of a drive shaft extending from a powered driver into the second end of the coupler assembly may result in an annular recess disposed in the one end of the drive shaft "snapping" into releasable engagement with the respective latch mechanism. Pushing one end of an intraosseous device into the first end of the coupler assembly may result in an annular recess in the one end of the intraosseous device "snapping" into releasable engagement with the respective latch mechanism.

For some embodiments, a coupler assembly or port assembly may be engaged with a containment bag or sterile sleeve in accordance with teachings of the present disclosure. Coupler assemblies and/or hub assemblies incorporating teachings of the present disclosure allow easy separation of an associated powered driver from an IO device such that the IO device may remain in place in a patient to allow bone marrow aspiration or removal of bone and/or bone marrow biopsy specimens. Such coupler assemblies and/or port assemblies may also allow an associated powered driver to "spin" or rotate an attached IO device while withdrawing an IO device from an insertion site or changing the depth of penetration of an TO device in a target area. Rotating the TO device during withdrawal or changing depth (power out) may substantially improve patient comfort and reduce potential trauma to bone and soft body tissue proximate an insertion site.

A powered driver may be used to insert an TO device incorporating teachings of the present disclosure into a selected target area or target site in ten seconds or less. However, various teachings of the present disclosure are not limited to use with powered drivers. Manual drivers and spring powered drivers may also be used with TO devices incorporating teachings of the present disclosure.

Examples of manual drivers are shown in U.S. patent application Ser. No. 11/042,912 entitled Manual Intraosseous Device filed Jan. 25, 2005 (now U.S. Pat. No. 8,641,715).

The term "fluid" may be used in this application to include liquids such as, but not limited to, blood, water, saline solutions, IV solutions, plasma or any mixture of liquids, particulate matter, dissolved medication and/or drugs associated with biopsy or aspiration of bone marrow or communication of fluids with bone marrow or other target sites. The term "fluid" may also be used in this patent application to include any body fluids and/or liquids containing particulate matter such as bone marrow and/or cells which may be withdrawn from a target area.

The terms "harvest" and "harvesting" may be used in this application to include bone and/or bone marrow biopsy and bone marrow aspiration. Bone and/or bone marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation and/or research purposes. For example some stem cell research techniques may require relatively large quantities of bone marrow.

The terms "insertion site," "penetration site," and "installation site" may be used in this application to describe a location on a bone at which an intraosseous device may be inserted or drilled into the bone and associated bone marrow. Insertion sites, penetration sites and installation sites are generally covered by skin and soft tissue.

The term "intraosseous (TO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set or aspiration needle set operable to provide access to an intraosseous space or interior portions of a bone. Such IO devices may be formed, at least in part, from metal alloys such as 304 stainless steel and other biocompatible materials associated with needles and similar medical devices.

Various types of IO devices may be formed in accordance with teachings of the present disclosure. Examples of such IO devices may include, but are not limited to, biopsy needles, biopsy needle sets, aspiration needles and aspiration needle sets. However, a wide variety of other IO devices may be formed in accordance with one or more teachings of the present disclosure. Such IO devices may or may not include a trocar or stylet.

For some applications, a trocar or stylet may be inserted into a generally hollow, longitudinal bore or lumen in an associated catheter or cannula. The first end of the second hub may be releasably engaged with second end of the first hub to releasably dispose the stylet or trocar within the longitudinal bore of the cannula or catheter. The present disclosure is not limited to aspiration needle sets or biopsy needle sets as discussed in this application.

The term "target area" may be used in this application to describe selected portions of a bone cavity or locations in a bone cavity from which associated bone marrow may be harvested in accordance with teachings of the present disclosure.

Many currently available techniques for harvesting bone and/or bone marrow may require more than one penetration into a bone and associated bone marrow to retrieve an adequate sample of bone and/or bone marrow. Multiple penetration sites may be required in the same bone if a biopsy specimen is not satisfactorily retrieved at the first penetration site. Medical personnel may need to insert an IO needle into several different penetration sites on the same bone to obtain adequate quantities of bone marrow for transplant or stem cell research. For example obtaining sufficient quantities of bone marrow from a patient's pelvis may require six or more insertion sites. Multiple insertions may be extremely painful for a patient and may deter some people from donating bone marrow. Multiple insertions may also cause fatigue in medical personnel performing such procedures with manual IO devices. Multiple scheduling for therapeutic procedures separate from diagnostic procedures also adds to trauma and cost for a patient.

Bone marrow transplant procedures and various research procedures such as stem cell research often require relatively large quantities of bone and/or bone marrow. Hip bones generally have a large bone cavity and are therefore frequently used as a target area for harvesting bone marrow for transplant procedures, stem cell research procedures or any other procedure requiring relatively large quantities of bone marrow.

For some applications, an IO needle or other IO device may be formed with a first end operable to penetrate bone and/or associated bone marrow. A connector or hub may be attached to a second end of the IO needle or other IO device. Such connectors or hubs may be operable to releasably engage the IO needle or IO device with a powered driver, a manual driver and/or a coupler assembly.

IO needle sets and other IO devices incorporating teachings of the present disclosure may include a first IO device such as a cannula, catheter or outer penetrator and a second IO device such as a stylet, trocar or inner penetrator. Various types of cutting surfaces may be formed proximate a first end of the first IO device and a first end of the second IO device. The cutting surface of the first IO device and the cutting surface of the second IO device may cooperate with each other to penetrate bone and/or associated bone marrow.

A first connector or first hub may be used to releasably engage the first IO needle or IO device with the second IO needle or IO device. For example an IO needle set may include a first connector or a first hub with a generally hollow cannula, catheter or outer penetrator attached thereto and extending from a first end of the first hub. A second end of the first hub may be operable to be releasably engaged with a first end of a second connector or a second hub. A stylet, trocar or inner penetrator may also be attached to and extend from the first end of the second hub. The second end of the first hub may include an opening sized to allow inserting the stylet, trocar or inner penetrator through the opening and a lumen in the cannula, catheter or outer penetrator.

A second end of the second hub may be operable to be releasably engaged with a first end of a coupler assembly incorporating teachings of the present disclosure. One end of a shaft extending from a powered driver or a manual driver may be releasably engaged with a second end of the coupler assembly. In some embodiments of the present disclosure, the dimensions of the hubs may be designed to be unobtrusive or minimally obtrusive to an imaging method that may be used to image the site of insertion and a medical procedure being performed such as the delivery of a medicament to a specific site.

Additional details concerning powered drivers, connectors, hubs and IO devices may be found in U.S. patent application Ser. No. 12/061,944 entitled "Powered Drivers, Intraosseous Devices and Methods to Access Bone Marrow" filed Apr. 3, 2008, now U.S. Pat. No. 9,451,968, which claims priority from a provisional patent application with the same title filed on Apr. 4, 2007.

Various features of the present disclosure may be described with respect to powered driver 200, 1200, coupler assemblies 250, 250a, 250b, 250c, 1250, 1250a, 1250b and 1250c, hub assemblies 130, 130a, 130b, 130c, 130d, 1130, 1130a, 1130b, 1130c and 1130d, hubs, 96, 140, 150, 1096, 1140, 1150, IO needle sets 100, 100a, 100b, 100c, 100d, 1100, 1100a, 1100b, 1100c and 1100d, including IO needles, vertebral needles, IO biopsy needles, IO aspiration needles, and containment bag 170, 1170. However, the present disclosure is not limited to such powered drivers, coupler assemblies, hub assemblies, IO needle sets, and/or containment bags. A wide variety of intraosseous devices, hub assemblies, coupler assemblies and/or containment bags may be formed in accordance with teachings of the present disclosure with various dimensions and/or configurations.

Figure 1B:
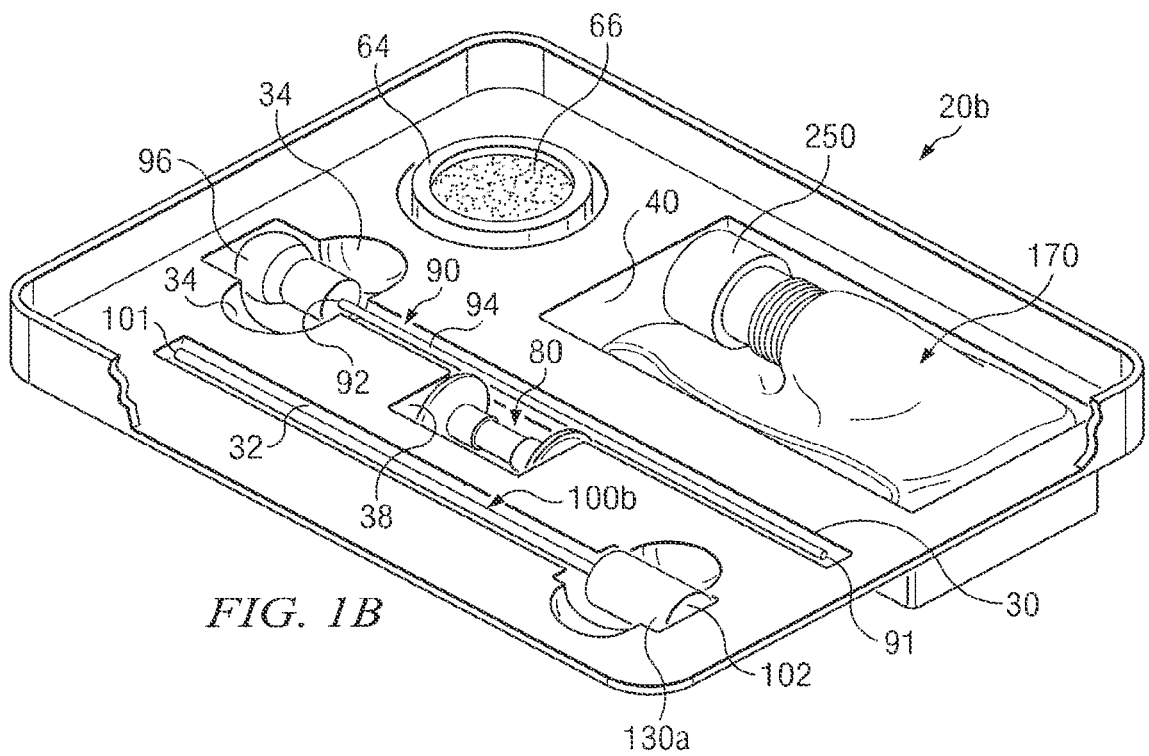
FIG. 1B is a schematic drawing showing an isometric view of one example of a biopsy needle set incorporating teachings of the present disclosure disposed in a kit.

FIGS. 1A-1J show some examples of medical procedure trays and/or kits which may contain one or more intraosseous devices and/or other components incorporating teachings of the present disclosure. For example, medical procedure tray 20a as shown in FIG. 1A may include intraosseous needle set or aspiration needle set 100 incorporating various teachings of the present disclosure. Medical procedure tray 20b as shown in FIG. 1B may include intraosseous needle set or biopsy needle set 100b, ejector 90, funnel 80 and/or containment bag or sterile sleeve 170. Medical procedure tray 20c as shown in FIGS. 1C-1I may also include various IO devices and other components incorporating teachings of the present disclosure including, but not limited to, biopsy needle set 100b, coupler assembly 250, containment bag 170, ejector 90 and/or funnel 80a.

Medical procedure trays and/or kits formed in accordance with teachings of the present disclosure may provide a support or base for various components such as a coupler assembly, funnel and/or sharps protector to allow an operator or user to perform various functions without requiring that the operator or user hold or manipulate the respective component. For example medical procedure tray 20c as shown in FIG. 1 may position and support coupler assembly 250 such that one end of a powered driver may be inserted (pushed) into releasable engagement with second end 252 of coupler assembly 250. The powered driver may then be used to withdraw coupler assembly 250 from medical procedure tray 20c without requiring an operator or user to directly hold or manipulate coupler assembly 250.

Funnel 80a may be positioned and supported within medical procedure tray 20c such that one end of an intraosseous device may be inserted (pushed) into funnel 80a. Funnel 80a may be withdrawn from medical procedure tray 20c without requiring that an operator or user directly hold or manipulate funnel 80a. Each sharps protector 64a may also be positioned and supported within medical procedure tray 20c to allow inserting (pushing) one end of an intraosseous device or any other medical device requiring sharps protection into sharps protector 64a without requiring that an operator or user to directly hold or manipulate the associated sharps protector 64a. Medical procedure trays, coupler assemblies and other components formed in accordance with teachings of the present disclosure may substantially reduce the number of opportunities for an accidental "needle stick" and/or dropping, contaminating or other problems associated with handling and manipulating various components disposed within an associated medical procedure tray.

Medical procedure trays and kits formed in accordance with teachings of the present disclosure may have a wide variety of configurations and/or dimensions. For some applications, a kit holding intraosseous devices in accordance with teachings of the present disclosure may have an overall length of approximately four and one-half inches, a width of approximately three inches and a depth of approximately two inches. Various heat sealing techniques may be satisfactorily used to place a removable cover (not expressly shown) over a medical procedure tray or kit incorporating teachings of the present disclosure.

Figure 1C:
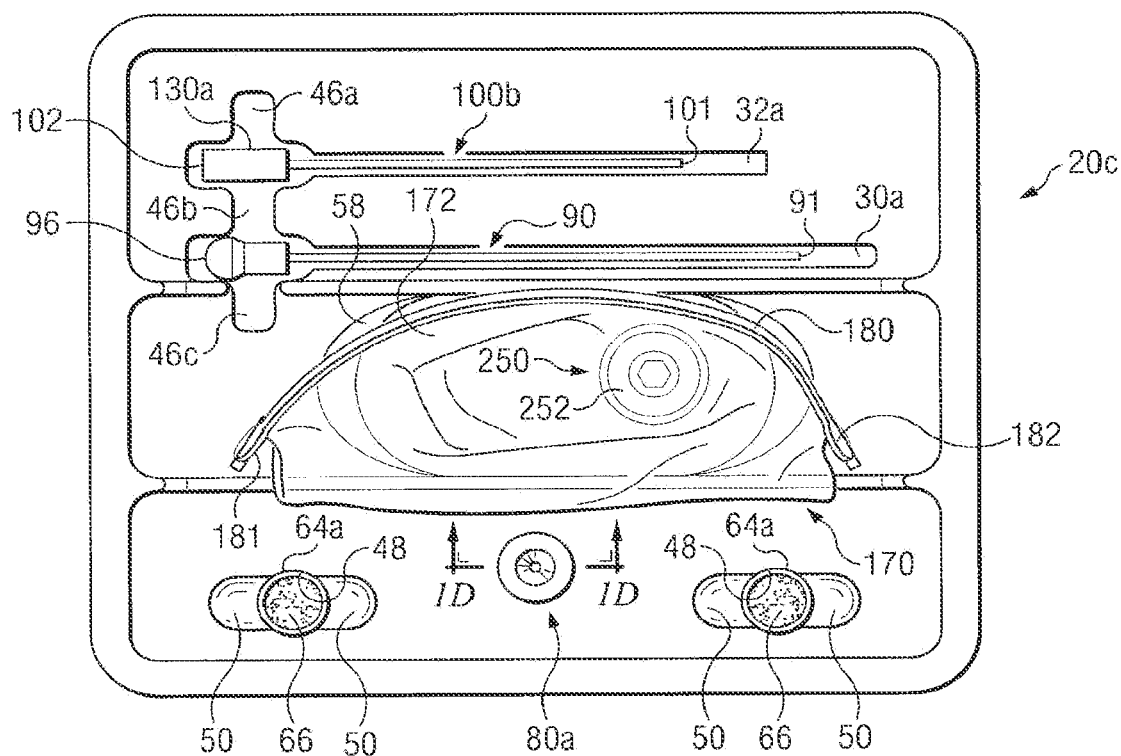
FIG. 1C is a schematic drawing showing an isometric view of one example of a medical procedure tray including a biopsy needle set and other components satisfactory for use with a powered driver in a sterile environment in accordance with teachings of the present disclosure.
Figure 1D:
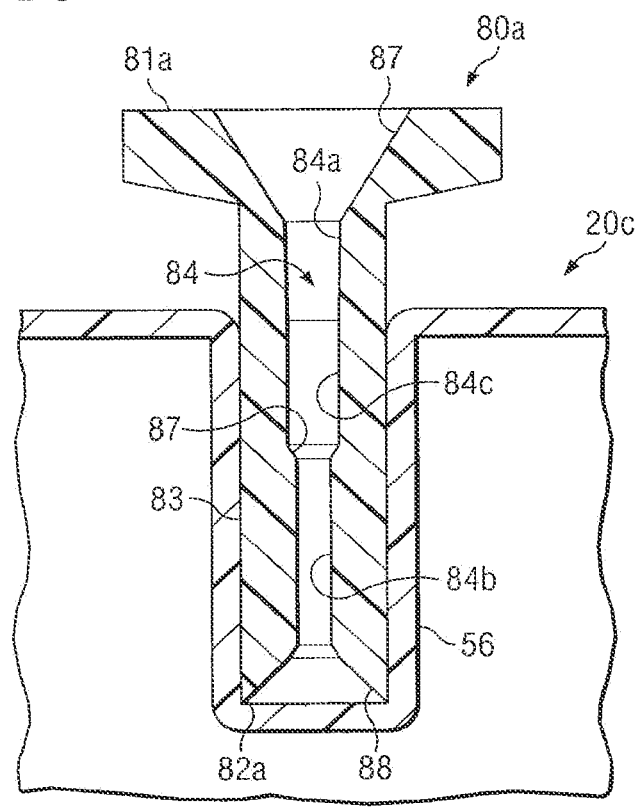
FIG. 1D is a drawing in section taken along lines 1D-1D of FIG. 1C.
Figure 1E:
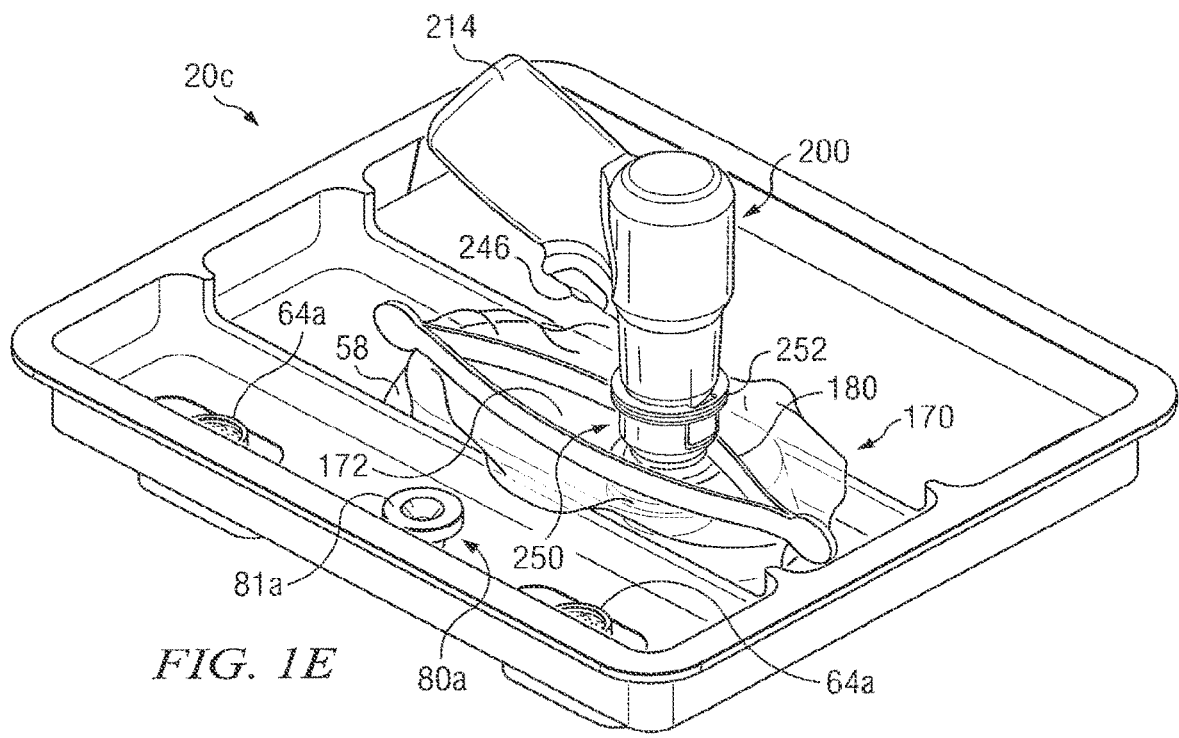
FIG. 1E is a schematic drawing showing an isometric view of the medical procedure tray of FIG. 1D with a non-sterile medical device disposed in a containment bag in accordance with teachings of the present disclosure.
Figure 1F:
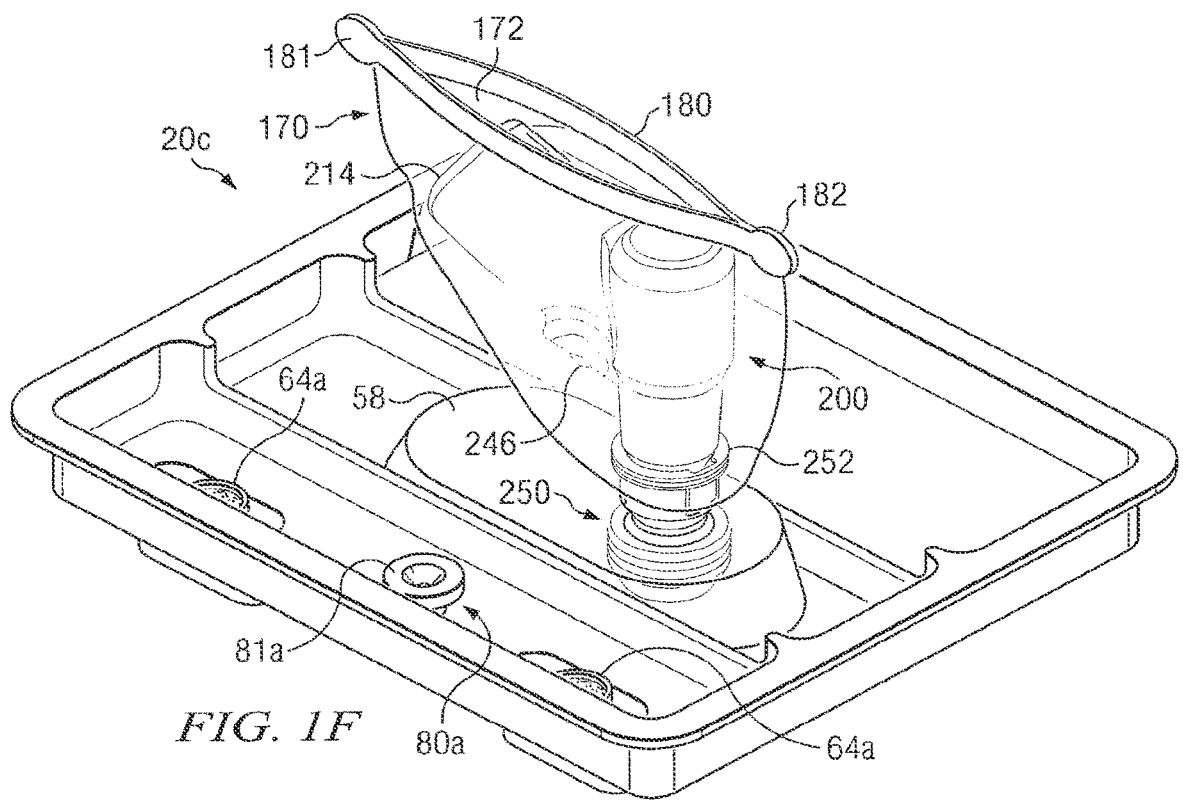
FIG. 1F is a schematic drawing showing still another isometric view of the medical procedure tray of FIG. 1D with the non-sterile medical device disposed in the containment bag in accordance with teachings of the present disclosure.

Medical procedure trays 20a, 20b and/or 20c may also contain a wide variety of other components including, but not limited to, one or more sharps protectors 64 as shown in FIGS. 1A and 1B or sharps protectors 64a as shown in FIGS. 1C, 1E and 1F. Sharps protectors 64 and 64a may include hard foam or claylike material 66 disposed therein. Intraosseous devices such as aspiration needle sets and biopsy needle sets typically have respective sharp tips and/or cutting surface operable to penetrate skin, soft tissue and bone. The sharp tips and/or cutting surface of such intraosseous devices may be inserted into hard foam or claylike material 66 after completion of a medical procedure using the respective intraosseous device.

For some applications, medical procedure tray 20a may be referred to as a "bone marrow aspiration tray," "aspiration procedure tray" or "bone marrow aspiration kit". For some applications, medical procedure trays 20b and 20c may sometimes be referred to as "bone and/or bone marrow biopsy procedure trays" or "biopsy procedure trays" or "bone marrow biopsy kits."

Medical procedure trays 20a, 20b and/or 20c may be formed from various polymeric materials compatible with sterile packaging and storage of various components disposed within each medical procedure tray. For some applications ethylene oxide sterilization techniques may be used during assembly and packaging of medical procedure trays 20a, 20b and 20c. However, other sterilization procedures may be used as appropriate.

Respective covers (not expressly shown) may be placed over each medical procedure tray 20a, 20b and 20c as part of an associated sterilization and packaging process. Such covers may be removed prior to use of various components disposed within each medical procedure tray.

Medical procedure tray or aspiration tray 20a (see FIG. 1A) may include elongated slot 22 with appropriate dimensions for an associated intraosseous device such as, but not limited to, aspiration needle set 100. The dimensions and configuration of slot 22 may be selected to accommodate the combined length of hub assembly 130 and cannula 110a extending therefrom. One end of slot 22 may be sized to accommodate the dimensions and configuration of hub assembly 130. Enlarged openings or finger slots 24 may also be provided to accommodate inserting and removing aspiration needle set 100 from slot 22. Various details associated with aspiration needle set 100 will be discussed later with respect to FIG. 3A.

Sharps protector 64 may be disposed within holder 26 of medical procedure tray 20a. A pair of finger slots 28 may also be formed in tray 20a to accommodate inserting and removing sharps protector 64 from holder 26a. Holder 26b may also be formed in tray 20a along with associated finger slots 28. An additional sharps protector or other components may be disposed within holder 26b. The dimensions/configurations of slot 22 and holders 26a and 26b may be varied as desired for respective components which will be disposed therein.

Medical procedure tray or biopsy tray 20b (See FIG. 1B) may include elongated slots 30 and 32. The dimensions and configuration of elongated slot 30 may be selected to accommodate placing ejector 90 therein. The dimensions and configuration of elongated slot 32 may be selected to accommodate placing intraosseous device or biopsy needle set 100b therein.

One end of elongated slot 30 may have configuration and dimensions selected to accommodate the configuration and dimensions of handle 96 disposed on second end 92 of injector rod 94. A pair of finger slots 34 may be formed as part of elongated slot 30 to allow installing and removing ejector 90. One end of elongated slot 32 may be operable to accommodate the configuration and dimensions associated with hub assembly 130a of biopsy needle set 100b. A pair of finger slots 36 may also be provided as part of elongated slot 32 to accommodate inserting and removing biopsy needle set 100b from elongated slot 32.

Tray 20b may also include holder 38 disposed adjacent to elongated slot 30. Holder 38 may have a configuration and dimensions compatible with releasably placing funnel 80 therein. Tray 20b may also include compartment or holder 40 with dimensions compatible with placing containment bag 170 with coupler assembly 250 attached thereto. One or more specimen or sample containers or cups (not expressly shown) may be provided in biopsy tray 20b. Biopsy specimen or sample containers may include a cavity sized to receive a biopsy specimen from biopsy needle set 100b. Funnel holders 38 may be formed in biopsy procedure tray 20b adjacent to ejector 90 to ensure that funnel 80 is readily available to assist with removing a biopsy specimen from biopsy needle set 100b.

Medical procedure tray or biopsy tray 20c as shown in FIGS. 1C-1I represents another example of a medical procedure tray formed in accordance with teachings of the present disclosure. Biopsy procedure tray 20c may include intraosseous device or biopsy needle set 100b releasably disposed in elongated slot 42 and ejector 90 disposed in elongated slot 44. Respective ends of elongated slots 42 and 44 may be disposed adjacent to each other so that finger slots 46a, 46b and 46c may be more easily manufactured. Biopsy procedure tray 20c also includes a pair of sharps protectors 64*a* disposed in respective holders 48. Each holder 48 includes a pair of finger slots 50.

Funnel 80*a* may be slidably disposed in holder 56 in medical procedure tray 20*c* in a generally vertical position. See FIG. 1D. As a result, first end 81*a* of funnel 80*a* may be oriented in a position to allow inserting one end of biopsy needle set 100*b* or outer cannula 110*b* therein. Longitudinal passageway 84 proximate first end 81*a* may include a sticking tapered portion operable to maintain contact with one end of biopsy needle set 100*b* or outer cannula 110*b*. Biopsy needle set 100*b* or cannula 110*b* may then be manipulated to pull funnel 80*a* from holder 56. Funnel 80*a* may serve as a sharps protector for the one end of an intraosseous device inserted therein.

One of the benefits of the present disclosure may include being able to releasably engage one end of a powered driver with one end of a coupler assembly, releasably engage one end of a biopsy needle with an opposite end of the coupler assembly, insert another end of the biopsy needle into a selected target area, "power out" the biopsy needle with a high degree of confidence that a biopsy specimen will be disposed therein and insert the other end of the biopsy needle into a funnel to provide both sharps protection and removal of the biopsy specimen. Any direct contact between an operator and the biopsy needle may be limited to pushing the one end of the biopsy needle into a respective end of the coupler assembly.

A pair of holders or clamps (not expressly shown) may also be formed in medical procedure tray 20*c* adjacent to holder for coupler assembly 250. Such clamps may be designed to accommodate first end 181 and second end 182 of flexible stay 180 disposed on second opening 172 of containment bag 170. Coupler assembly 250 may also be installed in holder 58 of biopsy procedure tray 20*c* with first end 251 down and second end 252 looking up.

FIGS. 1E and 1F show one procedure for placing a powered driver within a containment bag incorporating teachings of the present disclosure. Containment bag 170 may be formed from generally flexible, fluid impervious material which may also be sterilized using conventional sterilization techniques. Containment bag 170 may be used to prevent a non-sterile powered driver from contaminating a sterile intraosseous device and/or an injection site, particularly during a bone marrow biopsy procedure or a bone marrow aspiration procedure. Containment bag 170 may be operable to form a fluid barrier with adjacent portions of housing assembly 270. At the same time, coupler assembly 250 may allow powered driver to rotate an intraosseous device releasably engaged with first end 251 of coupler assembly 250 without damage to containment bag 170.

First opening 171 may be formed along one edge of containment bag or sleeve 170. Second opening 172 may be formed along an opposite edge of containment bag 170. The configuration and dimensions of second opening 172 may be selected to accommodate inserting and removing a powered driver or other non-sterile medical device therefrom.

Coupler assembly 250 may be securely engaged with and extend from first opening 171. The attachment between adjacent portions of first opening 171 and coupler assembly 250 may be selected to allow rotation of an intraosseous device by an associated powered drive. Housing assembly 270 and/or housing segments 280 and 290 of coupler assembly 250 may remain relatively stationary during rotation of elongated core 260. See FIG. 5F. For example portions of housing assembly 270 such as flange 254 extending from second end 252 of coupler assembly 250 may be attached to first opening 171 and remain relatively stationary while powered driver 200 rotates elongated core 260 and aspiration needle set 100 extending therefrom.

For some applications, powered driver 200 may be directly placed into a containment bag and engaged with coupler assembly 250. For other applications, a non-sterile powered driver may be inserted into containment bag 170 in connection with removing coupler assembly 250 from a medical procedure tray.

For some applications, a protective cover (not expressly shown) may be removed from medical procedure tray 20*c*. End 224 extending from drive shaft 222 of powered driver 200 may then be inserted through second opening 172 of containment bag 170 and releasably engaged with second end 252 of coupler assembly 250.

First end 181 and second end 182 of flexible stay 180 may then be removed from respective clamps or holders in medical procedure tray 20*c* to allow manually lifting second opening 172 upwardly relative to powered driver 200. See FIG. 1E. Containment bag 170 may continue to be raised to a fully extended position with powered driver 200 disposed therein. See FIG. 1F. Flap 174 may then be placed over second opening 172. Containment bag 170 with powered driver 200 disposed therein and coupler assembly 250 may then be removed from holder 58 of medical procedure tray 20*c*.

FIGS. 1G-1J show another procedure incorporating teachings of the present disclosure to place a non-sterile powered driver into a containment bag with a coupler assembly or port assembly extending therefrom and enclosing the non-sterile powered driver within the containment bag to allow engaging the coupler assembly with a sterile intraosseous device. The same procedure may be used to engage other non-sterile medical devices with sterile medical devices.

For some applications, medical procedure tray 20*c* may be placed in second tray 20*d* with first drape 51 disposed therebetween. See FIGS. 1G and 1J. Second drape 52 with opening or fenestration 54 may then be placed over medical procedure tray 20*c* with opening or fenestration 54 generally aligned with second opening 172 of containment bag 170 and second end 252 of coupler assembly 250. Second drape 52 may also cover portions of first drape 51 extending outwardly from between medical procedure tray 20*c* and the second medical procedure tray (not expressly shown).

For some applications portions of second drape 52 adjacent to fenestration 54 may be releasably engaged with portions of containment bag 170 adjacent to second opening 172. See FIG. 1J. Various commercially available low strength adhesive materials may be satisfactorily used to provide releasable engagement between second drape 52 proximate fenestration 54 and second opening 172 of containment bag 170.

Figure 1G:
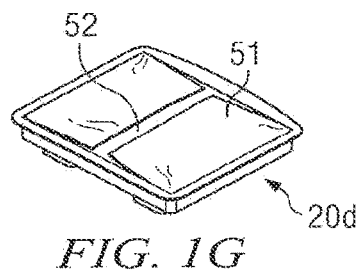
FIG. 1G is a schematic drawing showing a further isometric view of the medical procedure tray of FIG. 1C.

First drape 51 and second drape 52 may then be folded with each other and covering the contents of medical procedure tray 20*c* such as shown in FIG. 1G. A portion of second drape 52 may be seen in FIG. 1G between respective portions of first drape 51.

A protective cover (not expressly shown) may then be placed over both medical procedure trays and any exposed portions of drapes 51 and 52. The combined medical procedure tray (not expressly shown) may then be sterilized. One benefit of such sterilization include, but is not limited to, providing a sterilized containment bag which may be used to engage a non-sterile medical device with a sterile medical device in accordance with teachings of the present disclosure.

Figure 1H:
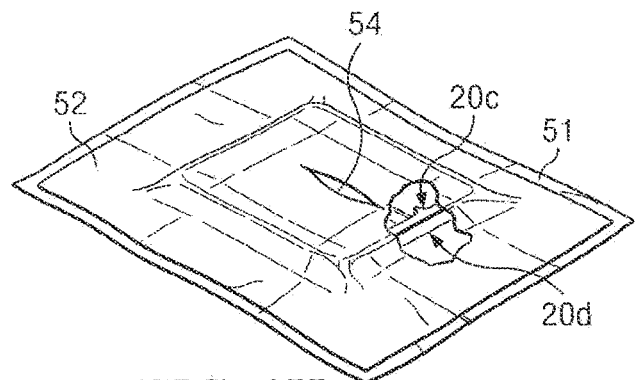
FIG. 1H is a schematic drawing showing an isometric view of the medical procedure tray of FIG. 1G after unfolding a first drape and a second drape.
Figure 1I:
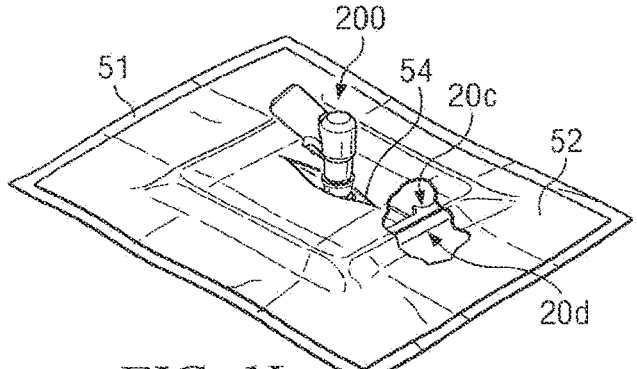
FIG. 1I is a schematic drawing showing an isometric view of the medical procedure tray of FIG. 1G after a powered driver has been engaged with a coupler assembly in accordance with teachings of the present disclosure.
Figure 1J:
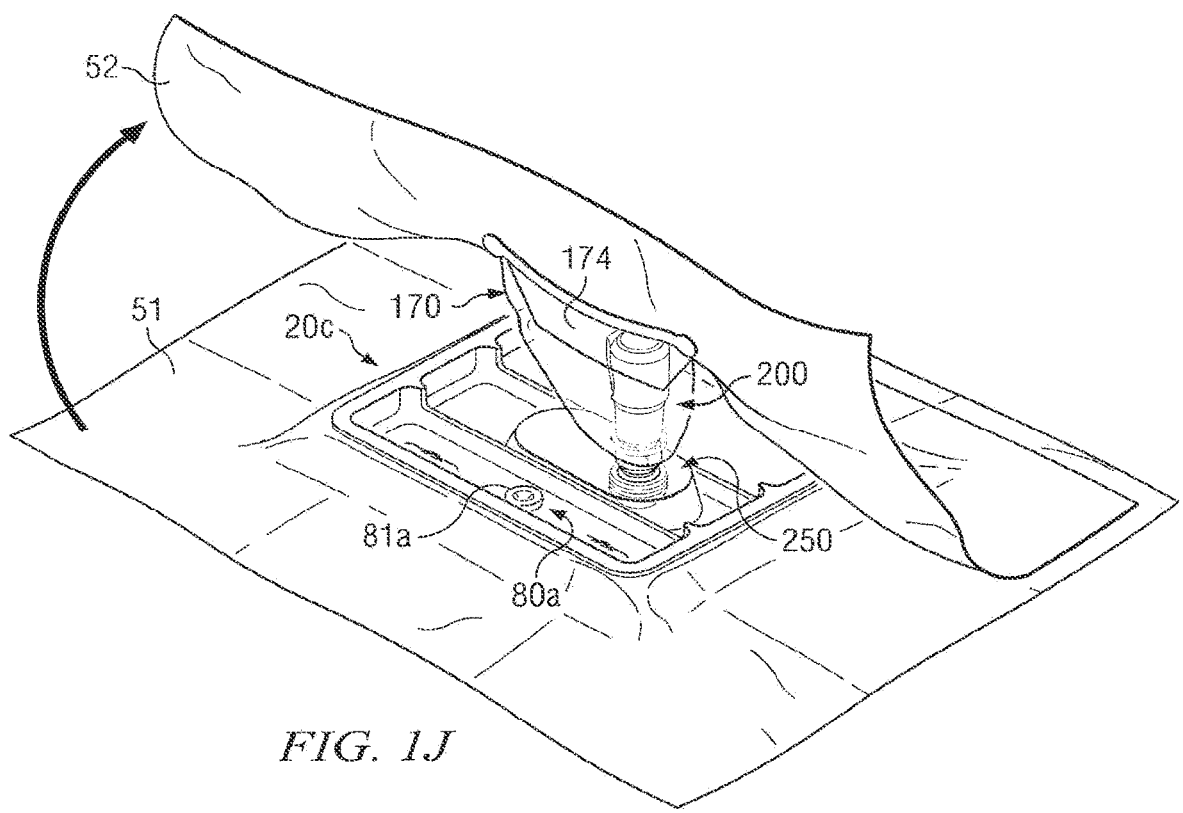
FIG. 1J is a schematic showing an isometric view of the medical procedure tray of FIG. 1G after lifting the second drape to enclose the powered driver (one example of a non-sterile medical device) in the containment bag.
Figure 2:
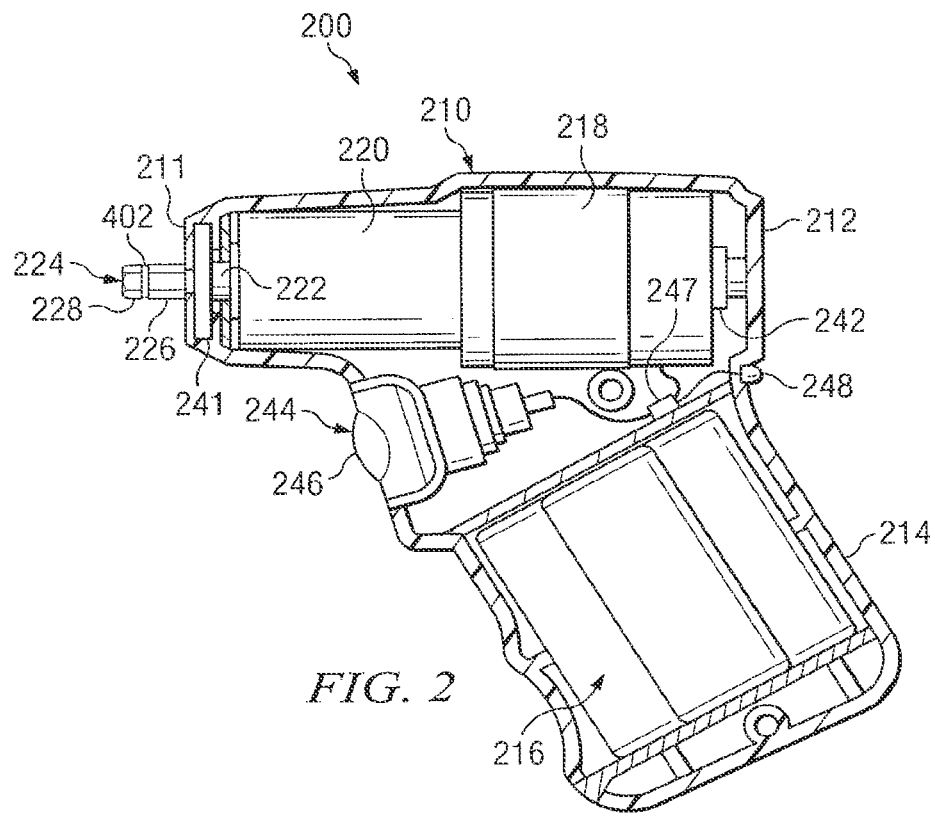
FIG. 2 is a schematic drawing showing one example of a powered driver operable for use with intraosseous (IO) devices incorporating teachings of the present disclosure.

First drape 51 and second drape 52 may then be unfolded as shown in FIG. 1H which will expose second opening 172 of containment bag 170 and second end 252 of coupler assembly 250 through fenestration 54 in second drape 52. A non-sterile person (not expressly shown) may next insert non-sterile powered driver 200 through opening or fenestration 54 and releasably engage end 224 of drive shaft 222 extending from non-sterile powered driver 200 with second end 252 of coupler assembly 250. The non-sterile person may then lift second drape 52 to a position such as shown in FIG. 1J with powered driver 200 disposed within containment bag 170. The non-sterile person may continue to lift second drape 52 to release engagement between portions of second drape 52 adjacent to fenestration 54 and portions of containment bag 170 adjacent to second opening 172.

Typical procedures associated with using a medical procedure tray or kit incorporating teachings of the present disclosure may include the following steps. Medical procedure tray 20d at a desired location for performing an associated medical procedure. For example medical procedure tray 20d may be placed on a table or cart adjacent to a surgical table on which a bone marrow aspiration procedure or a bone marrow biopsy procedure may be performed.

An associated cover may be removed from medical procedure tray 20d by a sterile person to expose folded drapes 51 and 52. Drapes 51 and 52 may then be unfolded by the sterile person such as shown in FIG. 1H. A non-sterile person may then pick up non-sterile powered driver 200 and insert powered driver 200 through fenestration 54 in second drape 52 such as shown in FIG. 1H. End 224 of drive shaft 222 of powered driver 200 may "snap" into place within second end 252 of coupler assembly 250. The non-sterile person may then lift second drape 52 such as shown in FIG. 1J which will result in lifting containment bag 170 up and over powered driver 200. The non-sterile person may then remove second drape 52.

A sterile person may next close flap 174 over second end 172 of containment bag 170. The sterile person may then grasp handle 214 of powered driver 200 through containment bag 170 and lift powered driver 200 with coupler assembly 250 attached thereto from holder 58 disposed in kit 20c. The sterile person may then remove an intraosseous device such as biopsy needle set 100b from medical procedure kit 20c and insert second end 102 of biopsy needle set 100b into first end 251 of coupler assembly 250. A "snap" may be felt when second end 102 of biopsy needle set 100b (or any other intraosseous device incorporating teachings of the present disclosure) is releasably latched within first end 251 of coupler assembly 250. A needle safety cap (not expressly shown) may be removed from first end 101 of biopsy needle 100b after releasably engaging second end 102 with first end 251 of coupler assembly 250.

Powered driver 200 disposed within containment bag 170 along with coupler assembly 250 and biopsy needle set 100b extending there from may be held in one hand while a sterile person identifies the insertion site with the other hand. Powered driver 200 may be positioned over the insertion site to introduce first end 101 of biopsy needle set 100b through the skin in the direction and towards the bone. Upon contact with the bone the operator may squeeze button or trigger 246 and apply relatively steady gentle pressure to handle 214 of powered driver 200. Upon penetration of the bone cortex, the operator may release trigger 246 to stop further insertion of first end 101 of biopsy needle set 100b.

First housing segment 280 may then be activated to release second end 102 of biopsy needle set 100b from engagement with coupler assembly 250. Second hub 150a may then be rotated counterclockwise to disengage second hub 150a and associated stylet 120 from first hub 140a. See FIG. 3B. Stylet 120 may then be pulled out and removed from biopsy needle or cannula 110b. First end 121 of stylet 120 may then be inserted into sharps protector 64a. Upon completion of an appropriate biopsy procedure second hub 150a may be reengaged with first hub 140a. First end 251 of coupler assembly 250 may then be reengaged with second end 102 of biopsy needle set 100b to rotate or spin biopsy needle set 100b while withdrawing from the insertion site. After removal from the insertion site, second end 102 of biopsy needle set 100b may be disengaged from coupler assembly 250. First end 101 of biopsy needle set 100b may then be inserted into sharps container 64a.

After second drape 52 has been removed from engagement with second opening 172, a sterile person (not expressly shown) may close flap 174 to seal non-sterile powered driver therein. The sterile person may then remove containment bag 170, powered driver 200 and coupler assembly 250 from holder 58. The sterile person may then releasably engage first end 251 of coupler assembly 250 with one end of a sterile intraosseous device disposed within medical procedure tray 20c in accordance with teachings of the present disclosure. After completion of a bone marrow aspiration procedure, bone and/or bone marrow biopsy procedure and/or other medical procedures using the intraosseous device, the sharp end or sharp tip of the intraosseous device may be inserted into material 66 in sharp protector 64a for further disposal in accordance with the appropriate procedures.

A wide variety of drapes may be satisfactory used with a medical procedure tray or kit incorporating teachings of the present disclosure. One example of a drape associated with medical procedures is shown in U.S. Pat. No. 4,553,539. However, first drape 51 and/or second drape 52 may be formed from a wide variety of materials and may have a wide variety of configurations and/or dimensions.

Figure 7A:
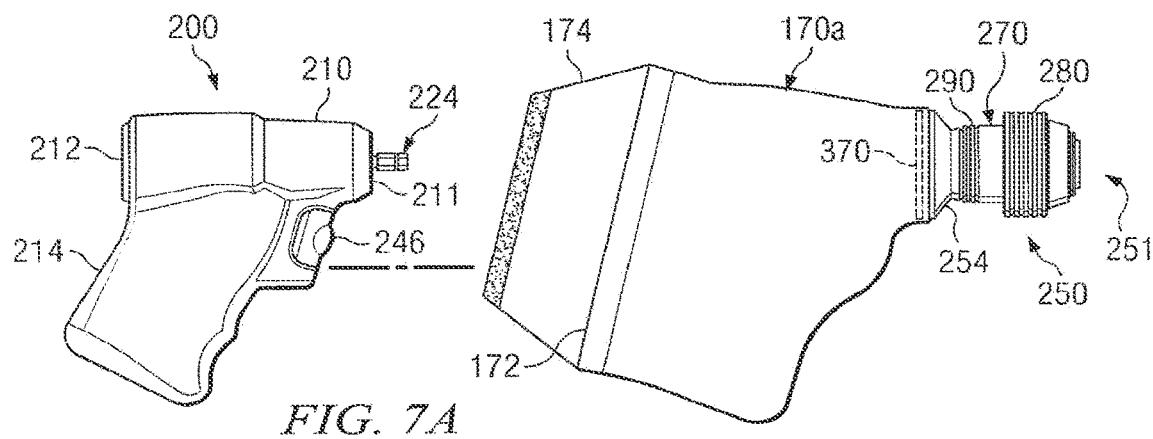
FIG. 7A is a schematic drawing showing an isometric view with portions broken away of a powered driver, containment bag or sterile sleeve and coupler assembly incorporating teachings of the present disclosure.
Figure 7B:
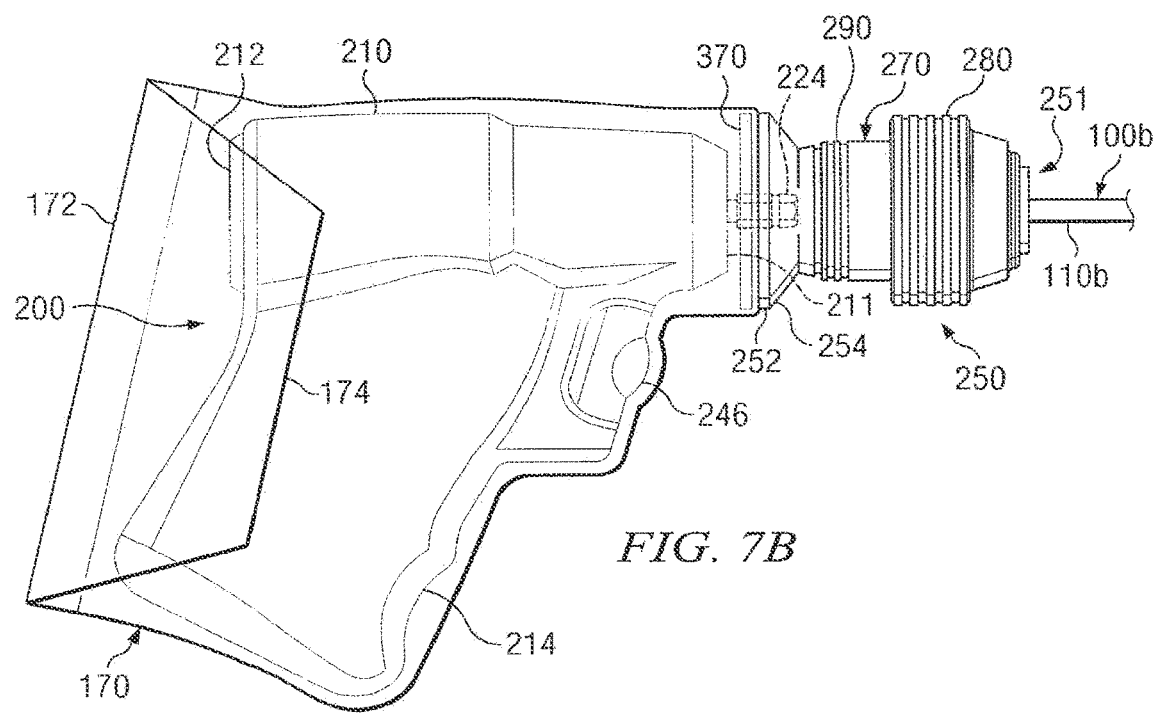
FIG. 7B is a schematic drawing showing another view of the powered driver disposed in the containment bag of FIG. 7A in accordance with teachings of the present disclosure.

Powered driver 200 as shown in FIGS. 1E, 1F, 1I, 2, and 5A and powered driver 200a as shown in FIGS. 7A and 7B may be satisfactorily used to insert an intraosseous device incorporating teachings of the present disclosure into a bone and associated bone marrow. Powered drivers 200 and 200a may be substantially similar except for respective ends 224 and 224a of drive shaft 222 extending from first end 211 of housing 210. See for example FIGS. 2 and 7A. Therefore, only powered driver 200 will be described in more detail.

Powered driver 200 may include housing 210 having a general configuration similar to a small pistol defined in part by handle 214. Various components associated with powered driver 200 may be disposed within housing 210 including handle 214. For example a power source such as battery pack 216 may be disposed within handle 214. Battery pack 216 may have various configurations and dimensions.

Housing 210 including handle 214 may be formed from relatively strong, heavy duty polymeric materials such as polycarbonate or other satisfactory materials. For some applications housing 210 may be formed in two halves (not expressly shown) which may be joined together with a fluid tight seal to protect various components of powered driver 200 disposed therein.

Motor 218 and gear assembly 220 may be disposed within portions of housing 210 adjacent to handle 214. Motor 218 and gear assembly 220 may be generally aligned with each other. Motor 218 may be rotatably engaged with one end of gear assembly 220. Drive shaft 222 may be rotatably engaged with and extend from another end of gear assembly 220 opposite from motor 218. For some applications both motor 218 and gear assembly 220 may have generally cylindrical configurations.

Motors and gear assemblies satisfactory for use with powered driver 200 may be obtained from various vendors. Such motor and gear assemblies may be ordered as "sets" with one end of each motor securely attached to an adjacent end of an associated gear assembly. A drive shaft having various dimensions and/or configurations may extend from the gear assembly opposite from the motor. Such gear assemblies may sometimes be referred to as "reduction gears" or "planetary gears". The dimensions and/or configuration of housing 210 may be modified to accommodate an associated motor and gear assembly.

Distal end or first end 211 of housing 210 may include an opening (not expressly shown) with portions of drive shaft 222 extending therefrom. For some applications end 224 or the portion of drive shaft 222 extending from first end 211 of housing 210 may have a generally hexagonal cross section with surfaces 226 disposed thereon. Receptacle 263 disposed in second end 252 of coupler assembly 250 may have a matching generally hexagonal cross section. See FIG. 5E.

Surfaces 226 may extend generally parallel with each other and parallel with respect to a longitudinal axis or rotational axis (not expressly shown) associated with drive shaft 222. One or more tapered surfaces 228 may also be formed on end 224 to assist with releasably engaging powered driver 200 with coupler assembly 250. See FIGS. 5E and 5G. The end of a drive shaft extending from a powered driver may have a wide variety of configurations. See for example FIGS. 6A and 6B.

A drive shaft having desired dimensions and configuration may extend from the gear assembly opposite from the motor. The drive shaft may be provided as part of each motor and gear assembly set. The dimensions and/or configuration of an associated housing may be modified in accordance with teachings of the present disclosure to accommodate various types of motors, gear assemblies and/or drive shafts. For example, powered drivers used with aspiration needles and/or biopsy needles may include gear assemblies with larger dimensions required to accommodate larger speed reduction ratios, for example between 60:1 and 80:1, resulting in slower drive shaft RPM's. Powered drivers used to provide intraosseous access during emergency medical procedures may operate at a higher speed and may include gear assemblies having a smaller speed reduction ratio, for example between 10:1 and 30:1, resulting in higher drive shaft RPM's. For some applications, the difference in size for gear assemblies may result in increasing the inside diameter of an associated housing by approximately two to three millimeters to accommodate larger gear assemblies associated with powered drivers used to insert biopsy needles and/or aspiration needles.

Coupler assemblies having corresponding openings or receptacles may be releasably engaged with end 224 extending from first end 211 of powered driver 200 or end 224a extending from first end 211 of powered driver 200a. For example, end 224 extending from first end 211 of housing 210 may be releasably engaged with receptacle 264 disposed proximate second end 252 of coupler assembly 250 as shown in FIGS. 1E, 1F, 5C and 5D.

For some applications thrust bearing 241 may be disposed between first end or distal end 211 of housing 210 and adjacent portions of gear assembly 220. Thrust bearing 242 may be disposed between second end or proximal end 212 of housing 210 and adjacent portions of motor 218. Thrust bearings 241 and 242 may limit longitudinal movement of motor 218, gear assembly 220 and drive shaft 222 within associated portions of housing 210.

Trigger assembly 244 may also be disposed within housing 210 proximate handle 214. Trigger assembly 244 may include trigger or contact switch 246. Motor 218 may be energized and deenergized by alternately depressing and releasing trigger 246. Electrical circuit board 247 may also be disposed within housing 210. Electrical circuit board 247 may be electrically coupled with trigger assembly 244, motor 218, power supply 216 and indicator light 248.

For some applications indicator light 248 may be a light emitting diode (LED) or a small more conventional light bulb. For some applications indicator light 248 may be activated when ninety percent (90%) of electrical storage capacity of battery pack 216 has been used.

The configuration and dimensions of an intraosseous device formed in accordance with teachings of the present disclosure may vary depending upon respective intended applications for each intraosseous device. For example the length of a biopsy needle formed in accordance with teachings of the present disclosure may vary from approximately five (5) millimeters to thirty (30) millimeters. However, biopsy needles having other lengths may also be formed in accordance with teachings of the present disclosure. Aspiration needles formed in accordance with teachings of the present disclosure may have lengths of approximately twenty five (25) millimeters, sixty (60) millimeters and ninety (90) millimeters. For some applications an aspiration needle having a length of ninety (90) millimeters or more may also include one or more side ports. See for example FIG. 3A. Intraosseous (IO) devices formed in accordance with teachings of the present disclosure may have outside diameters and longitudinal bores or lumens corresponding generally with eighteen (18) gauge to ten (10) gauge needles. The configuration and dimensions of each IO device may depend upon the size of an associated bone and desired depth of penetration of associated bone marrow.

Combining a powered driver with a coupler assembly and an aspiration needle set in accordance with teachings of the present disclosure may allow rapid access to the iliac crest or other insertion sites to extract associated bone marrow. Bone marrow aspiration systems incorporating teachings of the present disclosure may be capable of inserting an aspiration needle to a desired depth in cancellous bone in ten (10) to fifteen (15) seconds. This same capability may be used to obtain bone and/or bone marrow specimens depending upon the optimum speed for inserting a biopsy needle to obtain a reliable biopsy specimen in accordance with teachings of the present disclosure.

Bone marrow aspiration systems incorporating teachings of the present disclosure may provide a powered driver and a coupler assembly operable to insert an aspiration needle into cancellous bone and extract bone marrow. After an aspiration needle set has been inserted to a desired depth in a bone for extraction of bone marrow, a trocar or stylet may be removed from the lumen of an associated catheter or cannula. A hub assembly incorporating teachings of the present disclosure may be attached to the second end of the needle set allows relatively easy and quick removal of the trocar or stylet from the lumen of the cannula or catheter. A Luer lock fitting provided on a hub attached to the cannula or catheter may then be connected to a bone marrow aspiration system. See FIG. 10. For some applications hubs and hub assemblies may be formed using medical grade polycarbonate.

Upon completing aspiration of a desired volume or sample of bone marrow at a first target area, the trocar or stylet may be reinserted into the lumen of the outer penetrator or cannula. The first end of a hub attached to the trocar or stylet may be reengaged with the second end of a hub attached to the cannula or catheter. A powered driver and coupler assembly incorporating teachings of the present disclosure may then be used to insert the aspiration needle set to a second desired depth in the cancellous bone to obtain another bone marrow sample or the powered driver may be used to "power out" the aspiration needle set. Sharps safety capability for the stylet and/or cannula may be provided as part of such aspiration systems.

Figure 3A:
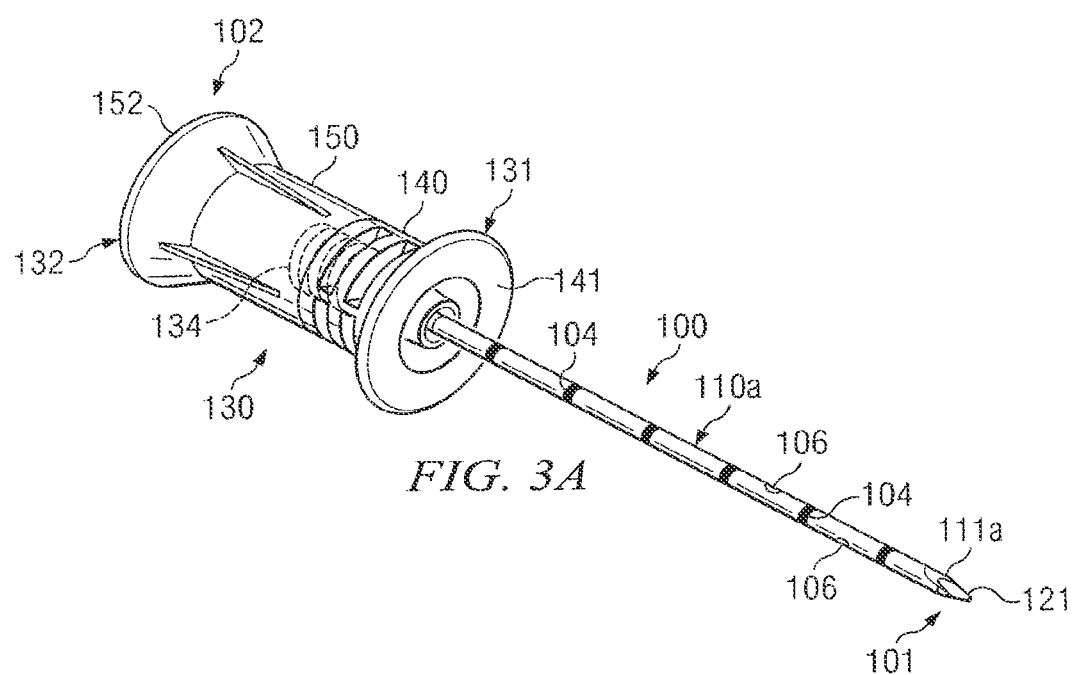
FIG. 3A is a schematic drawing showing an isometric view of the aspiration needle of FIG. 1A.
Figure 3B:
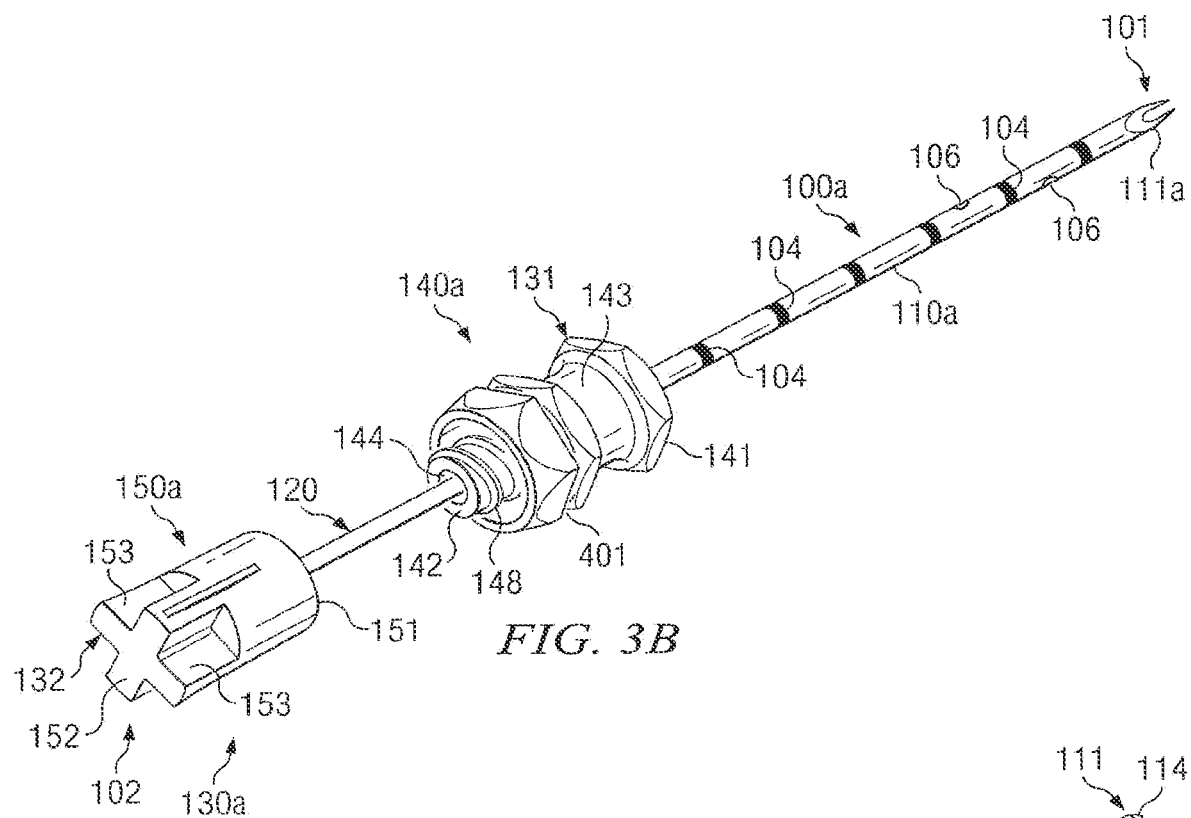
FIG. 3B is a schematic drawing showing an exploded view of the aspiration needle set of FIG. 3A.
Figure 3C:
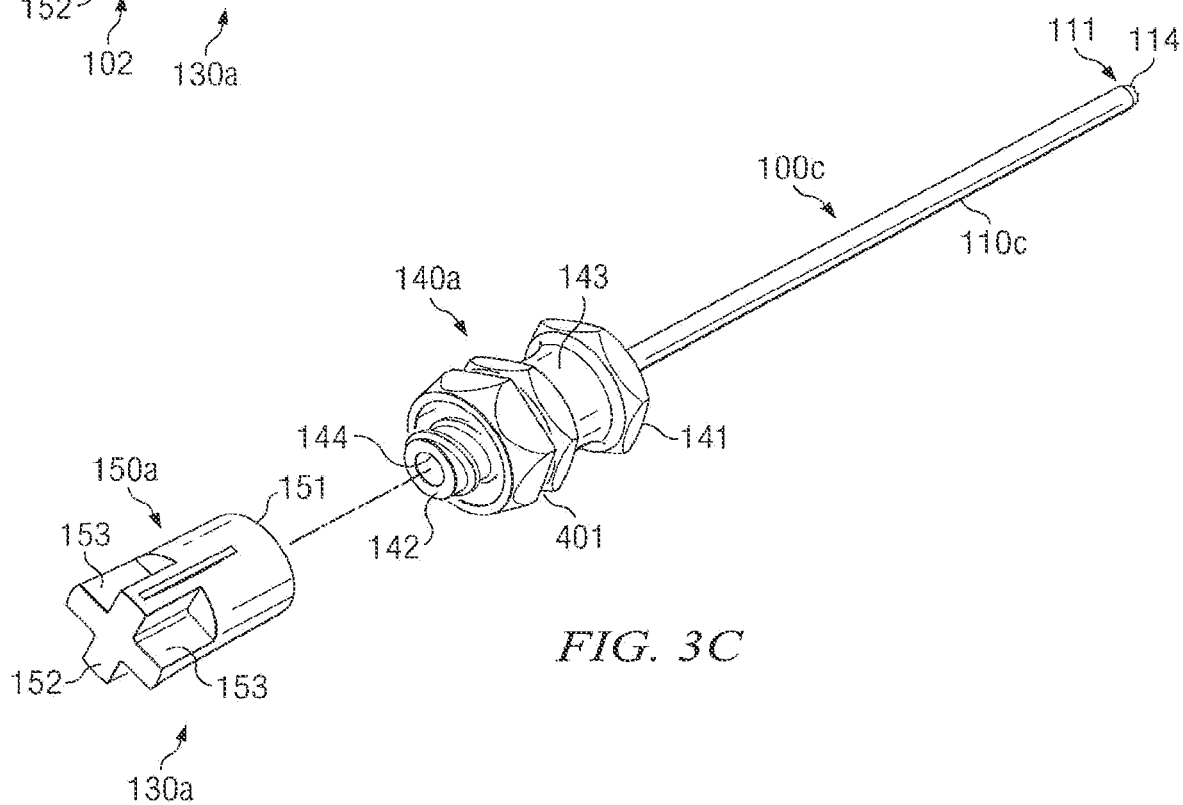
FIG. 3C is a schematic drawing showing an exploded, isometric view of one example of a biopsy needle incorporating teachings of the present disclosure.

Intraosseous (IO) needle sets or aspiration needle sets 100 and 100a as shown in FIG. 3A and FIG. 3B and biopsy needle 100c as shown in FIG. 3C represent only some examples of intraosseous devices formed in accordance with teachings of the present disclosure. Aspiration needle sets 100 and 100a may have similar outer penetrators or cannulas 110a and similar inner penetrators to stylets 120. See FIGS. 3A and 3B. However, IO needle set 100 may include hub assembly 130 while IO needle set 100a may include hub assembly 130a. See FIGS. 3A and 3B. Biopsy needle 100c may also include hub assembly 130a. See FIG. 3C.

For embodiments represented by IO needle sets 100 and 100a, first end 111a of cannula 110a and first end 121 of stylet 120 may be operable to penetrate a bone and associated bone marrow. Various features of first end 111a of cannula 110a and first end 121 of stylet 120 are shown in more detail in FIGS. 3D and 3F. First end 101 of IO needle sets 100 and 100a may correspond generally with first end 111a of cannula 110a and first end 121 of stylet 120.

Cannula 110a may have a plurality of markings 104 disposed on exterior portions thereof. Markings 104 may sometimes be referred to as "positioning marks" or "depth indicators." Markings 104 may be used to indicate the depth of penetration of aspiration needle set 100 or 100a into a bone and associated bone marrow. For some applications cannula 110a may have a length of approximately sixty (60) millimeters and may have a nominal outside diameter of approximately 0.017 inches corresponding generally with a sixteen (16) gauge needle. Cannula 110a may be formed from stainless steel or other suitable biocompatible materials. Positioning marks 104 may be spaced approximately one (1) centimeter from each other on exterior portions of cannula 110a. For some applications one or more side ports 106 may be formed in exterior portions of cannula 110a spaced from first end 111a.

Hub assembly 130 as shown in FIG. 3A may be used to releasably dispose stylet 120 within longitudinal bore or lumen 118 of cannula 110a. See FIG. 3E. Hub assembly 130 may include first hub 140 and second hub 150. The second end of cannula 110a, opposite from first end 111a, may be securely engaged with the second end of cannula 110a. The second end of stylet 120, opposite from first end 121, may be securely engaged with the first end of hub 150.

As shown in FIG. 3A cannula 110a may extend longitudinally from first end 141 of hub 140. Stylet 120 may also extend from the first end of hub 150 (not expressly shown). The second end of hub 140 may include a standard Luer lock fitting which may be releasably engaged with a corresponding Luer lock fitting disposed within the first end of second hub 150. Dotted lines 134 as shown in FIG. 3A may represent the resulting threaded connection between the second end of first hub 140 and the first end of second hub 150. Examples of Luer lock connections and/or fittings are shown in more detail in FIGS. 3B, 3C, 5E, 5F, 5I and 10. The Luer lock fitting disposed on the second end of hub 140 may be operable to be releasably engaged with a standard syringe type fitting and/or a standard intravenous (IV) connection.

Hub 150 includes second end 152 which generally corresponds with second end 132 of hub assembly 130 and second end 102 of IO needle set 100. Hub 140 may include first end 141 which may generally correspond with first end 131 of hub assembly 130. Cannula 110a may extend longitudinally from first end 141 of hub 140 and first end 131 of hub assembly 130.

Various types of receptacles may be satisfactory disposed in second end 152 of hub 150 for use in releasably engaging hub assembly 130 with a powered driver. For example, a receptacle having a generally tapered configuration corresponding with the tapered configuration of one end of a drive shaft extending from a powered driver may be releasably engaged with second end 152 of hub 150. Powered driver 200a as shown in FIGS. 6A and 6B may represent one example of a powered driver having a drive shaft extending from a housing with a tapered portion operable to be releasably engaged with a receptacle having a corresponding generally tapered configuration. For some applications such powered drivers may be secured to an intraosseous device by a magnet (not expressly shown) disposed on the end of the tapered shaft extending from the powered driver and a metal disk disposed within a corresponding receptacle in the intraosseous devices. Such powered drivers may also be used with intraosseous devices used to obtain emergency vascular access (EVA).

For other embodiments which may be discussed later, in more detail, the second end of a hub assembly may be operable to be disposed within a receptacle formed in a coupler assembly incorporating teachings of the present disclosure. One feature of the present disclosure may include forming a hub assembly which may be releasably engaged within a first receptacle disposed in a first end of a coupler assembly. See for example receptacle 263 proximate first end 261 of elongated core 260 as shown in FIG. 5E. The dimensions and configuration of receptacle 263 may be selected to prevent rotation of hub 150a relative to hub 140a while inserting (rotating) an IO device into a bone and associated bone marrow. The powered driver may be releasably engaged with a second receptacle disposed in a second end of the coupler assembly. See for example receptacle 264 proximate second end 262 of elongated core 260 as shown in FIG. 5E.

Intraosseous device or aspiration needle set 100a is shown in FIG. 3B with first end 151 of hub 150a spaced from second end 142 of hub 140a. Portions of stylet 120 extending from first end 151 of hub 150a are shown slidably disposed within lumen or longitudinal bore 118 of cannula 110a.

Hub assembly 130a as shown in FIG. 3B may include first end 131 which may correspond generally with first end 141 of hub 140a. Hub assembly 130a may also include second end 132 which may correspond generally with second end 152 of hub 150a and second end 102 of hub assembly 130a. See FIG. 3B. Cannula 110a may be attached to and extend from first end 141 of hub 140a.

Second end 142 of hub 140a may include one-half a typical Luer lock connection or fitting operable to be releasably engaged with corresponding portions of a Luer lock connection or fitting disposed in first end 151 of second hub 150a. For embodiments such as shown in FIGS. 3B and 3C, first end 131 of hub assembly 130a may correspond with first end 141 of first hub 140a. Second end 152 of second hub 150a may correspond with second end 132 of hub assembly 130a and second end 102 of aspiration needle set 100a.

At least one portion of hub assembly 130a may have a generally hexagonal cross section operable to be received within the generally hexagonal cross section of receptacle 264 disposed proximate first end 251 of coupler assembly 250. See FIG. 5E. For some embodiments portions of first hub 140a disposed adjacent to reduced outside diameter portion 143 may have generally hexagonal cross sections. See FIGS. 3B and 3C. Various cross sections other than hexagonal may be satisfactorily used to releasably engage a powered driver with one end of a coupler assembly and an intraosseous device with an opposite end of the coupler assembly.

Aspiration needle sets may often include a trocar, stylet or penetrator in combination with an associated cannula, catheter or outer penetrator. However, biopsy needles formed in accordance with teachings of the present disclosure may or may not include a trocar, stylet or inner penetrator. For example, biopsy needle 10c is shown in FIG. 3C attached to first end of hub 140a. A stylet or inner penetrator is not attached to first end 151 of hub 150a.

For embodiments represented by biopsy needle 100c, hub 140a may be used to releasably engage biopsy needle 100c in a receptacle formed in a coupler assembly incorporating teachings of the present disclosure. Hub 150a may be attached to close of end 141 of hub 140a. However, for many applications hub 140a without hub 150a may be connected with one end of a coupler assembly in accordance with teachings of the present disclosure. Biopsy needle 100c may be used to capture a biopsy specimen of a bone and associated bone marrow. Placing a trocar within biopsy needle 100c may result in substantial damage to the bone specimen during penetration of the bone by the combined tips of the trocar and biopsy needle 100c.

Hub 140a may include second end 142 with opening 144 formed therein. Passageway 146 may extend from second end 142 towards first end 141 of hub 140a. See FIGS. 5E, 5F and 5I. Passageway 146 may be operable to communicate fluids with lumen 118 of cannula 100a. Second end 142 of hub 140 may include various features of a conventional Luer lock connection or fitting, including threads 148. Corresponding threads 158 may be formed within first end 151 of hub 150a. See for example FIGS. 5E, 5F and 5I. The dimensions and configuration of receptacle 263 in first end 251 of coupler assembly 250 may be selected to prevent relative movement between hub 140a and hub 150a during insertion (rotation) of an IO device into a bone and associated bone marrow. If such relative movement occurs, threads 148 and 158 may be disconnected.

For some applications hub 140a and hub 150a may be formed using injection molding techniques. For such embodiments hub 140a may include reduced outside diameter portion 143 disposed between first end 141 and second end 142. See for example FIGS. 3B, 3C and 5C. In a similar manner a plurality of void spaces or cutouts 153 may be formed in hub 150a adjacent to and extending from second end 152 in the direction of first end 151. See for example FIGS. 3B, 3C and 5A. The configuration and dimensions of reduced diameter portion 143 and/or cutouts 153 may be varied to optimize associated injection molding techniques and at the same time provide required configurations, dimensions and material strength to allow associated hub assembly 130a to function in accordance with teachings of the present disclosure.

Figure 3D:
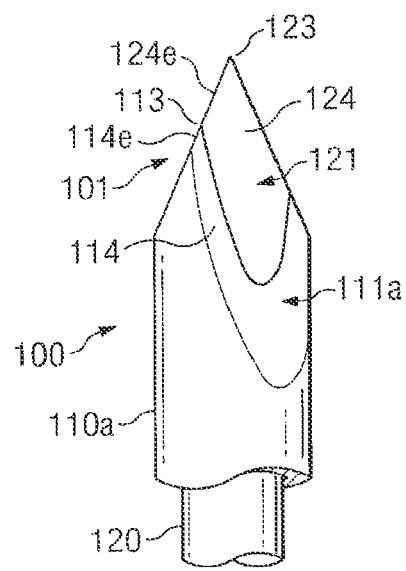
FIG. 3D is a schematic drawing showing an isometric view of another example of an intraosseous needle set incorporating teachings of the present disclosure.
Figure 3E:
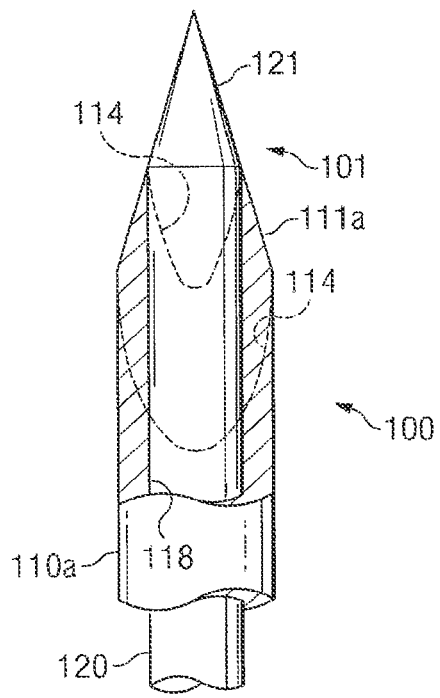
FIG. 3E is a schematic drawing showing an isometric view with portions broken away of the tips of the intraosseous needle set of FIG. 3A.

FIGS. 3D and 3E show one example of cutting surfaces and tips which may be formed adjacent to the ends of a cannula and an associated trocar in accordance with teachings of the present disclosure. For embodiments represented by cannula or outer penetrator 110a and trocar or inner penetrator 120a, tip 123 of stylet 120 may be disposed relatively close to tip 113 of cannula 110a. For some applications, first end 121 of trocar 120 and first end 111a of cannula 110a may be ground at the same time to form adjacent cutting surfaces 114 and 124. Grinding ends 111a and 121 at the same time may result in forming a single cutting unit to form generally matching cutting edges 124e and 114e such as shown in FIGS. 3D and 3E. Other types of cutting surfaces formed in accordance with teachings of the present disclosure may be discussed later.

First end 121 of trocar 120 may extend through opening 144 in second end 142 of hub 140a. See FIG. 3B. Hub 150a disposed on the second end of trocar 120 may be releasably engaged with the second end of cannula 110a represented by hub 140a. See FIG. 3B.

Oncologists and other health care provides may be unable to successfully obtain a suitable specimen of bone and/or bone marrow because currently available biopsy needles sometimes fail to capture a satisfactory specimen of bone and/or bone marrow. When a specimen is obtained, the specimen may sometimes be damaged or contaminated. Intraosseous devices incorporating teachings of the present disclosure may substantially reduce or eliminate problems associated with obtaining a suitable specimen of bone and/or bone marrow. Various teachings of the present disclosure may substantially increase the probability of obtaining a satisfactory biopsy specimen of cancellous bone and associated bone marrow.

Human bones may generally be described as having a hard outer lamellae or layer of osseous tissue known as "cortical bone". Cancellous bone (also known as trabecular or spongy bone) typically fills an inner cavity associated with cortical bone. Cancellous bone is another type of osseous tissue with generally low density and strength but high surface area. Cancellous bone typically includes spicules or trabeculae which form a latticework of interstices filled with connective tissue or bone marrow. Exterior portions of cancellous bone generally contain red bone marrow which produces blood cellular components. Most of the arteries and veins of a bone are located in the associated cancellous bone.

One of the benefits of the present disclosure may include providing various intraosseous devices including, but not limited to, biopsy needle sets and biopsy needles operable to reliably obtain biopsy specimens of cortical bone and/or cancellous bone without significant damage to associated biopsy specimens. For example, forming a plurality of cutting surfaces on the extreme end of an outer penetrator or cannula in accordance with teachings of the present disclosure may allow a resulting biopsy needle to more quickly penetrate a bone and associated bone marrow, may reduce the amount of time and force required to remove a bone and/or bone marrow specimen from a target area in accordance with teachings of the present disclosure.

The configuration of the tip of a cannula or outer penetrator may be modified in accordance with teachings of the present disclosure to provide optimum torque during insertion of the cannula or outer penetrator by a powered driver to obtain a bone and/or bone marrow biopsy specimen. A controlled, steady feed rate when using a powered driver may result in higher quality biopsy specimens as compared to manually inserted biopsy needles. At least one helical thread may be disposed within a hollow cannula proximate an associate tip or first end to assist with capturing a bone and/or bone marrow biopsy specimen.

The quality of a bone and/or bone marrow specimen and reliability of obtaining a bone and/or bone marrow specimen using a powered driver and biopsy needle incorporating teachings of the present disclosure may be substantially improved by using an optimum feed rate for inserting the biopsy needle into a bone and associated bone marrow. Feed rate or speed of insertion of a biopsy needle incorporating teachings of the present disclosure may be a function of the pitch of at least one thread disposed on an interior portion of the biopsy needle and revolutions per minute (RPM) of the biopsy needle.

RPM=Feed rate×Pitch of threads

Figure 4A:
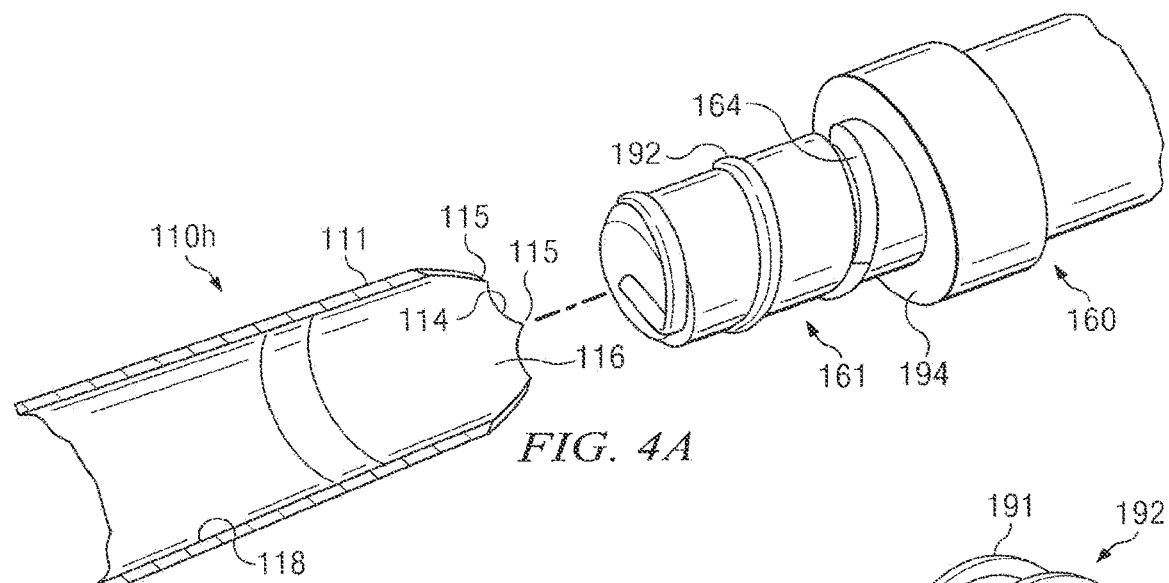
FIG. 4A is a schematic drawing partially in section and partially in elevation with portions broken away showing an exploded isometric view of a mandrel operable to install a thread insert within portions of a biopsy needle in accordance with teachings of the present disclosure.
Figure 4B:
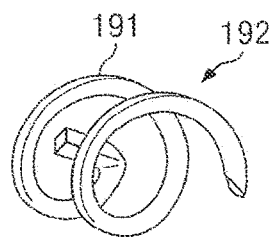
FIG. 4B is a schematic drawing showing one example of a thread insert which may be disposed within the longitudinal bore of a biopsy needle in accordance with teachings of the present disclosure.
Figure 4C:
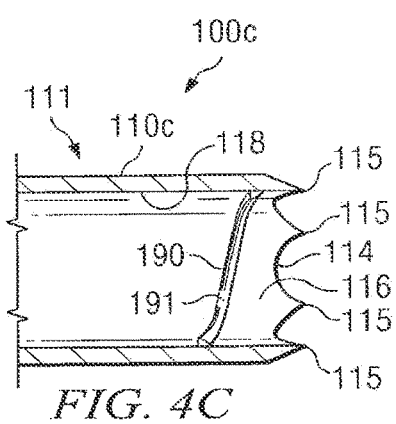
FIG. 4C is a schematic drawing in section with portions broken away showing one example of a biopsy needle with a single helical thread disposed within one end of the biopsy needle incorporating teachings of the present disclosure.
Figure 4D:
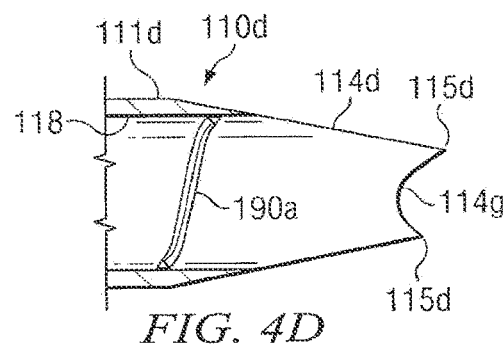
FIG. 4D is a schematic drawing in section with portions broken away showing another example of a biopsy needle with a single helical thread disposed within one end of the biopsy needle in accordance with teachings of the present disclosure.
Figure 4E:
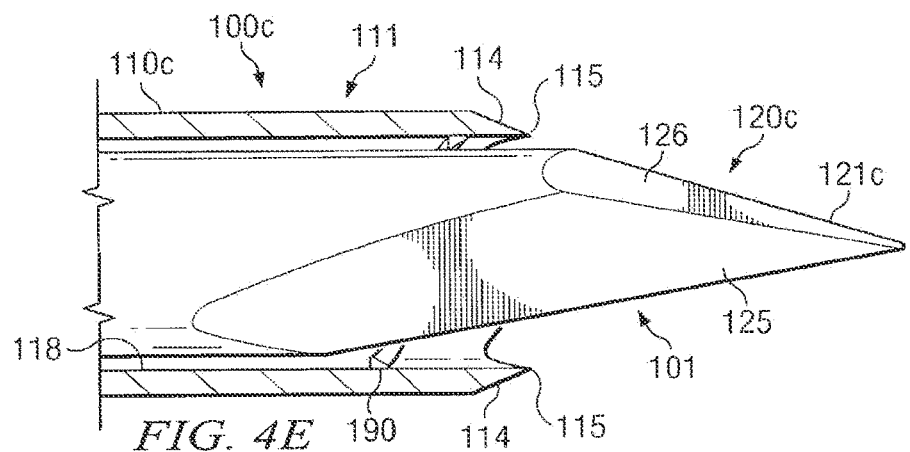
FIG. 4E is a schematic drawing in section and in elevation with portions broken away showing a biopsy needle set including a trocar and a single helical thread disposed proximate one end of a generally hollow cannula in accordance with teachings of the present disclosure.

Helical thread 190 as shown in FIGS. 4C, 4D and 4E may have a pitch of approximately twenty four (24) threads per inch. An optimum pitch may vary based on factors such as reduction gear ratio (77:1 for some embodiments) and load placed on an associated motor.

Further technical benefits may include reducing physical requirements and mental stress on users and decreasing pain and stress on patients by increasing speed and control of the needle set insertion during bone marrow biopsy and bone marrow aspiration procedures.

The combination of a powered driver and a biopsy needle set may be used to rapidly access the Iliac crest or other insertion sites to extract associated bone and/or bone marrow specimens. Bone marrow biopsy systems incorporating teachings of the present disclosure provide a powered alternative to current manual techniques for inserting biopsy needles into bone and bone marrow which are generally considered the industry standard.

For some applications, an aspiration needle or biopsy needle formed in accordance with teachings of the present disclosure may include a hollow cannula or catheter having one end formed by electrical discharge machining (EDM) techniques, grinding techniques and/or other machining techniques. A plurality of teeth may be formed on one end of the cannula or catheter using EDM techniques, grinding techniques and/or other machining techniques.

For some embodiments a stylet or trocar may also be disposed within the cannula or catheter with a first end of the stylet extending from a first end of the cannula or catheter. Increasing the length of the first end of the stylet or trocar extending from the first end of the cannula or catheter may reduce the amount of torque or force required to penetrate a bone and may reduce time required for an associated aspiration needle set or biopsy needle set to penetrate the bone and associated bone marrow.

A specific powered driver, intraosseous device and tip configuration will generally produce the same torque when drilling in a hard bone or a soft bone. However, the time required to drill to a first depth in a hard bone will generally be greater than the time required to drill to similar depth in a soft bone.

For still other embodiments, teeth formed on one end of a cannula or catheter may be bent radially outward to reduce the amount of time and/or force required to penetrate a bone and associated bone marrow using the cannula or catheter. For some applications a powered driver and aspiration needle set or biopsy needle set formed in accordance with teachings of the present disclosure may provide access to a patient's bone marrow using a similar amount of torque. The length of time for penetrating a relatively hard bone may be increased as compared with the length of time required to penetrate a relatively softer bone.

The tips of several stylets and cannulas incorporating teachings of the present disclosure were slowly ground with coolant to prevent possible thermal damage to metal alloys or spring material used to form the stylets and cannulas. The stylets and cannulas were assembled into respective IO needle sets. The tips of each needle set were inserted into sawbones blocks under controlled test conditions. Some testing was conducted with Pacific Research sawbones blocks. The tips of the needle sets were inserted to a depth of approximately two centimeters with ten pounds (10 lbs) of force and twelve volts direct current (12 VDC) applied to an associated powered driver. There was no measurable or visual wear of the stylet or cannula tips after completion of the testing.

For some embodiments a generally hollow biopsy needle may be substantially continuously rotated at an optimum speed or RPM during insertion into a selected target area to obtain a biopsy specimen. The biopsy needle may include a longitudinal bore extending from a first, open end of the needle to a second, open end of the needle. A small helical thread may be formed on interior portions of the longitudinal bore proximate the first end. For some embodiments the thread may have a pitch similar to threads used on conventional wood screws. The rate of rotation or revolutions per minute (RPM) of the biopsy needle may be selected by installing a gear assembly with a desired speed reduction ratio (typically between 60:1 and 80:1) between a motor and an associated drive shaft. For some applications the gear assembly may reduce speed of rotation of an attached motor at a ratio of approximately 66:1 or 77:1.

Figure 3F:
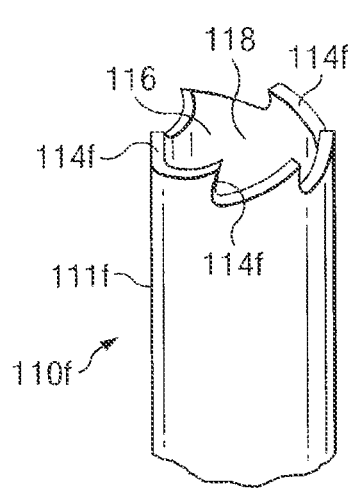
FIG. 3F is a schematic drawing showing an isometric view of one embodiment of the tip of an intraosseous device or cannula incorporating teachings of the present disclosure.

Outer penetrator or cannula 110f as shown in FIG. 3F may include first end 111f having a plurality of cutting surfaces 114f formed adjacent to opening 116 in first end 111f Opening 116 may communicate with and form a portion of an associated longitudinal bore or lumen 118. For some applications cutting surfaces 114f may be formed using electrical discharge machining (EDM) techniques.

Figure 3G:
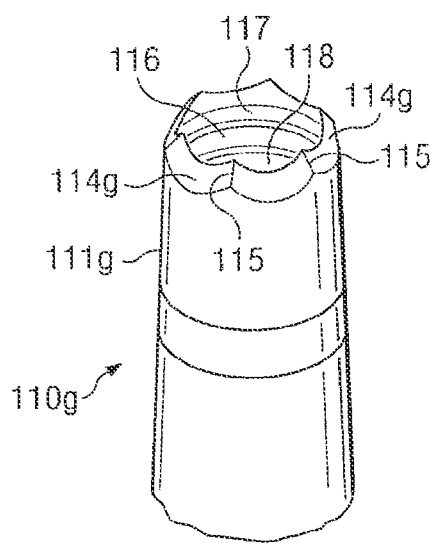
FIG. 3G is a schematic drawing showing an isometric view of another embodiment of the tip of a biopsy needle incorporating teachings of the present disclosure.
Figure 3H:
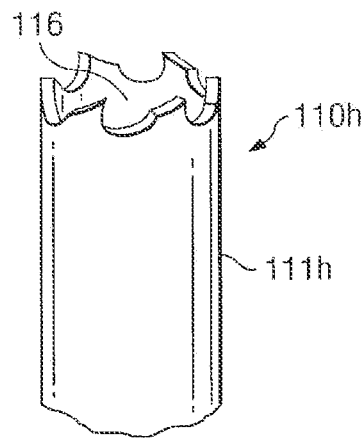
FIG. 3H is a schematic drawing showing an isometric view of still another embodiment of the tip of an intraosseous device or catheter incorporating teachings of the present disclosure.

For embodiments such as shown in FIG. 3G, outer penetrator or cannula 110g may include first end 111g having a generally tapered configuration or reduced outside diameter as compared with other portions of cannula 110g. A plurality of cutting surfaces 114g may be disposed on end 111g adjacent to respective opening 116. For some applications, cutting surfaces 114g may be formed using machine grinding techniques. For embodiments end 111g of cannula 110g may include six ground cutting surfaces 114g with respective crowns 115 may be formed therebetween. Forming a biopsy needle set and/or biopsy needle with tapered end 111g and a plurality of cutting surfaces 114g and crowns 115 may provide improved drilling performance when the resulting biopsy needle set and/or biopsy needle is used with a powered driver in accordance with teachings of the present disclosure.

For some applications, helical groove 117 may be formed within longitudinal bore 118 proximate respective opening 116. Helical groove 117 may assist with retaining a biopsy specimen or a bone marrow specimen within longitudinal bore 118.

Testing conducted with cannulas or outer penetrators formed in accordance with teachings of the present disclosure indicated that forming cutting surfaces or cutting teeth with electrical discharge machining (EDM) sometimes resulted in the associated cannula or outer penetrator being able to drill through a bone and associated bone marrow slightly faster than a cannula or outer penetrator having cutting surfaces formed using grinding techniques. Some test results also indicated that bending cutting surfaces formed on one end of a cannula or outer penetrator in accordance with teachings of the present disclosure may reduce the amount of time and/or the amount of force required to remove a bone and/or bone marrow specimen from a target area.

Figure 3I:
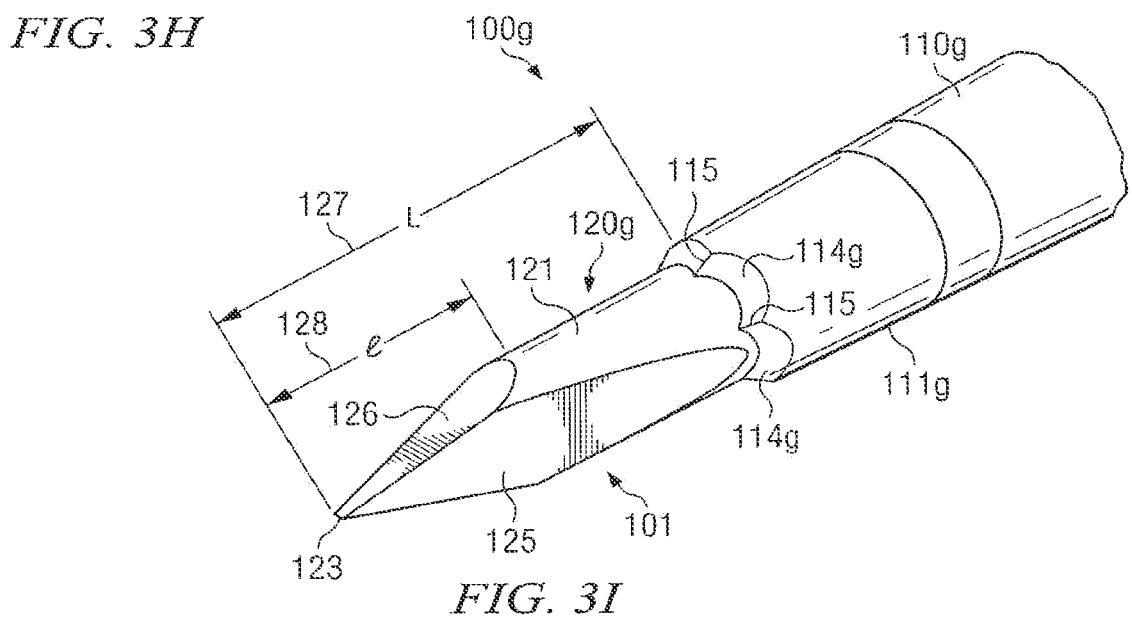
FIG. 3I is a schematic drawing showing an isometric view with portions broken away of a intraosseous needle set incorporating teachings of the present disclosure.
Figure 3J:
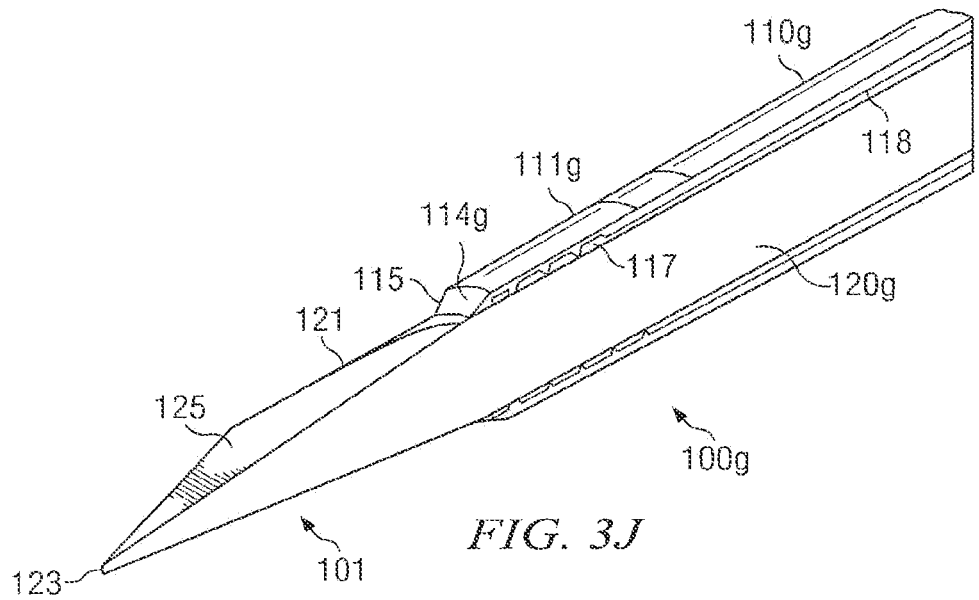
FIG. 3J is a schematic drawing showing an isometric view with portions broken away of another example of a biopsy needle set incorporating teachings of the present disclosure.

Intraosseous needle set or biopsy needle set 100g is shown in FIGS. 3I and 3J. Biopsy needle set 100g may include cannula or outer penetrator 110g with stylet or inner penetrator 120g slidably disposed therein. First end 101 of biopsy needle set 100g is shown in FIGS. 3I and 3J. For some applications first end 101 of biopsy needle set 100g may minimize damage to skin and soft body tissue at an insertion site.

For some applications inner penetrator or trocar 120g may include first end 121 having a plurality of cutting surfaces 125 and 126 formed on exterior portions thereof extending from associated tip 123 towards second end of trocar or inner penetrator 120g. For some applications one or more cutting surfaces 125 may be formed having length 127 extending from tip 123 to associated cutting surfaces 114g in associated cannula 110g. One or more cutting surfaces 126 may be formed adjacent to each cutting surface 125 with second length 128. First length 127 may be greater than second length 128. The ratio of first length 127 and second length 128 may be varied in accordance with teachings of the present disclosure to provide optimum performance for penetrating a selected bone and associated bone marrow.

For some applications, a single thread may be disposed within the longitudinal bore or lumen of a biopsy needle, cannula, catheter or outer penetrator in accordance with teachings of the present disclosure. Various techniques and procedures may be satisfactorily used to place the single thread within a generally hollow cannula or outer penetrator proximate one end of the cannula or outer penetrator having one end operable to penetrate a bone and/or associated bone marrow. For some embodiments, a helical coil having a configuration and dimensions associated with the resulting single thread may be placed on one end of a mandrel such as a spot welding electrode assembly. The mandrel or electrode assembly may then be inserted through an opening in the one end of the cannula or outer penetrator operable to penetrate a bone and/or associated bone marrow. The helical coil may then be bonded with adjacent portions of cannula. Coils having a wide variety of dimensions and configurations may be satisfactorily used to place a single thread in a biopsy needle.

For embodiments such as shown in FIGS. 4A-4E, examples of helical threads are shown disposed in biopsy needles or cannulas incorporating teachings of the present disclosure. Outer penetrator or cannula 110h as shown in FIG. 4A may be formed with longitudinal bore 118 or lumen 118 extending from open 116 through cannula 110h. Electrode assembly or mandrel 160 may be used to install (spot weld) a single helical thread in lumen 118 proximate opening 116.

Helical coil 192 as shown in FIG. 4B may be placed on first end 161 of electrode assembly 160. Helical coil 192 may have the cross section of a right triangle. First end or copper electrode 161 may have an appropriate configuration and dimensions to be slidably received within opening 116 formed in first end 111 of cannula or outer penetrator 110h. First end or copper electrode 161 of mandrel 160 may include corresponding groove 164 with a configuration and dimensions satisfactory to receive helical coil 192 therein. Groove 164 may be formed with a desired pitch for resulting thread 190 when attached to or bonded with interior portions of cannula 110h.

For some applications electrode assembly 160 may include enlarged outside diameter portion or plastic insulator 194 disposed adjacent to first end 161. The dimensions and/or configuration of copper electrode 161 and plastic insulator 194 may be selected to accommodate installing helical coil 192 at an optimum location relative to end 116 for retaining biopsy specimens in lumen 118. For example, the dimensions and configuration of plastic insulator 194 may be selected to contact the extreme end of outer penetrator or cannula 110h proximate crowns 115.

Copper electrode 161 of electrode assembly 160 with helical coil 192 attached thereto may be inserted into opening 116 in first end 111h of cannula 110h. Electrode assembly 160 may be operable to conduct electricity to copper electrode 161 to accommodate spot welding helical coil 192 with adjacent interior portions of longitudinal bore 118 of cannula 110h. For some embodiments mandrel 160 may be formed from materials compatible with laser welding helical coil 192 with interior portions of lumen or longitudinal bore 118 of cannula 110h. When attached to interior portions of a cannula or outer penetrator 110h, helical coil 192 may form a single thread having shoulder 191 extending generally perpendicular to adjacent interior portions of lumen 118. The resulting dimensions and configuration of helical thread 190 may be selected to optimize retaining a specimen of bone and/or bone marrow on shoulder 191 of thread 190 within lumen 118.

Cannula 110c of biopsy needle 100c is shown in FIG. 4C with helical thread 190 disposed therein. The combination of helical thread 190 with shoulder 191 extending substantially perpendicular to interior portions of lumen 118 may increase the reliability of biopsy needle 100c to retain a specimen of bone and/or bone marrow. For some applications combining helical thread 190 with cutting surfaces 114 and crowns 115 may substantially increase the reliability of obtaining a satisfactory bone specimen when using biopsy needle 100c with a powered driver in accordance with teachings of the present disclosure.

Helical thread 190 may be positioned at an optimum location relative to opening 116 in cannula 110c to begin capture of a bone marrow specimen or cancellous bone core. By inserting biopsy needle 100c at an optimum feed corresponding with the pitch of helical thread 190, helical thread 190 may be "screwed in" cancellous bone entering opening 116 to substantially increase the probability of capturing a satisfactory biopsy specimen or bone marrow core.

For embodiments such as shown in FIG. 4D cannula or outer penetrator 110d may include first end 111d having a plurality of exterior cutting surfaces 114d formed thereon and extending therefrom. The length of cutting surfaces 114d may be longer than the length of corresponding cutting surfaces 114. Respective crowns 115d may be formed between adjacent cutting surfaces 114d and 114g.

For some applications a helical thread having a generally "wedge shaped" cross section similar to an equilateral triangle may be disposed within the longitudinal bore or lumen of an outer penetrator or cannula incorporating teachings of the present disclosure. For example cannula 110d may include helical thread 190a having a generally wedge shaped cross section corresponding approximately with an equilateral triangle. Helical thread 190a may be installed within cannula 110d using apparatus and procedures as previously described with respect to helical thread 190.

FIG. 4E shows an example of combining inner penetrator or stylet 120c with cannula or outer penetrator 110c having helical thread 190 disposed therein to form biopsy needle set 100c in accordance with teachings of the present disclosure. Biopsy needle 100c is shown in FIGS. 3C and 4C without a stylet or trocar. Biopsy needle set 100c is shown in FIG.

4E with trocar or stylet 120c disposed in cannula 110c. Trocar 120c may include end 121c with a pair of cutting surfaces 125 and a pair of cutting surface 126 as shown in FIG. 3I. Surfaces 125 and 126 may cooperate with each other to form a cutting tip on trocar or stylet 120c similar to a "chisel point" drill bit. The pair of cutting surfaces 125 may be offset (relief angle) approximately eight degrees relative to the pair of cutting surfaces 126. The included angle of cutting surfaces 125 may be approximately thirty four degrees (34°) plus or minus four degrees (±4°). The included angle of cutting surfaces 126 may be approximately sixteen degrees (16°) plus or minus three degrees (±3°).

For some applications end 121 of trocar 120c may extend from end 111c of cannula 110c with respective cutting surfaces 114 of cannula 110g disposed adjacent to the end of each cutting surface 126 (short cutting surface) opposite from tip 123 of trocar 120c. See FIG. 4E. As a result portions of each cutting surface 125 (long cutting surface) of trocar 120c may be disposed within end 111 of cannula 110c. See FIG. 4E.

Placing portions of cutting surfaces 125 within end 111 of cannula 110c may result in more uniform forces being applied to end 101 of intraosseous device 100c while penetrating the cortex of an associated bone using biopsy needle set 100c and a powered driver in accordance with teachings of the present disclosure. When the cortex has been penetrated, forces applied to end 101 of biopsy needle set 100c may decrease sufficiently to indicate that end 101 has now entered associated bone marrow. An operator may then withdraw trocar 120c from cannula 110c and position end 111c of cannula 110c at a desired target area to perform a bone marrow biopsy.

For some embodiments threads 190 and 190a may extend approximately 0.005 inch from adjacent portions of an associated longitudinal bore or lumen 118. The outside diameter of an associated trocar such as trocar 120c as shown in FIG. 4E may be reduced to accommodate the height of thread 190 or 190a. The following test results were obtained during insertion of intraosseous devices such as biopsy needle set 100c shown in FIG. 4E into sawbones material or blocks with three millimeters (3 mm) of fifty pound (50 #) and forty millimeters (40 mm) of forty pound (40 #) material.

| Test # | Motor Torque(g-cm) | Time(s) |
|---|---|---|
| 44 | 1101 | 2.23 |
| 45 | 1081 | 2.49 |
| 46 | 1071 | 2.36 |
| 47 | 1081 | 2.50 |
| 48 | 1030 | 2.46 |
| 49 | 1070 | 2.33 |
| Average | 1072 | 2.40 |

The distance between the end of cutting surface 126 or trocar 120c and adjacent cutting surface 114 on cannula 110c was approximately 0.14 inches. End 111 of cannula 110c had six (6) ground cutting surfaces 114. The outside diameter of trocar 120c was approximately 0.086 inches.

Coupler assemblies incorporating teachings of the present disclosure may function as "quick release mechanisms" operable to engage and disengage an IO device from a powered driver disposed within a flexible containment bag or sterile sleeve. Such coupler assemblies may allow rotation of an IO device without damage to the flexible containment bag or sterile sleeve. For some applications the IO device may be an aspiration needle or a biopsy needle. One end of the coupler assembly may be operable to form a fluid seal or fluid barrier with adjacent portions of the containment bag or sterile sleeve. A coupler assembly incorporating teachings of the present disclosure may also be described as a port assembly attached to a containment bag. Such port assemblies may allow easy engagement or disengagement of a powered driver from an IO device and at the same time allow the powered driver to "power in and power out" an IO device from an insertion site.

A coupler assembly incorporating teachings of the present disclosure may be used in "non-sterile" environments and/or medical procedures which do not require the use of a containment bag or sterile sleeve.

FIGS. 5A-5I and 6A-6B show various examples of coupler assemblies or port assemblies incorporating teachings of the present disclosure. FIG. 5A-5I are schematic drawings showing various views of powered driver 200, coupler assemblies 250, 250a and 250b and intraosseous device 100b incorporating various teachings of the present disclosure. Coupler assemblies 250, 250a and 250a may each include respective first end 251 operable to be releasably engaged with one end of an intraosseous device such as, but not limited to, second end 102 of biopsy needle set 100b.

Coupler assembly 250 as shown in FIGS. 5E-5H may include second end 252 operable to be releasably engaged with a portion of a drive shaft extending from a powered driver, such as, but not limited to, end 224 of drive shaft 222 extending from first end 211 of housing 210 of powered driver 200. As discussed later, second end 252 of coupler assembly 250 may be securely engaged with an opening in a containment bag or sterile sleeve. Second end 252a of coupler assembly 250a and second end 252b of coupler assembly 250b do not include similar features. As a result coupler assemblies 250a and 250b may primarily be used in applications which do not require a sterile environment.

Coupler assemblies 250, 250a and 250b may have substantially the same or similar components, functions and features except for second end 252a of coupler assembly 250a and associated second end 272a of housing assembly 270a and second end 250b of coupler assembly 250b and associated second end 272b of housing assembly 270b. Therefore, various features of the present disclosure may be described with respect to coupler assembly 250 since both coupler assemblies 250a and 250b have substantially the same characteristics and features except for attachment with a containment bag or sterile sleeve.

Coupler assemblies incorporating various teachings of the present disclosure may be placed in a medical procedure tray or kit with one end down and an opposite end looking up to allow "hands free" releasable engagement with a powered driver or a manual driver. For example, coupler assembly 250 may be disposed in medical procedure tray 20c with first end 251 insert into holders 58 and second end 252 looking up. See FIGS. 1C, 1E and 1F. As a result, end 224 of drive shaft 222 extending from powered driver 200 may be inserted into and releasably engaged with second end 252 of coupler assembly 250 without requiring an operator or user (not expressly shown) to physically contact or manipulate any portion of coupler assembly 250. Various features of associated "hands free" latching mechanisms will be discussed with respect to FIGS. 5E, 5F, 5G and 5H.

Figure 5A:
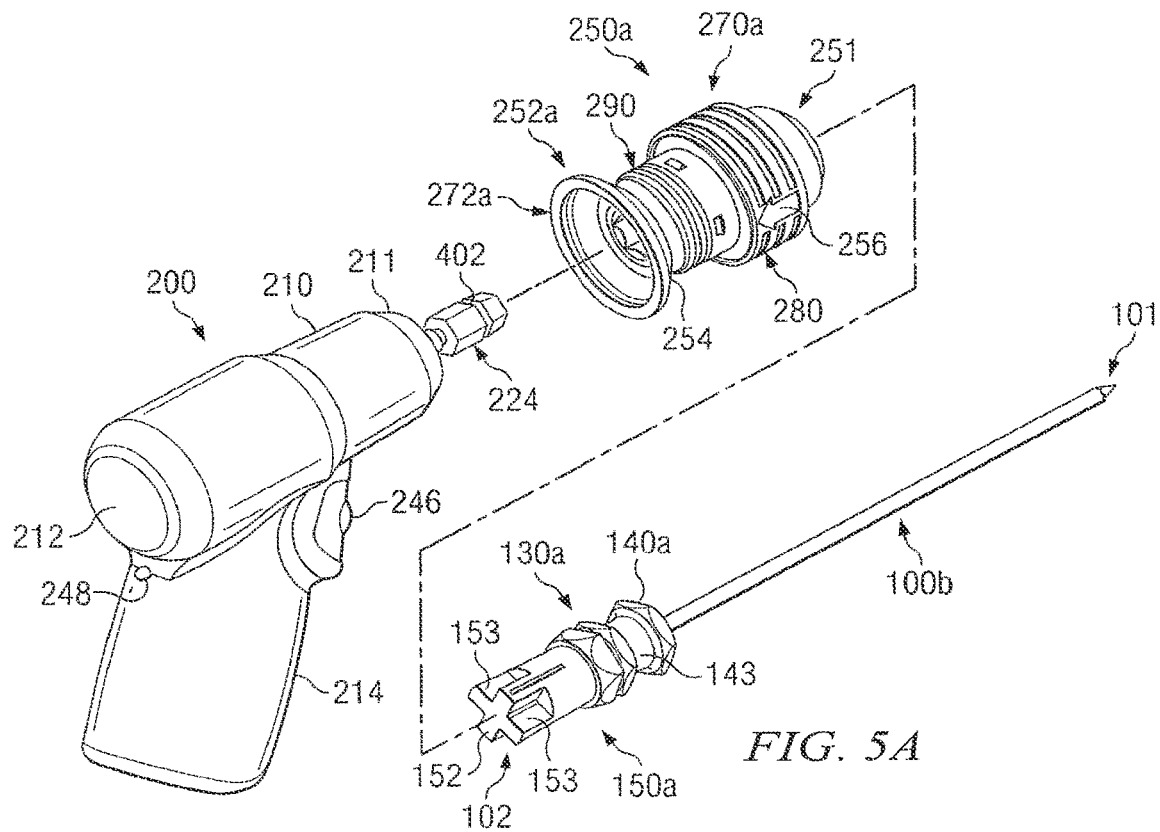
FIG. 5A is a schematic drawing showing an exploded, isometric view of a powered driver, coupler assembly and an intraosseous device incorporating teachings of the present disclosure.
Figure 5B:
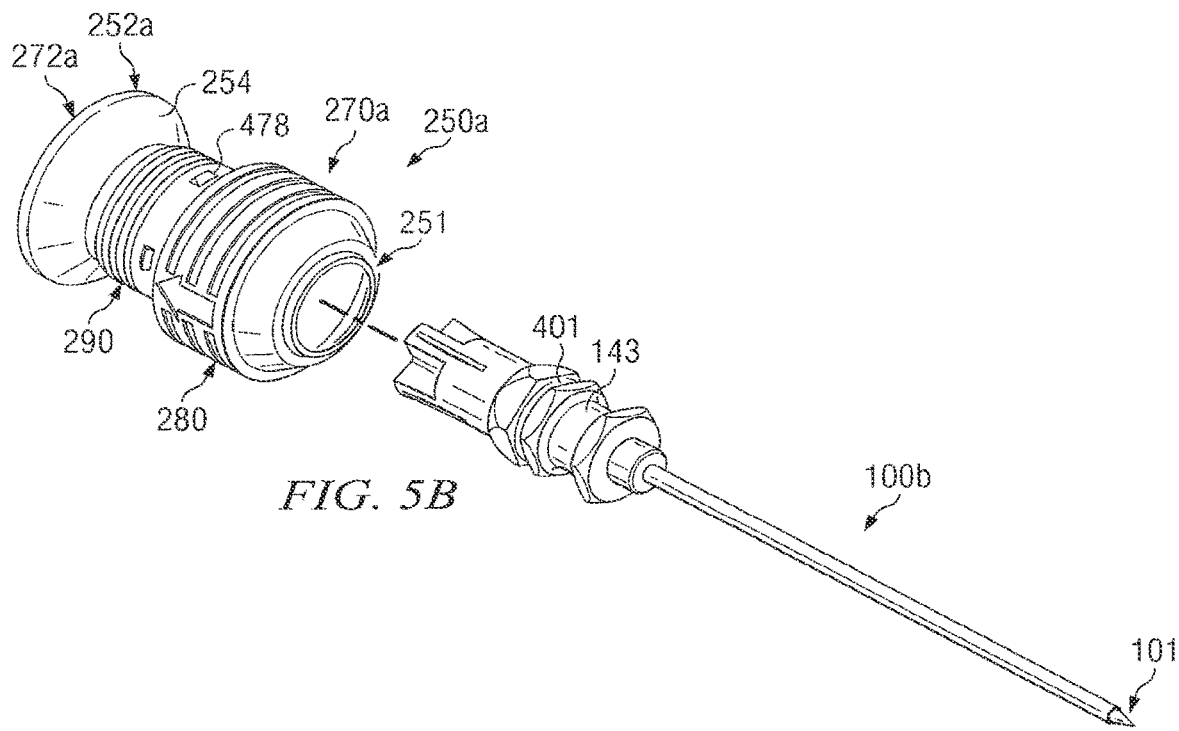
FIG. 5B is a schematic drawing showing another exploded, isometric view of the coupler assembly and intraosseous device of FIG. 5A.
Figure 5C:
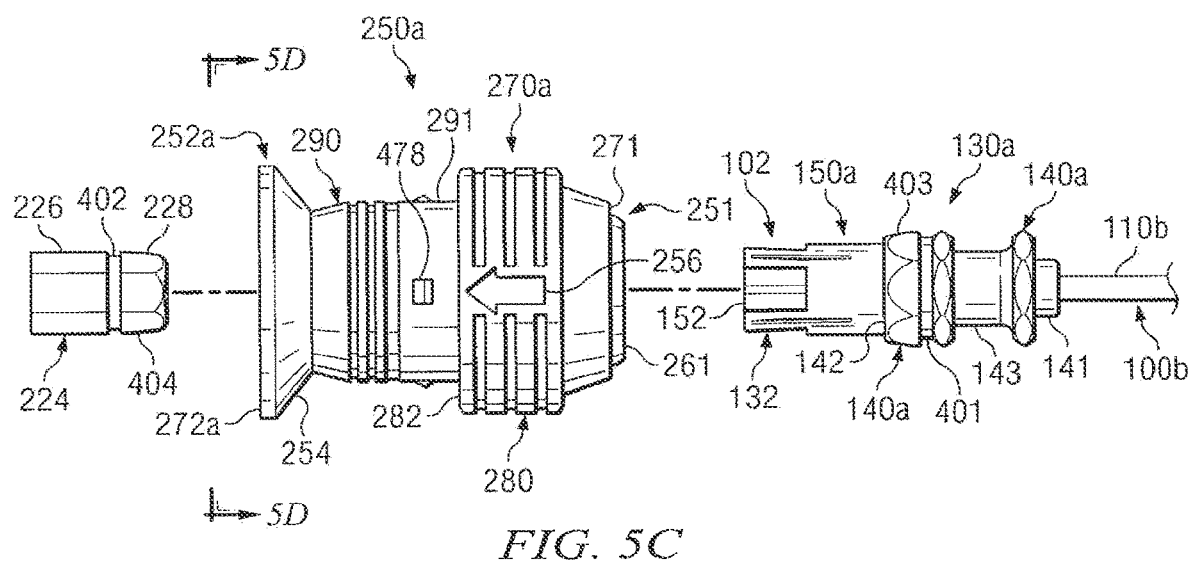
FIG. 5C is a schematic drawing in section with portions broken away showing another exploded view of the powered driver, coupler assembly and intraosseous device of FIG. 5A.
Figure 5D:
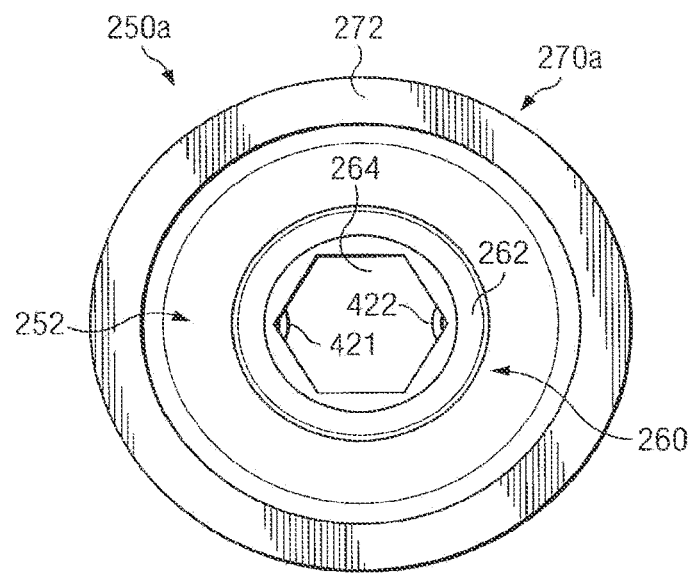
FIG. 5D is schematic drawing showing an end view of the coupler assembly taken along lines 5D-5D of FIG. 5C prior to insert one end of a device shaft therein.
Figure 5E:
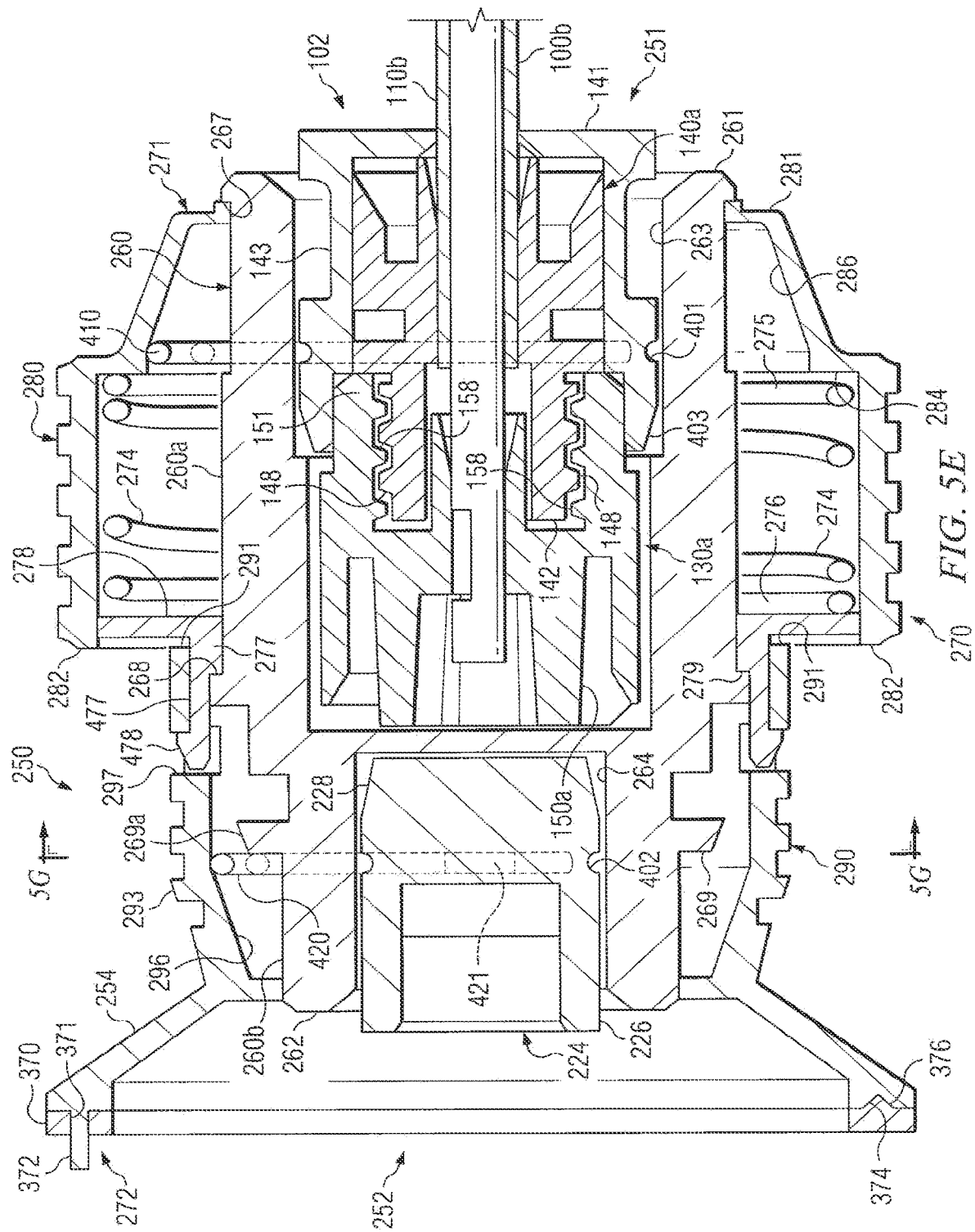
FIG. 5E is a schematic drawing in section with portions broken away showing the powered driver, coupler assembly and intraosseous device of FIG. 5A.
Figure 5F:
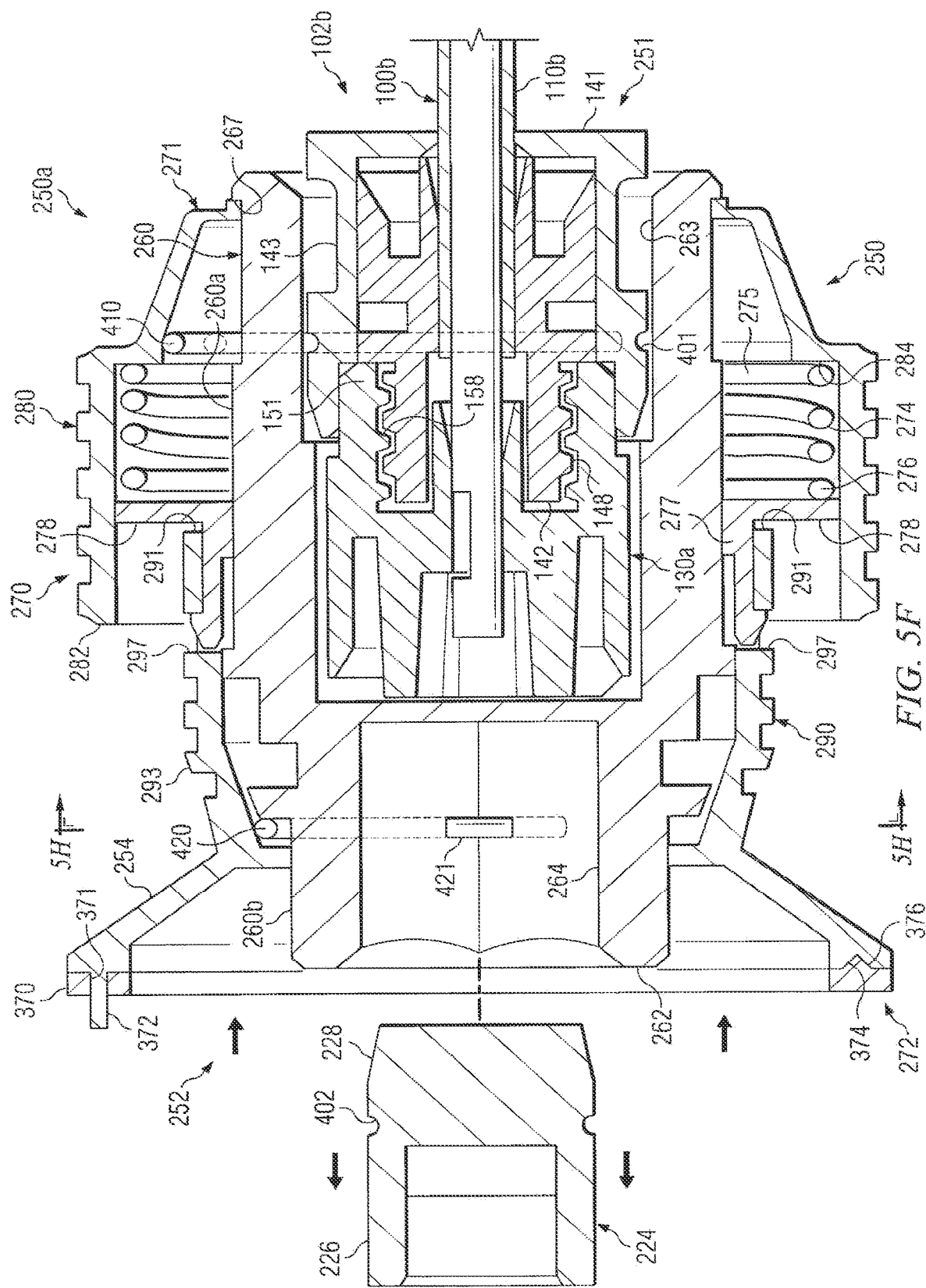
FIG. 5F is a schematic drawing in section with portions broken away showing the coupler assembly of FIG. 5D in a second position allowing release of a powered driver from a receptacle disposed in the first end of the coupler assembly.

As shown in FIGS. 5E and 5F, coupler assembly 250 may include elongated core 260 with housing assembly 270 slidably disposed on exterior portions of elongated core 260. Housing assembly 270 may include first end 271 and second end 272 which may be generally aligned with respective first end 261 and respective second end 262 of elongated core 260. For some applications, elongated core 260 may have a generally cylindrical configuration defined in first exterior portion 260a and second exterior portion 260b with various shoulders and/or recesses formed thereon. For some embodiments first exterior portion 260a may have a larger diameter than second exterior portion 260b.

Coupler assembly 250a and coupler assembly 250b may include respective elongated cores 260 having similar features and functions as described with respect to coupler assembly 250. Coupler assembly 250a may include housing assembly 270a with substantially the same components, functions and features as described with respect to housing assembly 270 except for second end 272a of housing assembly 270a. Coupler assembly 250b may include housing assembly 270b having substantially similar components, functions and features as described with respect to housing assembly 270 except for second end 272b of housing assembly 270b.

Housing assembly 270 may be described as having a generally hollow, cylindrical configuration defined in part by first housing segment 280 and second housing segment 290. See FIGS. 5E and 5F. The first end of housing segment 280 may generally correspond with first end 271 of housing assembly 270. The second end of second housing segment 290 may generally correspond with second end 272 of housing assembly 270.

First end 291 of second housing segment 290 may be described as having a generally cylindrical configuration with an outside diameter smaller than the adjacent inside diameter of second end 282 of first housing segment 280. First end 291 of second housing segment 290 may slide longitudinally from a first position (See FIG. 5E) to a second position (See FIG. 5F) within second end 282 of first housing segment 280 to release one end of a drive shaft engaged with second end 252 of coupler assembly 250.

A biasing mechanism such as coiled spring 274 may be disposed around exterior portion 260a of generally elongated core 260. See for example FIGS. 5E and 5F. First end 275 of coiled spring 274 may contact annular shoulder 284 formed on interior portions of first housing segment 280. Second end 276 of coiled spring 274 may contact annular shoulder 278 disposed proximate first end 291 of second housing segment 290. Coil spring 274, annular shoulder 284 and annular shoulder 278 may cooperate with each other to generally maintain first housing segment 280 and second housing segment 290 in a first extended position relative to each other. See FIGS. 5A, 5B, 5C, 5E and 5I. Other biasing mechanisms such as, but not limited to, leaf springs and bellows (not expressly shown) may also be disposed between annular shoulder 284 and annular shoulder 278.

Annular shoulder 278, associated with second end 276 of coiled spring 274, may extend radially outward from generally cylindrical ring 277. Generally cylindrical ring 277 may be slidably and rotatably disposed on exterior portion 260a of elongated core 260. Annular shoulder 279 may be disposed on interior portions of generally cylindrical ring 277 and may extend radially inward toward adjacent portions of elongated core 260.

Annular shoulder 268 may be formed on exterior portion 260a of elongated core 260 intermediate first end 261 and second end 262. The configuration and dimensions of annular shoulder 268 and annular shoulder 279 are selected to be compatible with each other such that engagement between annular shoulder 279 of generally cylindrical ring 277 with annular shoulder 268 of elongated core 260 may limit movement of second housing segment 290 longitudinally in the direction of second end 262 of elongated core 260.

For some applications a plurality of flexible collets or fingers 477 may extend from generally cylindrical ring 277 opposite from annular shoulder 278. Respective collet heads 478 may be formed on the end of each collet 477 opposite from annular shoulder 278. The dimensions and configuration of collet heads 478 may be selected to be received within respective slots or openings 297 formed in second housing 290. During manufacture of coupler assembly 250, each collet head 478 may be disposed within respective slot or opening 297 to securely engage generally cylindrical ring 277 and annular shoulder 278 proximate first end 291 of second housing segment 290. As a result, second housing segment 290 and annular shoulder 278 may generally move as a single unit relative to elongated core 260 and first housing segment 280.

During disengagement of an intraosseous device from first end 251 of coupler assembly 250, first housing segment 280 may move or slide longitudinally toward second housing segment 290. In a similar manner, second housing segment 290 may move or slide longitudinally toward first housing segment 280 during disengagement of a powered driver from second end 252 of coupler assembly 250.

Annular shoulder 267 may be formed on exterior portions of elongated core 260 proximate first end 261. Annular shoulder 267 may engage portions of first end 271 of housing 270 to limit longitudinal movement of first housing segment 280 during longitudinal movement of second housing segment 290 towards first end 261 of elongated core 260 during disengagement of a powered driver from second end 252 of coupler assembly 250.

As previously noted, annular shoulder 268 may be formed on exterior portions of elongated core 260 between first end 261 and second end 262. Engagement between annular shoulder 268 and annular shoulder 279 of generally cylindrical ring 277 may limit movement of second housing segment 290 toward second end 262 of elongated core 260. Contact between spring 274 and annular shoulder 278 and annular shoulder 284 of first housing segment 280 may limit the longitudinal movement of first housing segment 280 in the direction of second end 262 of elongated core 260 during disengagement of an intraosseous device from first end 251 of coupler assembly 250.

Generally cylindrical ring 277 and attached annular shoulder 279 may slide longitudinally on exterior portions of annular core 260 between annual shoulder 268 and annular shoulder 267. First housing segment 280 may move longitudinally toward second end 262 of elongated core 260 to release one end of intraosseous device from engagement with first end 251 of coupler assembly 250. In a similar manner, second housing segment 290 may move longitudinally toward first end 261 of elongated core 260 to release one end of a drive shaft extending from a powered driver engaged with second end 252 of coupler assembly 250.

A wide variety of latches and latch mechanisms may be satisfactorily used to releasably engage one end of an intraosseous device within a first end of a coupler assembly incorporating teachings of the present disclosure. In a similar manner, a wide variety of latches and latch mechanisms may be satisfactorily used to releasably engage one end of a drive shaft extending from a powered driver or manual driver within a second end of the coupler assembly incorporating teachings of the present disclosure.

For embodiments represented by coupler assemblies 250, 250a and 250b, first latch 410 may be disposed on exterior portions of elongated core 260 proximate receptacle 263 adjacent to first end 261 to releasably engage one end of an IO device such as second end 102 of biopsy needle set 100b within receptacle 263 of coupler assembly 250, 250a and/or 250b. Second latch mechanism 420 may be disposed on exterior portions of elongated core 260 proximate receptacle 264 adjacent to second end 262 to releasably engage one end of a drive shaft with second end 252 of coupler assembly 250. See FIGS. 5C, 5E and 5I.

Second latch 420 may be used to releasably engage one portion of a drive shaft such as end 224 of drive shaft 222 extending from powered driver 200 within second end 252 of coupler assembly 250, 250a and/or 250b. Latch 410 may releasably engage an intraosseous device with first end 251 of coupler assembly 250 substantially the same latch 420 may releasably engage a powered driver with second end 252 of coupler assembly 250.

For some applications, latches 410 and 420 may have similar configurations such as a general "omega" shape. See latch 420 in FIGS. 5G and 5H. However, latch 410 may have larger dimensions corresponding generally with exterior portion 260a of elongated core 260. Latch 420 may have smaller dimensions corresponding generally with exterior portion 260b of elongated core 260. Various features of the present disclosure may be described with respect to latch mechanism 420 as shown in FIGS. 5G and 5H along with adjacent portions of second housing segment 290 and exterior portion 260b of elongated core 260.

Respective detents 421 and 422 may be formed on opposite ends of generally omega shaped latch 420. See FIGS. 5D, 5G and 5H. In a similar manner, respective detents (not expressly shown) may be formed on the ends of generally omega shaped latch 410. The configuration and dimensions of detents 421 and 422 may be compatible with placing each detent 421 and 422 in respective slot or opening 431 and 432 extending between exterior portion 260b of elongated core 260 to interior portions of receptacle 264 disposed proximate second end 252 of coupler assembly 250.

Figure 5G:
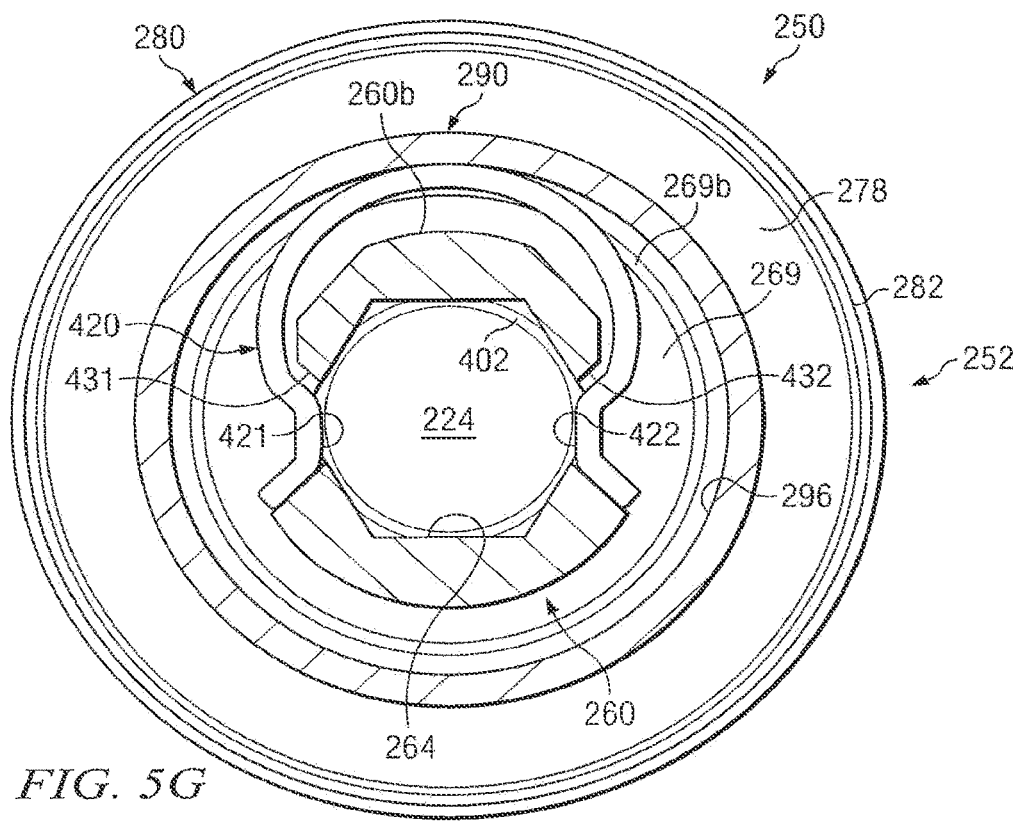
FIG. 5G is a schematic drawing in section showing various features of a coupler assembly and latch mechanism incorporating teachings of the present disclosure taken along lines 5G-5G of FIG. 5E.
Figure 5H:
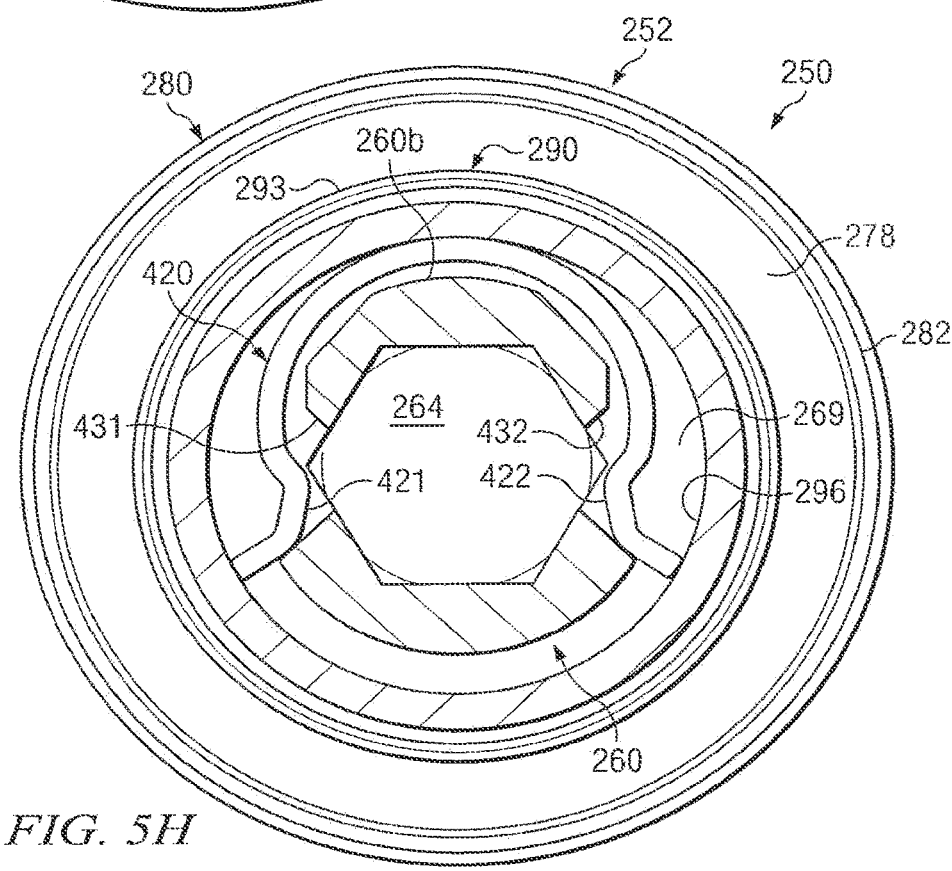
FIG. 5H is a schematic drawing in section showing various features of a coupler assembly and latch mechanism incorporating teachings of the present disclosure taken along lines 5H-5H of FIG. 5F.
Figure 5I:
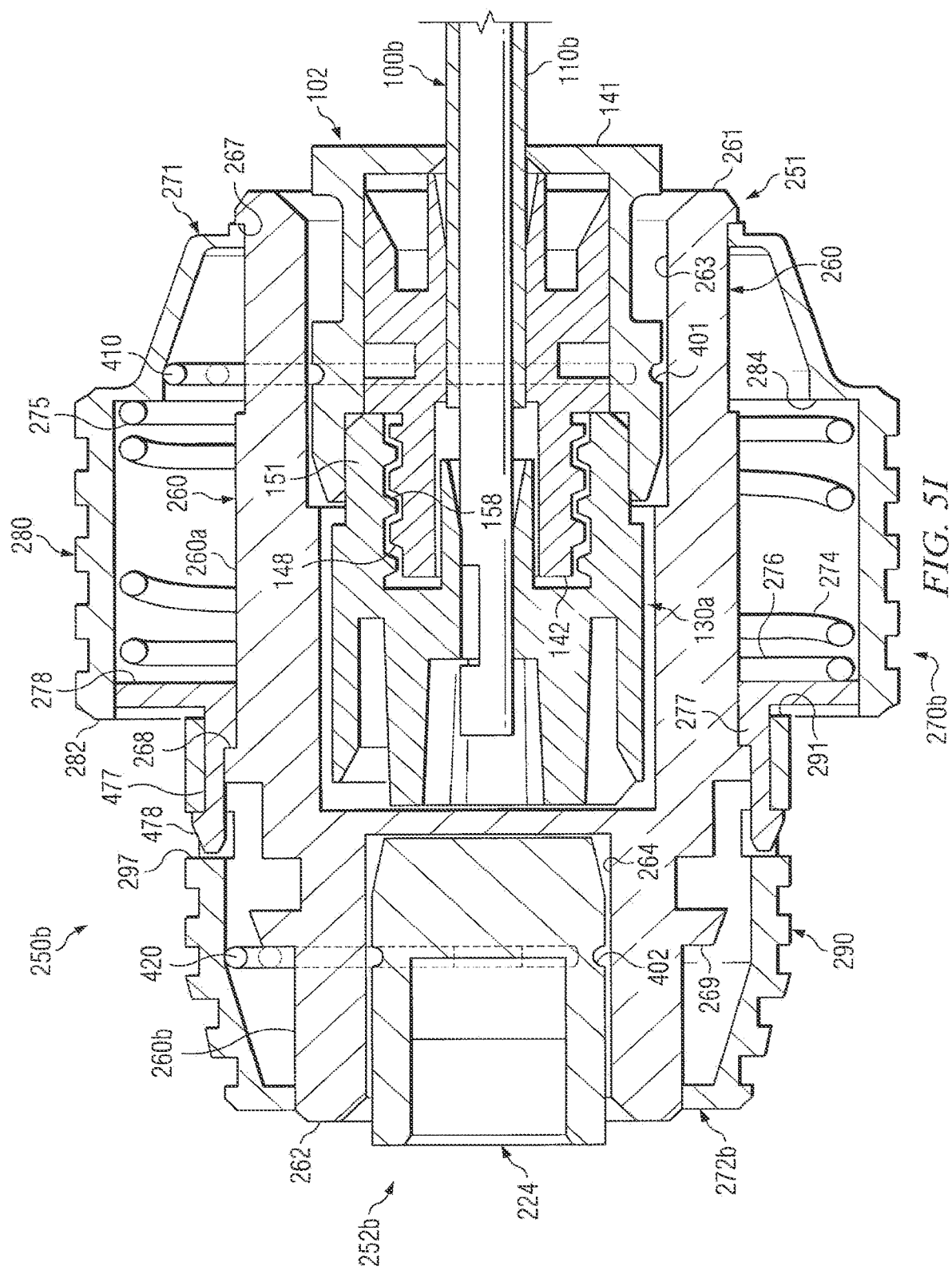
FIG. 5I is a schematic drawing in section with portions broken away showing another example of a coupler assembly incorporating teachings of the present disclosure.

Latch 420 may have a first position such as shown in FIGS. 5D and 5G in which portions of detents 421 and 422 may extend through respective slots 431 and 432. The dimensions and configuration of detent 421 and 422 may be operable to be securely engaged with annular groove 402 formed in end 224 of powered driver 200. In a similar manner, respective detents on associated latch 410 may be releasably engaged with annular groove 401 disposed in second end 102 of biopsy needle 100b.

For some applications, a plurality of tapered surfaces 403 may be formed on exterior portions of hub 140a proximate first end 142 (See FIG. 5C) to radially expand detent mechanisms associated with omega shaped latch 410 radially outward while inserting second end 102 of biopsy needle 100b into first end 251 of coupler assembly 250, 250a or 250b. The detent mechanism may "snap" into annular groove 401 when aligned therewith. In a similar manner, a plurality of tapered surfaces 228 may be formed on exterior portions of end 224 of drive shaft 222 extending from powered driver 200 to radially expand detent mechanisms 421 and 422 radially outward during the insertion of end 224 of powered driver 200 into second end 252 of coupler assembly 250. Detent mechanisms 421 and 422 will "snap" into annular groove 402 when aligned therewith. See FIG. 5F.

Engagement between detent mechanisms associated with latch 410 with annular groove 401 of hub assembly 130a will generally retain second end 102 of biopsy needle 100b securely engaged with first end 251 of coupler assembly 250. This engagement may allow powered driver 200 to rotate or spin cannula or biopsy needle 110b while withdrawing cannula or biopsy needle 110b from an insertion site. In a similar manner, engagement between detent mechanisms 421 and 422 of omega shaped latch 420 and annular groove 402 of end 224 of powered driver 200 will generally retain second end 252 of coupler assembly 250 engaged with powered driver 100 during withdrawal of cannula 110b from an insertion site.

Biopsy needle set 100b may be released from first end 251 of coupler assembly 250 by sliding first housing segment 280 longitudinally toward second end 262 of elongated core 260. Such movement of first housing segment 280 will result in interior tapered surface 286 contacting exterior portions of omega shaped latch 410 and compressing omega shaped latch 410 to radially expand associated detent mechanisms (not expressly shown) from engagement with annular groove 401 of hub assembly 130a. As a result, biopsy needle set 100b may be easily withdrawn from first end 251 of coupler assembly 250.

In a similar manner, longitudinal movement of second housing segment 290 toward first end 251 of coupler assembly 250 will result in interior tapered surface 296 contacting exterior portions of omega shaped latch 420 to compress generally omega shaped latch 420 and withdraw or retract detent mechanisms 421 and 422 from engagement with annular groove 402 of end 224. See FIGS. 5F and 5H. As a result, powered driver 200 and second end 222 of coupler assembly 250 may be easily disconnected from each other.

Coupler assemblies 250 and 250a may have substantially the same overall configuration and dimensions including respective flange 254 extending radially from second end 252 and 252a. Flange 254 may be generally described as having an enlarged funnel shaped or bell shaped configuration. The dimensions and configuration of flange 254 may be selected to be compatible with end 211 of powered driver 200. Coupler assembly 250b does not have a respective flange 254. See FIG. 5I. Second end 272b of housing assembly 270b may terminate proximate first end 262 of associated elongated core 260 and associated second end 252b of coupler assembly 250b.

As previously noted, coupler assembly 250 may be securely engaged with an opening formed in a containment bag or sterile sleeve in accordance with teachings of the present disclosure. For embodiments such as shown in FIGS. 5E and 5F second end 272 of housing 270 of coupler assembly 250 may include annular ring 370 operable to be securely engaged with adjacent portions of flange 254. The outside diameter of annular ring 370 may generally correspond with the outside diameter of adjacent portions of flange 254. The inside diameter of annular ring 370 may also generally correspond with the inside diameter of adjacent portions of flange 254.

For some embodiments a plurality of posts 372 and generally V shaped grooves 374 may be alternatingly disposed on the extreme end of flange 254. Annular ring 370 may include a plurality of holes 371 sized to received respective posts 372 therein. Annular ring 370 may also include a plurality of generally V shaped projections 376 sized to be received within respective generally V shaped grooves 374 formed in adjacent portions of flange 254.

For embodiments such as shown in FIGS. 1C, 1E, 1F, 7A and 7B portions of containment bag 170 adjacent to first opening 171 may be disposed between annular ring 370 and adjacent portions of flange 254. For example, post 372 may be inserted through respective holes (not expressly shown) in containment bag 170 adjacent to the perimeter of opening 171. Holes 371 in annular ring 370 may be aligned with respective posts 372. Other portions of bag 170 adjacent to opening 171 may be trapped between respective V shaped projections 376 and V shaped grooves 374. Various welding techniques including, but not limited to, laser welding may be applied to posts 372 to bond annular ring 370 with adjacent portions of flange 354. As a result, the perimeter of containment bag 170 adjacent to first opening 171 may be securely engaged with second end 252 of coupler assembly 250. See FIGS. 7A and 7B.

FIGS. 6A and 6B are schematic drawings showing powered driver 200a, coupler assembly 250b and biopsy needle set 100b incorporating various teachings of the present disclosure. Coupler assembly 250b may include first end 251 operable to be releasably engaged with second end 102 of intraosseous device 100b. Coupler assembly 250b may also include second end 252 operable to be releasably engaged with end 224a of drive shaft 222a extending from first end 211 of powered driver 200a.

As shown in FIG. 6B, second end 102 of biopsy needle set 100b may be releasably disposed within first end 251 of coupler assembly 250b. End 224a of drive shaft 222a extending from end 211 of powered driver 220a may be releasably engaged with second end 252b of coupler assembly 250. For embodiments represented by coupler assembly 250b, second end 252 of coupler assembly 250b may include tapered receptacle 264b having a configuration and dimensions corresponding generally with tapered end 224a of powered driver 220a.

Coupler assembly 250b may include generally elongated core 260b with housing assembly 270b slidably disposed on exterior portions of elongated core 260b adjacent to first end 251. Second end 272 of housing assembly 270b may be disposed adjacent to shoulder 278b formed on exterior portions of elongated core 260b. Coiled spring 274 may be disposed on exterior portions of elongated core 260b between shoulder 284b of housing 270b and shoulder 278b of elongated core 260b. Coiled spring 274 may bias housing assembly 270b to a first position with first end 271 of housing 270b generally aligned with first end 261 of elongated core 260b. See FIG. 6B.

For some applications, coupler assembly 250b may include latch mechanism 430 disposed proximate second end 252 of coupler assembly 250b. Latch mechanism 430 may be generally described as having an "L" shaped configuration defined in part by first segment 431 extending generally parallel with elongated core 260b and second segment 432 extending generally perpendicular with respect to elongated core 260b proximate second end 262. Second segment 432 may include an enlarged opening 434 sized to allow inserting end 224a of powered driver 200a into receptacle 264b. Segment 432 of latch mechanism 430 may also include detent mechanism 436 sized to be releasably engaged within annular groove 402 proximate end 224a of powered driver 200a. See FIG. 6B.

During attachment of coupler assembly 250b with end 224a of powered driver 200, first segment 431 may be manually depressed to compress spring 438 and to move detent mechanism 436 to allow full access to receptacle 264b disposed in second end 252b of coupler assembly 250b. End 224a of powered driver 200a may then be inserted through opening 434 into receptacle 264b. First segment 431 of latch mechanism 430 may next be released, which will allow detent mechanism 436 to be securely engaged within annular groove 402 of end 224a of powered driver 200a. As a result, coupler assembly 250b will remain securely engaged with powered driver 200a until first segment 431 is again depressed to disengage detent mechanism 436 from annular groove 402.

Latch mechanism 410b may be disposed on exterior portions of elongated core 260b proximate first end 261. Latch mechanism 410b may be operable to be releasably engaged with and disengaged from annular 401 in an associated intraosseous device such as annual groove 401 formed in second end 102 of biopsy needle 100b. See FIG. 6B. Housing 270b may slide longitudinally from first end 271 toward second end 252 of coupler assembly 250b to release engagement between latch mechanism 410b and annular groove 401 formed in second end 102 of biopsy needle set 100b.

For some embodiments, annular ring 440 may be disposed on exterior portions of coupler assembly 250b proximate second end 252. Annular ring 440 is shown in FIG. 6B. Annular ring 440 is not shown in FIG. 6A. Groove 442 may be formed in exterior portions of annular ring 440 to accommodate securely engaging the perimeter of a first opening in a containment bag therewith. The dimensions and configuration of annular ring 440 may be selected to allow rotation of coupler assembly 250b within annular ring 440. As a result a containment bag attached with annular ring 440 will generally not be damaged by rotation of coupler assembly 250b.

FIGS. 7A and 7B are schematic drawings showing one example of a containment bag or sterile sleeve engage with a coupler assembly in accordance with teachings of the present disclosure. FIG. 7A shows powered driver 200 prior to placing within containment bag 170. Containment bag 170 may be generally described as having first opening 171 and second opening 172. For some applications, containment bag 170 may be formed from generally clear, flexible plastic-like material.

First opening 171 may be sized to securely engage second end 252 of coupler assembly 250 therewith. For embodiments represented by coupler assembly 250, annular ring 370 may be used to securely engage portions of containment bag 170 proximate first opening 171 with second end 252 of coupler assembly 250. See FIGS. 5E and 5F. A fluid barrier may be formed between portions of containment bag 170 adjacent to first opening 171 and adjacent portions of second end 252 of coupler assembly 250.

The dimensions and configuration of second opening 172 of containment bag 170 are preferably selected to allow inserting powered driver 200 therethrough. Various closure mechanisms may be satisfactorily used to close second opening 172 after end 224 of powered driver 200 has been engaged with second end 252 of coupler assembly 250. For some applications, flap 174 may be folded over second opening 172. Various types of self sealing adhesive materials may be satisfactorily used to releasably engage portions of flap 174 with adjacent portions of containment bag 170. The present disclosure is not limited to using flaps and adhesive materials to close an opening in a containment bag.

Figure 8:
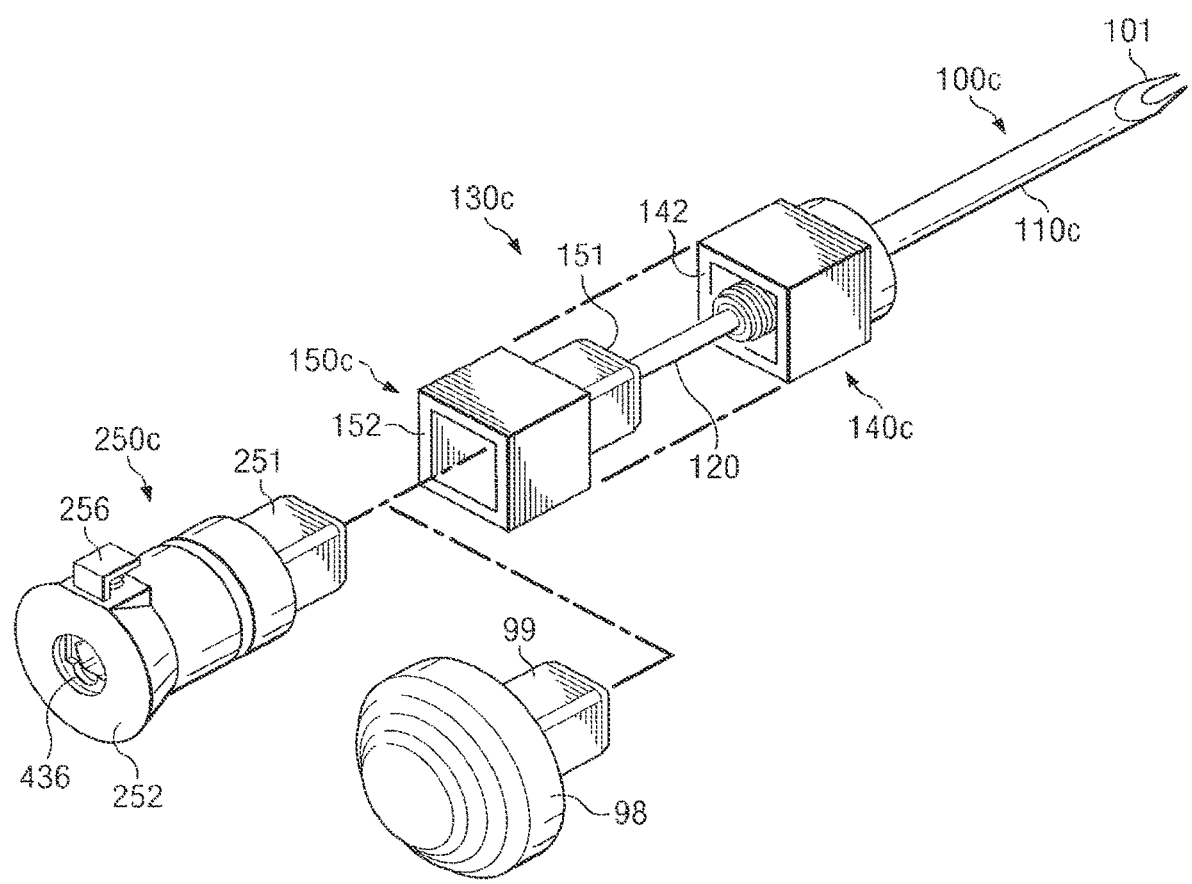
FIG. 8 is a schematic drawing showing an exploded isometric view of an intraosseous device and a coupler assembly incorporating teachings of the present disclosure which may be satisfactorily used with a powered driver in accordance with teachings of the present disclosure or a manual driver.

FIG. 8 is a schematic drawing showing an exploded isometric view of coupler assembly 250c and hub assembly 130c with intraosseous device 100d extending therefrom. First end 101 of intraosseous device 100d may be operable to be inserted into a bone and associated bone marrow. Intraosseous device 100d may include cannula 110c extending from hub 140c. Inner penetrator or trocar 120 may extend from first end 151 of hub 150c. First end 151 of hub 150c may be sized to be releasably inserted into second end 142 of hub 140c. First end 251 of coupler assembly 250c may be releasably inserted into second end 152 of hub 150c. For embodiments such as shown in FIG. 8, first end 251 of coupler assembly 250c, second end 152 of hub 150c, first end 151 of hub 150c and second end 142 of hub 140c may be described as having generally rectangular configurations.

Latch assembly 256 may be satisfactorily used to releasably engage one end of a drive shaft within second end 252d of coupler assembly 250c. For other applications, latch assembly 256 may include detent 436 operable to engage annular groove 402 in end 224a powered driver 200a. For other applications manual drive shaft 99 extending from manual driver 98 may also be releasably engaged with second end 152 of hub 150.

Various types of ejectors, ejector rods, funnels and/or ejector funnels may also be used with a biopsy needle, biopsy needle sets and/or other intraosseous devices incorporating teachings of the present disclosure. For some applications, funnels formed in accordance with teachings of the present disclosure may include a respective first opening formed at a first end and a respective second opening at a second end of the funnel. The first opening and the second opening may have different inside diameters.

For example, the first opening may be sized to accommodate inserting a biopsy needle therein while the second opening may have a reduced inside diameter which prevents inserting the biopsy needle therein. The second opening may be sized to only accommodate one end of an associated ejector rod. For some applications, a longitudinal passageway may extend between the first end and the second end of the funnel. Tapered surfaces may be formed within the longitudinal passageway adjacent to the first end. The tapered surfaces may function as a "one way" connector such that when a biopsy needle is inserted therein, the funnel will be securely engaged with the first end of the biopsy needle. The funnel may then function as a sharps protector for the first end of the biopsy needle.

Figure 9A:
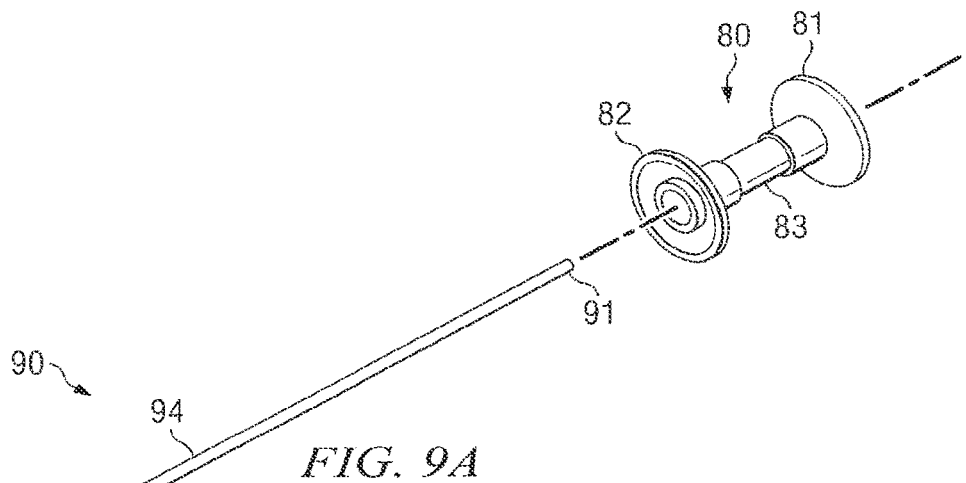
FIG. 9A is a schematic drawing showing an exploded, isometric view of a biopsy specimen ejector and associated funnel incorporating teachings of the present disclosure.
Figure 9B:
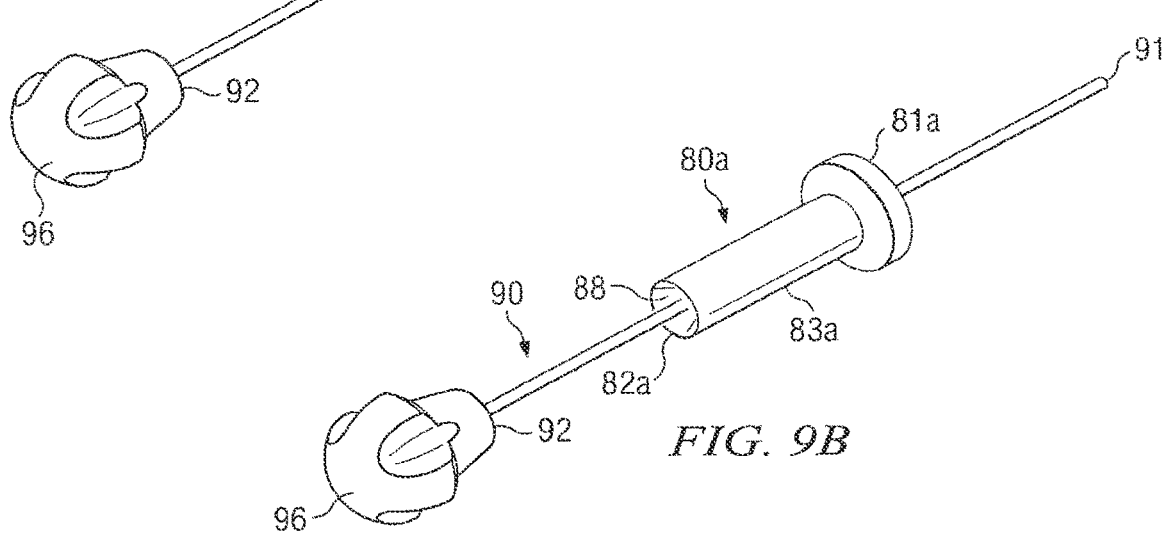
FIG. 9B is a schematic drawing showing an isometric view of another example of a biopsy specimen ejector and associated funnel incorporating teachings of the present disclosure.
Figure 9C:
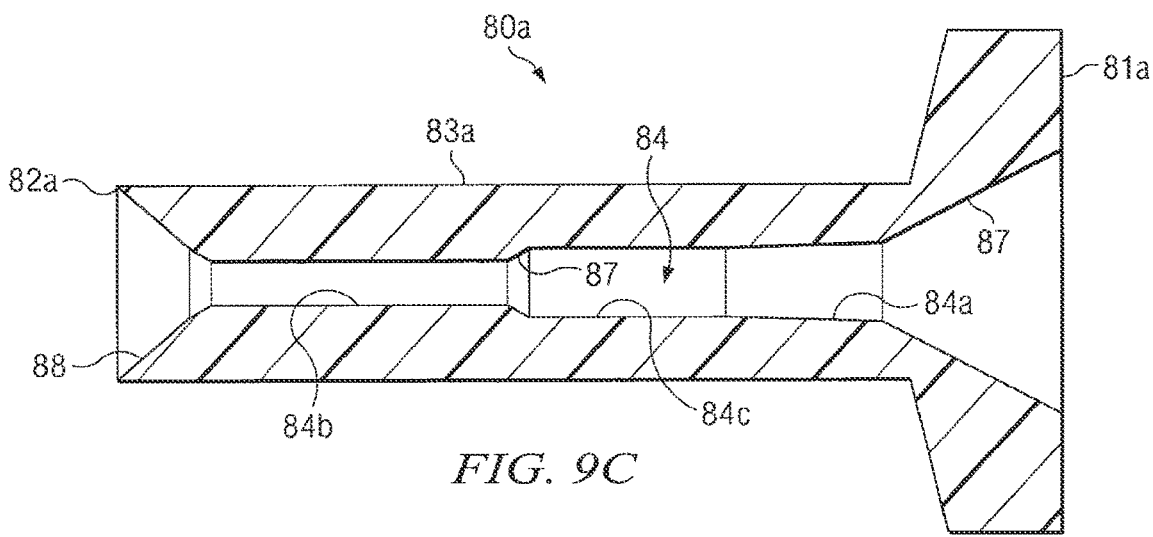
FIG. 9C is a schematic drawing in section of the funnel of FIG. 9B.

FIGS. 9A, 9B and 9C show some examples of apparatus and methods which may be used to remove a biopsy specimen from a generally hollow cannula or biopsy needle after inserting a first end of the generally hollow cannula or biopsy needle into a bone and/or associated bone marrow. Funnel 80 as shown in FIG. 9A may include first end 81 and second end 82 with a generally hollow, cylindrical portion 83 extending therebetween. Generally hollow, cylindrical portion 83 may include a longitudinal passageway (not expressly shown) sized to accommodate one end of an associated intraosseous device and first end 91 of ejector 90. For some applications ejector 90 may also be referred to as an "ejector rod".

The length of ejector 90 may be selected to be greater than the length of a lumen in an associated biopsy needle. Handle or hub 96 may be disposed on second end 92 of ejector 90. The dimensions and configuration of first end 91 of ejector rod 90 may be selected to be compatible with inserting first end 91 through an opening in the first end of an associated biopsy needle.

Funnel 80a as shown in FIGS. 9B and 9C represents an alternative embodiment of the present disclosure. First end 81a of funnel 80a may have a configuration and dimensions compatible with inserting the first end of an intraosseous device such as first end 101 of biopsy needle 100c therein. Second end 82a may have a modified configuration as compared with second end 82 of previously described funnel 80. The dimensions and configuration of second end 82a may be selected to be compatible with placing funnel 80a in a medical procedure tray with first end 81a oriented generally upward to allow inserting one end of an intraosseous device therein. See FIGS. 1C and 1D.

For embodiments such as shown in FIGS. 9B and 9C funnel 80a may include first end 81a sized to be securely engaged with one end of an intraosseous device such as first end 101 of biopsy needle 100c. Funnel 80a may include second end 82a sized to slidably receive first end 91 of ejector 90 therein. Longitudinal passageway 84 may be disposed in funnel 80a extending between first end 81a and second end 82a.

For some applications first tapered opening 87 may be formed proximate first end 81a. Second tapered opening 88 may be formed proximate second end 82a. First tapered opening 87 may be sized to allow inserting end 101 of biopsy needle 100c through and into first segment 84a of longitudinal passageway 84. Second tapered opening 88 may be sized to only allow inserting end 91 of ejector 90 therethrough and into reduced diameter portion 84b of longitudinal passageway 84. Reduced diameter portion 84b may be smaller than the outside diameter of biopsy needle 100c or other intraosseous devices.

For some applications longitudinal passageway 84 may include tapered inside diameter portion 84a disposed adjacent to and extending from first opening 87. The tapered inside diameter portion 84a may limit movement of the first end 101 of biopsy needle 100c or other intraosseous device therethrough. The configuration and dimensions associated with tapered inside diameter portion 84a may be described as a "sticking taper" which will result in securely engaging funnel 80a with the first end of an intraosseous device inserted therein. As a result of providing a "sticking taper" within longitudinal passageway 84, funnel 80a may then be withdrawn from a respective holder in a medical procedure kit to allow inserting injector rod 80 through second end 82a. Funnel 80a also may serve as a sharps protector since it is now securely engaged with the first end of the associated intraosseous device.

One of the benefits of the present disclosure may include the ability to securely engage one end of an intraosseous device with a funnel without requiring an operator to hold the funnel or the intraosseous device during such engagement. A powered driver and coupler assembly incorporating teachings of the present disclosure may be satisfactorily used to insert the one end of the intraosseous device into the funnel. The coupler assembly may then be releasably disengaged from an opposite end of the intraosseous device.

Benefits of the present disclosure may include reducing physical demands and mental stress on operators and patients by increasing speed and control of aspiration needle insertion during cancellous bone and bone marrow harvesting procedures. A bone marrow aspiration system incorporating teachings of the present disclosure may include a battery powered driver, a coupler assembly, a containment bag and an aspiration needle set. The powered driver, while disposed in a sterile containment bag, may rotate the coupler assembly and attached aspiration needle set to penetrate the cortex of a bone and associated cancellous bone to a desired depth to extract bone marrow. The driver and connector assembly may then be separated from the aspiration needle set. A hub assembly attached to one end of the aspiration needle set may be manipulated to leave an aspiration needle or cannula securely seated in the bone. A standard Luer lock fitting (part of the hub assembly) may be attached with a standard syringe or flexible tubing extending from a bone marrow aspiration system.

Figure 10:
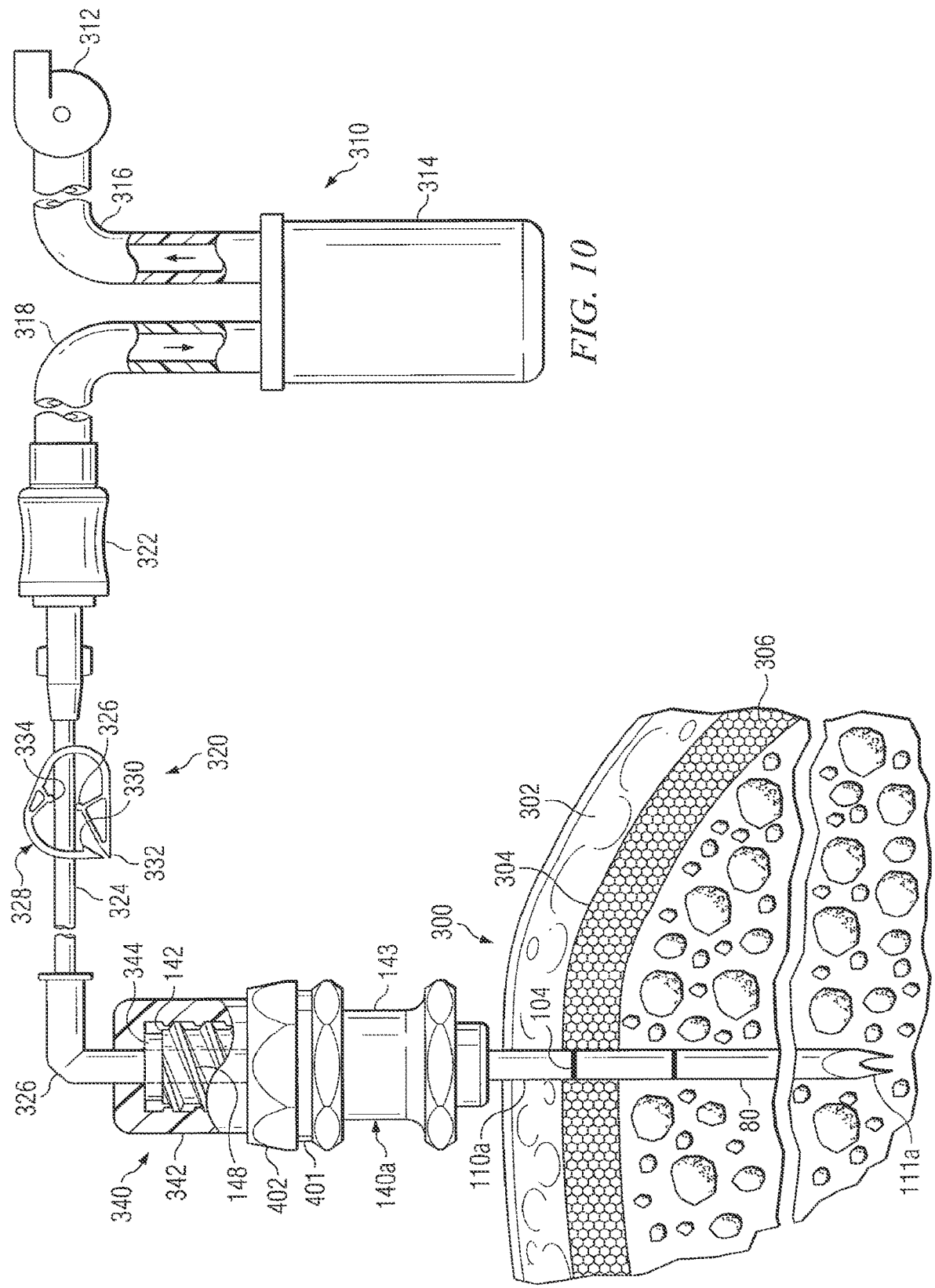
FIG. 10 is a schematic drawing in section and in elevation with portions broken away showing an aspiration needle disposed at a target site and communicating with a bone marrow aspiration system in accordance with teachings of the present disclosure.

FIG. 10 is a schematic drawing showing an aspiration needle disposed in a portion of a hip bone often referred to as the ilium. One of the penetration sites or insertion sites frequently used to obtain bone marrow from a hip bone may be the posterior iliac crest. Another insertion site may be the anterior iliac crest (not expressly shown). Bone marrow may also be aspirated from the tibia (leg bone) and sternum (chest).

Hip bone 300 as shown in FIG. 10 may include three segments—the ilium, the ischium and the pubis. These segments are generally distinct from each other in young patients but are generally fused together in adults. Skin and soft tissue 302 generally cover insertion sites in crest 304 of the ilium.

All bones generally include a tough, hard to penetrate layer of cortex. Crest 304 OF HIP BONE 300 typically includes cortex layer 306. FIG. 10 shows enlarged skin and soft tissue layer 302 and cortex layer 306 for illustration purposes only. A typical thickness for skin and soft tissue layer 302 may be seven to eight millimeters (7 mm to 8 mm). A typical thickness for cortex layer 306 may be approximately two millimeters (2 mm).

As previously discussed intraosseous (IO) device or aspiration needle set 100a may be inserted in the crest of the ilium or any other insertion site with minimum trauma to obtain bone and/or bone marrow samples in accordance with teachings of the present disclosure.

FIG. 10 shows one example of a system for aspirating bone marrow from a bone using apparatus and methods incorporating teachings of the present disclosure. Samples of bone and/or bone marrow may be obtained from any suitable bone including, but not limited to, tibia (leg bone), ilium (pelvis) or sternum (chest) using apparatus and methods incorporating teachings of the present disclosure. FIG. 10 shows cannula or aspiration needle 110a inserted into a target area in a patient's ilium.

For one embodiment, system 310 may include a source of vacuum or low pressure 312, collection container 314, vacuum tubing 316 and collection tubing 318. Source of vacuum 312 may be a pump such as shown in FIG. 10 or may be a portion of a hospital or operating suite low pressure vacuum system (not expressly shown). Vacuum tubing 316 may extend between vacuum source 312 and collection container 314. Various types of tubing may be satisfactorily used to form vacuum tubing 316 and/or collection tubing 318. The length of vacuum tubing 316 and/or collection tubing 318 may be varied depending upon each facility in which system 310 is used.

Collection tubing 318 may extend between collection container 314 and intraosseous (IO) connector assembly 320. Various types of connections and connector assemblies including, but not limited to, IO connector assembly 320 may be used to communicate fluids between an IO device such as aspiration needle 110a and collection tubing 318.

IO connector assembly 320 may include coupling or tubing connector 322 operable to be releasably engaged with one end of collection tubing 318 opposite from container 314. Various types of couplings associated with IV tubing may be satisfactorily used. Relatively short, flexible tubing 324 may extend between tubing connector 322 and right angle connector 326. For some applications, flow control device or tubing stop 328 may be attached to flexible tubing 324 between coupling 322 and right angle connector 326.

Flow control device 328 may have a first, open position as shown in FIG. 10 and a second, closed position (not expressly shown). Flow control device 328 may be used to prevent fluid flow from IO device 110a during engagement and disengagement with collection tubing 318 or any other apparatus such as IV tubing (not expressly shown) which may be attached to IO connector assembly 320.

Flow control device 328 may be formed from relatively flexible material which allows compressing or squeezing flow control device 328 to engage notch or hook 330 with end 332. Compression of flow control device 328 will preferably result in clamps 334 and 336 compressing or closing off fluid flow through the lumen of flexible tubing 324. Engagement of notch 330 with end 336 will hold flow control device 328 in its second, closed position.

Right angle connector 326 may be engaged with one end of flexible tubing 324 opposite from coupling 322. Right angle connector 326 allows flexible tubing 324 to be connected to aspiration needle 110a at an angle that will generally not kink or pinch off the lumen of tubing 324. Right angle connector 326 may also include Luer connector 340 operable to be releasably connected with second end 142 of first hub 140a. A tapered portion (not expressly shown) of Luer connector 340 may be inserted into tapered opening 144 formed in second end 142 of first hub 140a.

Lock nut 342 may be disposed on exterior portions of right angle connector 326 adjacent to Luer connector 340. Flange 344 may also be formed on the exterior of right angle connector 326 adjacent Luer connector 340. Lock nut 342 may be both rotatably and slidably disposed on the exterior portion of right angle connector 326 adjacent to Luer connector 340 with flange 344 disposed between lock nut 342 and Luer connector 340. Threads 346 formed on interior portions of lock nut 342 may be used to releasably engage right angle connector 326 with threads 148 formed adjacent to second end 142 of first hub 140a.

After aspirating a desired bone marrow sample from the target area shown in FIG. 10, IO connector assembly 320 may be disconnected from second end 142 of first hub 140a. Second hub 150a (with or without a trocar attached thereto) may be reconnected with second end 142 of first hub 140a. Powered driver 200 and coupler assembly 250 may be reconnected to hub assembly 130a to remove (power out) aspiration needle 110a or insert aspiration needle 110a to another target area in hip bone 300.

Figure 11A:
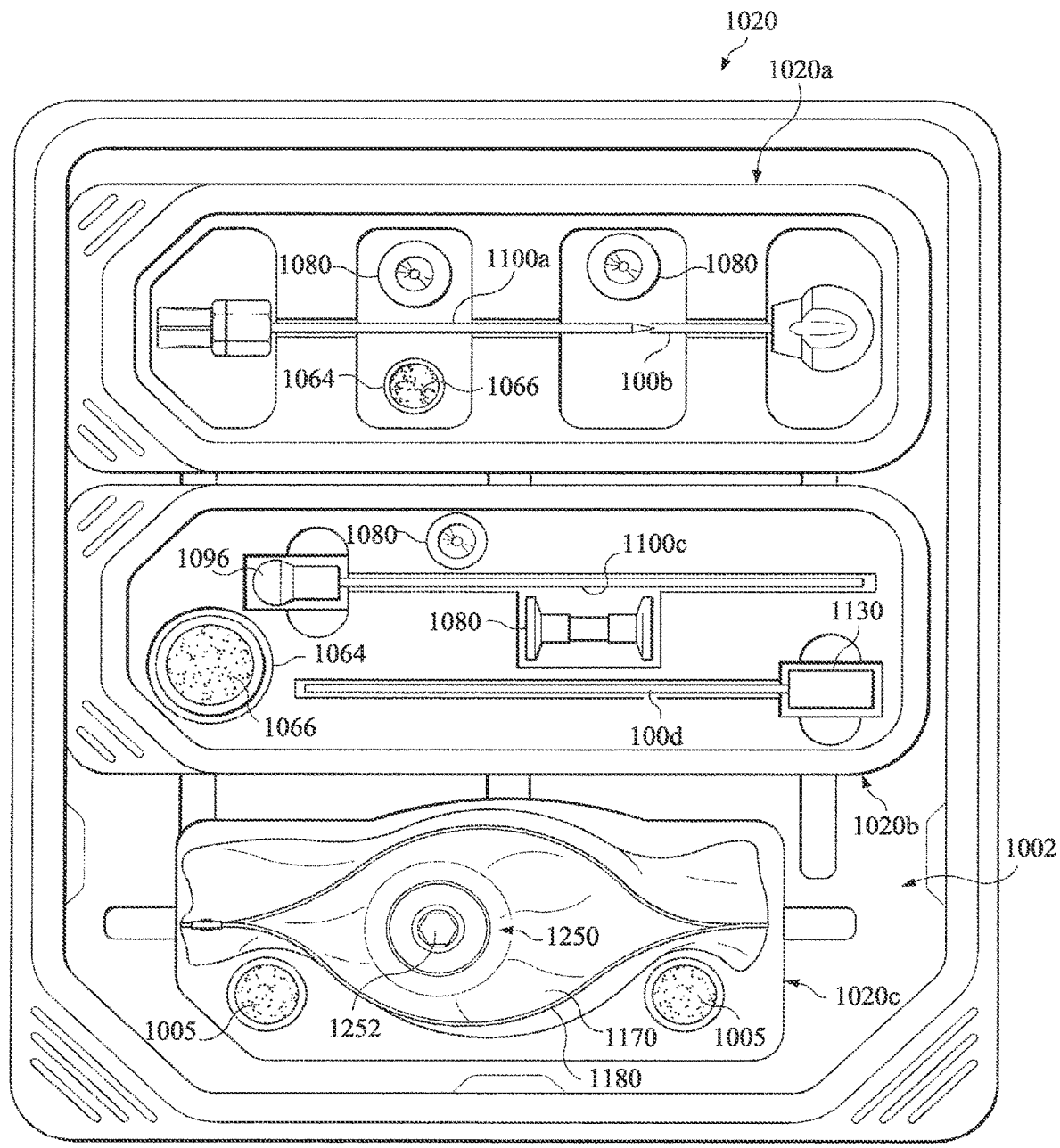
FIG. 11A is a schematic drawing showing a plan view of one example of a medical procedures tray comprising an intraosseous needle set and a biopsy needle set, each needle set disposed in a separate tray, and a coupler assembly operable to be releasably attached to each needle set and to a non-sterile medical device (e.g., a powered driver, not expressly shown), the coupler assembly further attached to a sterile container bag and disposed in another tray incorporating teachings of the present disclosure.
Figure 11B:
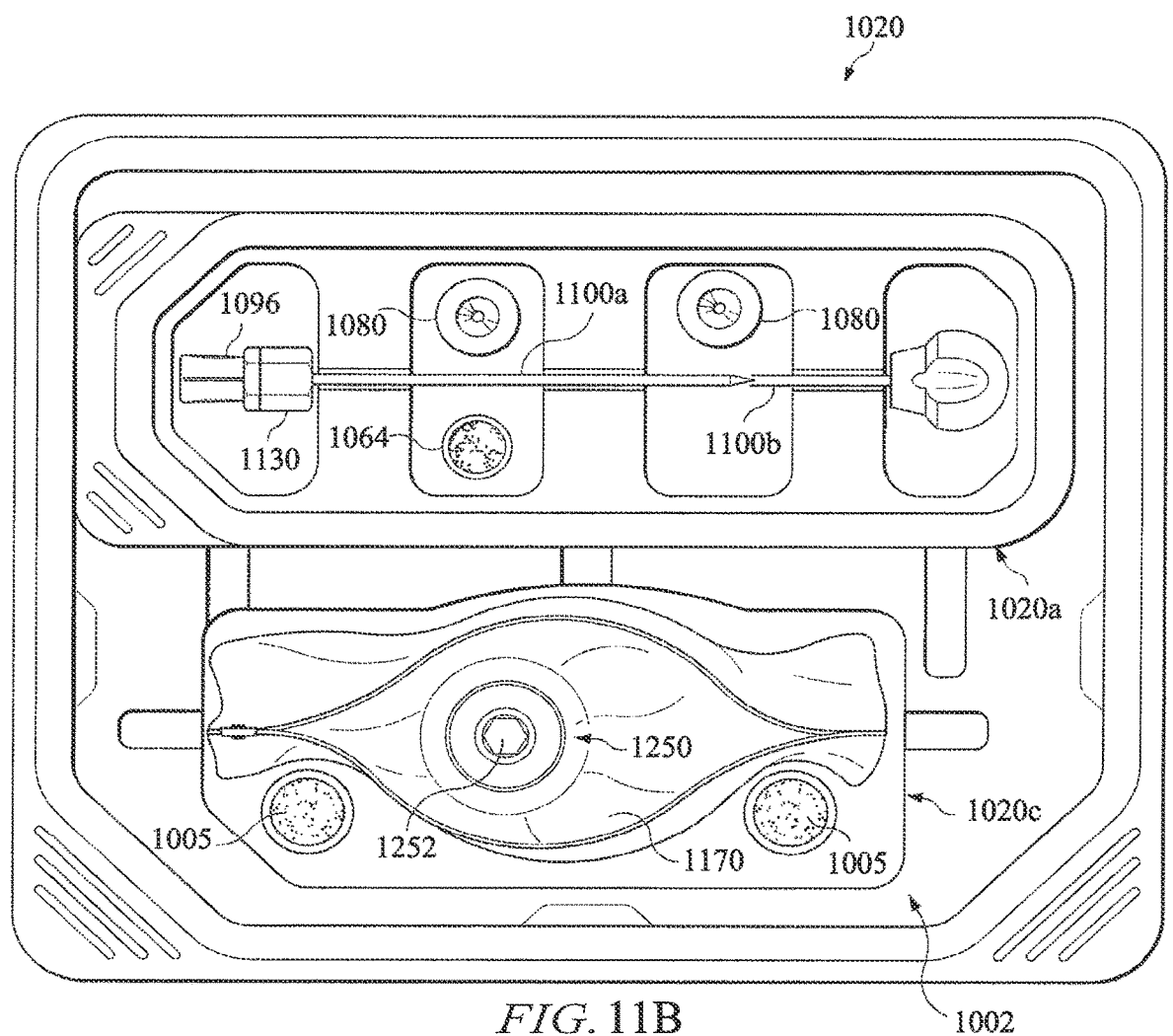
FIG. 11B is a schematic drawing showing a plan view of one example of a medical procedures tray comprising an intraosseous needle set enclosed in a tray and a coupler assembly operable to be releasably attached to the needle set and to a powered driver (not shown), the coupler assembly further attached to a sterile container bag incorporating teachings of the present disclosure.

FIGS. 11A and 11B show some examples of medical procedure trays and/or kits which may contain one or more intraosseous devices and/or other components incorporating teachings of the present disclosure. For example, medical procedure tray 1020 as shown in FIG. 11A may include a first tray 1020a comprising an intraosseous needle set with needles 1100a and 1100b (e.g., an IO needle set for penetration and delivery of a medicament to a vertebral bone), funnel 1080 and sharps container 1064; a second tray 1020b comprising an intraosseous biopsy needle set with needles 1100c and 1100d, funnel 1080 and sharps container 1064 incorporating various teachings of the present disclosure; and a third tray 1020c comprising a coupler assembly 1250, containment bag 1170, feet 1005 and second end of the coupler assembly 1252 that may be releasably attached to power driver 1200 (not expressly shown). Feet 1005 provide support for tray 1020c. Trays 1020a, 1020b and 1020c may be enclosed in tray 1020 and covered with a detachable paper or plastic wrap 1002. In some embodiments, an additional tray comprising an IO aspiration system for obtaining bone marrow may also be comprised in tray 1020 (not expressly depicted).

For delivery of a therapeutic agent to bone and/or for removal of a biological specimen from a bone the needles 1100b or 1100d as depicted in FIGS. 11A and 11B may also be referred to as an "ejector rod." An ejector rod, such as 1100b or 1100d, may be slidably disposed into a hollow cannula 1100 of an IO needle to deliver a medicament or obtain a biological sample from a bone. In the case of a biopsy ejector rod, a helical thread, operable to be wound back by a mandrel, may be disposed in the cannula. Upon contact with bone tissue the helical thread may be would back to retrieve the biopsy sample.

The length of ejectors 1100b or 1100d may be selected to be greater than the length of a lumen in an associated IO needle. Handle or hub 1096 may be disposed on second end 1092 of ejectors 1100b or 1100d. See FIG. 11D. The dimensions and configuration of first end 1091 of ejector rod 1100b or 1100d may be selected to be compatible with inserting first end 1091 through an opening in the first end 1111 of an associated IO and/or biopsy needle 1100. Various types of ejectors, ejector rods, funnels and/or ejector funnels may also be used with an IO needle, a vertebral needle, an IO biopsy needle, IO aspirator needle and/or other intraosseous devices incorporating teachings of the present disclosure.

Medical procedure tray 1020 as shown in FIG. 11B may include first tray 1020a comprising an intraosseous needle set 1100a and 1100b (for example, vertebral IO needles), funnels 1080 and sharps container 1064; and second tray 1020c comprising a coupler assembly 1250, containment bag 1170, feet 1005 and second end of the coupler assembly 1252 that may be releasably attached to power driver 1200 (not expressly shown). IO needle sets 1100 may comprise one or more cannulas, stylets, trocars, and/or cutting needle tips. Feet 1005 provide support for tray 1020c. Trays 1020a, 1020b and 1020c may be enclosed in tray 1020 and covered with a detachable paper or plastic wrap 1002.

Medical procedure trays and/or kits formed in accordance with teachings of the present disclosure may provide a support or base for various components such as one or more of the following: IO devices and needles 1100, coupler assembly 1250, funnel 1080 and/or sharps protector 1064 to allow an operator or user to perform various functions without requiring that the operator or user hold or manipulate the respective component. For example medical procedure tray 1020c as shown in FIGS. 11A and 11B may position and support coupler assembly 1250 such that one end of a powered driver 1200 may be inserted (pushed) into releasable engagement with second end 1252 of coupler assembly 1250. The powered driver 1200 may then be used to withdraw coupler assembly 1250 from medical procedure tray 1020c without requiring an operator or user to directly hold or manipulate coupler assembly 1250.

Figure 11C:
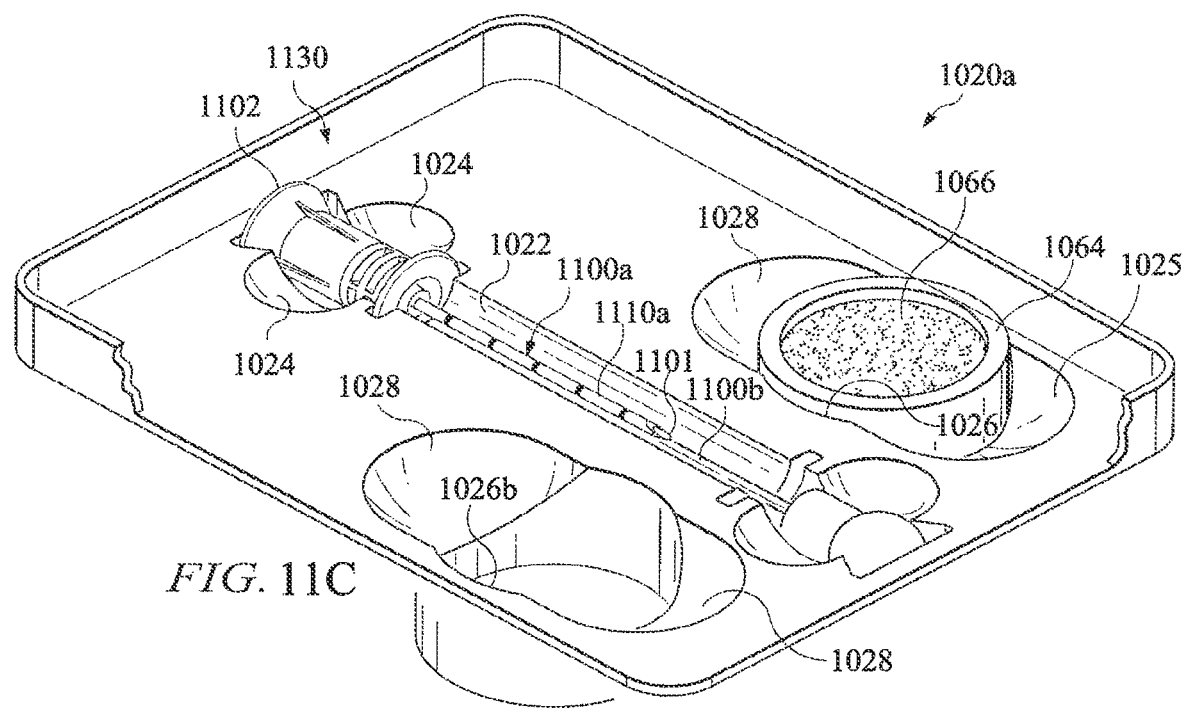
FIG. 11C is a schematic drawing showing an isometric view of one example of a medical procedures tray comprising an intraosseous needle set depicting details of the tray incorporating teachings of the present disclosure.
Figure 11D:
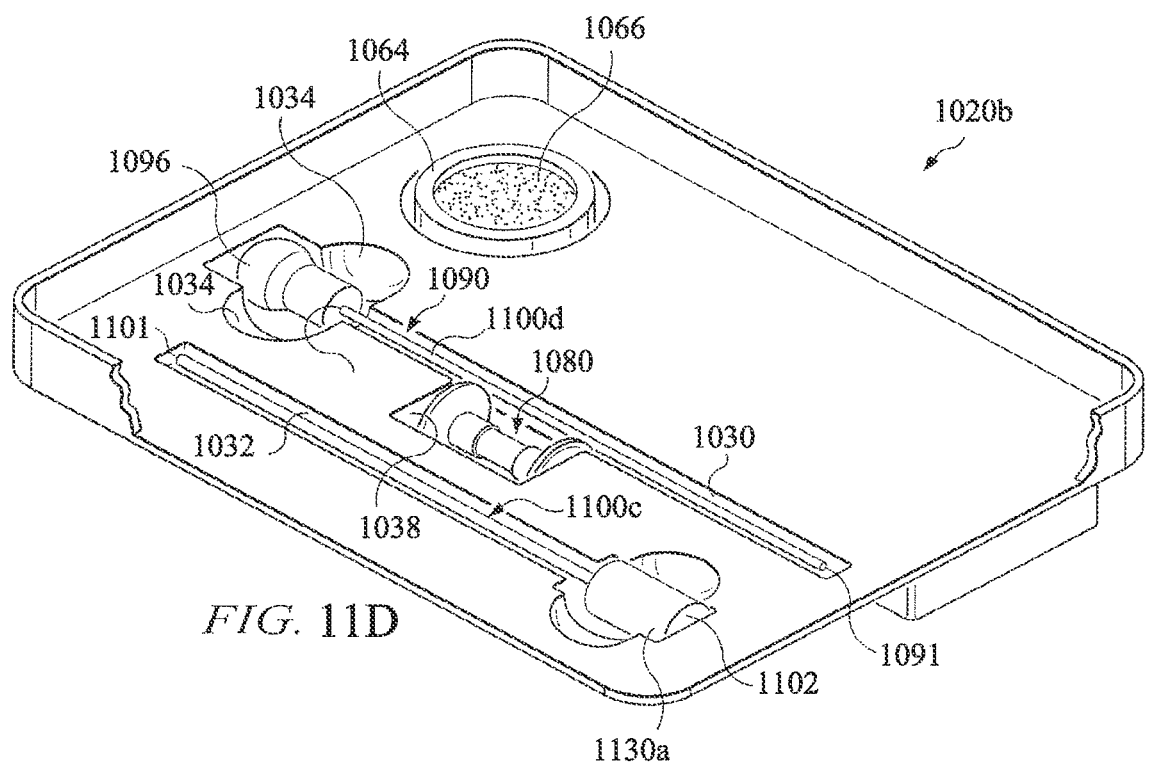
FIG. 11D is a schematic drawing showing an isometric view of one example of a medical procedures tray comprising an intraosseous biopsy needle set depicting details of the tray incorporating teachings of the present disclosure.
Figure 11E:
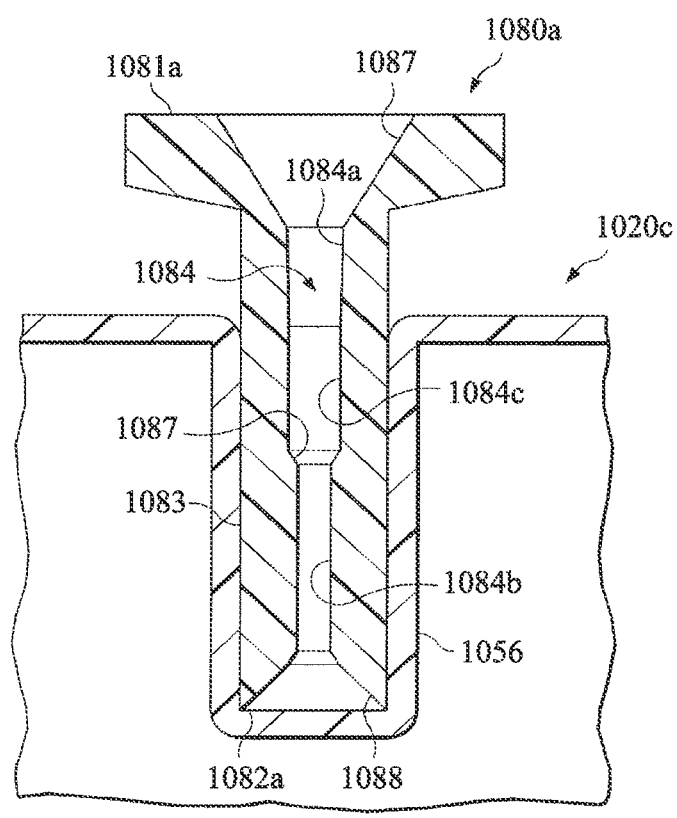
FIG. 11E is a schematic drawing in section with portions broken away showing one example funnel of a medical procedures tray incorporating the teachings of the present disclosure.

FIG. 11E depicts a detailed structure of funnels 1080 of FIGS. 11A, 11B, 11C and 11D. Funnel 1080a, as in FIG. 11E, may be positioned and supported within medical procedure trays 1020a or 1020b such that one end of an intraosseous device may be inserted (pushed) into funnel 1080a. Funnel 1080a may be withdrawn from medical procedure tray 1020a and/or 1020b without requiring that an operator or user directly hold or manipulate funnel 1080a.

Funnel 1080a may be slidably disposed in holder 1056 in medical procedure tray 1020a in a generally vertical position. See FIGS. 11A, 11B, 11C and 11D. As a result, first end 1081a of funnel 1080a may be oriented in a position to allow inserting one end of IO biopsy needles such as the cannula depicted herein as 1100a or 1100c therein. Longitudinal passageway 1084 proximate first end 1081a may include a sticking tapered portion operable to maintain contact with one end of an IO set such as the outer cannula 1100a or 1100c. An IO needle set or cannula may then be manipulated to pull funnel 1080a from holder 1056. Funnel 1080a may serve as a sharps protector for the one end of an intraosseous device inserted therein.

For some applications, funnels formed in accordance with teachings of the present disclosure may include a respective first opening formed at a first end and a respective second opening at a second end of the funnel. The first opening and the second opening may have different inside diameters. For example, the first opening may be sized to accommodate inserting an IO needle, a vertebral needle and/or a biopsy needle therein while the second opening may have a reduced inside diameter which prevents inserting the needle therein. The second opening may be sized to only accommodate one end of an associated ejector rod. For some applications, a longitudinal passageway may extend between the first end and the second end of the funnel. Tapered surfaces may be formed within the longitudinal passageway adjacent to the first end. The tapered surfaces may function as a "one way" connector such that when an IO needle, a vertebral needle, and/or an IO biopsy needle is inserted therein, the funnel will be securely engaged with the first end of the needle. The funnel may then function as a sharps protector for the first end of the needle.

Each sharps protector 1064 may also be positioned and supported within medical procedure trays 1020a and/or 1020b to allow inserting (pushing) one end of an intraosseous device or any other medical device requiring sharps protection into sharps protector 1064 without requiring that an operator or user to directly hold or manipulate the associated sharps protector 1064. Medical procedure trays 1020, 1020a, 1020b, 1020c, coupler assemblies 1250 and other components formed in accordance with teachings of the present disclosure may substantially reduce the number of opportunities for an accidental "needle stick" and/or dropping, contaminating or other problems associated with handling and manipulating various components disposed within an associated medical procedure tray.

Medical procedure trays and kits formed in accordance with teachings of the present disclosure may have a wide variety of configurations and/or dimensions. For some applications, a kit holding intraosseous devices in accordance with teachings of the present disclosure may have an overall length of approximately four and one-half inches, a width of approximately three inches and a depth of approximately two inches. Various heat sealing techniques may be satisfactorily used to place a removable cover (not expressly shown) over a medical procedure tray or kit incorporating teachings of the present disclosure.

Sharps protectors 1064 may include hard foam or claylike material 1066 disposed therein. Intraosseous devices such as vertebral needle sets, other IO needle sets, aspiration needle sets and biopsy needle sets typically have respective sharp tips and/or cutting surface operable to penetrate skin, soft tissue and bone. The sharp tips and/or cutting surface of such intraosseous devices may be inserted into hard foam or claylike material 1066 after completion of a medical procedure using the respective intraosseous device.

For some applications, medical procedure tray 1020 or 1020a may be referred to variously as a "vertebral procedure tray," and/or "vertebroplasty tray," and/or a "tray for providing access to deliver therapeutic agents to bone," and/or a "therapeutic and diagnostic procedures tray." For some applications, medical procedure tray 1020b may sometimes be referred to as "bone and/or bone marrow biopsy procedure trays" or "biopsy procedure trays" or "bone marrow biopsy kits." For some applications, medical procedure tray 1020a may be referred to as a "bone marrow aspiration tray," "aspiration procedure tray" or "bone marrow aspiration kit".

For some applications, medical procedures tray 1020c may be referred to as "coupler assembly tray" or "sterile glove tray."

Medical procedure trays 1020a, 1020b and/or 1020c may be formed from various polymeric materials compatible with sterile packaging and storage of various components disposed within each medical procedure tray. For some applications ethylene oxide sterilization techniques may be used during assembly and packaging of medical procedure trays 1020a, 1020b and 1020c. However, other sterilization procedures may be used as appropriate.

In some embodiments, medical procedures trays of the disclosure may be stored at temperatures ranging from between about −20° C. to about 50° C.

Respective covers (not expressly shown) may be placed over each medical procedure tray 1020a, 1020b and 1020c as part of an associated sterilization and packaging process. Such covers may be removed prior to use of various components disposed within each medical procedure tray. A respective cover 1002 may be placed on the main tray 1020 that comprises two or more of trays 1020a, 1020b and/or 1020c.

Medical procedure tray, vertebroplasty tray, vertebral procedure tray, diagnostic and therapeutic tray, or tray for providing a medicament to a bone, 1020a (see FIG. 11C) may include elongated slot 1022 with appropriate dimensions for an associated intraosseous device such as, but not limited to, IO needle set 1100, or 1100a and 1100b. The dimensions and configuration of slot 1022 may be selected to accommodate the combined length of hub assembly 1130 and cannula 110a extending therefrom. One end of slot 1022 may be sized to accommodate the dimensions and configuration of hub assembly 1130. Enlarged openings or finger slots 1024 may also be provided to accommodate inserting and removing IO needle set 1100 from slot 1022. Various details associated with IO needle set 1100 will be discussed later with respect to FIG. 16A-18E.

In FIGS. 11C and 11D, sharps protector 1064 may be disposed within holder 1026 of medical procedure tray 1020a or 1020b. A pair of finger slots 1028 may also be formed in tray 1020a or 1020b to accommodate inserting and removing sharps protector 1064 from holder 1026a. Holder 1026b may also be formed in tray 1020a along with associated finger slots 1028. An additional sharps protector or other components may be disposed within holder 1026b. The dimensions/configurations of slot 1022 and holders 1026a and 1026b may be varied as desired for respective components which will be disposed therein.

Medical procedure trays 1020b (See FIG. 11D) may include elongated slots 1030 and 1032. The dimensions and configuration of elongated slot 1030 may be selected to accommodate placing ejector 1110d therein. The dimensions and configuration of elongated slot 1032 may be selected to accommodate placing an intraosseous device such as a biopsy system with biopsy needle set 1100c and 1100d therein (as depicted) or an aspiration system with an aspiration needle (not depicted).

One end of elongated slot 1030 may have configuration and dimensions selected to accommodate the configuration and dimensions of handle 1096 disposed on second end 1092 of injector rod 1100d (See FIG. 11D). A pair of finger slots 1034 may be formed as part of elongated slot 1030 to allow installing and removing ejector 1100d. One end of elongated slot 1032 may be operable to accommodate the configuration and dimensions associated with hub assembly 1130a of IO biopsy needle set 1100c. A pair of finger slots 1036 may also be provided as part of elongated slot 1032 to accommodate inserting and removing IO biopsy needle set 1100c from elongated slot 1032.

Tray 1020b may also include holder 1038 disposed adjacent to elongated slot 1030. Holder 1038 may have a configuration and dimensions compatible with releasably placing funnel 1080 therein. One or more specimen or sample containers or cups (not expressly shown) may be provided in biopsy tray 1020b. Biopsy specimen or sample containers may include a cavity sized to receive a biopsy specimen from biopsy needle set 1100c and 1100d. Funnel holders 1038 may be formed in biopsy procedure tray 1020b adjacent to ejector 1100d to ensure that funnel 1080 is readily available to assist with removing a biopsy specimen from biopsy needle set 1100d.

Figure 12A:
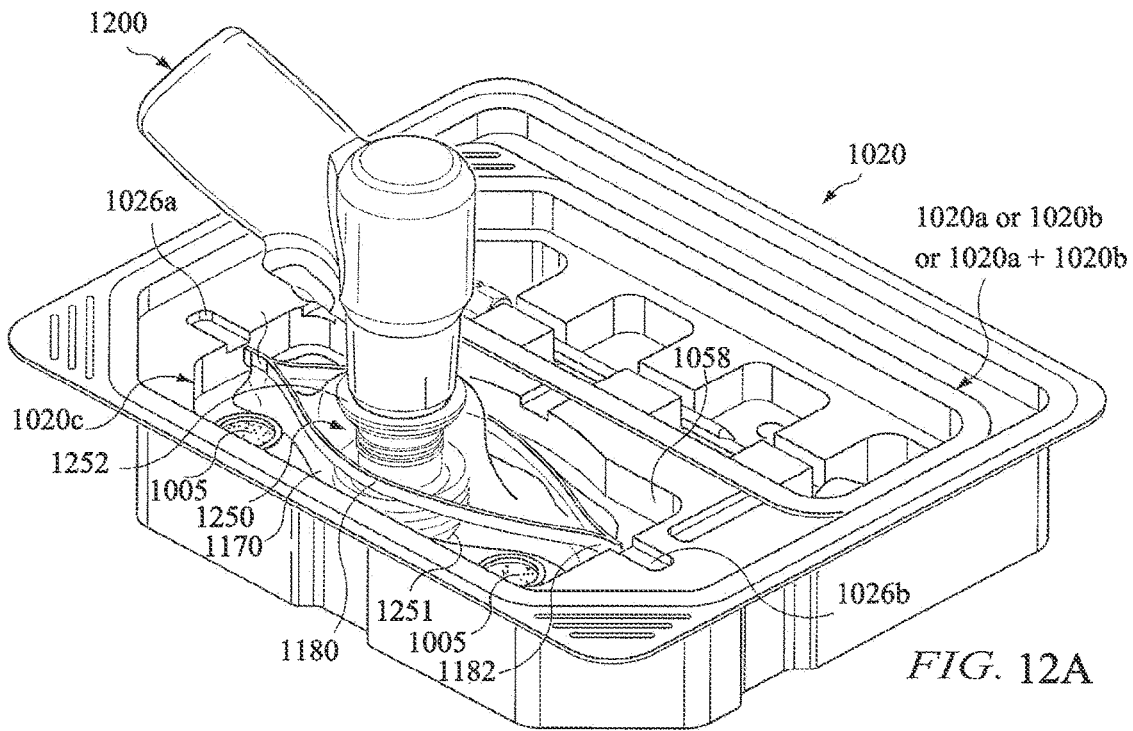
FIG. 12A is a schematic drawing showing an isometric view of one example of a medical procedure tray that may include an intraosseous needle set and/or a biopsy needle set enclosed, each optionally enclosed in a separate tray, and a coupler assembly attached to a sterile container bag disposed in another tray, the coupler operable to be releasably attached to a powered driver (one example of a non-sterile medical device) as depicted in accordance with teachings of the present disclosure.
Figure 12B:
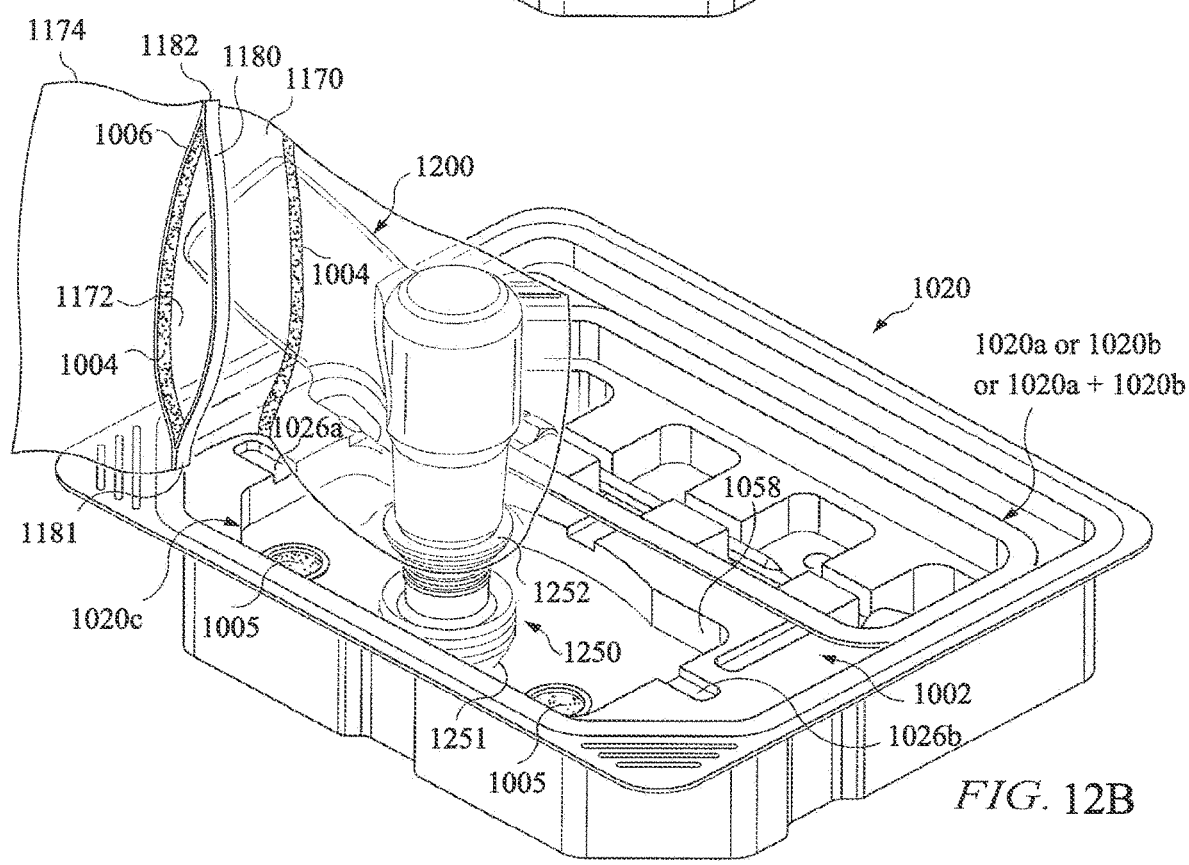
FIG. 12B is a drawing of a medical procedures tray showing one example of a sterile container bag with a non-sterile powered driver disposed therein and the driver attached releasably to a sterile coupler assembly in accordance with teachings of the present disclosure.

Medical procedure trays 1020 as shown in FIGS. 12A and 12B represent other example of a medical procedure tray formed in accordance with teachings of the present disclosure. FIGS. 12A and 12B depict trays that comprise medical procedure tray 1020c and either trays 1020a and 1020b; or 1020c and 1020a or 1020b. Containment bag 1170 and power driver 1200 are also shown. FIG. 12B shows power driver 1200 being enclosed in containment bag 1170. Containment bag 1170 may comprise a flexible stay 1180, a flap 1174, and may further comprise an adhesive strip 1004 all of which may be used to contain a non-sterile power driver 1200 and prevent contamination of IO devices, IO needles or coupler by the non-sterile power driver. Containment bag 1170 may also prevent contamination of the power driver 1200 by pathogens in bodily fluids that may leak out during a medical procedure. The configuration and dimensions of flexible stay 1180 may be selected to accommodate inserting and removing a powered driver or other non-sterile medical device therefrom.

A combined medical procedure tray(s) (such as 1020 in FIG. 11A or 1020 in FIG. 11B) may be sterilized after being assembled. One benefit of such sterilization may include, but is not limited to, providing a sterilized containment bag which may be used to engage a non-sterile medical device with a sterile medical device in accordance with teachings of the present disclosure.

One of the benefits of the present disclosure may include being able to releasably engage one end 1211 of a powered driver 1200 with one end 1252 of a coupler assembly 1250, releasably engage one end 1102 of an IO needle 1100 (such as a vertebral needle or a biopsy needle) with an opposite end 1251 of the coupler assembly 1250, insert "power in" another end 1101 of the IO needle 1100 into a selected target area, deliver one or more medicaments into the target area using one or more components of an IO device or needle set 1100, "power out" the 10 needle 1100 with a high degree of confidence that a specimen (such as a biopsy sample) will be disposed therein and insert the other end 1101 of the IO needle into a funnel to provide both sharps protection and removal/storage of the specimen. Any direct contact between an operator and the IO needle may be limited to pushing one end of the IO needle into a respective end of the coupler assembly.

Another benefit of the present disclosure is to insert "power in" a first IO needle (such as a cannula) into a bone to provide access to the bone followed by slidably inserting a second 10 needle (such as a trocar) into the first IO needle. The second needle may be operable to deliver a therapeutic agent to bone or may be operable to obtain a specimen from bone. The second needle may be slidably removed from the first IO needle. In one example, a second needle may be a biopsy needle that may be inserted into the cannula of a first needle to obtain a biopsy and slidably removed after the sample is obtained. Another needle, a third IO needle (a trocar) operable to deliver a therapeutic agent may then be slidably inserted into the first needle (cannula) and a therapeutic agent may be delivered. Multiple needles may be inserted for different diagnostic/therapeutic purposes repeatedly through the first cannula needle without the need for multiple insertions into bone. Upon completion of the medical procedures the first needle may then be "powered out". In some embodiments, the medical procedure devices and trays and methods of the present disclosure may be used to perform multiple procedures with one insertion into the bone.

A pair of holders or clamps 1026, 1026a, 1026b (FIGS. 12A and 12B) may also be formed in medical procedure tray 1020c adjacent to holder for coupler assembly 1250. Such clamps 1026a and 1026b may be designed to respectively accommodate first end 1181 and second end 1182 of flexible stay 1180 disposed on opening 1172 of containment bag 1170. Coupler assembly 1250 may also be installed in holder 1058 of coupler assembly tray 1020c with first end 1251 down and second end 1252 looking up. FIGS. 12A and 12B shows a power driver 1200 being placed on second end 1252 of a coupler assembly 1250 in exemplary tray 1020, where exemplary tray 1020 comprises tray 1020c as described above and may comprise trays 1020a and 1020b or tray 1020a or may even comprise a tray 1020d (not depicted). FIG. 12B depicts a raised bag 1170 covering powered driver 1200, showing features of the containment bag 1170 including flap 1174, opening 1172, flexible stay 1180, respective ends 1181 and 1182 of the flexible stay, and adhesive strip 1004 in an exemplary medical procedures tray as described earlier in this paragraph. However, the present disclosure is not limited to using flaps and adhesive materials to close an opening in a containment bag and other means may be used to close and seal a containment bag.

FIGS. 13A-13C illustrate one procedure for placing a powered driver 1200 within containment bag 1170 incorporating teachings of the present disclosure. Containment bag 1170 may be formed from generally flexible, fluid impervious material such as a plastic, which may also be sterilized using conventional sterilization techniques. Containment bag 1170 may be used to prevent a non-sterile powered driver 1200 from contaminating a sterile intraosseous device 1100 and/or a patient, particularly during an IO therapeutic and/or IO diagnostic procedure. Containment bag 1170 may be operable to form a fluid barrier with adjacent portions of housing assembly 1270 of coupler assembly 1250. At the same time, coupler assembly 1250 may allow powered driver to rotate an intraosseous device 1100 releasably engaged with first end 1251 of coupler assembly 1250 without damage to containment bag 1170.

A non-sterile person (not expressly shown) may next insert power driver 1200 into coupler assembly 1250 and extend containment bag 1170 (FIGS. 13A-13C). First end 1181 and second end 1182 of flexible stay 1180 may be removed from respective clamps or holders in medical procedure tray 1020c to allow manually lifting second opening 1172 upwardly relative to powered driver 1200. See FIGS. 12A-12B and 13A-13C. Containment bag 1170 may continue to be raised to a fully extended position with powered driver 1200 disposed therein. See FIG. 13B. Flap 1174 may then be placed over second opening 1172 and further sealed using the adhesive strip 1004 proximate 1172. Containment bag 1170 with powered driver 1200 disposed therein and coupler assembly 1250 may then be removed from holder 1058 of medical procedure tray 1020c (FIGS. 12A-12B). Various commercially available low strength adhesive materials may be satisfactorily used to provide releasable engagement between flap 1174 proximate opening 1172 of containment bag 1170.

Housing assembly 1270 and/or housing segments 1280 and 1290 of coupler assembly 1250 may remain relatively stationary during rotation of elongated core 1260. In some embodiments, spinner 1010 may be rotated for insertion and securing of IO device at end 1251. See FIGS. 13A-13C and 14A-14B. For example portions of housing assembly 1270 such as flange 1254 extending from second end 1252 of coupler assembly 1250 may be attached to containment bag 1170 and remain relatively stationary while powered driver 1200 rotates elongated core 1260 and IO needle set 1100 extending therefrom.

For some applications, powered driver 1200 may be directly placed into a containment bag 1170 and engaged with coupler assembly 1250. For other applications, a non-sterile powered driver may be inserted into containment bag 1170 in connection with removing coupler assembly 1250 from a medical procedure tray.

For some applications, a protective cover (not expressly shown) may be removed from medical procedure tray 1020c. End 1224 extending from drive shaft 1222 of powered driver 1200 may then be inserted through opening 1172 of containment bag 1170 and releasably engaged with second end 1252 of coupler assembly 1250 (see FIG. 14C and FIGS. 13A-13C).

Typical procedures associated with using a medical procedure tray or kit incorporating teachings of the present disclosure may include the following steps. Medical procedure tray 1020 may be placed at a desired location for performing an associated medical procedure. For example medical procedure tray 1020 may be placed on a table or cart adjacent to a surgical table on which a bone therapeutic procedure, a vertebral procedure, a bone or bone marrow biopsy procedure, and/or a bone marrow aspiration procedure may be performed.

An associated cover 1002 may be removed from medical procedure tray 1020 by a sterile person. A non-sterile person may then pick up and insert non-sterile powered driver 1200 into flexible stay 180 such as shown in FIG. 13A. End 1224 of drive shaft 1222 of powered driver 1200 may "snap" into place within second end 1252 of coupler assembly 1250. A sterile person may then lift containment bag 1170 up and over powered driver 1200 (as shown in FIG. 13B), and fold flap 174 over to secure with adhesive strip 1004 which will result in containing the power driver 1200 (not expressly shown).

The sterile person may then grasp handle 1214 of powered driver 1200 through containment bag 1170 and lift powered driver 1200 with coupler assembly 1250 attached thereto from holder 1058 disposed in tray 1020c. The sterile person may then remove an intraosseous (IO) device/needle 1100 from medical procedure trays 1020a or 1020b and insert second end 1102 of IO device/needle 1100 into first end 1251 of coupler assembly 1250. A "snap" may be felt when second end 1102 of IO device/needle 1100 (or any other intraosseous device incorporating teachings of the present disclosure) is releasably latched within first end 1251 of coupler assembly 1250. A needle safety cap (not expressly shown) may be removed from first end 1101 of IO needle 1100 after releasably engaging second end 1102 with first end 1251 of coupler assembly 1250.

Powered driver 1200 disposed within containment bag 1170 along with coupler assembly 1250 and IO needle 1100 extending there from may be held in one hand while a sterile person identifies the insertion site with the other hand.

Powered driver 1200 may be positioned over the insertion site to introduce first end 1101 of IO needle set 1100 through the skin in the direction and towards the bone. Upon contact with the bone the operator may squeeze button or trigger 1246 and apply relatively steady gentle pressure to handle 1214 of powered driver 1200. Upon penetration of the bone cortex, the operator may release trigger 1246 to stop further insertion of first end 1101 of IO needle 1100.

First housing segment 1280 may then be activated to release second end 1102 of 10 needle 1110a from engagement with coupler assembly 1250. Second hub 1150a may then be rotated counterclockwise to disengage second hub 1150a and associated stylet 1120 from first hub 1140a. See FIGS. 15A-15B and 16A-16C. Stylet 1120 may then be pulled out and removed from IO needle or cannula 1111a. First end 1121 of stylet 1120 (FIG. 16C) may then be inserted into sharps protector 1064 of medical procedure tray 1020. Upon completion of an appropriate IO procedure second hub 1150a may be reengaged with first hub 1140a (see FIGS. 16A and 16B). First end 1251 of coupler assembly 1250 may then be reengaged with second end 1102 of IO needle set 1100a to rotate or spin IO needle set 1100a while withdrawing from the insertion site. After removal from the insertion site, second end 1102 of IO needle set 1100a may be disengaged from coupler assembly 1250. First end 1101 of IO needle set 1100a may then be inserted into sharps container 1064.

In general, after completion of a bone related medical procedure, such as vertebroplasty, other spinal procedures, delivery of a medicament to a bone, a bone marrow aspiration procedure, a bone and/or bone marrow biopsy procedure and/or other medical procedures using an IO device 1100, the sharp end or sharp tip of all components of the intraosseous device may be inserted into material 1066 in sharp protector 1064 for further disposal in accordance with the appropriate procedures.

Powered driver 1200 as shown in FIGS. 13A-13C, and 14A-14C may be satisfactorily used to insert an intraosseous device incorporating teachings of the present disclosure into a bone and associated bone marrow. However the disclosure is not limited to this particular power driver and any power driver may be used to practice the present embodiments.

Powered driver 1200 may include housing 1210 having a general configuration similar to a small pistol defined in part by handle 1214. Various components associated with powered driver 1200 may be disposed within housing 1210 including handle 1214. For example a power source such as battery pack 1216 may be disposed within handle 1214. Battery pack 1216 may have various configurations and dimensions. Battery pack may comprise a lithium chloride battery.

Housing 1210 including handle 1214 may be formed from relatively strong, heavy duty polymeric materials such as polycarbonates or other satisfactory materials. For some applications housing 1210 may be formed in two halves (not expressly shown) which may be joined together with a fluid tight seal to protect various components of powered driver 1200 disposed therein.

Motor 1218 and gear assembly 1220 may be disposed within portions of housing 1210 adjacent to handle 1214. Motor 1218 and gear assembly 1220 may be generally aligned with each other. Motor 1218 may be rotatably engaged with one end of gear assembly 1220. Drive shaft 1222 may be rotatably engaged with and extend from another end of gear assembly 1220 opposite from motor 1218. For some applications both motor 1218 and gear assembly 1220 may have generally cylindrical configurations.

Motors and gear assemblies satisfactory for use with powered driver 1200 may be obtained from various vendors. Such motor and gear assemblies may be ordered as "sets" with one end of each motor securely attached to an adjacent end of an associated gear assembly. A drive shaft having various dimensions and/or configurations may extend from the gear assembly opposite from the motor. Such gear assemblies may sometimes be referred to as "reduction gears" or "planetary gears". The dimensions and/or configuration of housing 1210 may be modified to accommodate an associated motor and gear assembly.

Distal end or first end 1211 of housing 1210 may include an opening (not expressly shown) with portions of drive shaft 1222 extending therefrom. For some applications end 1224 or the portion of drive shaft 1222 extending from first end 1211 of housing 1210 may have a generally hexagonal cross section with surfaces 1226 disposed thereon. Receptacle 1263 disposed in second end 1252 of coupler assembly 1250 may have a matching generally hexagonal cross section. See FIGS. 15A-15B.

Surfaces 1226 may extend generally parallel with each other and parallel with respect to a longitudinal axis or rotational axis (not expressly shown) associated with drive shaft 1222. One or more tapered surfaces 1228 may also be formed on end 1224 to assist with releasably engaging powered driver 1200 with coupler assembly 1250. See FIGS. 15A-15B. The end of a drive shaft extending from a powered driver may have a wide variety of configurations.

A drive shaft having desired dimensions and configuration may extend from the gear assembly opposite from the motor. The drive shaft may be provided as part of each motor and gear assembly set. The dimensions and/or configuration of an associated housing may be modified in accordance with teachings of the present disclosure to accommodate various types of motors, gear assemblies and/or drive shafts. For example, powered drivers used with vertebral IO needles, aspiration needles and/or biopsy needles may include gear assemblies with larger dimensions required to accommodate larger speed reduction ratios, for example between 60:1 and 80:1, resulting in slower drive shaft RPM's. Powered drivers used to provide intraosseous access during emergency medical procedures may operate at a higher speed and may include gear assemblies having a smaller speed reduction ratio, for example between 10:1 and 30:1, resulting in higher drive shaft RPM's. For some applications, the difference in size for gear assemblies may result in increasing the inside diameter of an associated housing by approximately two to three millimeters to accommodate larger gear assemblies associated with powered drivers used to insert vertebral IO needles, biopsy needles and/or aspiration needles.

Coupler assemblies having corresponding openings or receptacles may be releasably engaged with end 1224 extending from first end 1211 of powered driver 1200 or end 1224a extending from first end 1211 of powered driver 1200a. For example, end 1224 extending from first end 1211 of housing 1210 may be releasably engaged with receptacle 1264 disposed proximate second end 1252 of coupler assembly 1250 as shown in FIGS. 11A-11B, 12A-12B, 13A-13C and 15A-15D.

For some applications thrust bearing 1241 may be disposed between first end or distal end 1211 of housing 1210 and adjacent portions of gear assembly 1220. See FIG. 14C. Thrust bearing 1242 may be disposed between second end or proximal end 1212 of housing 1210 and adjacent portions of motor 1218. Thrust bearings 1241 and 1242 may limit longitudinal movement of motor 1218, gear assembly 1220 and drive shaft 1222 within associated portions of housing 1210.

Trigger assembly 1244 may also be disposed within housing 1210 proximate handle 1214. Trigger assembly 1244 may include trigger or contact switch 1246. See FIG. 14C. Motor 1218 may be energized and deenergized by alternately depressing and releasing trigger 1246. Electrical circuit board 1247 may also be disposed within housing 1210. Electrical circuit board 1247 may be electrically coupled with trigger assembly 1244, motor 1218, power supply 1216 and indicator light 1248.

For some applications indicator light 1248 may be a light emitting diode (LED) or a small more conventional light bulb. For some applications indicator light 1248 may be activated when ninety percent (90%) of electrical storage capacity of battery pack 1216 has been used.

The configuration and dimensions of an intraosseous device formed in accordance with teachings of the present disclosure may vary depending upon respective intended applications for each intraosseous device. For example, the length of a vertebral IO needle formed in accordance with teachings of the present disclosure may vary from approximately about 5 inches to about 10 inches. In one non-limiting example a vertebral IO needle may be about 6 inches (or 152 millimeters). However, vertebral needles with other lengths may also be made in accordance with the teachings of this disclosure.

The length of a biopsy needle formed in accordance with teachings of the present disclosure may vary from approximately five (5) millimeters to thirty (30) millimeters. However, biopsy needles having other lengths may also be formed in accordance with teachings of the present disclosure.

Aspiration needles formed in accordance with teachings of the present disclosure may have lengths of approximately twenty five (25) millimeters, sixty (60) millimeters and ninety (90) millimeters. For some applications an aspiration needle having a length of ninety (90) millimeters or more may also include one or more side ports. See for example FIGS. 16A-16C.

Further details about IO biopsy systems and needle sets and IO aspirations systems may be found in U.S. patent application Ser. No. 11/853,678 filed on Sep. 11, 2007 (now U.S. Pat. No. 8,668,698).

Intraosseous (IO) devices formed in accordance with teachings of the present disclosure may have outside diameters and longitudinal bores or lumens corresponding generally with eighteen (18) gauge to ten (10) gauge needles. For example, a vertebral IO needle may have a cannula with an eight (8) gauge to eleven (11) gauge diameter while an biopsy needle that may be inserted inside the vertebral cannula may have a diameter of fifteen (15) gauge to sixteen (16) gauge. The configuration and dimensions of each IO device may depend upon the size of an associated bone and desired depth of penetration of associated bone marrow. In one specific non-limiting example, a vertebral IO needle set may comprise a beveled cutting tip and a stylet and may be an 11 gauge, 152 millimeter needle, made of 304 stainless steel.

Combining a powered driver with a coupler assembly and a vertebral needle set in accordance with teachings of the present disclosure may allow rapid access to the vertebral or spinal bones or other insertion sites. Vertebral access systems incorporating teachings of the present disclosure may be capable of inserting a vertebral needle to a desired depth in cancellous bone in ten (10) to fifteen (15) seconds. This same capability may be used to obtain bone marrow using the bone marrow aspiration systems as well as biopsy specimen of bone and/or bone marrow using the biopsy needles of the present disclosure.

Figure 16A:
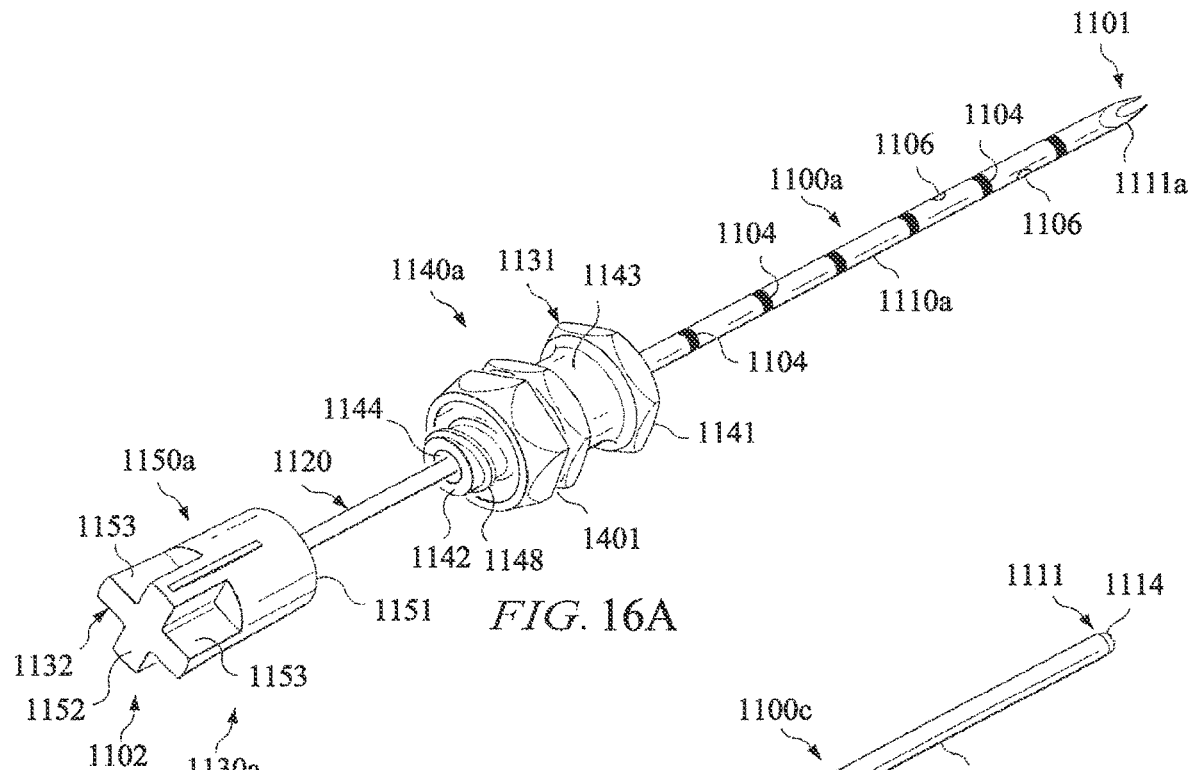
FIG. 16A is a schematic drawing showing an exploded of one example of an intraosseous needle incorporating teachings of the present disclosure.
Figure 16B:
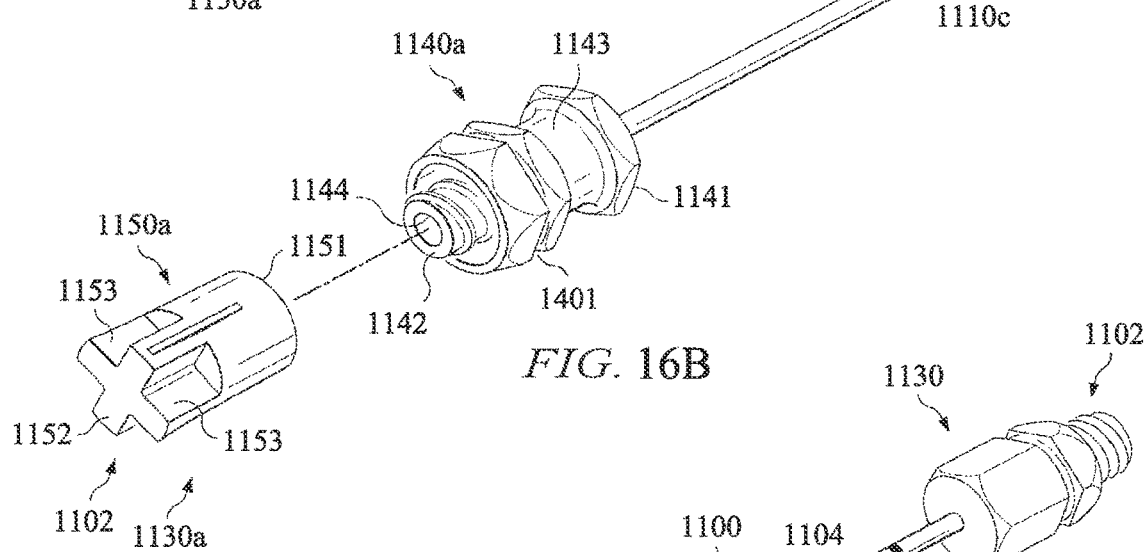
FIG. 16B is a schematic drawing showing an isometric view of an intraosseous biopsy needle incorporating teachings of the present disclosure.
Figure 16C:
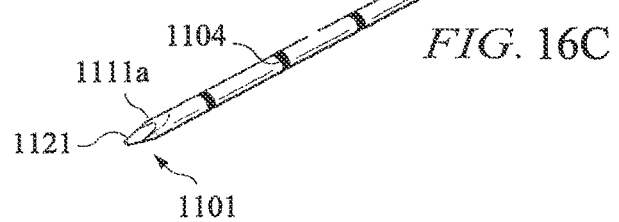
FIG. 16C is a schematic drawing showing an isometric view of another intraosseous needle incorporating teachings of the present disclosure.

Intraosseous (IO) needle sets, such as vertebral IO needles 1100a and 1100b, biopsy needles 1100c and 1100d and aspiration needle 1100e as shown in FIGS. 11A-11B and/or FIGS. 16A-16C represent only some examples of intraosseous devices formed in accordance with teachings of the present disclosure. All the IO needles may have similar outer penetrators or cannulas 110a and similar inner penetrators to stylets 1120. See FIGS. 16A-16C. Similar or different hub assemblies 1130 or 1130a may be used.

For embodiments represented by IO needle sets 1100 and 1100a, first end 1111a of cannula 1110a and first end 1121 of stylet 1120 may be operable to penetrate a bone and/or associated bone marrow. Various features of first end 1111a of cannula 1110a and first end 1121 of stylet 1120 are shown in more detail in FIGS. 17A-17F. First end 1101 of IO needle sets 1100 and 1100a may correspond generally with first end 1111a of cannula 1110a and first end 1121 of stylet 1120.

Cannula 1110a may have a plurality of markings 1104 disposed on exterior portions thereof. Markings 1104 may sometimes be referred to as "positioning marks" or "depth indicators." Markings 1104 may be used to indicate the depth of penetration of the IO needle set 1100 or 1100a into a bone (e.g. vertebral bone) and/or associated bone marrow. For some applications cannula 1110a may have a length of approximately sixty (60) millimeters and may have a nominal outside diameter of approximately 0.017 inches corresponding generally with a sixteen (16) gauge needle. In some applications, a cannula 1110a may be an 8-11 gauge needle and an inner trocar such as a biopsy or cement trocar may be a 15-16 gauge needle. Cannula 111a may be formed from stainless steel or other suitable biocompatible materials. Positioning marks 1104 may be spaced approximately one (1) centimeter from each other on exterior portions of cannula 1110a.

Hub assembly 1130 as shown in FIGS. 16A-16C may be used to releasably dispose stylet 1120 within longitudinal bore or lumen 1118 of cannula 1110a. Hub assembly 1130 may include first hub 1140 and second hub 1150. The second end of cannula 1110a, opposite from first end 111a, may be securely engaged with the second end of cannula 1110a. The second end of stylet 1120, opposite from first end 1121, may be securely engaged with the first end of hub 1150.

As shown in FIG. 16A cannula 1110a may extend longitudinally from first end 1141 of hub 1140. Stylet 1120 may also extend from the first end of hub 1150 (not expressly shown). The second end of hub 1140 may include a standard Luer lock fitting which may be releasably engaged with a corresponding Luer lock fitting disposed within the first end of second hub 1150. Threaded connections may be present between the second end of first hub 1140 and the first end of second hub 1150 (not expressly shown). Examples of Luer lock connections and/or fittings are shown in more detail in FIGS. 16A-16C. The Luer lock fitting disposed on the second end of hub 1140 may be operable to be releasably engaged with a standard syringe type fitting and/or a standard intravenous (IV) connection.

Hub 1150 includes second end 1152 which generally corresponds with second end 1132 of hub assembly 1130 and second end 1102 of IO needle set 1100. Hub 1140 may include first end 1141 which may generally correspond with first end 1131 of hub assembly 1130. Cannula 1110a may extend longitudinally from first end 1141 of hub 1140 and first end 1131 of hub assembly 1130.

Figure 14A:
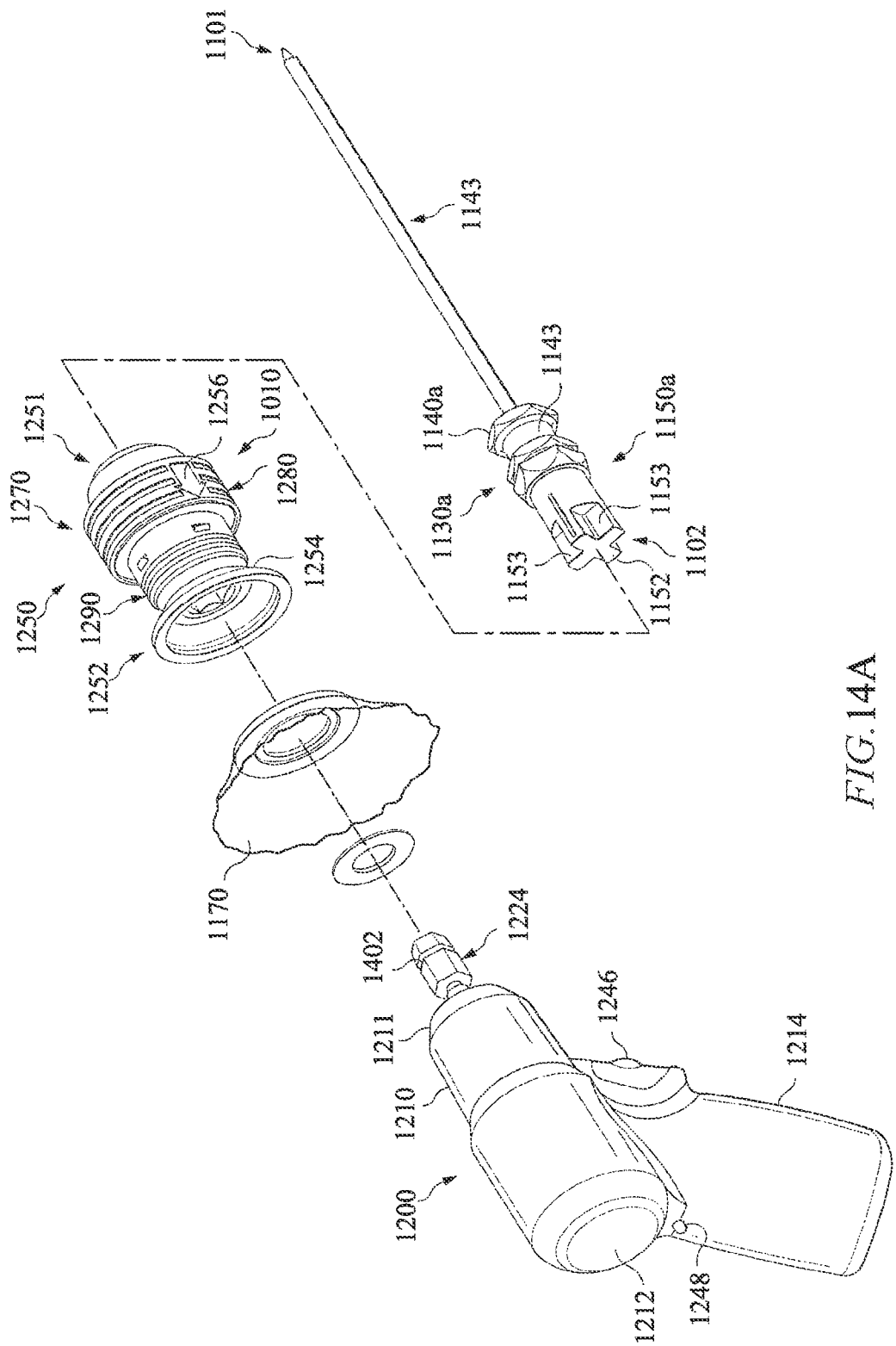
FIG. 14A is a schematic drawing showing an exploded, isometric view of a powered driver, coupler assembly with a sterile bag and an intraosseous device incorporating teachings of the present disclosure.
Figure 14B:
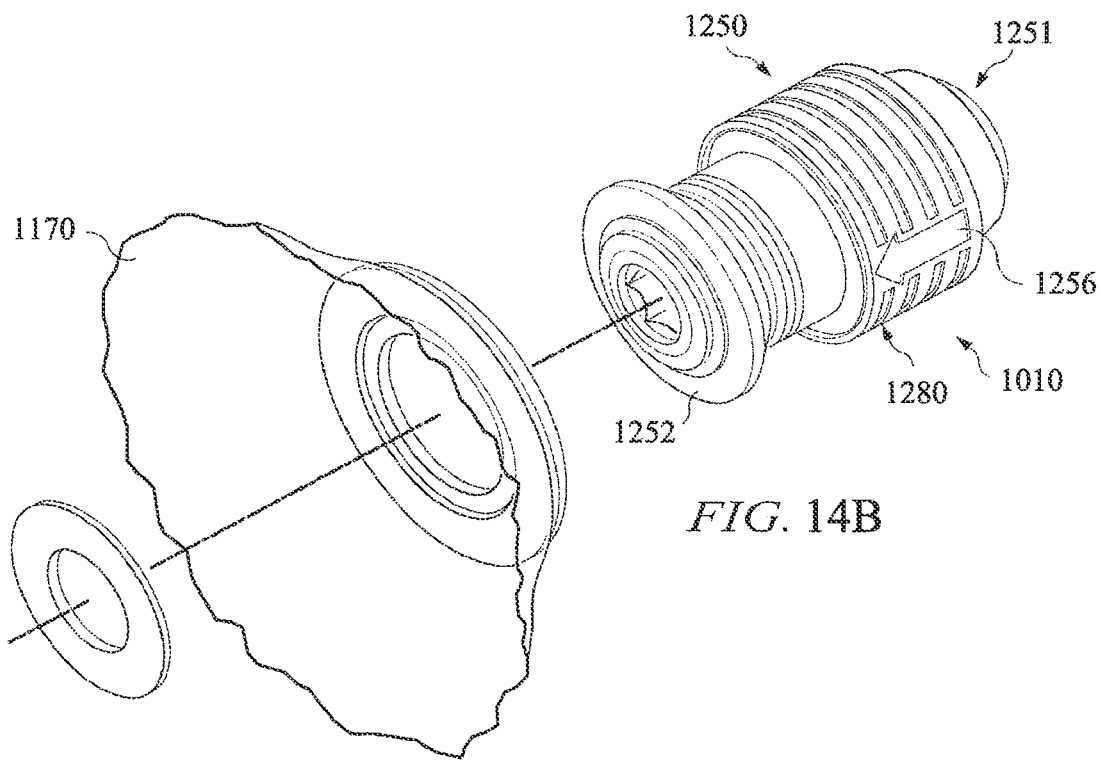
FIG. 14B is a schematic drawing showing another exploded, isometric view of the coupler assembly with the sterile bag of FIG. 14A incorporating teachings of the present disclosure.
Figure 14C:
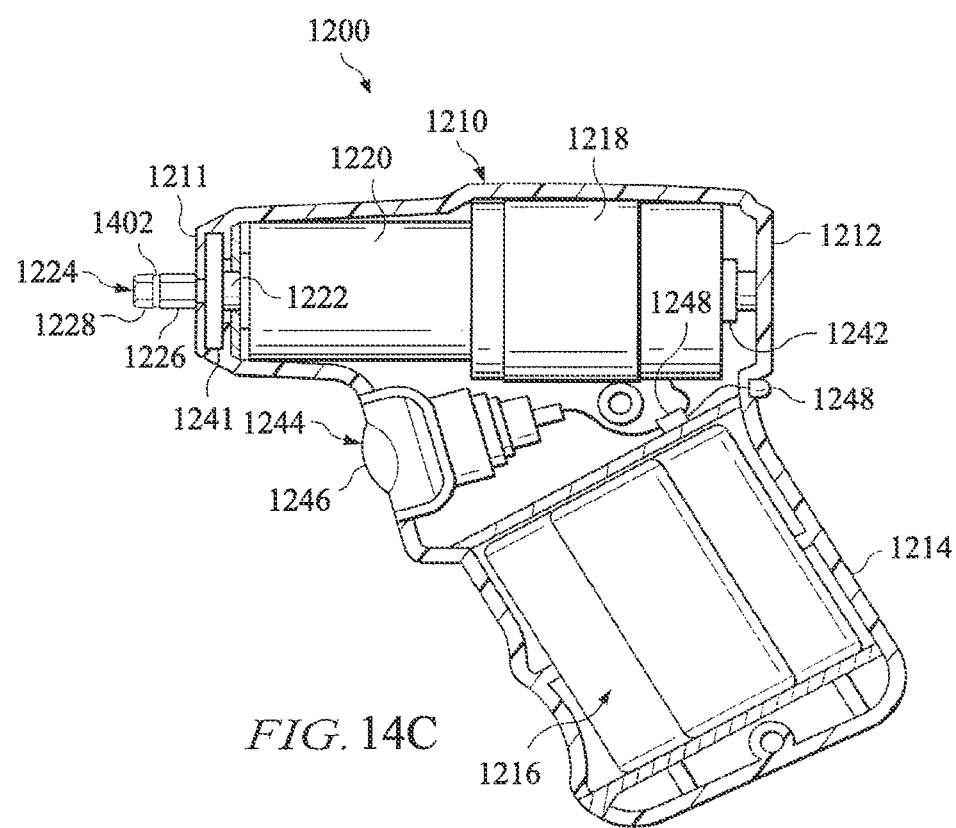
FIG. 14C is a schematic drawing showing one example of a powered driver operable for use with intraosseous (IO) devices incorporating teachings of the present disclosure.

Various types of receptacles may be satisfactory disposed in second end 1152 of hub 1150 for use in releasably engaging hub assembly 1130 with a powered driver. For example, a receptacle having a generally tapered configuration corresponding with the tapered configuration of one end of a drive shaft extending from a powered driver may be releasably engaged with second end 1152 of hub 1150. Powered driver 1200 as shown in FIGS. 14A-14C may represent one example of a powered driver having a drive shaft extending from a housing with a tapered portion operable to be releasably engaged with a receptacle having a corresponding generally tapered configuration. For some applications such powered drivers may be secured to an intraosseous device by a magnet (not expressly shown) disposed on the end of the tapered shaft extending from the powered driver and a metal disk disposed within a corresponding receptacle in the intraosseous devices. Such powered drivers may also be used with intraosseous devices used to obtain emergency vascular access (EVA).

Figure 15A:
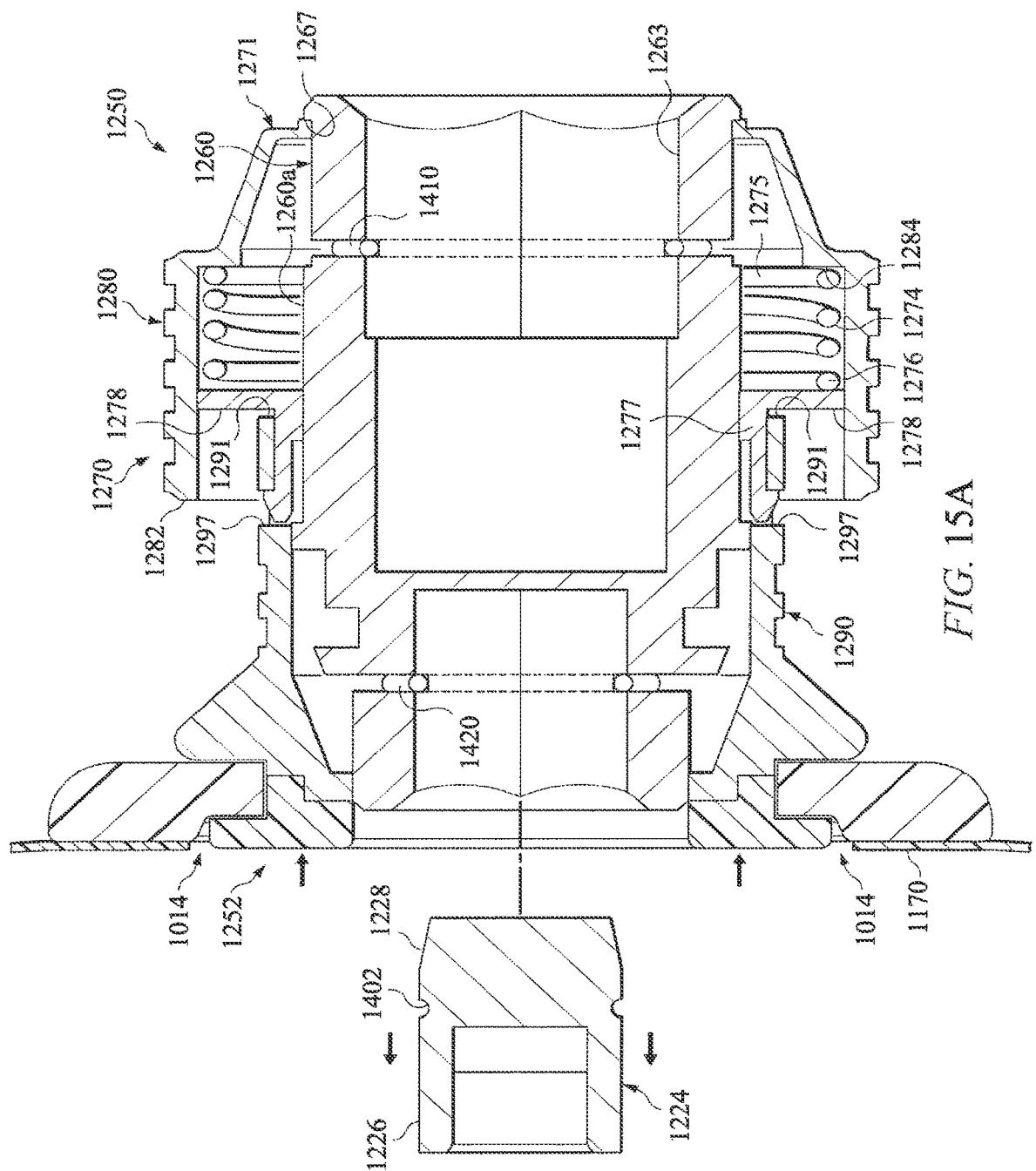
FIG. 15A is a schematic drawing in section with portions broken away showing a coupler assembly such as in FIGS. 14A and 14B in a second position showing release of a powered driver from a receptacle disposed in the first end of the coupler assembly and showing attachment of a sterile containment bag and a tortuous path disposed proximate attachment site of containment bag, incorporating the teachings of the present disclosure.
Figure 15B:
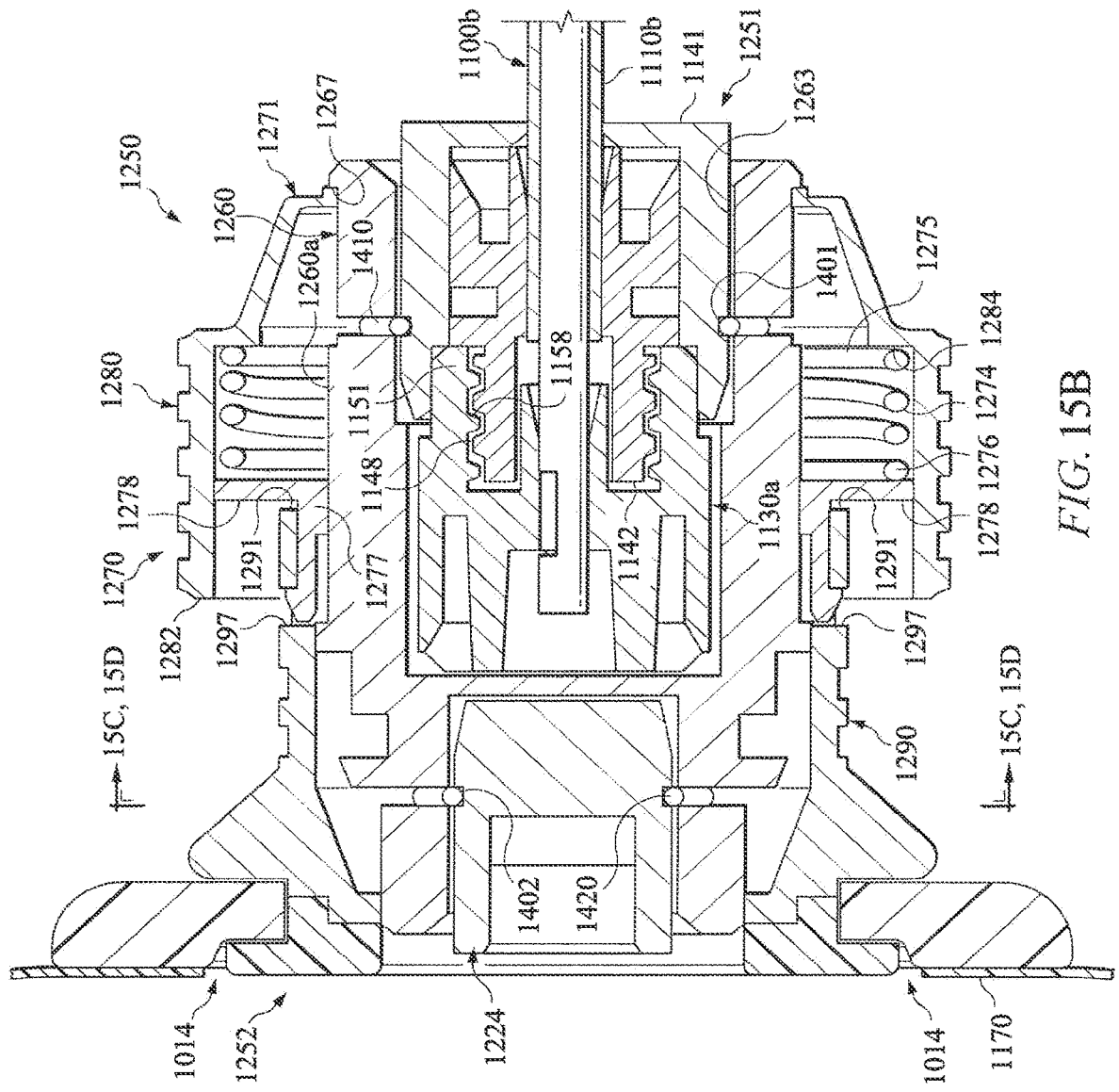
FIG. 15B is a schematic drawing in section with portions broken away showing another example of a coupler assembly incorporating teachings of the present disclosure.

The coupler assembly as depicted in FIGS. 15A and 15B depicts how containment bag 1170 is attached to the coupler. Containment bag 1170 is attached proximate end 1252 of the coupler. In some embodiments, the containment bag may be attached using a hot glue gun. However, a wide variety of attachment mechanisms such as but not limited to coupler assemblies, port assemblies, connectors, receptacles, fittings, hubs, hub assemblies, latching mechanisms and/or other types of connecting devices incorporating teachings of the present disclosure may be satisfactorily used to attach the container bag with the coupler assembly.

A "tortuous path" 1014 is defined proximate attachment of bag 1170 and the body of the coupler. A tortuous path 1014 may be a non-linear path such that bodily fluids that may contain bacteria, viruses or other pathogens cannot easily traverse to cause contamination of a sterile IO device attached at end 1251 of the coupler. A tortuous path may comprise sharp curves. If a pathogen falls into a part of the tortuous path the sharp curves and edges prevent the pathogen from reaching sterile surfaces on the other side.

For other embodiments, the second end of a hub assembly may be operable to be disposed within a receptacle formed in a coupler assembly incorporating teachings of the present disclosure. One feature of the present disclosure may include forming a hub assembly which may be releasably engaged within a first receptacle disposed in a first end 1251 of a coupler assembly 1250. See for example receptacle 1263 proximate first end 1261 of elongated core 1260 as shown in FIG. 15A-15D. The dimensions and configuration of receptacle 1263 may be selected to prevent rotation of hub 1150*a* relative to hub 1140*a* while inserting (rotating) an IO device into a bone and associated bone marrow. The powered driver may be releasably engaged with a second receptacle disposed in a second end 1252 of the coupler assembly. See for example receptacle 1264 proximate second end 1262 of elongated core 1260 as shown in FIGS. 15A-15B.

At least one portion of hub assembly 1130*a* may have a generally hexagonal cross section operable to be received within the generally hexagonal cross section of receptacle 1264 disposed proximate first end 1251 of coupler assembly 1250. See FIGS. 15C and 15D. For some embodiments portions of first hub 1140*a* disposed adjacent to reduced outside diameter portion 1143 may have generally hexagonal cross sections. See FIGS. 16A and 16B. Various cross sections other than hexagonal may be satisfactorily used to releasably engage a powered driver with one end of a coupler assembly and an intraosseous device with an opposite end of the coupler assembly.

Aspiration needle sets may often include a trocar, stylet or penetrator in combination with an associated cannula, catheter or outer penetrator. However, biopsy needles formed in accordance with teachings of the present disclosure may or may not include a trocar, stylet or inner penetrator. For example, biopsy needle 1100*c* is shown in FIG. 16B attached to first end of hub 1140*a*. A stylet or inner penetrator is not attached to first end 1151 of hub 1150*a*.

For embodiments represented by biopsy needle 1100*c*, hub 1140*a* may be used to releasably engage biopsy needle 1100*c* in a receptacle formed in a coupler assembly incorporating teachings of the present disclosure. Hub 1150*a* may be attached to close of end 1141 of hub 1140*a*. However, for many applications hub 1140*a* without hub 1150*a* may be connected with one end of a coupler assembly in accordance with teachings of the present disclosure. Biopsy needle 1100*c* may be used to capture a biopsy specimen of a bone and associated bone marrow. Placing a trocar within biopsy needle 1100*c* may result in substantial damage to the bone specimen during penetration of the bone by the combined tips of the trocar and biopsy needle 1100*c*.

Hub 1140*a* may include second end 1142 with opening 1144 formed therein. Passageway 1146 may extend from second end 1142 towards first end 1141 of hub 1140*a*. Passageway 1146 may be operable to communicate fluids with lumen 1118 of cannula 1100*a*. See FIGS. 16A-16C and FIGS. 17A-17F. Second end 1142 of hub 1140 may include various features of a conventional Luer lock connection or fitting, including threads 1148. Corresponding threads 1158 may be formed within first end 1151 of hub 1150*a*. The dimensions and configuration of receptacle 1263 in first end 1251 of coupler assembly 1250 may be selected to prevent relative movement between hub 1140*a* and hub 1150*a* during insertion (rotation) of an IO device into a bone and associated bone marrow. If such relative movement occurs, threads 1148 and 1158 may be disconnected.

For some applications hub 1140*a* and hub 1150*a* may be formed using injection molding techniques. For such embodiments hub 1140*a* may include reduced outside diameter portion 1143 disposed between first end 1141 and second end 1142. In a similar manner a plurality of void spaces or cutouts 1153 may be formed in hub 1150*a* adjacent to and extending from second end 1152 in the direction of first end 1151. See for example FIGS. 16A, 16B and 14A. The configuration and dimensions of reduced diameter portion 1143 and/or cutouts 1153 may be varied to optimize associated injection molding techniques and at the same time provide required configurations, dimensions and material strength to allow associated hub assembly 1130*a* to function in accordance with teachings of the present disclosure.

Figure 17A:
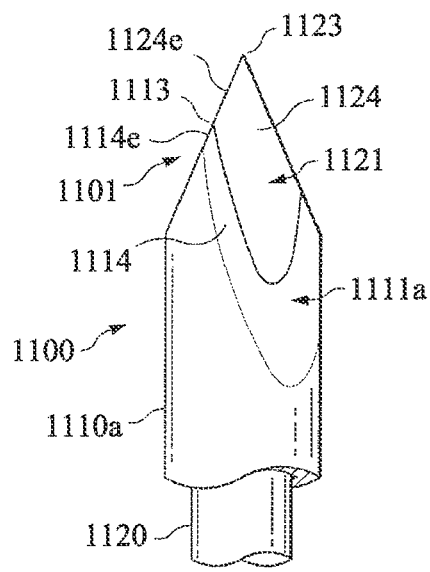
FIG. 17A is a schematic drawing showing an exploded view with portions broken away of the tips of an intraosseous needle set incorporating teachings of the present disclosure.
Figure 17B:
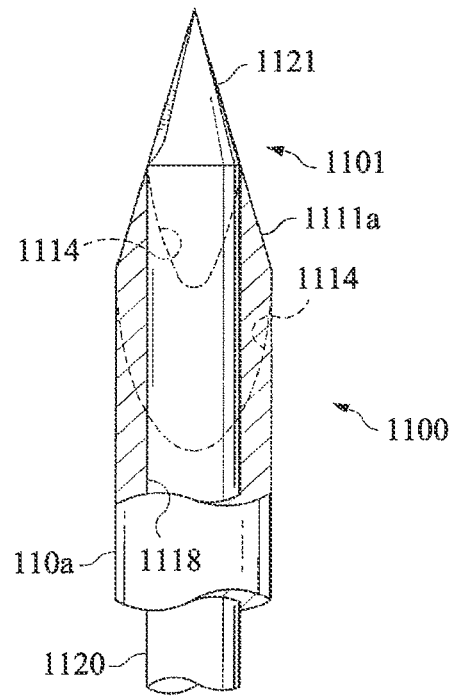
FIG. 17B is a schematic drawing showing an exploded view with portions broken away of a beveled tip of an intraosseous needle set incorporating teachings of the present disclosure.

FIGS. 17A and 17B show one example of cutting surfaces and tips which may be formed adjacent to the ends of a cannula and an associated trocar in accordance with teachings of the present disclosure. For embodiments represented by cannula or outer penetrator 1110*a* and trocar or inner penetrator 1120*a*, tip 1123 of stylet 1120 may be disposed relatively close to tip 1113 of cannula 1110*a*. For some applications, first end 1121 of trocar 1120 and first end 1111*a* of cannula 1110*a* may be ground at the same time to form adjacent cutting surfaces 1114 and 1124. Grinding ends 1111*a* and 1121 at the same time may result in forming a single cutting unit to form generally matching cutting edges 1124*e* and 1114*e* such as shown in FIGS. 17A and 17B. Beveled cutting surfaced and/or serrated cutting surfaces may be used in some embodiments. Other types of cutting surfaces formed in accordance with teachings of the present disclosure may be discussed later.

First end 1121 of trocar 1120 may extend through opening 1144 in second end 1142 of hub 1140a. See FIG. 16A. Hub 1150a disposed on the second end of trocar 1120 may be releasably engaged with the second end of cannula 1110a represented by hub 1140a. See FIG. 16B.

Human bones may generally be described as having a hard outer lamellae or layer of osseous tissue known as "cortical bone". Cancellous bone (also known as trabecular or spongy bone) typically fills an inner cavity associated with cortical bone. Cancellous bone is another type of osseous tissue with generally low density and strength but high surface area. Cancellous bone typically includes spicules or trabeculae which form a latticework of interstices filled with connective tissue or bone marrow. Exterior portions of cancellous bone generally contain red bone marrow which produces blood cellular components. Most of the arteries and veins of a bone are located in the associated cancellous bone.

One of the benefits of the present disclosure may include providing various vertebral intraosseous devices including, but not limited to, vertebroplasty needles, vertebral biopsy needle sets configured to reliably provide a therapeutic agent and adapted to obtain biopsy specimens of cortical bone and/or cancellous bone by reducing need for multiple procedures/insertions in a patient.

The configuration of the tip of a cannula or outer penetrator may be modified in accordance with teachings of the present disclosure to provide optimum torque during insertion of the cannula or outer penetrator by a powered driver to penetrate bone for a therapeutic or diagnostic procedure. A controlled, steady feed rate when using a powered driver may result in higher quality delivery of therapeutic agent (cement) and/or obtaining biopsy specimens as compared to manually inserted IO needles. A needle comprising a beveled cutting tip, such as a stylet may be used to initially penetrate bone. The cutting tip may be retractable and withdrawn after insertion of a cannula comprising the beveled cutting tip. A rod shaped needle/cannula, containing one or more therapeutic agents (such as but not limited to a bone cement), configured to inject the therapeutic agent, may be disposed within the hollow cannula that has a tip making contact with the interior of the bone. In embodiments wherein a biopsy sample is desired, a biopsy rod/trocar may also be inserted into the hollow cannula. A biopsy rod may have a helical thread disposed within proximate an associate tip or first end to assist with capturing a bone and/or bone marrow biopsy specimen.

The quality and reliability of a medical procedure incorporating teachings of the present disclosure may be substantially improved by using an optimum feed rate for inserting and IO needle into a bone and associated bone marrow. Feed rate or speed of insertion of an IO biopsy needle incorporating teachings of the present disclosure may be a function of the pitch of at least one thread disposed on an interior portion of the biopsy needle and revolutions per minute (RPM) of the biopsy needle.

RPM=Feed rate×Pitch of threads

A helical thread may have a pitch of approximately twenty four (24) threads per inch. An optimum pitch may vary based on factors such as reduction gear ratio (77:1 for some embodiments) and load placed on an associated motor.

Further technical benefits may include reducing physical requirements and mental stress on users and decreasing pain and stress on patients by increasing speed and control of the needle set insertion during vertebral procedures or other bone procedures and by decreasing the number of procedures performed and the number of times a bone is drilled into.

For some applications, an IO needle formed in accordance with teachings of the present disclosure may include a hollow cannula or catheter having one end formed by electrical discharge machining (EDM) techniques, grinding techniques and/or other machining techniques. A plurality of teeth may be formed on one end of the cannula or catheter using EDM techniques, grinding techniques and/or other machining techniques.

For some embodiments a stylet or trocar may also be disposed within the cannula or catheter with a first end of the stylet extending from a first end of the cannula or catheter. Increasing the length of the first end of the stylet or trocar extending from the first end of the cannula or catheter may reduce the amount of torque or force required to penetrate a bone and may reduce time required for an associated IO needle set, vertebral needle set, biopsy needle set, aspiration needle set or to penetrate the bone and associated bone marrow.

A specific powered driver, intraosseous device and tip configuration will generally produce the same torque when drilling in a hard bone or a soft bone. However, the time required to drill to a first depth in a hard bone will generally be greater than the time required to drill to similar depth in a soft bone.

For still other embodiments, teeth formed on one end of a cannula or catheter may be bent radially outward to reduce the amount of time and/or force required to penetrate a bone and associated bone marrow using the cannula or catheter. For some applications a powered driver and vertebral needle set, aspiration needle set or biopsy needle set formed in accordance with teachings of the present disclosure may provide access to a patient's bone using a similar amount of torque. The length of time for penetrating a relatively hard bone may be increased as compared with the length of time required to penetrate a relatively softer bone.

The tips of several stylets and cannulas incorporating teachings of the present disclosure were slowly ground with coolant to prevent possible thermal damage to metal alloys or spring material used to form the stylets and cannulas. The stylets and cannulas were assembled into respective IO needle sets. The tips of each needle set were inserted into sawbones blocks under controlled test conditions. Some testing was conducted with Pacific Research sawbones blocks. The tips of the needle sets were inserted to a depth of approximately two centimeters with ten pounds (10 lbs) of force and twelve volts direct current (12 VDC) applied to an associated powered driver. There was no measurable or visual wear of the stylet or cannula tips after completion of the testing.

For some embodiments a generally hollow biopsy needle may be substantially continuously rotated at an optimum speed or RPM during insertion into a selected target area to obtain a biopsy specimen. The biopsy needle may include a longitudinal bore extending from a first, open end of the needle to a second, open end of the needle. A small helical thread may be formed on interior portions of the longitudinal bore proximate the first end. For some embodiments the thread may have a pitch similar to threads used on conventional wood screws. The rate of rotation or revolutions per minute (RPM) of the biopsy needle may be selected by installing a gear assembly with a desired speed reduction ratio (typically between 60:1 and 80:1) between a motor and an associated drive shaft. For some applications the gear assembly may reduce speed of rotation of an attached motor at a ratio of approximately 66:1 or 77:1.

Figure 17C:
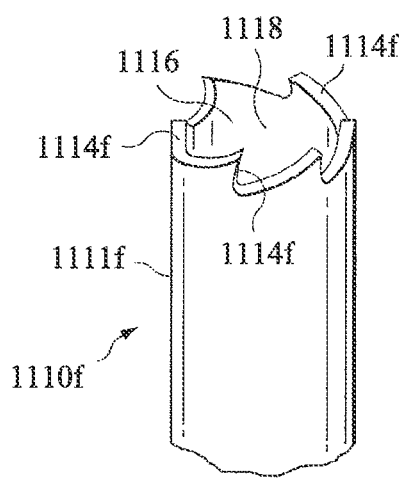
FIG. 17C is a schematic drawing showing an exploded view with portions broken away of the tips of an intraosseous needle set or a cannula incorporating teachings of the present disclosure.

Outer penetrator or cannula 1110f as shown in FIG. 17C may include first end 1111f having a plurality of cutting surfaces 1114f formed adjacent to opening 1116 in first end 111f. Opening 1116 may communicate with and form a portion of an associated longitudinal bore or lumen 1118. For some applications cutting surfaces 1114f may be formed using electrical discharge machining (EDM) techniques. Cannula 1110f as shown in FIG. 17C may have a cutting surface or tooth 1114f protruding outward followed by the next cutting surface or tooth 1114f protruding inward resulting in a cross-cut saw-type pattern. For some medical applications, a cannula such as 1110f may be used effectively. The pattern of the cutting surfaces may be effective to obtain a biopsy sample since the teeth extending outward may form a passageway (not expressly shown) with an inside diameter larger than a corresponding outside diameter of the cannula. The teeth extending inward may form a sample of bone and/or bone marrow (not expressly shown), having a generally cylindrical configuration with an outside diameter smaller than a corresponding inside diameter of the cannula. The result of such "cross cutting" may be less friction between exterior portions of the cannula and adjacent bone and/or bone marrow and less damage to a biopsy sample disposed within the lumen of the cannula.

Figure 17D:
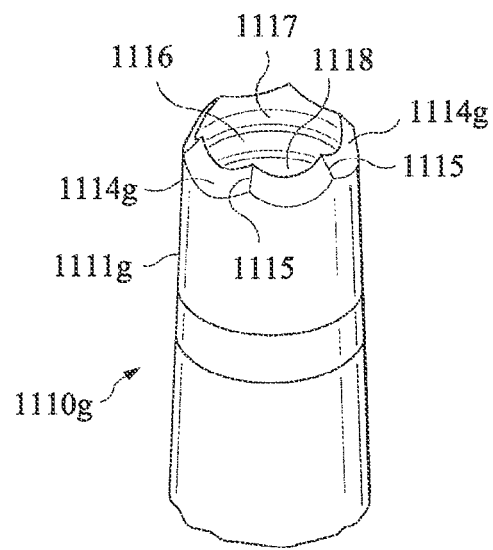
FIG. 17D is a schematic drawing showing an exploded view with portions broken away of the tips of an intraosseous needle set or a cannula incorporating teachings of the present disclosure.

For embodiments such as shown in FIG. 17D, outer penetrator or cannula 1110g may include first end 111g having a generally tapered configuration or reduced outside diameter as compared with other portions of cannula 1110g. A plurality of cutting surfaces 1114g may be disposed on end 1111g adjacent to respective opening 1116. For some applications, cutting surfaces 114g may be formed using machine grinding techniques. For embodiments end 1111g of cannula 1110g may include six ground cutting surfaces 1114g with respective crowns 1115 may be formed therebetween. Forming a biopsy needle set and/or biopsy needle with tapered end 1111g and a plurality of cutting surfaces 1114g and crowns 1115 may provide improved drilling performance when the resulting biopsy needle set and/or biopsy needle is used with a powered driver in accordance with teachings of the present disclosure.

For some applications, helical groove 1117 may be formed within longitudinal bore 1118 proximate respective opening 1116. Helical groove 1117 may assist with retaining a biopsy specimen or a bone marrow specimen within longitudinal bore 1118.

Testing conducted with cannulas or outer penetrators formed in accordance with teachings of the present disclosure indicated that forming cutting surfaces or cutting teeth with electrical discharge machining (EDM) sometimes resulted in the associated cannula or outer penetrator being able to drill through a bone and associated bone marrow slightly faster than a cannula or outer penetrator having cutting surfaces formed using grinding techniques. Some test results also indicated that bending cutting surfaces formed on one end of a cannula or outer penetrator in accordance with teachings of the present disclosure may reduce the amount of time and/or the amount of force required to remove a bone and/or bone marrow specimen from a target area.

Figure 17E:
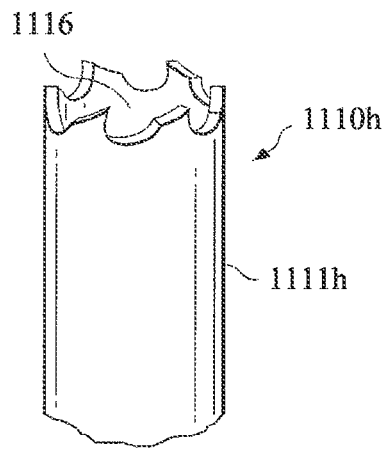
FIG. 17E is a schematic drawing showing an exploded view of one embodiment of the tip of an intraosseous device or cannula incorporating teachings of the present disclosure.
Figure 17F:
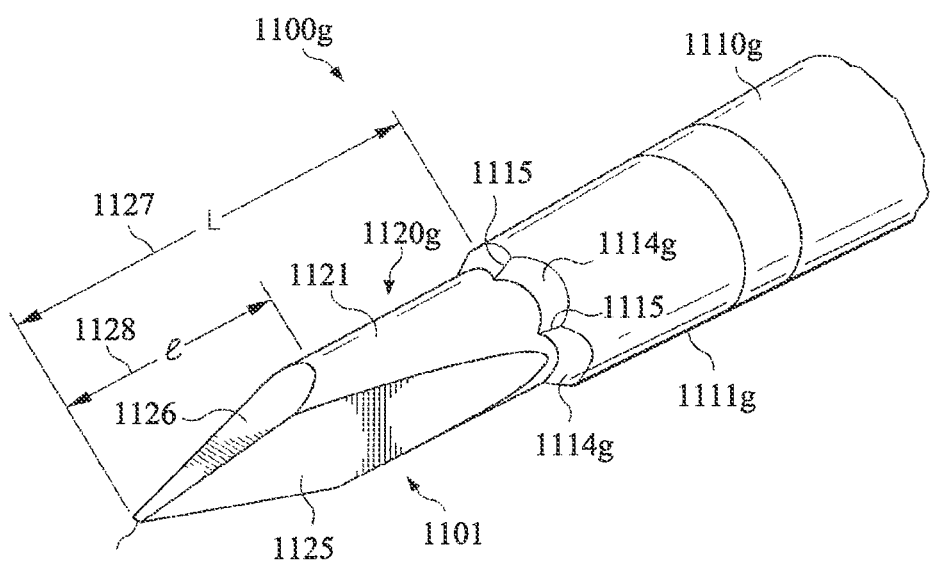
FIG. 17F is a schematic drawing showing an exploded view of still another embodiment of a tip of an intraosseous needle or device incorporating teachings of the present disclosure.

Intraosseous needle set or biopsy needle set 1100g is shown in FIGS. 17E and 17F. Biopsy needle set 1100g may include cannula or outer penetrator 1110g with stylet or inner penetrator 1120g slidably disposed therein. First end 1101 of biopsy needle set 1100g is shown in FIGS. 17E and 17F. For some applications first end 1101 of biopsy needle set 1100g may minimize damage to skin and soft body tissue at an insertion site.

For some applications inner penetrator or trocar 1120g may include first end 1121 having a plurality of cutting surfaces 1125 and 1126 formed on exterior portions thereof extending from associated tip 1123 towards second end of trocar or inner penetrator 1120g. For some applications one or more cutting surfaces 1125 may be formed having length 1127 extending from tip 1123 to associated cutting surfaces 1114g in associated cannula 1110g. One or more cutting surfaces 1126 may be formed adjacent to each cutting surface 1125 with second length 1128. First length 1127 may be greater than second length 1128. The ratio of first length 1127 and second length 1128 may be varied in accordance with teachings of the present disclosure to provide optimum performance for penetrating a selected bone and associated bone marrow.

For some applications, a single thread may be disposed within the longitudinal bore or lumen of a biopsy needle, cannula, catheter or outer penetrator in accordance with teachings of the present disclosure. Various techniques and procedures may be satisfactorily used to place the single thread within a generally hollow cannula or outer penetrator proximate one end of the cannula or outer penetrator having one end operable to penetrate a bone and/or associated bone marrow. For some embodiments, a helical coil having a configuration and dimensions associated with the resulting single thread may be placed on one end of a mandrel such as a spot welding electrode assembly. The mandrel or electrode assembly may then be inserted through an opening in the one end of the cannula or outer penetrator operable to penetrate a bone and/or associated bone marrow. The helical coil may then be bonded with adjacent portions of cannula. Coils having a wide variety of dimensions and configurations may be satisfactorily used to place a single thread in a biopsy needle.

Coupler assemblies incorporating various teachings of the present disclosure may be placed in a medical procedure tray or kit with one end down and an opposite end looking up to allow "hands free" releasable engagement with a powered driver or a manual driver. For example, coupler assembly 1250 may be disposed in medical procedure tray 1020c with first end 1251 insert into holders 1058 and second end 1252 looking up. See FIGS. 11C and 11D. As a result, end 1224 of drive shaft 1222 extending from powered driver 1200 may be inserted into and releasably engaged with second end 1252 of coupler assembly 1250 without requiring an operator or user (not expressly shown) to physically contact or manipulate any portion of coupler assembly 1250. Various features of associated "hands free" latching mechanisms are depicted in FIGS. 15A-15B.

As shown in FIGS. 15A-15D, coupler assembly 1250 may include elongated core 1260 with housing assembly 1270 slidably disposed on exterior portions of elongated core 1260. Housing assembly 1270 may include first end 1271 and second end 1272 which may be generally aligned with respective first end 1261 and respective second end 1262 of elongated core 1260. For some applications, elongated core 1260 may have a generally cylindrical configuration defined in first exterior portion 1260a and second exterior portion 1260b with various shoulders and/or recesses formed thereon. For some embodiments first exterior portion 1260a may have a larger diameter than second exterior portion 1260b.

Coupler assembly 1250a and coupler assembly 1250b may include respective elongated cores 1260a and 1260b having similar features and functions as described with respect to coupler assembly 1250. Coupler assembly 1250a may include housing assembly 1270a with substantially the same components, functions and features as described with respect to housing assembly 1270 except for second end 272a of housing assembly 1270a. Coupler assembly 1250b may include housing assembly 1270b having substantially similar components, functions and features as described with respect to housing assembly 1270 except for second end 272b of housing assembly 1270b.

Housing assembly 1270 may be described as having a generally hollow, cylindrical configuration defined in part by first housing segment 1280 and second housing segment 1290. See FIGS. 15A and 15B. The first end of housing segment 1280 may generally correspond with first end 1271 of housing assembly 1270. The second end of second housing segment 1290 may generally correspond with second end 272 of housing assembly 1270.

First end 1291 of second housing segment 1290 may be described as having a generally cylindrical configuration with an outside diameter smaller than the adjacent inside diameter of second end 1282 of first housing segment 1280. First end 1291 of second housing segment 1290 may slide longitudinally from a first position to a second position within second end 1282 of first housing segment 1280 to release one end of a drive shaft engaged with second end 1252 of coupler assembly 1250 (See FIGS. 15A-15D).

A biasing mechanism such as coiled spring 1274 may be disposed around exterior portion 1260a of generally elongated core 1260. See for example FIGS. 15A, 15B, 15C and 15D. First end 1275 of coiled spring 1274 may contact annular shoulder 1284 formed on interior portions of first housing segment 1280. Second end 1276 of coiled spring 1274 may contact annular shoulder 278 disposed proximate first end 1291 of second housing segment 1290. Coil spring 1274, annular shoulder 1284 and annular shoulder 278 may cooperate with each other to generally maintain first housing segment 1280 and second housing segment 1290 in a first extended position relative to each other. See FIGS. 14A and 15A-15D. Other biasing mechanisms such as, but not limited to, leaf springs and bellows (not expressly shown) may also be disposed between annular shoulder 1284 and annular shoulder 1278.

Annular shoulder 1278, associated with second end 1276 of coiled spring 1274, may extend radially outward from generally cylindrical ring 1277. Generally cylindrical ring 1277 may be slidably and rotatably disposed on exterior portion 1260a of elongated core 1260. Annular shoulder 1279 may be disposed on interior portions of generally cylindrical ring 1277 and may extend radially inward toward adjacent portions of elongated core 1260.

Annular shoulder 1268 may be formed on exterior portion 1260a of elongated core 1260 intermediate first end 1261 and second end 1262. The configuration and dimensions of annular shoulder 268 and annular shoulder 1279 are selected to be compatible with each other such that engagement between annular shoulder 1279 of generally cylindrical ring 1277 with annular shoulder 1268 of elongated core 1260 may limit movement of second housing segment 1290 longitudinally in the direction of second end 1262 of elongated core 1260.

For some applications a plurality of flexible collets or fingers 1477 may extend from generally cylindrical ring 1277 opposite from annular shoulder 1278. Respective collet heads 1478 may be formed on the end of each collet 1477 opposite from annular shoulder 1278. The dimensions and configuration of collet heads 1478 may be selected to be received within respective slots or openings 1297 formed in second housing 1290. During manufacture of coupler assembly 1250, each collet head 1478 may be disposed within respective slot or opening 1297 to securely engage generally cylindrical ring 1277 and annular shoulder 1278 proximate first end 1291 of second housing segment 1290. As a result, second housing segment 1290 and annular shoulder 1278 may generally move as a single unit relative to elongated core 1260 and first housing segment 1280.

During disengagement of an intraosseous device from first end 1251 of coupler assembly 1250, first housing segment 1280 may move or slide longitudinally toward second housing segment 1290. In a similar manner, second housing segment 1290 may move or slide longitudinally toward first housing segment 1280 during disengagement of a powered driver from second end 1252 of coupler assembly 1250.

Annular shoulder 1267 may be formed on exterior portions of elongated core 1260 proximate first end 1261. Annular shoulder 1267 may engage portions of first end 1271 of housing 1270 to limit longitudinal movement of first housing segment 1280 during longitudinal movement of second housing segment 1290 towards first end 1261 of elongated core 1260 during disengagement of a powered driver from second end 1252 of coupler assembly 1250.

As previously noted, annular shoulder 1268 may be formed on exterior portions of elongated core 1260 between first end 1261 and second end 1262. Engagement between annular shoulder 1268 and annular shoulder 1279 of generally cylindrical ring 1277 may limit movement of second housing segment 1290 toward second end 1262 of elongated core 1260. Contact between spring 1274 and annular shoulder 1278 and annular shoulder 1284 of first housing segment 1280 may limit the longitudinal movement of first housing segment 1280 in the direction of second end 1262 of elongated core 1260 during disengagement of an intraosseous device from first end 1251 of coupler assembly 1250.

Generally cylindrical ring 1277 and attached annular shoulder 1279 may slide longitudinally on exterior portions of annular core 1260 between annual shoulder 1268 and annular shoulder 1267. First housing segment 1280 may move longitudinally toward second end 1262 of elongated core 1260 to release one end of intraosseous device from engagement with first end 1251 of coupler assembly 1250. In a similar manner, second housing segment 1290 may move longitudinally toward first end 1261 of elongated core 1260 to release one end of a drive shaft extending from a powered driver engaged with second end 1252 of coupler assembly 1250.

A wide variety of latches and latch mechanisms may be satisfactorily used to releasably engage one end of an intraosseous device within a first end of a coupler assembly incorporating teachings of the present disclosure. In a similar manner, a wide variety of latches and latch mechanisms may be satisfactorily used to releasably engage one end of a drive shaft extending from a powered driver or manual driver within a second end of the coupler assembly incorporating teachings of the present disclosure.

For embodiments represented by coupler assemblies 1250, 1250a and 1250b, first latch 1410 may be disposed on exterior portions of elongated core 1260 proximate receptacle 1263 adjacent to first end 1261 to releasably engage one end of an IO device such as second end 1102 of an IO needle set 1100 within receptacle 1263 of coupler assembly 1250, 1250a and/or 1250b. Second latch mechanism 1420 may be disposed on exterior portions of elongated core 1260 proximate receptacle 1264 adjacent to second end 1262 to releasably engage one end of a drive shaft with second end 1252 of coupler assembly 1250. See FIGS. 14A-14C and FIGS. 15A-15D.

Second latch 1420 may be used to releasably engage one portion of a drive shaft such as end 1224 of drive shaft 1222 extending from powered driver 1200 within second end 1252 of coupler assembly 1250, 1250a and/or 1250b. Latch 1410 may releasably engage an intraosseous device with first end 1251 of coupler assembly 1250 substantially the same latch 1420 may releasably engage a powered driver with second end 1252 of coupler assembly 1250.

Figure 15C:
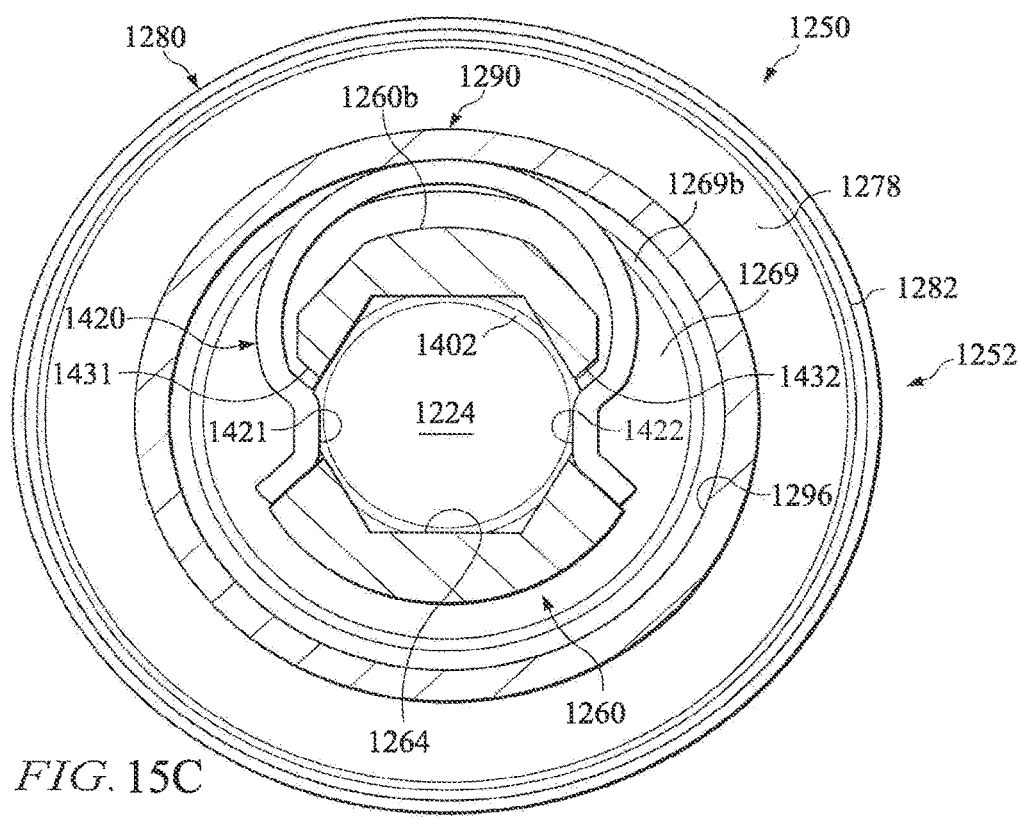
FIG. 15C is a schematic drawing in section taken along lines 15C-15C of FIG. 15B, incorporating teachings of the present disclosure.
Figure 15D:
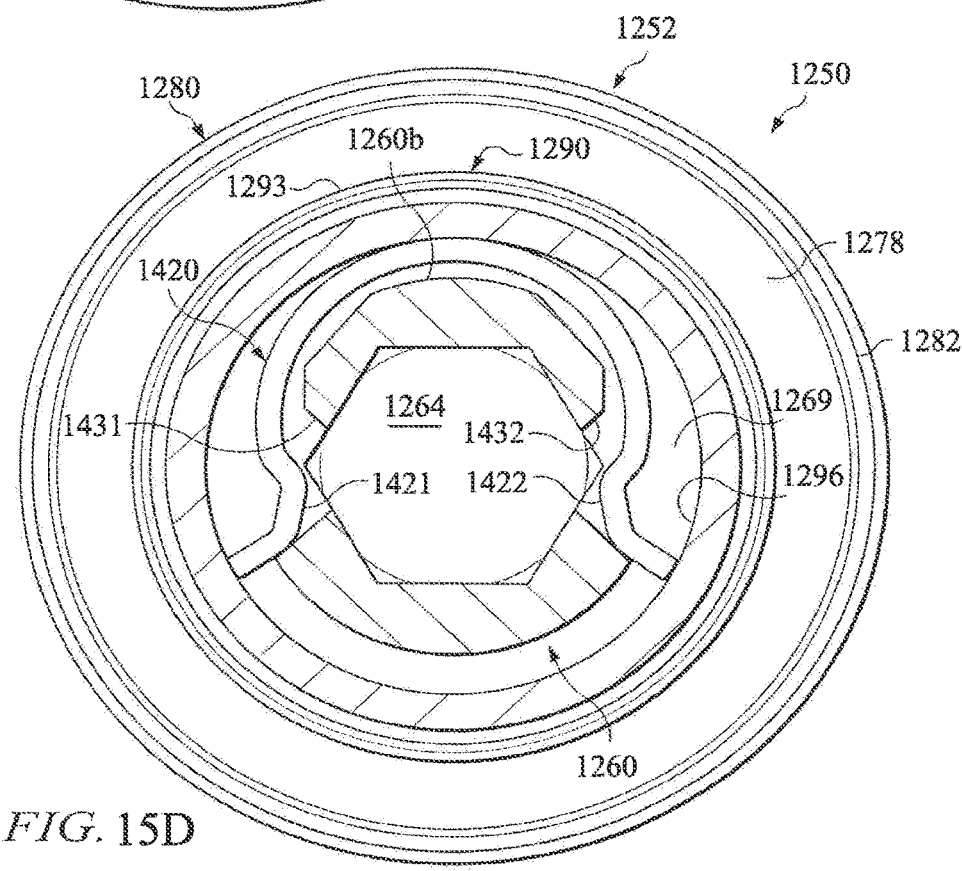
FIG. 15D is a schematic drawing in section taken along lines 15D-15D of FIG. 15A, incorporating teachings of the present disclosure.

For some applications, latches 1410 and 1420 may have similar configurations such as a general "omega" shape. See latch 1420 in FIGS. 15C and 15D. However, latch 1410 may have larger dimensions corresponding generally with exterior portion 1260a of elongated core 1260. Latch 1420 may have smaller dimensions corresponding generally with exterior portion 1260b of elongated core 1260. Various features of the present disclosure may be described with respect to latch mechanism 1420 as shown in FIGS. 15C and 15D along with adjacent portions of second housing segment 1290 and exterior portion 1260b of elongated core 1260.

Respective detents 1421 and 1422 may be formed on opposite ends of generally omega shaped latch 1420. See FIGS. 15C and 15D. In a similar manner, respective detents (not expressly shown) may be formed on the ends of generally omega shaped latch 1410. The configuration and dimensions of detents 1421 and 1422 may be compatible with placing each detent 1421 and 1422 in respective slot or opening 1431 and 1432 extending between exterior portion 1260b of elongated core 1260 to interior portions of receptacle 1264 disposed proximate second end 1252 of coupler assembly 1250.

Latch 1420 may have a first position such as shown in FIGS. 15A-15D in which portions of detents 1421 and 1422 may extend through respective slots 1431 and 1432. The dimensions and configuration of detent 1421 and 1422 may be operable to be securely engaged with annular groove 1402 formed in end 1224 of powered driver 1200. In a similar manner, respective detents on associated latch 1410 may be releasably engaged with annular groove 1401 disposed in second end 1102 of an IO needle 1100.

For some applications, a plurality of tapered surfaces 1403 may be formed on exterior portions of hub 1140a proximate first end 1142 (See FIG. 15A) to radially expand detent mechanisms associated with omega shaped latch 1410 radially outward while inserting second end 1102 of biopsy needle 1100b into first end 1251 of coupler assembly 1250, 1250a or 1250b. The detent mechanism may "snap" into annular groove 1401 when aligned therewith. In a similar manner, a plurality of tapered surfaces 1228 may be formed on exterior portions of end 1224 of drive shaft 1222 extending from powered driver 1200 to radially expand detent mechanisms 1421 and 1422 radially outward during the insertion of end 1224 of powered driver 1200 into second end 1252 of coupler assembly 1250. Detent mechanisms 1421 and 1422 will "snap" into annular groove 1402 when aligned therewith. See FIG. 15A.

Engagement between detent mechanisms associated with latch 1410 with annular groove 1401 of hub assembly 1130a will generally retain second end 1102 of biopsy needle 1100b securely engaged with first end 1251 of coupler assembly 1250. This engagement may allow powered driver 1200 to rotate or spin cannula or biopsy needle 1110 while withdrawing cannula or biopsy needle 1110 from an insertion site. In a similar manner, engagement between detent mechanisms 1421 and 1422 of omega shaped latch 1420 and annular groove 1402 of end 1224 of powered driver 1200 will generally retain second end 1252 of coupler assembly 1250 engaged with powered driver 1100 during withdrawal of cannula 1110b from an insertion site.

IO needle set 1100 may be released from first end 1251 of coupler assembly 1250 by sliding first housing segment 1280 longitudinally toward second end 1262 of elongated core 1260. Such movement of first housing segment 1280 will result in interior tapered surface 1286 contacting exterior portions of omega shaped latch 1410 and compressing omega shaped latch 1410 to radially expand associated detent mechanisms (not expressly shown) from engagement with annular groove 1401 of hub assembly 1130a. As a result, IO needle set 1100 may be easily withdrawn from first end 1251 of coupler assembly 1250.

In a similar manner, longitudinal movement of second housing segment 1290 toward first end 1251 of coupler assembly 1250 will result in interior tapered surface 1296 contacting exterior portions of omega shaped latch 1420 to compress generally omega shaped latch 1420 and withdraw or retract detent mechanisms 1421 and 1422 from engagement with annular groove 1402 of end 1224. See FIG. 15B. As a result, powered driver 1200 and second end 1252 of coupler assembly 1250 may be easily disconnected from each other.

Coupler assemblies 1250 and 1250a may have substantially the same overall configuration and dimensions including respective flange 1254 extending radially from second end 1252 and 1252a. Flange 1254 may be generally described as having an enlarged funnel shaped or bell shaped configuration. The dimensions and configuration of flange 1254 may be selected to be compatible with end 1211 of powered driver 1200. In some embodiments a coupler assembly 1250b may not have a respective flange 1254 (not expressly shown). Second end 1272b of housing assembly 1270b may terminate proximate first end 1262 of associated elongated core 1260 and associated second end 1252b of coupler assembly 1250b.

Further details about coupler assemblies and other latch mechanisms and release mechanisms may be found in co-pending U.S. patent application Ser. No. 11/853,678, filed on Sep. 11, 2007, now U.S. Pat. No. 8,668,698, entitled "Apparatus And Methods For Biopsy And Aspiration Of Bone Marrow."

Figure 18:
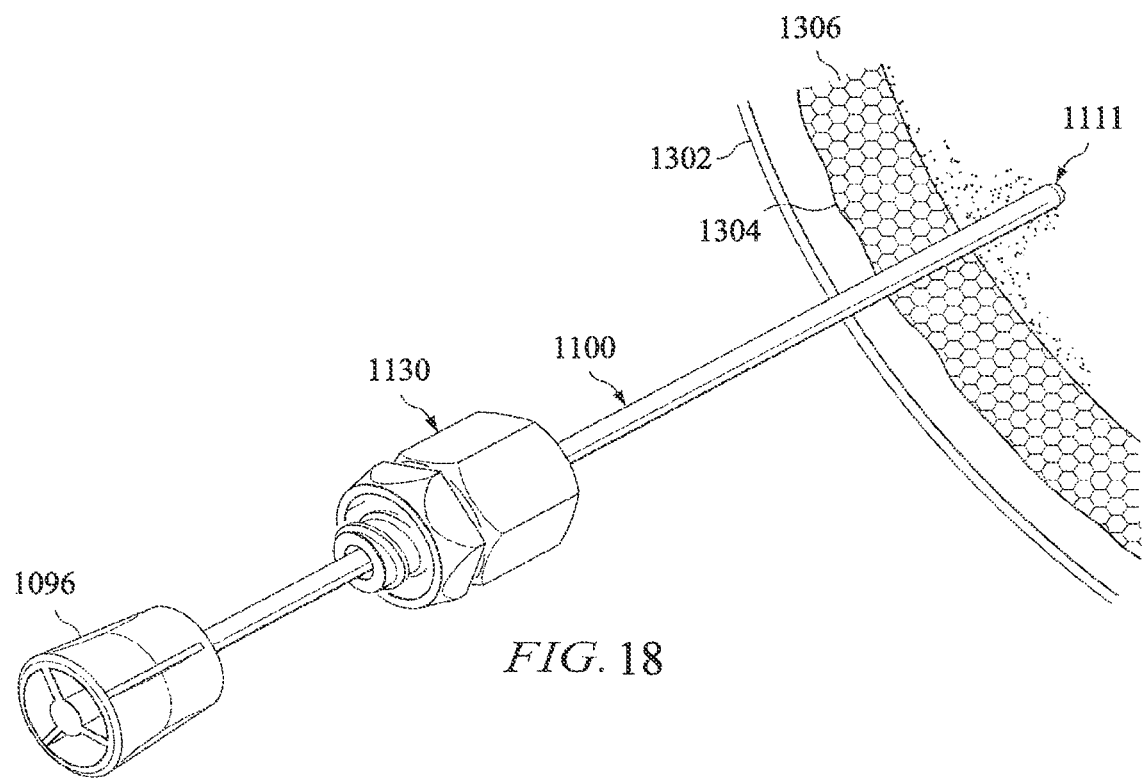
FIG. 18 is a schematic drawing partially in section showing an isometric view of an intraosseous needle set penetrating bone incorporating teachings of the present disclosure.

FIG. 18 depicts an example of apparatus and methods which may be used to insert a first end 1111 of the generally hollow cannula or IO needle 1100 into the cortex of a bone and/or associated bone marrow. Skin and soft tissue 1302 generally cover insertion sites in crest 1304 of the bone. All bones generally include a tough, hard to penetrate layer of cortex 1306. FIG. 18 shows enlarged skin and soft tissue layer 1302 and cortex layer 1306 for illustration purposes only. A typical thickness for skin and soft tissue layer 1302 may be seven to eight millimeters (7 mm to 8 mm). A typical thickness for cortex layer 1306 may be approximately two millimeters (2 mm).

As previously discussed an intraosseous (IO) device or IO needle set 1100 may be inserted in the cortex of a bone with minimum trauma to deliver a therapeutic medicament and/or obtain bone and/or bone marrow samples in accordance with teachings of the present disclosure.

The medical devices, medical procedure trays, kits and diagnostic methods and therapeutic methods of the present disclosure may be used to treat or evaluate any bone, such as but not limited to, bones of the vertebrae, neck bones, sternum, rib, clavicle, femoral, pelvic, wrist and the distal ends of the long bones. Some exemplary conditions that may be diagnosed or treated may include fractures, osteoporosis, degenerative bone diseases, bone cancers, metastatic bone disease, osteolytic bone disease, osteomalacia, osteitis fibrosa, Paget's disease, bone deficiency, hyperparathyroidism. Fractures or degeneration of bone may result from osteoporosis which may be age-related osteoporosis, postmenopausal osteoporosis, juvenile osteoporosis, Cushing's syndrome osteoporosis, multiple myeloma osteoporosis, leukemia osteoporosis, Turner's syndrome osteoporosis, alcohol osteoporosis, chronic liver disease osteoporosis, glucocorticoid-induced osteoporosis, chronic inflammatory disease induced osteoporosis and disuse osteoporosis.

FIGS. 19A-19D depict an exemplary medical procedure performed on a vertebral disc of a human patient using the methods, devices, medical procedure trays and kits of the disclosure. In a non-limiting example, the vertebral procedure may be vertebroplasty. The teachings of the present disclosure are however not limited to vertebroplasty or vertebral procedures and medicaments or therapeutic agents of any type may be delivered to a vertebral bone (or any other bone) and/or a biological sample may be obtained for analysis during the same procedure.

In an example vertebroplasty procedure, depicted in FIGS. 19A-19D, an operator may obtain a medical procedures tray 1020 comprising a vertebral IO device as set forth in the present disclosure, comprising a vertebral IO needle system/set 1100, power driver 1200, coupler assembly 1250 comprising sterile sleeve 1170. An example vertebral IO device may comprise a vertebroplasty needle set and may include a beveled needle comprising a cannula 1100a and a stylet with a beveled cutting tip and a serrated cutting edge (see FIGS. 17B and 17F). The IO device may also comprise a biopsy needle set, and may comprise a cannula with a helical thread for capturing a bone sample. The coupler assembly 1250 may be operable to releasably attach different vertebral IO needles 1100 at end 1251 and releasably attach power driver 1200 at end 1252.

The operator may assemble the vertebral system apparatus by unwrapping a sterile medical procedure tray and attaching a non-sterile power driver 1200 to end 1252 of the coupler assembly 1250 and covering power driver 1250 with sterile glove 1170 as shown in FIGS. 13A and 13B. Sterile vertebral needle 1100a may be then attached to end 1251 of the coupler 1250 as shown in FIG. 13C. The sterile vertebral needle 1100a attached to the vertebral apparatus as in FIG. 13C may then be inserted into a vertebral disc "powered in." Generally, an operator trained to perform such a procedure, may insert a vertebral needle 1100 through the cortex 1306 of a vertebral bone into the vertebral body 1307 using powered drill 200 under the guidance of fluoroscopy or other visual imaging methods. Following powering in, driver 1200 may be released from the coupler 1250 and the stylet comprising a beveled cutting tip and/or a serrated cutting surface and/or any other suitable cutting tip may be withdrawn from the cannula 1100 of the vertebral needle, thereby leaving the cannula 1100 firmly seated in the vertebral body 1307 (see FIG. 19B).

Figure 19A:
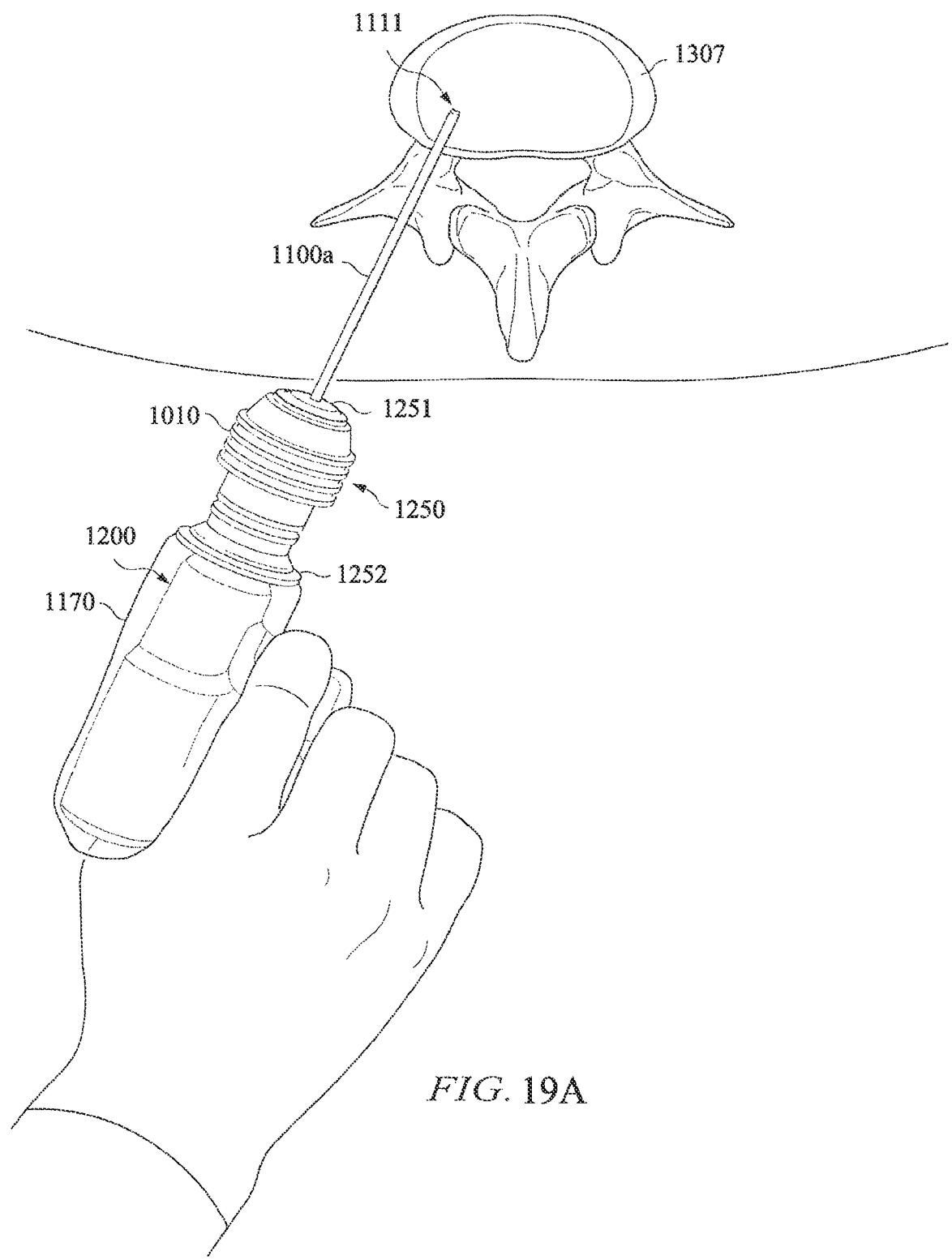
FIG. 19A is a schematic drawing partially in section showing an example of a vertebral procedure using the intraosseous (IO) medical devices and medical procedures tray, wherein a powered driver is used to insert an IO device (needle/cannula) into a vertebral bone, incorporating teachings of the present disclosure.
Figure 19B:
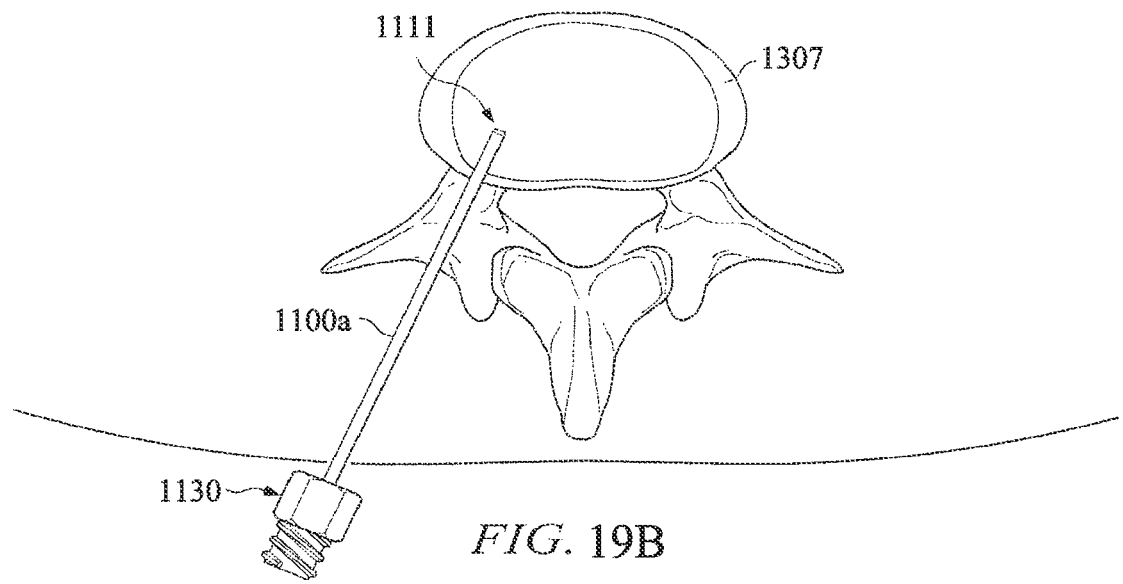
FIG. 19B is a schematic drawing showing partially in section an example of a vertebral procedure using the intraosseous (IO) medical devices and medical procedures tray, wherein the powered device is detached from the intraosseous medical devices leaving the IO needle/cannula attached to the vertebral bone, incorporating teachings of the present disclosure.
Figure 19C:
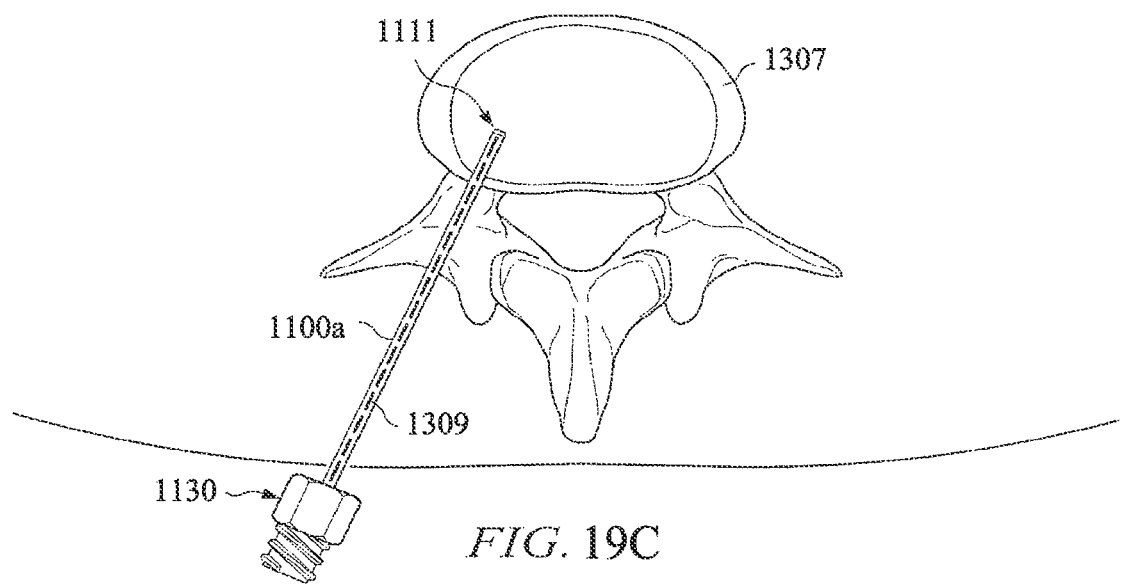
FIG. 19C is a schematic drawing partially in section showing an example of a vertebral procedure using the intraosseous medical devices and medical procedures tray, a therapeutic agent may be delivered into the IO needle/cannula, incorporating teachings of the present disclosure.

A trocar, and/or needle, and/or ejector rod, and/or syringe filled with a bone cement 1309 (and/or other medicaments) may be slidably disposed into cannula 1100a as shown in FIG. 19C (trocar/needle/rod/syringe 1100b not expressly shown) and bone cement 1309 may be injected into the vertebral body 1307. A connection (such as a Luer lock) may be used to attach 1100b with 1100a. The trocar 1100b may comprise one or more therapeutic agents to be delivered into a bone such as a vertebral disc. For example, a bone strengthening agent/factor may be delivered with the bone cement. In some embodiments, the bone cement or therapeutic agent may be delivered directly through the cannula 1100a into the vertebral body (without requiring trocar 1100b). The injected bone cement will typically solidify and strengthen a fractured and/or compressed vertebra.

Figure 19D:
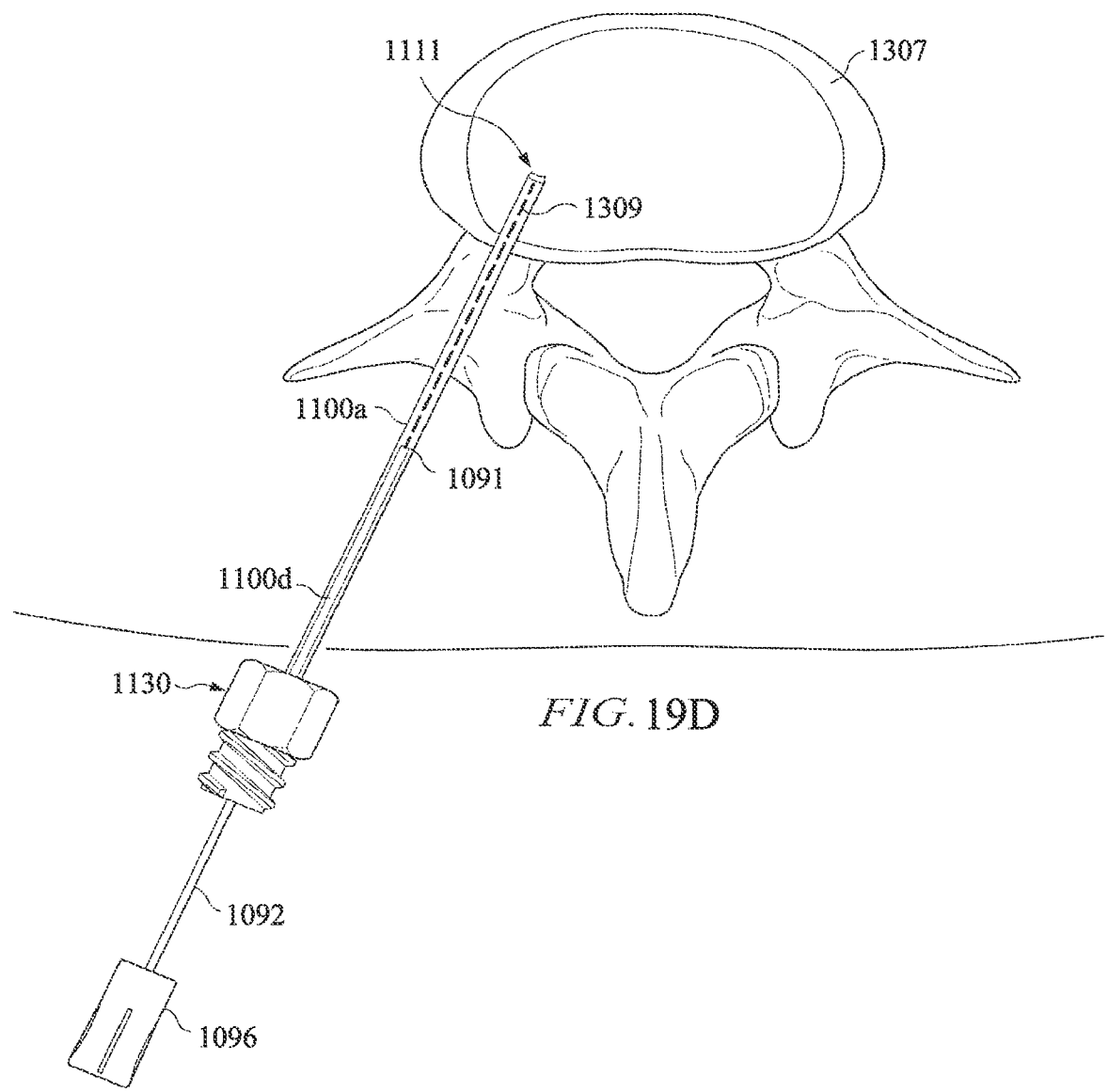
FIG. 19D is a schematic drawing partially in section showing an example of a vertebral procedure using the intraosseous medical devices and medical procedures tray, wherein a trocar (e.g., for delivering a therapeutic agent, or for obtaining a biopsy) is inserted into the cannula attached to a vertebral bone, incorporating teachings of the present disclosure.

Either preceding or following injection of the bone cement 1309 into the vertebral body 1307, a biopsy needle 1100d comprising handle 1096, first end 1091 and second end 1092 may be inserted into cannula 1100 and used to obtain a specimen of bone tissue for diagnostic analysis (see FIG. 19D). The biopsy needle 1100d may then be withdrawn, power driver 1200 reattached to coupler assembly 1250 at end 1251 and the cannula 1100 may be withdrawn from the patient "powered out" (not expressly shown). Thus, a therapeutic procedure may be combined with a diagnostic procedure using the IO needles, IO devices, methods, kits and trays of the present disclosure.

Following the medical and/or diagnostic procedures, the driver 1200 may be detached from the coupler assembly and cleaned and stored for further use. A non-sterile power driver 1200 maybe used with disposable needles 1100 and a disposable coupler 1250, comprising a sterile sleeve 1170, thereby allowing multiple use of the non-sterile power driver.

As described above, for delivery of a therapeutic agent to bone and/or for removal of a biological specimen from a bone the needles 1100b or 1100d as depicted in FIGS. 19A-19D may also be referred to as an "ejector rod". An ejector rod, such as 1100b or 1100d, may be slidably disposed into a hollow cannula 1100a of an IO needle to deliver a medicament or obtain a biological sample from a bone.

The length of ejector 1100b or 1100d may be selected to be greater than the length of a lumen in an associated IO needle 1100a. Handle or hub 1096 may be disposed on second end 1092 of ejector 1100b or 1100d. The dimensions and configuration of first end 1091 of ejector rod 1100b or 1100d may be selected to be compatible with inserting first end 1091 through an opening in the first end of an associated IO needle 1100a. As set forth above, the teachings of the present disclosure are not limited to vertebroplasty or vertebral procedures and medical procedures for delivery of a therapeutic agent and possibly combining such a therapeutic procedure with a diagnostic procedure are provided by this disclosure for any bone and any bone related condition.

Benefits of the present disclosure may include reducing physical requirements and mental stress on operators and decreasing pain and stress on patients by increasing speed and control of the needle set insertion during vertebral procedures or other bone procedures and by decreasing the number of procedures performed and the number of times a bone is drilled into.

Although the present disclosure and its advantages have been described in detail, it should be understood that various changes, substitutions and alternations can be made herein without departing from the spirit and scope of the invention as defined by the following claims.

What is claimed is:

1. An apparatus for obtaining a biopsy sample of a bone and/or associated bone marrow, the apparatus comprising:
   an intraosseous device operable to penetrate the bone and associated bone marrow, the intraosseous device comprising:
      a cannula extending from a first hub, the cannula having a longitudinal bore through the cannula; and
      a stylet extending from a second hub, the second hub configured to releasably engage the first hub, and the cannula configured to slidably receive the stylet within the longitudinal bore of the cannula when the first hub is engaged to the second hub;

a powered driver including a housing defining a handle configured to be sized and shaped to fit a hand of an operator of the apparatus, the housing enclosing a motor and a power supply, the housing further including a trigger assembly electrically coupled to the power supply and operable to activate the motor to rotate the intraosseous device when the intraosseous device is releasably coupled to the powered driver;

a coupler assembly operable to releasably couple the intraosseous device to the powered driver, a first end portion of the coupler assembly configured to receive a portion of the intraosseous device, and a second end portion of the coupler assembly configured to receive a portion of the powered driver, the coupler assembly further configured to releasably engage the portion of the intraosseous device and the portion of the powered driver; and a containment bag attached to the coupler assembly, the containment bag including an opening configured to receive and enclose the powered driver such that the operator may grasp the handle of the powered driver over the containment bag to prevent contamination of the handle, wherein the coupler assembly defines a first receptacle configured to receive the portion of the intraosseous device, and wherein the coupler assembly comprises a housing segment slidably disposed over an exterior portion of an elongated core of the coupler assembly, the housing segment operable to move along a longitudinal length of the coupler assembly from a first position to a second position to allow release of the portion of the intraosseous device from within the first receptacle.

2. The apparatus according to claim 1, wherein the containment bag further includes a second opening attached to the coupler assembly and forms a fluid barrier between an inner volume defined by the containment bag configured to enclose the handle and the intraosseous device.

3. The apparatus according to claim 2, wherein the coupler assembly is operable to allow the powered driver to rotate the intraosseous device without damage to the containment bag.

4. The apparatus according to claim 1, wherein the power supply comprises a battery disposed within the housing and configured to supply power to the motor.

5. The apparatus according to claim 4, wherein the housing of the powered driver further includes an indicator light.

6. The apparatus according to claim 5, wherein the indicator light is disposed on a proximal end of the housing.

7. The apparatus according to claim 5, wherein the indicator light is operable to indicate a level of the battery.

8. The apparatus according to claim 5, wherein the indicator light is a light emitting diode.

9. The apparatus according to claim 5, wherein the indicator light is operable to activate when a predetermined amount of electrical storage capacity of the battery has been used.

10. The apparatus according to claim 1, wherein the powered driver further comprises a drive shaft configured to releasably engage the coupler assembly.

11. The apparatus according to claim 10, wherein the drive shaft extends from a distal end of the housing.

12. The apparatus according to claim 11, further comprising a tapered surface formed on an exterior portion of a distal end of the drive shaft.

13. The apparatus according to claim 1, wherein the cannula comprises a cutting tip, and the cutting tip of the cannula and a tip of the stylet are operable to penetrate the bone as a single cutting unit.

14. The apparatus according to claim 1, wherein an end of the first hub further comprises a Luer lock fitting.

15. The apparatus according to claim 1, wherein the housing of the powered driver further includes an indicator light operable to indicate a level of the power supply, and wherein the cannula and the stylet are operable to penetrate the bone as a single cutting unit.

16. The apparatus according to claim 15, wherein the powered driver further comprises a drive shaft with a distal end having an exterior portion including a tapered surface.

* * * * *